United States Patent
Fujimoto et al.

(10) Patent No.: US 7,030,138 B2
(45) Date of Patent: Apr. 18, 2006

(54) BENZAMIDINE DERIVATIVES

(75) Inventors: Koichi Fujimoto, Yokohama (JP); Naoki Tanaka, Matsudo (JP); Ikuko Shimada, Yokohama (JP); Fumitoshi Asai, Nishitokyo (JP)

(73) Assignee: Sankyo Company, Limited, Tokyo (JP)

( * ) Notice: Subject to any disclaimer, the term of this patent is extended or adjusted under 35 U.S.C. 154(b) by 131 days.

(21) Appl. No.: 10/679,215

(22) Filed: Oct. 3, 2003

(65) Prior Publication Data
US 2004/0147555 A1 Jul. 29, 2004

Related U.S. Application Data

(63) Continuation-in-part of application No. PCT/JP02/03355, filed on Apr. 3, 2002.

(30) Foreign Application Priority Data
Apr. 5, 2001 (JP) .............................. 2001-107615

(51) Int. Cl.
*C07D 211/06* (2006.01)
*A61K 31/445* (2006.01)

(52) U.S. Cl. ................. 514/317; 514/212.01; 514/424; 546/192; 540/484; 548/541

(58) Field of Classification Search ........... 514/212.01, 514/317, 424; 546/192; 540/484; 548/541
See application file for complete search history.

(56) References Cited

U.S. PATENT DOCUMENTS

| 6,555,556 B1 | 4/2003 | Fujimoto et al. |
| 2004/0010009 A1 | 1/2004 | Fujimoto et al. |

FOREIGN PATENT DOCUMENTS

| EP | 0 540 051 A1 | 5/1993 |
| EP | 0 798 295 A1 | 10/1997 |
| EP | 0 976 722 A1 | 2/2000 |
| WO | WO 00/47553 A2 | 8/2000 |
| WO | WO 01/09093 A1 | 2/2001 |
| WO | WO 01/30756 A1 | 5/2001 |

OTHER PUBLICATIONS

English-language International Preliminary Examination Report transmitted on Nov. 4, 2003 of International Application No. PCT/JP02/03355; Applicants: Sankyo Company, Limited.
E.L. Smith et al., *Principles of Biochemistry: Mammalian Biochemistry*, 7th Edition, McGraw-Hill, Inc. (1983), pp. 16 to 37.
Sebastian Harder and Petra Thürmann, "Clinically Important Drug Interactions with Anticoagulants", *Clin. Pharmacokinet, 30*, 416 to 444 (1996).
Marc Verstraete and Pierre Zoldhelyi, "Novel Antithrombotic Drugs in Development", *Drugs, 49*, 856 to 884 (1995).

*Primary Examiner*—Zinna Northington Davis
(74) *Attorney, Agent, or Firm*—Frishauf, Holtz, Goodman & Chick, P.C.

(57) ABSTRACT

A compound of a formula (1) and pharmacologically acceptable salts thereof:

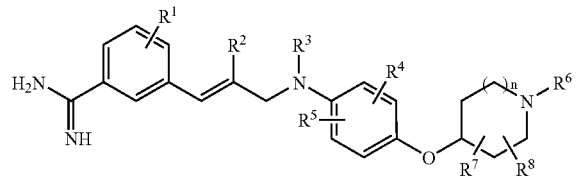

(1)

wherein $R^1$ represents hydrogen, halogen, alkyl or hydroxyl; $R^2$ represents hydrogen or halogen; $R^3$ represents hydrogen, alkyl, hydroxyl, carboxyalkyl, alkoxycarbonylalkyl, alkylsulfonyl, alkoxycarbonylalkylsulfonyl, craboxyalkylsulfonyl or carboxyalkylcarbonyl; each of $R^4$ and $R^5$ represents hydrogen, halogen, alkyl, carbamoyl, alkoxy, carboxyl, alkoxycarbonyl, monoalkylcarbamoyl or dialkylcarbamoyl; $R^6$ represents a heterocycle, hydrogen, alkyl, cycloalkyl, aralkyl, carboxyalkyl, alkoxycarbonylalkyl, aliphatic or aromatic acyl, carbamoyl, alkylsulfonyl, aryl, formimidoyl, 1-iminoalkyl, N-alkylforminidoyl or iminoarylmethyl; each of $R^7$ and $R^8$ represents hydrogen or alkyl; n represents 0, 1 or 2. The compound exhibits excellent activated blood coagulation factor X inhibitory activity and prevents or treats blood coagulation-related diseases.

34 Claims, No Drawings

BENZAMIDINE DERIVATIVES

CROSS REFERENCE TO RELATED APPLICATION

This application is a continuation-in-part application of International application PCT/JP02/03355 filed Apr. 3, 2002, the entire contents of which are hereby incorporated by reference herein.

BACKGROUND OF THE INVENTION

1. Field of the Invention

The present invention relates to benzamidine derivatives, and pharmacologically acceptable salts and prodrugs thereof, which have excellent activated blood coagulation factor X inhibitory activity. The present invention also concerns a pharmaceutical composition for the prevention or treatment of blood coagulation-related diseases, comprising said benzamidine derivative, or a pharmacologically acceptable salt or prodrug thereof. The present invention is further directed to the use of said benzamidine derivative, or a pharmacologically acceptable salt or prodrug thereof for the preparation of a medicament for the prevention or treatment of blood coagulation-related diseases. The present invention also relates to a method for the prevention or treatment of blood coagulation-related diseases comprising administering to a warm blooded animal in need of such prevention or treatment a pharmacologically effective amount of said benzamidine derivative, or a pharmacologically acceptable salt or prodrug thereof. The present invention also involves processes for the preparation of said benzamidine derivatives, and pharmacologically acceptable salts and prodrugs thereof.

2. Background Information

Recently the proportion of the population of an advanced age is increasing and the increase of patients with circulatory disease accompanying aging is remarkable. Of the diseases, thromboses such as cerebral embolus, myocardial infarction, peripheral circulatory disease and the like not only directly become the cause of a person's death, but also lead to a private and social burden, which comprise unsatisfactory recuperation of the patient and a restricted private life of the patient. It is considered that anti-coagulation treatment will be increasingly important as a thrombosis treatment.

Blood coagulation is caused by formation of fibrin. Fibrin is formed by the selective decomposition of fibrinogen, which is a soluble serum protein, by activated thrombin, which is produced at the end of an amplified multi-step enzyme reaction activated by some stimulus. Fibrin is an insoluble protein and causes coagulation. This process is known as a blood coagulation cascade and comprises an internally caused process and an externally caused process. Both processes come together at the activation of blood coagulation factor X. The activated blood coagulation factor X thus formed is an important enzyme in the blood coagulation cascade. The activated blood coagulation factor X ultimately forms a complex with divalent calcium ions, phosphatide, activated blood coagulation factor V and the like, effectively converting pro-thrombin to thrombin and enhancing the blood coagulation reaction (for example, see E. L. Smith, A. White et al., "Principles of Biochemistry: Mammalian Biochemistry 7$^{th}$ edition", McGraw-Hill, Inc. (1983)).

At the present time, warfarin and anti-thrombin agents are known as anti-blood coagulation agents. Warfarin has widely been used as an oral anti-thrombus agent. However it is known that the control of blood coagulation activity with warfarin is difficult, because it is a vitamin K antagonist and often has an interaction with a meal and with agents combined with warfarin (for example, *Clin. Pharmacokinet.*, 30, 416 (1996) and the like). Recently bleeding has been obserbed as an adverse effect of anti-thrombin agents. Therefore an improved anti-blood coagulation agent has been expected. It has been known that the activated blood coagulation factor X is directly involved in the formation of thrombin and that inhibitors of activated blood coagulation factor X exhibit anti-blood coagulation activity. The possibility that such an inhibitor might become a new anti-blood coagulation agent has been suggested (for example, *Drugs*, 49, 856 (1995) and the like).

Incidentally some aromatic amidine derivatives and amidinonaphthyl derivatives are disclosed in Japanese patent application publication number Hei 5-208946 (EP 540051), WO 96/16940 (EP 798295) and WO 00/47553 as competitive-antagonistic activated blood coagulation factor X inhibitors. Some benzamidine derivatives, for example N-[4-[1-acetimidoyl-4-piperidyloxy]phenyl]-N-[2-(3-amidinophenoxy)ethyl]sulfamoylacetic acid ditrifluoroacetate are described in WO 98/31661 (EP 976722).

SUMMARY OF THE INVENTION

The inventors have made a great effort for a long time to find a compound having excellent activated blood coagulation factor X inhibitory activity and have studied the pharmacologically activity of various benzamidine derivatives. They have found that specific benzamidine derivatives having a novel chemical structure have excellent activated blood coagulation factor X inhibitory activity and do not have trypsin inhibitory activity, and found that said derivatives are useful for the prevention or treatment (particularly treatment) of blood coagulation-related diseases. Thereby they have completed the present invention.

The present invention provides benzamidine derivatives, and pharmacologically acceptable salts or prodrugs thereof, which exhibit excellent activated blood coagulation factor X inhibitory activity; processes for the preparation of thereof; useful intermediates for preparation of thereof; pharmaceutical compositions for the prevention or treatment of blood coagulation-related diseases comprising thereof; use of said benzamidine derivative, or a pharmacologically acceptable salt or prodrug thereof for preparing a medicament for the prevention or treatment of blood coagulation-related diseases; a method for the prevention or treatment of blood coagulation-related diseases, comprising administering to a warm blooded animal (such as a human) a pharmacologically effective amount of said benzamidine derivative, or a pharmacologically acceptable salt or prodrug thereof.

The present invention provides compounds of the following general formula (1) and pharmacologically acceptable salts and prodrugs thereof:

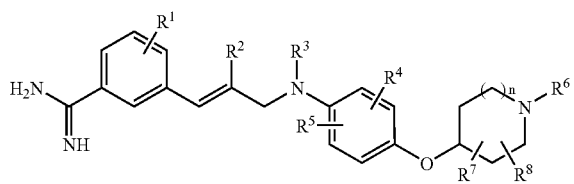

(1)

wherein

R[1] represents a hydrogen atom, a halogen atom, an alkyl group having from 1 to 6 carbon atoms or a hydroxyl group;

R[2] represents a hydrogen atom or a halogen atom;

R[3] represents a hydrogen atom, an alkyl group having from 1 to 6 carbon atoms, an alkyl group having from 1 to 6 carbon atoms substituted with a hydroxyl group, a carboxyalkyl group having from 2 to 7 carbon atoms, an alkoxycarbonylalkyl group having from 3 to 13 carbon atoms, an alkylsulfonyl group having from 1 to 6 carbon atoms, an alkoxycarbonylalkylsulfonyl group having from 3 to 13 carbon atoms, a carboxyalkylsulfonyl group having from 2 to 7 carbon atoms or a carboxyalkylcarbonyl group having from 3 to 8 carbon atoms;

R[4] and R[5] are the same or different and each represents a hydrogen atom, a halogen atom, an alkyl group having from 1 to 6 carbon atoms, an alkyl group having from 1 to 6 carbon atoms substituted with a halogen atom, an alkoxy group having from 1 to 6 carbon atoms, a carboxyl group, an alkoxycarbonyl group having from 2 to 7 carbon atoms, a carbamoyl group, a monoalkylcarbamoyl group having from 2 to 7 carbon atoms or a dialkylcarbamoyl group having from 3 to 13 carbon atoms;

R[6] represents a hydrogen atom, an alkyl group having from 1 to 6 carbon atoms, a cycloalkyl group having from 3 to 8 carbon atoms, an aralkyl group having from 7 to 16 carbon atoms, an alkyl group having from 1 to 6 carbon atoms substituted with a heterocycle, a carboxyalkyl group having from 2 to 7 carbon atoms, an alkoxycarbonylalkyl group having from 3 to 13 carbon atoms, an aliphatic acyl group having from 2 to 7 carbon atoms, an aromatic acyl group having from 7 to 11 carbon atoms, a carbamoyl group, an alkylsulfonyl group having from 1 to 6 carbon atoms, an aryl group having from 6 to 10 carbon atoms, a heterocycle, a formimidoyl group, a 1-iminoalkyl group having from 3 to 7 carbon atoms, an N-alkylformimidoyl group having from 2 to 7 carbon atoms or an iminoarylmethyl group having from 7 to 11 carbon atoms;

each of R[7] and R[8] represents a hydrogen atom or an alkyl group having from 1 to 6 carbon atoms; or R[6] and R[7] taken together or R[7] and R[8] taken together form an alkylene group having from 2 to 5 carbon atoms; and n represents 0, 1 or 2.

DETAILED DESCRIPTION OF THE INVENTION

The "halogen atom" in the definition of R[1], R[2], R[4], and R[5] includes, for example, an iodine atom, a bromine atom, a chlorine atom and a fluorine atom; a preferred halogen atom for R[1] is a bromine atom, a chlorine atom, a fluorine atom or the like, and a particularly preferred halogen atom for R[1] is a fluorine atom; a preferred halogen atom for R[2] is a bromine atom, a chlorine atom or a fluorine atom and a particularly preferred halogen atom for R[2] is a fluorine atom; a preferred halogen atom for each of R[4] and R[5] is a bromine atom, a chlorine atom or a fluorine atom, a more preferred halogen atom for each of R[4] and R[5] is a fluorine atom or chlorine atom, and the most preferred is a chlorine atom.

The "alkyl group having from 1 to 6 carbon atoms" in the definition of R[1], R[3], R[4], R[5], R[6], R[7] and R[8] includes, for example, methyl, ethyl, propyl, isopropyl, butyl, isobutyl, s-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups and the like; a preferred alkyl group for R[1] is a methyl group; a preferred alkyl group for R[3] is a methyl, ethyl or isopropyl group and a particularly preferred alkyl group for R[3] is a isopropyl group; a preferred alkyl group for each of R[4] and R[5] is a methyl group; a preferred alkyl group for R[6] is a methyl, ethyl, isopropyl or butyl group and a particularly preferred alkyl group for R[6] is a methyl, ethyl or isopropyl group; a preferred alkyl group for R[7] is a methyl group; and a preferred alkyl group for R[8] is a methyl group.

The alkyl moiety of the "alkyl group having from 1 to 6 carbon atoms substituted with a hydroxyl group" in the definition of R[3] has the same meaning as that indicated above for the definition of the "alkyl group having from 1 to 6 carbon atoms"; a preferred alkyl moiety is an alkyl group having from 1 to 3 carbon atoms; a more preferred alkyl moiety is an ethyl group and a preferred "alkyl group having from 1 to 6 carbon atoms substituted with a hydroxyl group" is a 2-hydroxyethyl group.

The alkyl moiety of the "carboxyalkyl group having from 2 to 7 carbon atoms" in the definition of R[3] has the same meaning as that indicated above for the definition of the "alkyl group having from 1 to 6 carbon atoms"; a preferred alkyl moiety is an alkyl group having from 1 to 3 carbon atoms; a more preferred alkyl moiety is a methyl group and a preferred "carboxyalkyl group having from 2 to 7 carbon atoms" is a carboxymethyl group.

The alkyl moiety, and the alkyl moiety of the alkoxy part of the "alkoxycarbonylalkyl group having from 3 to 13 carbon atoms" in the definition of R[3] has the same meaning as that indicated above for the definition of the "alkyl group having from 1 to 6 carbon atoms"; a preferred alkyl moiety is an alkyl group having from 1 to 4 carbon atoms; a preferred "alkoxycarbonylalkyl group having from 3 to 13 carbon atoms" is a methoxycarbonylmethyl group, an ethoxycarbonylmethyl group, a propoxycarbonylmethyl group or a butoxycarbonylmethyl group; a more preferred is a methoxycarbonylmethyl group or an ethoxycarbonylmethyl group and a particularly preferred is an ethoxycarbonylmethyl group.

The alkyl moiety of the "carboxyalkylsulfonyl group having from 2 to 7 carbon atoms" in the definition of R[3] has the same meaning as that indicated above for the definition of the "alkyl group having from 1 to 6 carbon atoms"; a preferred alkyl moiety is an alkyl group having from 1 to 4 carbon atoms; a more preferred is a methyl group, and a preferred "carboxyalkylsulfonyl group having from 2 to 7 carbon atoms" is a carboxymethanesulfonyl group.

The alkyl moiety of the "alkylsulfonyl group having from 1 to 6 carbon atoms" in the definition of R[3] has the same meaning as that indicated above for the definition of the "alkyl group having from 1 to 6 carbon atoms"; a preferred alkyl moiety is an alkyl group having from 1 to 4 carbon atoms; a more preferred alkyl moiety is an ethyl group, and a preferred "alkylsulfonyl group having from 1 to 6 carbon atoms" is an ethanesulfonyl group.

The alkyl moiety, and the alkyl moiety of the alkoxy part, of the "alkoxycarbonylalkylsulfonyl group having from 3 to 13 carbon atoms" in the definition of R[3] has the same meaning as that indicated above for the definition of the "alkyl group having from 1 to 6 carbon atoms"; a preferred alkyl moiety is an alkyl group having from 1 to 4 carbon atoms; a more preferred is an alkyl group having 1 or 2 carbon atoms, and a preferred "alkoxycarbonylalkylsulfonyl group having from 3 to 13 carbon atoms" is an ethoxycarbonylmethanesulfonyl group.

The alkyl moiety of the "carboxyalkylcarbonyl group having from 3 to 8 carbon atoms" in the definition of R[3] has the same meaning as that indicated above for the definition of the "alkyl group having from 1 to 6 carbon atoms"; a preferred alkyl moiety is an alkyl group having from 1 to 4 carbon atoms; a more preferred is an alkyl group having 1 carbon atom, and a preferred "carboxyalkylcarbonyl group having from 3 to 8 carbon atoms" is a carboxyacetyl group.

The alkyl moiety of the "alkyl group having from 1 to 6 carbon atoms substituted with a halogen atom" in the definition of $R^4$ and $R^5$ has the same meaning as that indicated above for the definition of the "alkyl group having from 1 to 6 carbon atoms"; a preferred alkyl moiety is an alkyl group having 1 or 2 carbon atoms, and a preferred "alkyl group having from 1 to 6 carbon atoms substituted with a halogen atom" is a trifluoromethyl group.

The alkyl moiety of the "alkoxy group having from 1 to 6 carbon atoms" in the definition of $R^4$ and $R^5$ has the same meaning as that indicated above for the definition of the "alkyl group having from 1 to 6 carbon atoms"; a preferred alkyl moiety is an alkyl group having from 1 to 4 carbon atoms; a more preferred alkyl moiety is an alkyl group having 1 carbon atom, and a preferred "alkoxy group having from 1 to 6 carbon atoms" is a methoxy group.

The alkyl moiety of the "alkoxycarbonyl group having from 2 to 7 carbon atoms" in the definition of $R^4$ and $R^5$ has the same meaning as that indicated above for the definition of the "alkyl group having from 1 to 6 carbon atoms"; a preferred alkyl moiety is an alkyl group having 1 or 2 carbon atoms and a preferred "alkoxycarbonyl group having from 2 to 7 carbon atoms" is an ethoxycarbonyl group.

The alkyl moiety of the "monoalkylcarbamoyl group having from 2 to 7 carbon atoms" in the definition of $R^4$ and $R^5$ has the same meaning as that indicated above for the definition of the "alkyl group having from 1 to 6 carbon atoms"; a preferred alkyl moiety is an alkyl group having 1 or 2 carbon atoms and a preferred "monoalkylcarbamoyl group having from 2 to 7 carbon atoms" is an N-methylcarbamoyl group.

The alkyl moieties of the "dialkylcarbamoyl group having from 3 to 13 carbon atoms" in the definition of $R^4$ and $R^5$ each have the same meaning as that indicated above for the definition of the "alkyl group having from 1 to 6 carbon atoms"; a preferred alkyl moiety is an alkyl group having 1 or 2 carbon atoms and a preferred "dialkylcarbamoyl group having from 3 to 13 carbon atoms" is an N,N-dimethylcarbamoyl group.

The "cycloalkyl group having from 3 to 8 carbon atoms" in the definition of $R^6$ includes, for example, cyclopropyl, cyclobutyl, cyclopentyl, cyclohexyl, cycloheptyl and cyclooctyl groups and the like and preferably is a cyclopentyl group.

The "aralkyl group having from 7 to 16 carbon atoms" in the definition of $R^6$ includes, for example, benzyl, 1-naphthylmethyl, 2-naphthylmethyl, and phenethyl groups and the like and is preferably a benzyl or phenethyl group.

The alkyl moiety of the "alkyl group having from 1 to 6 carbon atoms substituted with a heterocycle" in the definition of $R^6$ has the same meaning as that indicated above for the definition of the "alkyl group having from 1 to 6 carbon atoms"; a preferred alkyl moiety is an alkyl group having 1 or 2 carbon atoms, and the heterocyclyl moiety is a 5- to 7-membered heterocyclyl group containing from 1 to 3 sulfur atoms, oxygen atoms and/or nitrogen atoms, and for example, includes aromatic heterocyclyl groups such as furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, and pyrazinyl groups; and heterocyclyl groups, which are partially or fully hydrogenated aromatic heterocyclyl groups corresponding to the aromatic heterocyclyl groups indicated above, such as morpholinyl, thiomorpholinyl, pyrrolidinyl, pyrrolinyl, imidazolidinyl, imidazolinyl, pyrazolidinyl, pyrazolinyl, piperidyl, and piperazinyl groups; preferably it is a 5- to 7-membered heterocycle, which contains at least one nitrogen atom and may optionally contain an oxygen atom or a sulfur atom, for example, an aromatic heterocyclyl group such as pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl, or pyrazinyl; or a heterocyclyl group, which is a partially or fully hydrogenated aromatic heterocyclyl group corresponding to the aromatic heterocyclyl group indicated above, such as morpholinyl, thiomorpholinyl, pyrrolidinyl, pyrrolinyl, imidazolidinyl, imidazolinyl, pyrazolidinyl, pyrazolinyl, piperidyl, or piperazinyl (for example, 4,5-dihydro-3H-pyrrol-2-yl, 2,3,4,5-tetrahydropyridin-6-yl, 4,5-dihydrooxazole-2-yl, or 5,6-dihydro-2H-[1,4]thiazin-3-yl); and said "5- to 7-membered heterocyclyl group" may optionally be fused to another cyclic group, and such fused cyclic groups include, for example, isobenzofuranyl, chromenyl, xanthenyl, phenoxatiinyl, indolizinyl, isoindolyl, indolyl, indazolyl, purinyl, quinolidinyl, isoquinolyl, quinolyl, phthalazinyl, naphthyridinyl, quinoxalinyl, quinazolinyl, carbazolyl, carbolinyl, acridinyl, isoindolinyl and the like and a preferred heterocyclyl group is a pyridyl group. A preferred "alkyl group having from 1 to 6 carbon atoms substituted with a heterocycle" is a 2-pyridylmethyl, 3-pyridylmethyl, 4-pyridylmethyl, 2-(2-pyridyl)ethyl, 2-(3-pyridyl)ethyl or 2-(4-pyridyl)ethyl group.

The alkyl moiety of the "carboxyalkyl group having from 2 to 7 carbon atoms" in the definition of $R^6$ has the same meaning as that indicated above for the definition of the "alkyl group having from 1 to 6 carbon atoms"; a preferred alkyl moiety is an alkyl group having 1 or 2 carbon atoms. A preferred "carboxyalkyl group having from 2 to 7 carbon atoms" is a carboxymethyl group.

The alkyl moiety of the "alkoxycarbonylalkyl group having from 3 to 13 carbon atoms" in the definition of $R^6$ has the same meaning as that indicated above for the definition of the "alkyl group having from 1 to 6 carbon atoms"; a preferred alkyl moiety is an alkyl group having 1 or 2 carbon atoms. A preferred "alkoxycarbonylalkyl group having from 3 to 13 carbon atoms" is a methoxycarbonylmethyl group.

The "aliphatic acyl group having from 2 to 7 carbon atoms" in the definition of $R^6$ includes, for example, acetyl, propionyl, butyryl, isobutyryl, pivaloyl, valeryl, isovaleryl, hexanoyl, heptanoyl and octanoyl groups and the like and is preferably an acetyl group.

The "aromatic acyl group having from 7 to 11 carbon atoms" in the definition of $R^6$ includes, for example, a benzoyl, 1-naphthylcarbonyl, and 2-naphthylcarbonyl group and the like and is preferably a benzoyl group.

The alkyl moiety of the "alkylsulfonyl group having from 1 to 6 carbon atoms" in the definition of $R^6$ has the same meaning as that indicated above for the definition of the "alkyl group having from 1 to 6 carbon atoms"; a preferred alkyl moiety is an alkyl group having 1 or 2 carbon atoms. A preferred "alkylsulfonyl group having from 1 to 6 carbon atoms" is a methanesulfonyl group.

The "aryl group having from 6 to 10 carbon atoms" in the definition of $R^6$ includes, for example, phenyl, 1-naphthyl, 2-naphthyl and phenanthryl groups and the like and is preferably a phenyl group.

The "heterocycle" in the definition of $R^6$ has the same meaning as that indicated above for the "alkyl group having from 1 to 6 carbon atoms substituted with a heterocycle", a preferred heterocycle is a group of the following formula, which is a 4,5-dihydro-3H-pyrrol-2-yl of formua (A), 2,3,4,5-tetrahydropyridin-6-yl of formula (B), 4,5-dihydrooxazol-2-yl of formula (C), 5,6-dihydro-2H-[1,4]-thiazin-3-yl of formula (D) or 4-pyridyl group.

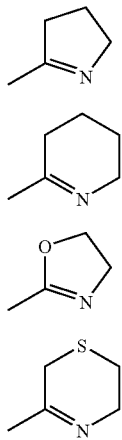

The alkyl moiety of the "1-iminoalkyl group having from 3 to 7 carbon atoms" in the definition of $R^6$ has the same meaning as that indicated above for the definition of the "alkyl group having from 1 to 6 carbon atoms"; a preferred alkyl moiety is an alkyl group having 3 carbon atoms. A preferred "1-iminoalkyl group having from 3 to 7 carbon atoms" is a 1-iminopropyl group.

The alkyl moiety of the "N-alkylformimidoyl group having from 2 to 7 carbon atoms" in the definition of $R^6$ has the same meaning as that indicated above for the definition of the "alkyl group having from 1 to 6 carbon atoms"; a preferred alkyl moiety is an alkyl group having 1 or 2 carbon atoms. A preferred "N-alkylformimidoyl group having from 2 to 7 carbon atoms" is an N-ethylformimidoyl group.

The "iminoarylmethyl group having from 7 to 11 carbon atoms" in the definition of $R^6$ includes, for example, an iminophenylmethyl, iminonaphthylmethyl group and the like and is preferably an iminophenylmethyl group.

The "alkylene group having from 2 to 5 carbon atoms", which $R^6$ and $R^7$ taken together or $R^7$ and $R^8$ taken together form, includes, for example, ethylene, trimethylene, tetramethylene and pentamethylene groups and the like and is preferably an ethylene or trimethylene group.

n is preferably 1.

Preferred compounds of the present invention include:

(1) a compound wherein $R^1$ is a hydrogen atom or a hydroxyl group, (2) a compound wherein $R^2$ is a hydrogen atom, (3) a compound wherein $R^3$ is an alkoxycarbonylalkylsulfonyl group having from 3 to 13 carbon atoms or a carboxyalkylsulfonyl group having from 2 to 7 carbon atoms, (4) a compound wherein $R^3$ is an ethoxycarbonylmethanesulfonyl group or a carboxymethanesulfonyl group, (5) a compound wherein $R^4$ and $R^5$ are the same or different and each represents a hydrogen atom, a halogen atom, an alkyl group having from 1 to 6 carbon atoms, an alkyl group having from 1 to 6 carbon atoms substituted with a halogen atom or a carbamoyl group, (6) a compound wherein $R^4$ and $R^5$ are the same or different and each represents a hydrogen atom, a chlorine atom, a methyl group, a trifluoromethyl group or a carbamoyl group, (7) a compound wherein $R^6$ is an alkyl group having from 1 to 6 carbon atoms, a cycloalkyl group having from 3 to 8 carbon atoms, an aralkyl group having from 7 to 16 carbon atoms, an alkyl group having from 1 to 6 carbon atoms substituted with a heterocycle, an aryl group having from 6 to 10 carbon atoms, a heterocycle, a formimidoyl group, a 1-iminoalkyl group having from 3 to 7 carbon atoms, an iminoarylmethyl group having from 7 to 11 carbon atoms or an N-alkylformimidoyl group having from 2 to 7 carbon atoms, (8) a compound wherein $R^6$ is a methyl, ethyl or isopropyl group, a cyclopentyl group, a benzyl or phenethyl group, a 2-pyridylmethyl, 3-pyridylmethyl, 4-pyridylmethyl, 2-(2-pyridyl)ethyl, 2-(3-pyridyl)ethyl or 2-(4-pyridyl)ethyl group, a phenyl group, a 4,5-dihydro-3H-pyrrol-2-yl, 2,3,4,5-tetrahydropyridin-6-yl, 4,5-dihydrooxazol-2-yl, 5,6-dihydro-2H-[1,4]thiazin-3-yl or 4-pyridyl group, a formimidoyl group, a 1-iminopropyl group, an iminophenylmethyl group or an N-ethylformimidoyl group, (9) a compound wherein each of $R^7$ and $R^8$ is a hydrogen atom or an alkyl group having from 1 to 6 carbon atoms,

(10) a compound wherein $R^6$ and $R^7$ taken together or $R^7$ and $R^8$ taken together form an alkylene group having from 2 to 5 carbon atoms,

(11) a compound wherein $R^6$ and $R^7$ taken together or $R^7$ and $R^8$ taken together form an ethylene or trimethylene group,

(12) a compound wherein n is 1, and a compound comprising a combination of these compounds, for example, a compound comprising a combination of (1), (2), (3), (5), (7), (9) and (12), or comprising a combination of (1), (2), (4), (6), (8), (9) and (12), and the like.

The compounds of the present invention can be-converted to salts thereof and preferred salts includes an alkali metal salt such as a sodium salt, potassium salt or lithium salt; an alkaline earth metal salt such as a calcium salt or magnesium salt; a metal salt such as an aluminum salt, iron salt, zinc salt, copper salt, nickel salt or cobalt salt; an inorganic salt such as an ammonium salt or an organic amine salt such as a t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt or tris(hydroxymethyl)aminomethane salt; an inorganic acid salt, for example, a hydrohalogenic acid salt such as a hydrofluoric acid salt, a hydrochloric acid salt, hydrobromic acid salt or hydroiodic acid salt, a nitric acid salt, a perchloric acid salt, a sulfuric acid salt, or a phosphoric acid salt; a lower alkanesulfonic acid salt such as a methanesulfonic acid salt, trifluoromethanesulfonic acid salt or ethanesulfonic acid salt; an arylsulfonic acid salt such as a benzenesulfonic acid salt or p-toluenesulfonic acid salt; an organic acid salt such as an acetic acid salt, malic acid salt, fumaric acid salt, succinic acid salt, citric acid salt, tartaric acid salt, oxalic acid salt, maleic acid salt or trifluoroacetic acid salt; or an amino acid salt such as a glycine salt, lysine salt, arginine salt, ornithine salt, glutamic acid salt or aspartic acid salt.

When a compound of the present invention is allowed to stand in contact with the atmosphere, it may absorb water or water may attach to it to form a hydrate. The present invention encompasses such hydrates.

The compound of the present invention may absorb a solvent to form a solvate. The present invention encompasses such solvates.

When a compound of this invention has a hydroxyl group, an amino group, an amidino group or a carboxyl group, the "prodrug thereof" is a compound having a protecting group for these groups respectively, wherein said protecting group can be cleaved by a chemical reaction in vivo or can be biochemically cleaved. When a parent compound has a hydroxyl group, an amino group or an amidino group, a group forming a prodrug of said compound is a "protecting group which can be cleaved by a chemical process" or a "protecting group which can be cleaved by a biological process such as hydrolysis in vivo".

Such a "protecting group which can be cleaved by a chemical process" includes an "aliphatic acyl group", for example, an alkylcarbonyl group such as a formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl or henicosanoyl group, a carboxylated alkylcarbonyl group such as a succinoyl, glutaroyl or adipoyl group, a halogenated lower alkylcarbonyl group such as a chloroacetyl, dichloroacetyl, trichloroacetyl or trifluoroacetyl group, a lower alkoxy lower alkylcarbonyl group such as a methoxyacetyl group, an unsaturated alkylcarbonyl group such as a (E)-2-methyl-2-butenoyl group, or the like; an "aromatic acyl group", for example an arylcarbonyl group such as a benzoyl, α-naphthoyl or β-naphthoyl group, a halogenated arylcarbonyl group such as a 2-bromobenzoyl, or 4-chlorobenzoyl group, a lower alkylated arylcarbonyl group such as a 2,4,6-trimethylbenzoyl or 4-toluoyl group, a lower alkoxylated arylcarbonyl group such as a 4-anisoyl group, a carboxylated arylcarbonyl group such as a 2-carboxybenzoyl, 3-carboxybenzoyl or 4-carboxybenzoyl group, a nitrated arylcarbonyl group such as a 4-nitrobenzoyl or 2-nitrobenzoyl group, a lower alkoxycarbonylated arylcarbonyl group such as a 2-(methoxycarbonyl)benzoyl group, an arylated arylcarbonyl group such as a 4-phenylbenzoyl group, or the like; a "tetrahydropyranyl or tetrahydrothiopyranyl group" such as a tetrahydropyran-2-yl, 3-bromotetrahydropyran-2-yl, 4-methoxytetrahydropyran-4-yl, tetrahydrothiopyran-2-yl, or 4-methoxytetrahydrothiopyran-4-yl group; a "tetrahydrofuranyl or tetrahydrothiofuranyl group" such as a tetrahydrofuran-2-yl or tetrahydrothiofuran-2-yl group; a "silyl group", for example, a lower trialkylsilyl group such as a trimethylsilyl, triethylsilyl, isopropyldimethylsilyl, t-butyldimethylsilyl, methyldiisopropylsilyl, methyl-di-t-butylsilyl, or triisopropylsilyl group or a tri-loweralkylsilyl group substituted with 1 or 2 aryl groups such as a diphenylmethylsilyl, diphenylbutylsilyl, diphenylisopropylsilyl or phenyldiisopropylsilyl group, or the like; an "alkoxymethyl group", for example, a lower alkoxymethyl group such as a methoxymethyl, 1,1-dimethyl-1-methoxymethyl, ethoxymethyl, propoxymethyl, isopropoxymethyl, butoxymethyl or t-butoxymethyl group, a lower alkokylated lower alkoxymethyl group such as a 2-methoxyethoxymethyl group, or a halogenated lower alkoxymethyl group such as a 2,2,2-trichloroethoxymethyl or bis(2-chloroethoxy)methyl group; a "substituted ethyl group", for example, a lower alkoxylated ethyl group such as a 1-ethoxyethyl or 1-(isopropoxy)ethyl group, a halogenated ethyl group such as a 2,2,2-trichloroethyl group, or the like; an "aralkyl group", for example, a lower alkyl group substituted with from 1 to 3 aryl groups such as a benzyl, α-naphthylmethyl, β-naphthylmethyl, diphenylmethyl, triphenylmethyl, α-naphthyldiphenylmethyl or 9-anthrylmethyl group, or a lower alkyl group substituted with from 1 to 3 aryl groups, wherein said aryl group is substituted with a lower alkyl, lower alkoxy, halogen or cyano group, such as a 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl or 4-cyanobenzyl group; an "alkoxycarbonyl group", for example, a lower alkoxycarbonyl group such as a methoxycarbonyl, ethoxycarbonyl, t-butoxycarbonyl or isobutoxycarbonyl group or a lower alkoxycarbonyl group substituted with a halogen atom or a tri-loweralkylsilyl group such as a 2,2,2-trichloroethoxycarbonyl or 2-trimethylsilylethoxycarbonyl group, or the like; an "alkenyloxycarbonyl group" such as a vinyloxycarbonyl or allyloxycarbonyl group; an "aryloxycarbonyl group", wherein said aryl group may optionally be substituted with 1 or 2 lower alkoxy groups, nitro groups or halogen atoms, such as a phenoxycarbonyl, 4-methoxyphenoxycarbonyl, 3,4-dimethoxyphenoxycarbonyl, 2-nitrophenoxycarbonyl, 4-nitrophenoxycarbonyl or 4-fluorophenoxycarbonyl group; or an "aralkyloxycarbonyl group", wherein said aryl group may optionally be substituted with 1 or 2 lower alkoxy or nitro groups, such as a benzyloxycarbonyl, 4-methoxybenzyloxycarbonyl, 3,4-dimethoxybenzyloxycarbonyl, 2-nitrobenzyloxycarbonyl or 4-nitrobenzyloxycarbonyl group.

On the other hand the "protecting group which can be cleaved by a biological process such as hydrolysis in vivo" includes a "carbonyloxyalkyl group", for example, an acyloxyalkyl group such as an ethylcarbonyloxymethyl, pivaloyloxymethyl, dimethylaminoacetoxymethyl or 1-acetoxyethyl group; a 1-(alkoxycarbonyloxy)alkyl group such a 1-(methoxycarbonyloxy)ethyl, 1-(ethoxycarbonyloxy) ethyl, ethoxycarbonyloxymethyl, 1-(isopropoxycarbonyloxy)ethyl, 1-(t-butoxycarbonyloxy)ethyl, 1-(ethoxycarbonyloxy)propyl or 1-(cyclohexyloxycarbonyloxy)ethyl; a phthalidyl group; an oxodioxolenylmethyl group such as a 4-methyl-oxodioxolenylmethyl or 4-phenyl-oxodioxolenylmethyl, 2-oxo-1,3-dioxolenylmethyl group or the like; an "aliphatic acyl group" described hereinbefore; an "aromatic acyl group" described hereinbefore; a "residual group of a succinic acid half-ester"; a "residual group of a phosphoric acid ester"; a "residual group forming an amino acid ester or the like"; a carbamoyl group; a carbamoyl group substituted with 1 or 2 lower alkyl groups; or a "carbonyloxyalkyloxycarbonyl group" such as a pivaloyloxymethyloxycarbonyl group. Such a derivative under investigation is administered intravenously to a test animal such as a rat or a mouse and the body fluids of the test animal are thereafter studied. If the parent compound or a pharmacologically acceptable salt thereof is detected in the body fluids of the test animal, the derivative under investigation is judged to have a protecting group which can be cleaved by a biological process such as hydrolysis in vivo; and a preferred protecting group is an acetyl group.

An amino or amidino protecting group is not particularly restricted and preferably includes, an "aliphatic acyl group", for example, an alkylcarbonyl group such as a formyl, acetyl, propionyl, butyryl, isobutyryl, pentanoyl, pivaloyl, valeryl, isovaleryl, octanoyl, lauroyl, palmitoyl or stearoyl group, a halogenated lower alkylcarbonyl group such as a chloroacetyl, dichloroacetyl, trichloroacetyl, or trifluoroacetyl group, a lower alkoxy lower alkylcarbonyl group such as a methoxyacetyl group, an unsaturated alkylcarbonyl group such as an (E)-2-methyl-2-butenoyl group, or the like; an "aromatic acyl group", for example an arylcarbonyl group such as a benzoyl, α-naphthoyl or β-naphthoyl group, a halogenated arylcarbonyl group such as a 2-bromobenzoyl or 4-chlorobenzoyl group, a lower alkylated arylcarbonyl group such as a 2,4,6-trimethylbenzoyl or 4-toluoyl group, a lower alkoxylated arylcarbonyl group such as a 4-anisoyl group, a nitrated arylcarbonyl group such as a 4-nitrobenzoyl or 2-nitrobenzoyl group, a lower alkoxycarbonylated arylcarbonyl group such as a 2-(methoxycarbonyl)benzoyl group, an arylated arylcarbonyl group such as a 4-phenylbenzoyl group, or the like; an "alkoxycarbonyl group", for example, a lower alkoxycarbonyl group such as a methoxycarbonyl, ethoxycarbonyl, t-butoxycarbonyl or isobutoxycarbonyl group or a lower alkoxycarbonyl group substituted with a halogen atom or a tri-loweralkylsilyl group such as a 2,2,2-trichloroethoxycarbonyl or 2-trimethylsilylethoxycarbonyl group; an "alkenyloxycarbonyl group" such as a vinyloxycarbonyl or allyloxycarbonyl group; an "aryloxycarbonyl group", wherein said aryl group may optionally be substituted with 1 or 2 lower alkoxy or nitro groups or halogen atoms, such as a phenoxycarbonyl, 4-methoxyphenoxycarbonyl, 3,4-dimethoxyphenoxycarbonyl, 2-nitrophenoxycarbonyl, 4-nitrophenoxycarbonyl or 4-fluorophenoxycarbonyl group; a preferred protecting group is an ethoxycarbonyl group, a 1-(propionyloxy)ethoxycarbonyl group, or a 4-methoxyphenoxycarbonyl group, or 4-fluorophenoxycarbonyl group.

A carboxyl protecting group represents a "protecting group which can be cleaved by a biological process such as hydrolysis in vivo" and a "protecting group which can be cleaved by a chemical process such as hydrogenolysis, hydrolysis, electrolysis or photolysis". A "protecting group which can be cleaved by a chemical process" includes a "lower alkyl group" such as a methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group; an "alkenyl group" such as an ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl or 5-hexenyl group; an "alkynyl group" such as an ethynyl, 2-propynyl, 1-methyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl or 5-hexynyl group; a "halogenated lower alkyl group" such as a trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl or 2,2-dibromoethyl group; a "hydroxyl lower alkyl group" such as a 2-hydroxyethyl, 2,3-dihydroxypropyl, 3-hydroxypropyl, 3,4-dihydroxybutyl or 4-hydroxybutyl group; an "aliphatic acyl lower alkyl group" such as an acetylmethyl group; a lower alkyl group substituted with 1 to 3 aryl groups such as a benzyl, phenethyl, 3-phenylpropyl, α-naphthylmethyl, β-naphthylmethyl, diphenylmethyl, triphenylmethyl, 6-phenylhexyl, α-naphthyldiphenylmethyl, or 9-anthrylmethyl group; or an "aralkyl group" which is a lower alkyl group substituted with 1 to 3 aryl groups wherein said aryl group is substituted with a lower alkyl, lower alkoxy, nitro, halogen, cyano or alkoxycarbonyl group such as a 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl, piperonyl or 4-methoxycarbonylbenzyl group; or a "silyl group" such as a trimethylsilyl, triethylsilyl, isopropyldimethylsilyl, tert-butyldimethylsilyl, methyldiisopropylsilyl, methyl-di-tert-butylsilyl, triisopropylsilyl, methyldiphenylsilyl, isopropyldiphenylsilyl, butyldiphenylsilyl or phenyldiisopropylsilyl group.

The compound having a "protecting group which can be cleaved by a biological process such as hydrolysis in vivo" is an ester which forms a free acid or a salt thereof by hydrolysis or the like in the human body. A protecting group "which can be cleaved by biological process such as hydrolysis in vivo" includes an "alkoxy lower alkyl group", for example, a lower alkoxy lower alkyl group such as a methoxymethyl, 1-ethoxyethyl, 1-methyl-1-methoxyethyl, 1-(isopropoxy)ethyl, 2-methoxyethyl, 2-ethoxyethyl, 1,1-dimethyl-1-methoxymethyl, ethoxymethyl, n-propoxymethyl, isopropoxymethyl, n-butoxymethyl or t-butoxymethyl group, a lower alkoxylated lower alkoxy lower alkyl group such as 2-methoxyethoxymethyl group, an aryloxy lower alkyl group such as a phenoxymethyl group, a halogenated lower alkoxy lower alkyl group such as a 2,2,2-trichloroethoxymethyl or bis(2-chloroethoxy)methyl group, or the like; a "lower alkoxycarbonyl lower alkyl group" such as a methoxycarbonylmethyl group; a "cyano lower alkyl group" such as a cyanomethyl or 2-cyanoethyl group; a "lower alkyl thiomethyl group" such as a methylthiomethyl or ethylthiomethyl group; an "aryl thiomethyl group" such as a phenylthiomethyl or naphthylthiomethyl group; a "lower alkylsulfonyl lower alkyl group which may optionally be substituted with a halogen atom" such as a 2-methanesulfonylethyl or 2-trifluoromethanesulfonylethyl group; an "arylsulfonyl lower alkyl group" such as a 2-benzenesulfonylethyl or 2-toluenesulfonylethyl group; an "acyloxy lower alkyl group" for example, an aliphatic acyloxy lower alkyl group such as a formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 2-formyloxyethyl, 2-acetoxyethyl, 2-propionyloxyethyl, 2-butyryloxyethyl, 2-pivaloyloxyethyl, 2-valeryloxyethyl, 2-isovaleryloxyethyl, 2-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl or 1-pivaloyloxyhexyl group, a cycloalkylcarbonyloxy lower alkyl group such as a cyclopentanoyloxymethyl, cyclohexanoyloxymethyl, 1-cyclopentanoyloxyethyl, 1-cyclohexanoyloxyethyl, 1-cyclopentanoyloxypropyl, 1-cyclohexanoyloxypropyl, 1-cyclopentanoyloxybutyl, or 1-cyclohexaoyloxybutyl group, an aromatic acyloxy lower alkyl group such as a benzoyloxymethyl group, or the like; a "carbonyloxyalkyl group" for example, an (alkoxycarbonyloxy)alkyl group such as a methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy(cyclohexyl)methyl, 1-(methoxycarbonyloxy)ethyl, 1-(ethoxycarbonyloxy)ethyl, 1-(propoxycarbonyloxy)ethyl, 1-(isopropoxycarbonyloxy)ethyl, 1-(butoxycarbonyloxy)ethyl, 1-(isobutoxycarbonyloxy)ethyl, 1-(tert-butoxycarbonyloxy)ethyl, 1-(pentyloxycarbonyloxy)ethyl, 1-(hexyloxycarbonyloxy)ethyl, 1-(cyclopenytyloxycarbonyloxy)ethyl, 1-(cyclopenytyloxycarbonyloxy)propyl, 1-(cyclohexyloxycarbonyloxy)propyl, 1-(cyclopentyloxycarbonyloxy)butyl, 1-(cyclohexyloxycarbonyloxy)butyl, 1-(cyclohexyloxycarbpnyloxy)ethyl, 1-(ethoxycarbonyloxy)propyl, 2-(methoxycarbonyloxy)ethyl, 2-(ethoxycarbonyloxy)ethyl, 2-(propoxycarbonyloxy)ethyl, 2-(isopropoxycarbonyloxy)ethyl, 2-(butoxycarbonyloxy)ethyl, 2-(isobutoxycarbonyloxy)ethyl, 2-(pentyloxycarbonyloxy)ethyl, 2-(hexyloxycarbonyloxy)ethyl, 1-(methoxycarbonyloxy)propyl, 1-(ethoxycarbonyloxy)propyl, 1-(propoxycarbonyloxy)propyl, 1-(isopropoxycarbonyloxy)propyl, 1-(butoxycarbonyloxy)propyl, 1-(isobutoxycarbonyloxy)propyl, 1-(pentyloxycarbonyloxy)propyl, 1-(hexyloxycarbonyloxy)propyl, 1-(methoxycarbonyloxy)butyl, 1-(ethoxycarbonyloxy)butyl, 1-(propoxycarbonyloxy)butyl, 1-(isopropoxycarbonyloxy)butyl, 1-(butoxycarbonyloxy)butyl, 1-(isobutoxycarbonyloxy)butyl, 1-(methoxycarbonyloxy)pentyl, 1-(ethoxycarbonyloxy)pentyl, 1-(methoxycarbonyloxy)hexyl or 1-(ethoxycarbonyloxy)hexyl group; an oxodioxolenylmethyl group such as a (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl or (5-butyl-2-oxo-1,3-dioxolen-4-yl)methyl group, or the like; a "phthalidyl group" such as a phthalidyl, dimethylphthalidyl or dimethoxyphthalidyl group; an "aryl group" such as a phenyl or indanyl group; an "alkyl group" described hereinbefore; a "carboxyalkyl group" such as a carboxymethyl group; or a "residual group forming an amide of an amino acid" such as a phenylalanine. Such a derivative under investigation is administered intravenously to a test animal such as a rat or a mouse and the body fluids of the test animal are thereafter studied. If the parent compound or a pharmacologically acceptable salt thereof is detected in the body fluids of the test animal, the derivative under investigation is judged to have a protecting group which can be cleaved by a biological process such as hydrolysis in vivo; and a preferred group is an ethyl group.

The compounds of the present invention are exemplified in Table 1. In Table 1 the following abbreviations are used: Et represents an ethyl group; MS represents a —CH$_2$SO$_2$ group; Ph represents a phenyl group; Pyr represents a pyridyl group; Pyrm represents a pyrimidinyl group; cPn represents a cyclopentyl group, —(CH$_2$)$_3$-(5) represents a 5-membered cyclic group wherein R$^6$ and R$^7$ taken together form a trimethylene group; C$_3$H$_4$NO represents a 4,5-dihydrooxazol-2-yl group; C$_4$H$_6$N represents a 4,5-dihydro-3H-pyrrol-2-yl group; C$_3$H$_4$NS represents a 4,5-dihydrothiazol-2-yl group; C$_5$H$_8$N represents a 2,3,4,5-tetrahydropyridin-6-yl group; C$_6$H$_{10}$N represents a 3,4,5,6-tetrahydro-2H-azepin-7-yl group; C$_4$H$_6$NS represents a 5,6-dihydro-2H-[1,4]thiazin-3-yl group; C$_5$F$_4$N represents a 2,3,5,6-tetrafluoropyridin-4-yl group; H(CH$_3$CH$_2$N)C represents a N-ethylformimidoyl group; —(CH$_2$)$_2$— represents an ethylene group which R$^7$ at 2 position and R$^8$ at 6 position taken together form; and C$_8$H$_{14}$N represents a 3,4,5,6,7,8-hexahydro-2H-azonin-9-yl group.

TABLE 1

(1)

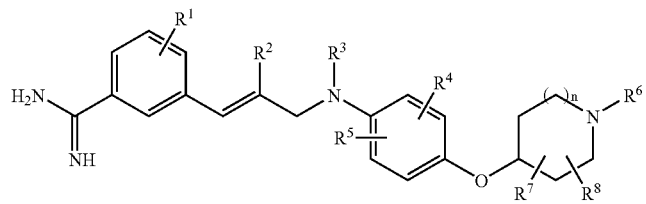

| No. | R$^1$ | R$^2$ | R$^3$ | R$^4$ | R$^5$ | R$^6$ | R$^7$ | R$^8$ | n |
|---|---|---|---|---|---|---|---|---|---|
| 1 | H | H | EtOOC-MS | 3-Cl | H | CH$_3$ | H | H | 1 |
| 2 | H | H | EtOOC-MS | 3-Cl | H | CH$_3$CH$_2$ | H | H | 1 |
| 3 | H | H | EtOOC-MS | 3-Cl | H | CH$_3$(CH$_3$)CH | H | H | 1 |
| 4 | H | H | EtOOC-MS | 3-Cl | H | CH$_3$(CH$_2$)$_2$CH$_2$ | H | H | 1 |
| 5 | H | H | EtOOC-MS | 3-Cl | H | PhCH$_2$ | H | H | 1 |
| 6 | H | H | EtOOC-MS | 3-Cl | H | Ph(CH$_2$)$_2$ | H | H | 1 |
| 7 | H | H | EtOOC-MS | 3-Cl | H | Ph | H | H | 1 |
| 8 | H | H | EtOOC-MS | 3-Cl | H | CH$_3$OCOCH$_2$ | H | H | 1 |
| 9 | H | H | EtOOC-MS | 3-Cl | H | CH$_3$CO | H | H | 1 |
| 10 | H | H | EtOOC-MS | 3-Cl | H | H$_2$NCO | H | H | 1 |
| 11 | H | H | EtOOC-MS | 3-Cl | H | CH$_3$SO$_2$ | H | H | 1 |
| 12 | H | H | EtOOC-MS | 3-Cl | H | 2-Pyr | H | H | 1 |
| 13 | H | H | EtOOC-MS | 3-Cl | H | 3-Pyr | H | H | 1 |

TABLE 1-continued (1)

| No. | R¹ | R² | R³ | R⁴ | R⁵ | R⁶ | R⁷ | R⁸ | n |
|---|---|---|---|---|---|---|---|---|---|
| 14 | H | H | EtOOC-MS | 3-Cl | H | 4-Pyr | H | H | 1 |
| 15 | H | H | EtOOC-MS | 3-Cl | H | 2-Pyrm | H | H | 1 |
| 16 | H | H | EtOOC-MS | 3-Cl | H | Pyr-3-CH₂ | H | H | 1 |
| 17 | H | H | EtOOC-MS | 3-Cl | H | Pyr-4-CH₂ | H | H | 1 |
| 18 | H | H | EtOOC-MS | 3-Cl | H | Pyr-2-(CH₂)₂ | H | H | 1 |
| 19 | H | H | EtOOC-MS | 3-Cl | H | cPn | H | H | 1 |
| 20 | H | H | EtOOC-MS | 3-Cl | H | CH₃ | 2-CH₃ | H | 1 |
| 21 | H | H | EtOOC-MS | 3-Cl | H | —(CH₂)₃-(5) | — | H | 1 |
| 22 | H | H | EtOOC-MS | 3-Cl | H | H(NH)C | H | H | 1 |
| 23 | H | H | EtOOC-MS | 3-Cl | H | CH₃CH₂(NH)C | H | H | 1 |
| 24 | H | H | EtOOC-MS | 3-Cl | H | Ph(NH)C | H | H | 1 |
| 25 | H | H | EtOOC-MS | 3-Cl | H | C₄H₆N | H | H | 1 |
| 26 | H | H | EtOOC-MS | 3-Cl | H | C₅H₈N | H | H | 1 |
| 27 | H | H | EtOOC-MS | 3-Cl | H | C₆H₁₀N | H | H | 1 |
| 28 | H | H | EtOOC-MS | 3-Cl | H | C₄H₆NS | H | H | 1 |
| 29 | H | H | EtOOC-MS | 3-CH₃ | H | CH₃ | H | H | 1 |
| 30 | H | H | EtOOC-MS | 3-CH₃ | H | CH₃CH₂ | H | H | 1 |
| 31 | H | H | EtOOC-MS | 3-CH₃ | H | CH₃(CH₃)CH | H | H | 1 |
| 32 | H | H | EtOOC-MS | 3-CH₃ | H | CH₃(CH₂)₂CH₂ | H | H | 1 |
| 33 | H | H | EtOOC-MS | 3-CH₃ | H | PhCH₂ | H | H | 1 |
| 34 | H | H | EtOOC-MS | 3-CH₃ | H | Ph(CH₂)₂ | H | H | 1 |
| 35 | H | H | EtOOC-MS | 3-CH₃ | H | Ph | H | H | 1 |
| 36 | H | H | EtOOC-MS | 3-CH₃ | H | CH₃OCOCH₂ | H | H | 1 |
| 37 | H | H | EtOOC-MS | 3-CH₃ | H | CH₃CO | H | H | 1 |
| 38 | H | H | EtOOC-MS | 3-CH₃ | H | H₂NCO | H | H | 1 |
| 39 | H | H | EtOOC-MS | 3-CH₃ | H | CH₃SO₂ | H | H | 1 |
| 40 | H | H | EtOOC-MS | 3-CH₃ | H | 2-Pyr | H | H | 1 |
| 41 | H | H | EtOOC-MS | 3-CH₃ | H | 3-Pyr | H | H | 1 |
| 42 | H | H | EtOOC-MS | 3-CH₃ | H | 4-Pyr | H | H | 1 |
| 43 | H | H | EtOOC-MS | 3-CH₃ | H | 2-Pyrm | H | H | 1 |
| 44 | H | H | EtOOC-MS | 3-CH₃ | H | Pyr-3-CH₂ | H | H | 1 |
| 45 | H | H | EtOOC-MS | 3-CH₃ | H | Pyr-4-CH₂ | H | H | 1 |
| 46 | H | H | EtOOC-MS | 3-CH₃ | H | Pyr-2-(CH₂)₂ | H | H | 1 |
| 47 | H | H | EtOOC-MS | 3-CH₃ | H | cPn | H | H | 1 |
| 48 | H | H | EtOOC-MS | 3-CH₃ | H | CH₃ | 2-CH₃ | H | 1 |
| 49 | H | H | EtOOC-MS | 3-CH₃ | H | —(CH₂)₃-(5) | — | H | 1 |
| 50 | H | H | EtOOC-MS | 3-CH₃ | H | H(NH)C | H | H | 1 |
| 51 | H | H | EtOOC-MS | 3-CH₃ | H | CH₃CH₂(NH)C | H | H | 1 |
| 52 | H | H | EtOOC-MS | 3-CH₃ | H | Ph(NH)C | H | H | 1 |
| 53 | H | H | EtOOC-MS | 3-CH₃ | H | C₄H₆N | H | H | 1 |
| 54 | H | H | EtOOC-MS | 3-CH₃ | H | C₅H₈N | H | H | 1 |
| 55 | H | H | EtOOC-MS | 3-CH₃ | H | C₆H₁₀N | H | H | 1 |
| 56 | H | H | EtOOC-MS | 3-CH₃ | H | C₄H₆NS | H | H | 1 |
| 57 | H | H | EtOOC-MS | H | H | CH₃ | H | H | 1 |
| 58 | H | H | EtOOC-MS | H | H | CH₃CH₂ | H | H | 1 |
| 59 | H | H | EtOOC-MS | H | H | CH₃(CH₃)CH | H | H | 1 |
| 60 | H | H | EtOOC-MS | H | H | CH₃(CH₂)₂CH₂ | H | H | 1 |
| 61 | H | H | EtOOC-MS | H | H | PhCH₂ | H | H | 1 |
| 62 | H | H | EtOOC-MS | H | H | Ph(CH₂)₂ | H | H | 1 |
| 63 | H | H | EtOOC-MS | H | H | Ph | H | H | 1 |
| 64 | H | H | EtOOC-MS | H | H | CH₃OCOCH₂ | H | H | 1 |
| 65 | H | H | EtOOC-MS | H | H | CH₃CO | H | H | 1 |
| 66 | H | H | EtOOC-MS | H | H | H₂NCO | H | H | 1 |
| 67 | H | H | EtOOC-MS | H | H | CH₃SO₂ | H | H | 1 |
| 68 | H | H | EtOOC-MS | H | H | 2-Pyr | H | H | 1 |
| 69 | H | H | EtOOC-MS | H | H | 3-Pyr | H | H | 1 |
| 70 | H | H | EtOOC-MS | H | H | 4-Pyr | H | H | 1 |
| 71 | H | H | EtOOC-MS | H | H | 2-Pyrm | H | H | 1 |
| 72 | H | H | EtOOC-MS | H | H | Pyr-3-CH₂ | H | H | 1 |
| 73 | H | H | EtOOC-MS | H | H | Pyr-4-CH₂ | H | H | 1 |
| 74 | H | H | EtOOC-MS | H | H | Pyr-2-(CH₂)₂ | H | H | 1 |
| 75 | H | H | EtOOC-MS | H | H | cPn | H | H | 1 |
| 76 | H | H | EtOOC-MS | H | H | CH₃ | 2-CH₃ | H | 1 |
| 77 | H | H | EtOOC-MS | H | H | —(CH₂)₃-(5) | — | H | 1 |
| 78 | H | H | EtOOC-MS | H | H | H(NH)C | H | H | 1 |

TABLE 1-continued (1)

[Structure: H$_2$N-C(=NH)-phenyl(R$^1$)-CH=C(R$^2$)-CH$_2$-N(R$^3$)-phenyl(R$^4$,R$^5$)-O-piperidine(R$^7$,R$^8$,(CH$_2$)$_n$)-N-R$^6$]

| No. | R$^1$ | R$^2$ | R$^3$ | R$^4$ | R$^5$ | R$^6$ | R$^7$ | R$^8$ | n |
|---|---|---|---|---|---|---|---|---|---|
| 79 | H | H | EtOOC-MS | H | H | CH$_3$CH$_2$(NH)C | H | H | 1 |
| 80 | H | H | EtOOC-MS | H | H | Ph(NH)C | H | H | 1 |
| 81 | H | H | EtOOC-MS | H | H | C$_4$H$_6$N | H | H | 1 |
| 82 | H | H | EtOOC-MS | H | H | C$_5$H$_8$N | H | H | 1 |
| 83 | H | H | EtOOC-MS | H | H | C$_6$H$_{10}$N | H | H | 1 |
| 84 | H | H | EtOOC-MS | H | H | C$_4$H$_6$NS | H | H | 1 |
| 85 | H | H | EtOOC-MS | 3-CF$_3$ | H | CH$_3$ | H | H | 1 |
| 86 | H | H | EtOOC-MS | 3-CF$_3$ | H | CH$_3$CH$_2$ | H | H | 1 |
| 87 | H | H | EtOOC-MS | 3-CF$_3$ | H | CH$_3$(CH$_3$)CH | H | H | 1 |
| 88 | H | H | EtOOC-MS | 3-CF$_3$ | H | CH$_3$(CH$_2$)$_2$CH$_2$ | H | H | 1 |
| 89 | H | H | EtOOC-MS | 3-CF$_3$ | H | PhCH$_2$ | H | H | 1 |
| 90 | H | H | EtOOC-MS | 3-CF$_3$ | H | Ph(CH$_2$)$_2$ | H | H | 1 |
| 91 | H | H | EtOOC-MS | 3-CF$_3$ | H | Ph | H | H | 1 |
| 92 | H | H | EtOOC-MS | 3-CF$_3$ | H | CH$_3$OCOCH$_2$ | H | H | 1 |
| 93 | H | H | EtOOC-MS | 3-CF$_3$ | H | CH$_3$CO | H | H | 1 |
| 94 | H | H | EtOOC-MS | 3-CF$_3$ | H | H$_2$NCO | H | H | 1 |
| 95 | H | H | EtOOC-MS | 3-CF$_3$ | H | CH$_3$SO$_2$ | H | H | 1 |
| 96 | H | H | EtOOC-MS | 3-CF$_3$ | H | 2-Pyr | H | H | 1 |
| 97 | H | H | EtOOC-MS | 3-CF$_3$ | H | 3-Pyr | H | H | 1 |
| 98 | H | H | EtOOC-MS | 3-CF$_3$ | H | 4-Pyr | H | H | 1 |
| 99 | H | H | EtOOC-MS | 3-CF$_3$ | H | 2-Pyrm | H | H | 1 |
| 100 | H | H | EtOOC-MS | 3-CF$_3$ | H | Pyr-3-CH$_2$ | H | H | 1 |
| 101 | H | H | EtOOC-MS | 3-CF$_3$ | H | Pyr-4-CH$_2$ | H | H | 1 |
| 102 | H | H | EtOOC-MS | 3-CF$_3$ | H | Pyr-2-(CH$_2$)$_2$ | H | H | 1 |
| 103 | H | H | EtOOC-MS | 3-CF$_3$ | H | cPn | H | H | 1 |
| 104 | H | H | EtOOC-MS | 3-CF$_3$ | H | CH$_3$ | 2-CH$_3$ | H | 1 |
| 105 | H | H | EtOOC-MS | 3-CF$_3$ | H | —(CH$_2$)$_3$-(5) | — | H | 1 |
| 106 | H | H | EtOOC-MS | 3-CF$_3$ | H | H(NH)C | H | H | 1 |
| 107 | H | H | EtOOC-MS | 3-CF$_3$ | H | CH$_3$CH$_2$(NH)C | H | H | 1 |
| 108 | H | H | EtOOC-MS | 3-CF$_3$ | H | Ph(NH)C | H | H | 1 |
| 109 | H | H | EtOOC-MS | 3-CF$_3$ | H | C$_4$H$_6$N | H | H | 1 |
| 110 | H | H | EtOOC-MS | 3-CF$_3$ | H | C$_5$H$_8$N | H | H | 1 |
| 111 | H | H | EtOOC-MS | 3-CF$_3$ | H | C$_6$H$_{10}$N | H | H | 1 |
| 112 | H | H | EtOOC-MS | 3-CF$_3$ | H | C$_4$H$_6$NS | H | H | 1 |
| 113 | H | H | EtOOC-MS | 3-H$_2$NCO | H | CH$_3$ | H | H | 1 |
| 114 | H | H | EtOOC-MS | 3-H$_2$NCO | H | CH$_3$CH$_2$ | H | H | 1 |
| 115 | H | H | EtOOC-MS | 3-H$_2$NCO | H | CH$_3$(CH$_3$)CH | H | H | 1 |
| 116 | H | H | EtOOC-MS | 3-H$_2$NCO | H | CH$_3$(CH$_2$)$_2$CH$_2$ | H | H | 1 |
| 117 | H | H | EtOOC-MS | 3-H$_2$NCO | H | PhCH$_2$ | H | H | 1 |
| 118 | H | H | EtOOC-MS | 3-H$_2$NCO | H | Ph(CH$_2$)$_2$ | H | H | 1 |
| 119 | H | H | EtOOC-MS | 3-H$_2$NCO | H | Ph | H | H | 1 |
| 120 | H | H | EtOOC-MS | 3-H$_2$NCO | H | CH$_3$OCOCH$_2$ | H | H | 1 |
| 121 | H | H | EtOOC-MS | 3-H$_2$NCO | H | CH$_3$CO | H | H | 1 |
| 122 | H | H | EtOOC-MS | 3-H$_2$NCO | H | H$_2$NCO | H | H | 1 |
| 123 | H | H | EtOOC-MS | 3-H$_2$NCO | H | CH$_3$SO$_2$ | H | H | 1 |
| 124 | H | H | EtOOC-MS | 3-H$_2$NCO | H | 2-Pyr | H | H | 1 |
| 125 | H | H | EtOOC-MS | 3-H$_2$NCO | H | 3-Pyr | H | H | 1 |
| 126 | H | H | EtOOC-MS | 3-H$_2$NCO | H | 4-Pyr | H | H | 1 |
| 127 | H | H | EtOOC-MS | 3-H$_2$NCO | H | 2-Pyrm | H | H | 1 |
| 128 | H | H | EtOOC-MS | 3-H$_2$NCO | H | Pyr-3-CH$_2$ | H | H | 1 |
| 129 | H | H | EtOOC-MS | 3-H$_2$NCO | H | Pyr-4-CH$_2$ | H | H | 1 |
| 130 | H | H | EtOOC-MS | 3-H$_2$NCO | H | Pyr-2-(CH$_2$)$_2$ | H | H | 1 |
| 131 | H | H | EtOOC-MS | 3-H$_2$NCO | H | cPn | H | H | 1 |
| 132 | H | H | EtOOC-MS | 3-H$_2$NCO | H | CH$_3$ | 2-CH$_3$ | H | 1 |
| 133 | H | H | EtOOC-MS | 3-H$_2$NCO | H | —(CH$_2$)$_3$-(5) | — | H | 1 |
| 134 | H | H | EtOOC-MS | 3-H$_2$NCO | H | H(NH)C | H | H | 1 |
| 135 | H | H | EtOOC-MS | 3-H$_2$NCO | H | CH$_3$CH$_2$(NH)C | H | H | 1 |
| 136 | H | H | EtOOC-MS | 3-H$_2$NCO | H | Ph(NH)C | H | H | 1 |
| 137 | H | H | EtOOC-MS | 3-H$_2$NCO | H | C$_4$H$_6$N | H | H | 1 |
| 138 | H | H | EtOOC-MS | 3-H$_2$NCO | H | C$_5$H$_8$N | H | H | 1 |
| 139 | H | H | EtOOC-MS | 3-H$_2$NCO | H | C$_6$H$_{10}$N | H | H | 1 |
| 140 | H | H | EtOOC-MS | 3-H$_2$NCO | H | C$_4$H$_6$NS | H | H | 1 |
| 141 | H | H | EtOOC-MS | 3-F | H | CH$_3$ | H | H | 1 |
| 142 | H | H | EtOOC-MS | 3-F | H | CH$_3$CH$_2$ | H | H | 1 |
| 143 | H | H | EtOOC-MS | 3-F | H | CH$_3$(CH$_3$)CH | H | H | 1 |

TABLE 1-continued (1)

| No. | R¹ | R² | R³ | R⁴ | R⁵ | R⁶ | R⁷ | R⁸ | n |
|---|---|---|---|---|---|---|---|---|---|
| 144 | H | H | EtOOC-MS | 3-F | H | CH₃(CH₂)₂CH₂ | H | H | 1 |
| 145 | H | H | EtOOC-MS | 3-F | H | PhCH₂ | H | H | 1 |
| 146 | H | H | EtOOC-MS | 3-F | H | Ph(CH₂)₂ | H | H | 1 |
| 147 | H | H | EtOOC-MS | 3-F | H | Ph | H | H | 1 |
| 148 | H | H | EtOOC-MS | 3-F | H | CH₃OCOCH₂ | H | H | 1 |
| 149 | H | H | EtOOC-MS | 3-F | H | CH₃CO | H | H | 1 |
| 150 | H | H | EtOOC-MS | 3-F | H | H₂NCO | H | H | 1 |
| 151 | H | H | EtOOC-MS | 3-F | H | CH₃SO₂ | H | H | 1 |
| 152 | H | H | EtOOC-MS | 3-F | H | 2-Pyr | H | H | 1 |
| 153 | H | H | EtOOC-MS | 3-F | H | 3-Pyr | H | H | 1 |
| 154 | H | H | EtOOC-MS | 3-F | H | 4-Pyr | H | H | 1 |
| 155 | H | H | EtOOC-MS | 3-F | H | 2-Pyrm | H | H | 1 |
| 156 | H | H | EtOOC-MS | 3-F | H | Pyr-3-CH₂ | H | H | 1 |
| 157 | H | H | EtOOC-MS | 3-F | H | Pyr-4-CH₂ | H | H | 1 |
| 158 | H | H | EtOOC-MS | 3-F | H | Pyr-2-(CH₂)₂ | H | H | 1 |
| 159 | H | H | EtOOC-MS | 3-F | H | cPn | H | H | 1 |
| 160 | H | H | EtOOC-MS | 3-F | H | CH₃ | 2-CH₃ | H | 1 |
| 161 | H | H | EtOOC-MS | 3-F | H | —(CH₂)₃-(5) | — | H | 1 |
| 162 | H | H | EtOOC-MS | 3-F | H | H(NH)C | H | H | 1 |
| 163 | H | H | EtOOC-MS | 3-F | H | CH₃CH₂(NH)C | H | H | 1 |
| 164 | H | H | EtOOC-MS | 3-F | H | Ph(NH)C | H | H | 1 |
| 165 | H | H | EtOOC-MS | 3-F | H | C₄H₆N | H | H | 1 |
| 166 | H | H | EtOOC-MS | 3-F | H | C₅H₈N | H | H | 1 |
| 167 | H | H | EtOOC-MS | 3-F | H | C₆H₁₀N | H | H | 1 |
| 168 | H | H | EtOOC-MS | 3-F | H | C₄H₆NS | H | H | 1 |
| 169 | H | H | EtOOC-MS | 3-Cl | H | CH₃ | H | H | 0 |
| 170 | H | H | EtOOC-MS | 3-Cl | H | CH₃CH₂ | H | H | 0 |
| 171 | H | H | EtOOC-MS | 3-Cl | H | CH₃(CH₃)CH | H | H | 0 |
| 172 | H | H | EtOOC-MS | 3-Cl | H | CH₃(CH₂)₂CH₂ | H | H | 0 |
| 173 | H | H | EtOOC-MS | 3-Cl | H | PhCH₂ | H | H | 0 |
| 174 | H | H | EtOOC-MS | 3-Cl | H | Ph(CH₂)₂ | H | H | 0 |
| 175 | H | H | EtOOC-MS | 3-Cl | H | Ph | H | H | 0 |
| 176 | H | H | EtOOC-MS | 3-Cl | H | CH₃OCOCH₂ | H | H | 0 |
| 177 | H | H | EtOOC-MS | 3-Cl | H | CH₃CO | H | H | 0 |
| 178 | H | H | EtOOC-MS | 3-Cl | H | H₂NCO | H | H | 0 |
| 179 | H | H | EtOOC-MS | 3-Cl | H | CH₃SO₂ | H | H | 0 |
| 180 | H | H | EtOOC-MS | 3-Cl | H | 2-Pyr | H | H | 0 |
| 181 | H | H | EtOOC-MS | 3-Cl | H | 3-Pyr | H | H | 0 |
| 182 | H | H | EtOOC-MS | 3-Cl | H | 4-Pyr | H | H | 0 |
| 183 | H | H | EtOOC-MS | 3-Cl | H | 2-Pyrm | H | H | 0 |
| 184 | H | H | EtOOC-MS | 3-Cl | H | Pyr-3-CH₂ | H | H | 0 |
| 185 | H | H | EtOOC-MS | 3-Cl | H | Pyr-4-CH₂ | H | H | 0 |
| 186 | H | H | EtOOC-MS | 3-Cl | H | Pyr-2-(CH₂)₂ | H | H | 0 |
| 187 | H | H | EtOOC-MS | 3-Cl | H | cPn | H | H | 0 |
| 188 | H | H | EtOOC-MS | 3-Cl | H | CH₃ | 2-CH₃ | H | 0 |
| 189 | H | H | EtOOC-MS | 3-Cl | H | —(CH₂)₃-(5) | — | H | 0 |
| 190 | H | H | EtOOC-MS | 3-Cl | H | H(NH)C | H | H | 0 |
| 191 | H | H | EtOOC-MS | 3-Cl | H | CH₃CH₂(NH)C | H | H | 0 |
| 192 | H | H | EtOOC-MS | 3-Cl | H | Ph(NH)C | H | H | 0 |
| 193 | H | H | EtOOC-MS | 3-Cl | H | C₄H₆N | H | H | 0 |
| 194 | H | H | EtOOC-MS | 3-Cl | H | C₅H₈N | H | H | 0 |
| 195 | H | H | EtOOC-MS | 3-Cl | H | C₆H₁₀N | H | H | 0 |
| 196 | H | H | EtOOC-MS | 3-Cl | H | C₄H₆NS | H | H | 0 |
| 197 | H | H | EtOOC-MS | 3-CH₃ | H | CH₃ | H | H | 0 |
| 198 | H | H | EtOOC-MS | 3-CH₃ | H | CH₃CH₂ | H | H | 0 |
| 199 | H | H | EtOOC-MS | 3-CH₃ | H | CH₃(CH₃)CH | H | H | 0 |
| 200 | H | H | EtOOC-MS | 3-CH₃ | H | CH₃(CH₂)₂CH₂ | H | H | 0 |
| 201 | H | H | EtOOC-MS | 3-CH₃ | H | PhCH₂ | H | H | 0 |
| 202 | H | H | EtOOC-MS | 3-CH₃ | H | Ph(CH₂)₂ | H | H | 0 |
| 203 | H | H | EtOOC-MS | 3-CH₃ | H | Ph | H | H | 0 |
| 204 | H | H | EtOOC-MS | 3-CH₃ | H | CH₃OCOCH₂ | H | H | 0 |
| 205 | H | H | EtOOC-MS | 3-CH₃ | H | CH₃CO | H | H | 0 |
| 206 | H | H | EtOOC-MS | 3-CH₃ | H | H₂NCO | H | H | 0 |
| 207 | H | H | EtOOC-MS | 3-CH₃ | H | CH₃SO₂ | H | H | 0 |
| 208 | H | H | EtOOC-MS | 3-CH₃ | H | 2-Pyr | H | H | 0 |

TABLE 1-continued (1)

| No. | R¹ | R² | R³ | R⁴ | R⁵ | R⁶ | R⁷ | R⁸ | n |
|---|---|---|---|---|---|---|---|---|---|
| 209 | H | H | EtOOC-MS | 3-CH₃ | H | 3-Pyr | H | H | 0 |
| 210 | H | H | EtOOC-MS | 3-CH₃ | H | 4-Pyr | H | H | 0 |
| 211 | H | H | EtOOC-MS | 3-CH₃ | H | 2-Pyrm | H | H | 0 |
| 212 | H | H | EtOOC-MS | 3-CH₃ | H | Pyr-3-CH₂ | H | H | 0 |
| 213 | H | H | EtOOC-MS | 3-CH₃ | H | Pyr-4-CH₂ | H | H | 0 |
| 214 | H | H | EtOOC-MS | 3-CH₃ | H | Pyr-2-(CH₂)₂ | H | H | 0 |
| 215 | H | H | EtOOC-MS | 3-CH₃ | H | cPn | H | H | 0 |
| 216 | H | H | EtOOC-MS | 3-CH₃ | H | CH₃ | 2-CH₃ | H | 0 |
| 217 | H | H | EtOOC-MS | 3-CH₃ | H | —(CH₂)₃-(5) | — | H | 0 |
| 218 | H | H | EtOOC-MS | 3-CH₃ | H | H(NH)C | H | H | 0 |
| 219 | H | H | EtOOC-MS | 3-CH₃ | H | CH₃CH₂(NH)C | H | H | 0 |
| 220 | H | H | EtOOC-MS | 3-CH₃ | H | Ph(NH)C | H | H | 0 |
| 221 | H | H | EtOOC-MS | 3-CH₃ | H | C₄H₆N | H | H | 0 |
| 222 | H | H | EtOOC-MS | 3-CH₃ | H | C₅H₈N | H | H | 0 |
| 223 | H | H | EtOOC-MS | 3-CH₃ | H | C₆H₁₀N | H | H | 0 |
| 224 | H | H | EtOOC-MS | 3-CH₃ | H | C₄H₆NS | H | H | 0 |
| 225 | H | H | EtOOC-MS | H | H | CH₃ | H | H | 0 |
| 226 | H | H | EtOOC-MS | H | H | CH₃CH₂ | H | H | 0 |
| 227 | H | H | EtOOC-MS | H | H | CH₃(CH₃)CH | H | H | 0 |
| 228 | H | H | EtOOC-MS | H | H | CH₃(CH₂)₂CH₂ | H | H | 0 |
| 229 | H | H | EtOOC-MS | H | H | PhCH₂ | H | H | 0 |
| 230 | H | H | EtOOC-MS | H | H | Ph(CH₂)₂ | H | H | 0 |
| 231 | H | H | EtOOC-MS | H | H | Ph | H | H | 0 |
| 232 | H | H | EtOOC-MS | H | H | CH₃OCOCH₂ | H | H | 0 |
| 233 | H | H | EtOOC-MS | H | H | CH₃CO | H | H | 0 |
| 234 | H | H | EtOOC-MS | H | H | H₂NCO | H | H | 0 |
| 235 | H | H | EtOOC-MS | H | H | CH₃SO₂ | H | H | 0 |
| 236 | H | H | EtOOC-MS | H | H | 2-Pyr | H | H | 0 |
| 237 | H | H | EtOOC-MS | H | H | 3-Pyr | H | H | 0 |
| 238 | H | H | EtOOC-MS | H | H | 4-Pyr | H | H | 0 |
| 239 | H | H | EtOOC-MS | H | H | 2-Pyrm | H | H | 0 |
| 240 | H | H | EtOOC-MS | H | H | Pyr-3-CH₂ | H | H | 0 |
| 241 | H | H | EtOOC-MS | H | H | Pyr-4-CH₂ | H | H | 0 |
| 242 | H | H | EtOOC-MS | H | H | Pyr-2-(CH₂)₂ | H | H | 0 |
| 243 | H | H | EtOOC-MS | H | H | cPn | H | H | 0 |
| 244 | H | H | EtOOC-MS | H | H | CH₃ | 2-CH₃ | H | 0 |
| 245 | H | H | EtOOC-MS | H | H | —(CH₂)₃-(5) | — | H | 0 |
| 246 | H | H | EtOOC-MS | H | H | H(NH)C | H | H | 0 |
| 247 | H | H | EtOOC-MS | H | H | CH₃CH₂(NH)C | H | H | 0 |
| 248 | H | H | EtOOC-MS | H | H | Ph(NH)C | H | H | 0 |
| 249 | H | H | EtOOC-MS | H | H | C₄H₆N | H | H | 0 |
| 250 | H | H | EtOOC-MS | H | H | C₅H₈N | H | H | 0 |
| 251 | H | H | EtOOC-MS | H | H | C₆H₁₀N | H | H | 0 |
| 252 | H | H | EtOOC-MS | H | H | C₄H₆NS | H | H | 0 |
| 253 | H | H | EtOOC-MS | 3-CF₃ | H | CH₃ | H | H | 0 |
| 254 | H | H | EtOOC-MS | 3-CF₃ | H | CH₃CH₂ | H | H | 0 |
| 255 | H | H | EtOOC-MS | 3-CF₃ | H | CH₃(CH₃)CH | H | H | 0 |
| 256 | H | H | EtOOC-MS | 3-CF₃ | H | CH₃(CH₂)₂CH₂ | H | H | 0 |
| 257 | H | H | EtOOC-MS | 3-CF₃ | H | PhCH₂ | H | H | 0 |
| 258 | H | H | EtOOC-MS | 3-CF₃ | H | Ph(CH₂)₂ | H | H | 0 |
| 259 | H | H | EtOOC-MS | 3-CF₃ | H | Ph | H | H | 0 |
| 260 | H | H | EtOOC-MS | 3-CF₃ | H | CH₃OCOCH₂ | H | H | 0 |
| 261 | H | H | EtOOC-MS | 3-CF₃ | H | CH₃CO | H | H | 0 |
| 262 | H | H | EtOOC-MS | 3-CF₃ | H | H₂NCO | H | H | 0 |
| 263 | H | H | EtOOC-MS | 3-CF₃ | H | CH₃SO₂ | H | H | 0 |
| 264 | H | H | EtOOC-MS | 3-CF₃ | H | 2-Pyr | H | H | 0 |
| 265 | H | H | EtOOC-MS | 3-CF₃ | H | 3-Pyr | H | H | 0 |
| 266 | H | H | EtOOC-MS | 3-CF₃ | H | 4-Pyr | H | H | 0 |
| 267 | H | H | EtOOC-MS | 3-CF₃ | H | 2-Pyrm | H | H | 0 |
| 268 | H | H | EtOOC-MS | 3-CF₃ | H | Pyr-3-CH₂ | H | H | 0 |
| 269 | H | H | EtOOC-MS | 3-CF₃ | H | Pyr-4-CH₂ | H | H | 0 |
| 270 | H | H | EtOOC-MS | 3-CF₃ | H | Pyr-2-(CH₂)₂ | H | H | 0 |
| 271 | H | H | EtOOC-MS | 3-CF₃ | H | cPn | H | H | 0 |
| 272 | H | H | EtOOC-MS | 3-CF₃ | H | CH₃ | 2-CH₃ | H | 0 |
| 273 | H | H | EtOOC-MS | 3-CF₃ | H | —(CH₂)₃-(5) | — | H | 0 |

TABLE 1-continued (1)

$$\text{H}_2\text{N}-\text{C}(=\text{NH})-\text{C}_6\text{H}_3(\text{R}^1)-\text{CH}=\text{C}(\text{R}^2)-\text{CH}_2-\text{N}(\text{R}^3)-\text{C}_6\text{H}_3(\text{R}^4)(\text{R}^5)-\text{O}-\text{C}_5\text{H}_{7}(\text{R}^7)(\text{R}^8)(\text{CH}_2)_n-\text{N}-\text{R}^6$$

| No. | R¹ | R² | R³ | R⁴ | R⁵ | R⁶ | R⁷ | R⁸ | n |
|---|---|---|---|---|---|---|---|---|---|
| 274 | H | H | EtOOC-MS | 3-CF₃ | H | H(NH)C | H | H | 0 |
| 275 | H | H | EtOOC-MS | 3-CF₃ | H | CH₃CH₂(NH)C | H | H | 0 |
| 276 | H | H | EtOOC-MS | 3-CF₃ | H | Ph(NH)C | H | H | 0 |
| 277 | H | H | EtOOC-MS | 3-CF₃ | H | C₄H₆N | H | H | 0 |
| 278 | H | H | EtOOC-MS | 3-CF₃ | H | C₅H₈N | H | H | 0 |
| 279 | H | H | EtOOC-MS | 3-CF₃ | H | C₆H₁₀N | H | H | 0 |
| 280 | H | H | EtOOC-MS | 3-CF₃ | H | C₄H₆NS | H | H | 0 |
| 281 | H | H | EtOOC-MS | 3-H₂NCO | H | CH₃ | H | H | 0 |
| 282 | H | H | EtOOC-MS | 3-H₂NCO | H | CH₃CH₂ | H | H | 0 |
| 283 | H | H | EtOOC-MS | 3-H₂NCO | H | CH₃(CH₃)CH | H | H | 0 |
| 284 | H | H | EtOOC-MS | 3-H₂NCO | H | CH₃(CH₂)₂CH₂ | H | H | 0 |
| 285 | H | H | EtOOC-MS | 3-H₂NCO | H | PhCH₂ | H | H | 0 |
| 286 | H | H | EtOOC-MS | 3-H₂NCO | H | Ph(CH₂)₂ | H | H | 0 |
| 287 | H | H | EtOOC-MS | 3-H₂NCO | H | Ph | H | H | 0 |
| 288 | H | H | EtOOC-MS | 3-H₂NCO | H | CH₃OCOCH₂ | H | H | 0 |
| 289 | H | H | EtOOC-MS | 3-H₂NCO | H | CH₃CO | H | H | 0 |
| 290 | H | H | EtOOC-MS | 3-H₂NCO | H | H₂NCO | H | H | 0 |
| 291 | H | H | EtOOC-MS | 3-H₂NCO | H | CH₃SO₂ | H | H | 0 |
| 292 | H | H | EtOOC-MS | 3-H₂NCO | H | 2-Pyr | H | H | 0 |
| 293 | H | H | EtOOC-MS | 3-H₂NCO | H | 3-Pyr | H | H | 0 |
| 294 | H | H | EtOOC-MS | 3-H₂NCO | H | 4-Pyr | H | H | 0 |
| 295 | H | H | EtOOC-MS | 3-H₂NCO | H | 2-Pyrm | H | H | 0 |
| 296 | H | H | EtOOC-MS | 3-H₂NCO | H | Pyr-3-CH₂ | H | H | 0 |
| 297 | H | H | EtOOC-MS | 3-H₂NCO | H | Pyr-4-CH₂ | H | H | 0 |
| 298 | H | H | EtOOC-MS | 3-H₂NCO | H | Pyr-2-(CH₂)₂ | H | H | 0 |
| 299 | H | H | EtOOC-MS | 3-H₂NCO | H | cPn | H | H | 0 |
| 300 | H | H | EtOOC-MS | 3-H₂NCO | H | CH₃ | 2-CH₃ | H | 0 |
| 301 | H | H | EtOOC-MS | 3-H₂NCO | H | —(CH₂)₃-(5) | — | H | 0 |
| 302 | H | H | EtOOC-MS | 3-H₂NCO | H | H(NH)C | H | H | 0 |
| 303 | H | H | EtOOC-MS | 3-H₂NCO | H | CH₃CH₂(NH)C | H | H | 0 |
| 304 | H | H | EtOOC-MS | 3-H₂NCO | H | Ph(NH)C | H | H | 0 |
| 305 | H | H | EtOOC-MS | 3-H₂NCO | H | C₄H₆N | H | H | 0 |
| 306 | H | H | EtOOC-MS | 3-H₂NCO | H | C₅H₈N | H | H | 0 |
| 307 | H | H | EtOOC-MS | 3-H₂NCO | H | C₆H₁₀N | H | H | 0 |
| 308 | H | H | EtOOC-MS | 3-H₂NCO | H | C₄H₆NS | H | H | 0 |
| 309 | H | H | EtOOC-MS | 3-F | H | CH₃ | H | H | 0 |
| 310 | H | H | EtOOC-MS | 3-F | H | CH₃CH₂ | H | H | 0 |
| 311 | H | H | EtOOC-MS | 3-F | H | CH₃(CH₃)CH | H | H | 0 |
| 312 | H | H | EtOOC-MS | 3-F | H | CH₃(CH₂)₂CH₂ | H | H | 0 |
| 313 | H | H | EtOOC-MS | 3-F | H | PhCH₂ | H | H | 0 |
| 314 | H | H | EtOOC-MS | 3-F | H | Ph(CH₂)₂ | H | H | 0 |
| 315 | H | H | EtOOC-MS | 3-F | H | Ph | H | H | 0 |
| 316 | H | H | EtOOC-MS | 3-F | H | CH₃OCOCH₂ | H | H | 0 |
| 317 | H | H | EtOOC-MS | 3-F | H | CH₃CO | H | H | 0 |
| 318 | H | H | EtOOC-MS | 3-F | H | H₂NCO | H | H | 0 |
| 319 | H | H | EtOOC-MS | 3-F | H | CH₃SO₂ | H | H | 0 |
| 320 | H | H | EtOOC-MS | 3-F | H | 2-Pyr | H | H | 0 |
| 321 | H | H | EtOOC-MS | 3-F | H | 3-Pyr | H | H | 0 |
| 322 | H | H | EtOOC-MS | 3-F | H | 4-Pyr | H | H | 0 |
| 323 | H | H | EtOOC-MS | 3-F | H | 2-Pyrm | H | H | 0 |
| 324 | H | H | EtOOC-MS | 3-F | H | Pyr-3-CH₂ | H | H | 0 |
| 325 | H | H | EtOOC-MS | 3-F | H | Pyr-4-CH₂ | H | H | 0 |
| 326 | H | H | EtOOC-MS | 3-F | H | Pyr-2-(CH₂)₂ | H | H | 0 |
| 327 | H | H | EtOOC-MS | 3-F | H | cPn | H | H | 0 |
| 328 | H | H | EtOOC-MS | 3-F | H | CH₃ | 2-CH₃ | H | 0 |
| 329 | H | H | EtOOC-MS | 3-F | H | —(CH₂)₃-(5) | — | H | 0 |
| 330 | H | H | EtOOC-MS | 3-F | H | H(NH)C | H | H | 0 |
| 331 | H | H | EtOOC-MS | 3-F | H | CH₃CH₂(NH)C | H | H | 0 |
| 332 | H | H | EtOOC-MS | 3-F | H | Ph(NH)C | H | H | 0 |
| 333 | H | H | EtOOC-MS | 3-F | H | C₄H₆N | H | H | 0 |
| 334 | H | H | EtOOC-MS | 3-F | H | C₅H₈N | H | H | 0 |
| 335 | H | H | EtOOC-MS | 3-F | H | C₆H₁₀N | H | H | 0 |
| 336 | H | H | EtOOC-MS | 3-F | H | C₄H₆NS | H | H | 0 |
| 337 | H | H | EtOOC-MS | 3-Cl | H | CH₃ | H | H | 2 |
| 338 | H | H | EtOOC-MS | 3-Cl | H | CH₃CH₂ | H | H | 2 |

TABLE 1-continued (1)

$$\text{Structure: } H_2N-C(=NH)-C_6H_3(R^1)-CH=C(R^2)-CH_2-N(R^3)-C_6H_3(R^4)(R^5)-O-\text{piperidine}(R^7)(R^8)(CH_2)_n-N-R^6$$

| No. | R¹ | R² | R³ | R⁴ | R⁵ | R⁶ | R⁷ | R⁸ | n |
|-----|----|----|-----|------|----|------|------|----|---|
| 339 | H | H | EtOOC-MS | 3-Cl | H | CH₃(CH₃)CH | H | H | 2 |
| 340 | H | H | EtOOC-MS | 3-Cl | H | CH₃(CH₂)₂CH₂ | H | H | 2 |
| 341 | H | H | EtOOC-MS | 3-Cl | H | PhCH₂ | H | H | 2 |
| 342 | H | H | EtOOC-MS | 3-Cl | H | Ph(CH₂)₂ | H | H | 2 |
| 343 | H | H | EtOOC-MS | 3-Cl | H | Ph | H | H | 2 |
| 344 | H | H | EtOOC-MS | 3-Cl | H | CH₃OCOCH₂ | H | H | 2 |
| 345 | H | H | EtOOC-MS | 3-Cl | H | CH₃CO | H | H | 2 |
| 346 | H | H | EtOOC-MS | 3-Cl | H | H₂NCO | H | H | 2 |
| 347 | H | H | EtOOC-MS | 3-Cl | H | CH₃SO₂ | H | H | 2 |
| 348 | H | H | EtOOC-MS | 3-Cl | H | 2-Pyr | H | H | 2 |
| 349 | H | H | EtOOC-MS | 3-Cl | H | 3-Pyr | H | H | 2 |
| 350 | H | H | EtOOC-MS | 3-Cl | H | 4-Pyr | H | H | 2 |
| 351 | H | H | EtOOC-MS | 3-Cl | H | 2-Pyrm | H | H | 2 |
| 352 | H | H | EtOOC-MS | 3-Cl | H | Pyr-3-CH₂ | H | H | 2 |
| 353 | H | H | EtOOC-MS | 3-Cl | H | Pyr-4-CH₂ | H | H | 2 |
| 354 | H | H | EtOOC-MS | 3-Cl | H | Pyr-2-(CH₂)₂ | H | H | 2 |
| 355 | H | H | EtOOC-MS | 3-Cl | H | cPn | H | H | 2 |
| 356 | H | H | EtOOC-MS | 3-Cl | H | CH₃ | 2-CH₃ | H | 2 |
| 357 | H | H | EtOOC-MS | 3-Cl | H | —(CH₂)₃-(5) | — | H | 2 |
| 358 | H | H | EtOOC-MS | 3-Cl | H | H(NH)C | H | H | 2 |
| 359 | H | H | EtOOC-MS | 3-Cl | H | CH₃CH₂(NH)C | H | H | 2 |
| 360 | H | H | EtOOC-MS | 3-Cl | H | Ph(NH)C | H | H | 2 |
| 361 | H | H | EtOOC-MS | 3-Cl | H | C₄H₆N | H | H | 2 |
| 362 | H | H | EtOOC-MS | 3-Cl | H | C₅H₈N | H | H | 2 |
| 363 | H | H | EtOOC-MS | 3-Cl | H | C₆H₁₀N | H | H | 2 |
| 364 | H | H | EtOOC-MS | 3-Cl | H | C₄H₆NS | H | H | 2 |
| 365 | H | H | EtOOC-MS | 3-CH₃ | H | CH₃ | H | H | 2 |
| 366 | H | H | EtOOC-MS | 3-CH₃ | H | CH₃CH₂ | H | H | 2 |
| 367 | H | H | EtOOC-MS | 3-CH₃ | H | CH₃(CH₃)CH | H | H | 2 |
| 368 | H | H | EtOOC-MS | 3-CH₃ | H | CH₃(CH₂)₂CH₂ | H | H | 2 |
| 369 | H | H | EtOOC-MS | 3-CH₃ | H | PhCH₂ | H | H | 2 |
| 370 | H | H | EtOOC-MS | 3-CH₃ | H | Ph(CH₂)₂ | H | H | 2 |
| 371 | H | H | EtOOC-MS | 3-CH₃ | H | Ph | H | H | 2 |
| 372 | H | H | EtOOC-MS | 3-CH₃ | H | CH₃OCOCH₂ | H | H | 2 |
| 373 | H | H | EtOOC-MS | 3-CH₃ | H | CH₃CO | H | H | 2 |
| 374 | H | H | EtOOC-MS | 3-CH₃ | H | H₂NCO | H | H | 2 |
| 375 | H | H | EtOOC-MS | 3-CH₃ | H | CH₃SO₂ | H | H | 2 |
| 376 | H | H | EtOOC-MS | 3-CH₃ | H | 2-Pyr | H | H | 2 |
| 377 | H | H | EtOOC-MS | 3-CH₃ | H | 3-Pyr | H | H | 2 |
| 378 | H | H | EtOOC-MS | 3-CH₃ | H | 4-Pyr | H | H | 2 |
| 379 | H | H | EtOOC-MS | 3-CH₃ | H | 2-Pyrm | H | H | 2 |
| 380 | H | H | EtOOC-MS | 3-CH₃ | H | Pyr-3-CH₂ | H | H | 2 |
| 381 | H | H | EtOOC-MS | 3-CH₃ | H | Pyr-4-CH₂ | H | H | 2 |
| 382 | H | H | EtOOC-MS | 3-CH₃ | H | Pyr-2-(CH₂)₂ | H | H | 2 |
| 383 | H | H | EtOOC-MS | 3-CH₃ | H | cPn | H | H | 2 |
| 384 | H | H | EtOOC-MS | 3-CH₃ | H | CH₃ | 2-CH₃ | H | 2 |
| 385 | H | H | EtOOC-MS | 3-CH₃ | H | —(CH₂)₃-(5) | — | H | 2 |
| 386 | H | H | EtOOC-MS | 3-CH₃ | H | H(NH)C | H | H | 2 |
| 387 | H | H | EtOOC-MS | 3-CH₃ | H | CH₃CH₂(NH)C | H | H | 2 |
| 388 | H | H | EtOOC-MS | 3-CH₃ | H | Ph(NH)C | H | H | 2 |
| 389 | H | H | EtOOC-MS | 3-CH₃ | H | C₄H₆N | H | H | 2 |
| 390 | H | H | EtOOC-MS | 3-CH₃ | H | C₅H₈N | H | H | 2 |
| 391 | H | H | EtOOC-MS | 3-CH₃ | H | C₆H₁₀N | H | H | 2 |
| 392 | H | H | EtOOC-MS | 3-CH₃ | H | C₄H₆NS | H | H | 2 |
| 393 | H | H | EtOOC-MS | H | H | CH₃ | H | H | 2 |
| 394 | H | H | EtOOC-MS | H | H | CH₃CH₂ | H | H | 2 |
| 395 | H | H | EtOOC-MS | H | H | CH₃(CH₃)CH | H | H | 2 |
| 396 | H | H | EtOOC-MS | H | H | CH₃(CH₂)₂CH₂ | H | H | 2 |
| 397 | H | H | EtOOC-MS | H | H | PhCH₂ | H | H | 2 |
| 398 | H | H | EtOOC-MS | H | H | Ph(CH₂)₂ | H | H | 2 |
| 399 | H | H | EtOOC-MS | H | H | Ph | H | H | 2 |
| 400 | H | H | EtOOC-MS | H | H | CH₃OCOCH₂ | H | H | 2 |
| 401 | H | H | EtOOC-MS | H | H | CH₃CO | H | H | 2 |
| 402 | H | H | EtOOC-MS | H | H | H₂NCO | H | H | 2 |
| 403 | H | H | EtOOC-MS | H | H | CH₃SO₂ | H | H | 2 |

TABLE 1-continued (1)

[Structure: H2N-C(=NH)-phenyl(R1)-CH=C(R2)-CH2-N(R3)-phenyl(R4,R5)-O-piperidine ring with (CH2)n, R6 on N, R7, R8 substituents]

| No. | R¹ | R² | R³ | R⁴ | R⁵ | R⁶ | R⁷ | R⁸ | n |
|---|---|---|---|---|---|---|---|---|---|
| 404 | H | H | EtOOC-MS | H | H | 2-Pyr | H | H | 2 |
| 405 | H | H | EtOOC-MS | H | H | 3-Pyr | H | H | 2 |
| 406 | H | H | EtOOC-MS | H | H | 4-Pyr | H | H | 2 |
| 407 | H | H | EtOOC-MS | H | H | 2-Pyrm | H | H | 2 |
| 408 | H | H | EtOOC-MS | H | H | Pyr-3-CH₂ | H | H | 2 |
| 409 | H | H | EtOOC-MS | H | H | Pyr-4-CH₂ | H | H | 2 |
| 410 | H | H | EtOOC-MS | H | H | Pyr-2-(CH₂)₂ | H | H | 2 |
| 411 | H | H | EtOOC-MS | H | H | cPn | H | H | 2 |
| 412 | H | H | EtOOC-MS | H | H | CH₃ | 2-CH₃ | H | 2 |
| 413 | H | H | EtOOC-MS | H | H | —(CH₂)₃-(5) | — | H | 2 |
| 414 | H | H | EtOOC-MS | H | H | H(NH)C | H | H | 2 |
| 415 | H | H | EtOOC-MS | H | H | CH₃CH₂(NH)C | H | H | 2 |
| 416 | H | H | EtOOC-MS | H | H | Ph(NH)C | H | H | 2 |
| 417 | H | H | EtOOC-MS | H | H | C₄H₆N | H | H | 2 |
| 418 | H | H | EtOOC-MS | H | H | C₅H₈N | H | H | 2 |
| 419 | H | H | EtOOC-MS | H | H | C₆H₁₀N | H | H | 2 |
| 420 | H | H | EtOOC-MS | H | H | C₄H₆NS | H | H | 2 |
| 421 | H | H | EtOOC-MS | 3-CF₃ | H | CH₃ | H | H | 2 |
| 422 | H | H | EtOOC-MS | 3-CF₃ | H | CH₃CH₂ | H | H | 2 |
| 423 | H | H | EtOOC-MS | 3-CF₃ | H | CH₃(CH₃)CH | H | H | 2 |
| 424 | H | H | EtOOC-MS | 3-CF₃ | H | CH₃(CH₂)₂CH₂ | H | H | 2 |
| 425 | H | H | EtOOC-MS | 3-CF₃ | H | PhCH₂ | H | H | 2 |
| 426 | H | H | EtOOC-MS | 3-CF₃ | H | Ph(CH₂)₂ | H | H | 2 |
| 427 | H | H | EtOOC-MS | 3-CF₃ | H | Ph | H | H | 2 |
| 428 | H | H | EtOOC-MS | 3-CF₃ | H | CH₃OCOCH₂ | H | H | 2 |
| 429 | H | H | EtOOC-MS | 3-CF₃ | H | CH₃CO | H | H | 2 |
| 430 | H | H | EtOOC-MS | 3-CF₃ | H | H₂NCO | H | H | 2 |
| 431 | H | H | EtOOC-MS | 3-CF₃ | H | CH₃SO₂ | H | H | 2 |
| 432 | H | H | EtOOC-MS | 3-CF₃ | H | 2-Pyr | H | H | 2 |
| 433 | H | H | EtOOC-MS | 3-CF₃ | H | 3-Pyr | H | H | 2 |
| 434 | H | H | EtOOC-MS | 3-CF₃ | H | 4-Pyr | H | H | 2 |
| 435 | H | H | EtOOC-MS | 3-CF₃ | H | 2-Pyrm | H | H | 2 |
| 436 | H | H | EtOOC-MS | 3-CF₃ | H | Pyr-3-CH₂ | H | H | 2 |
| 437 | H | H | EtOOC-MS | 3-CF₃ | H | Pyr-4-CH₂ | H | H | 2 |
| 438 | H | H | EtOOC-MS | 3-CF₃ | H | Pyr-2-(CH₂)₂ | H | H | 2 |
| 439 | H | H | EtOOC-MS | 3-CF₃ | H | cPn | H | H | 2 |
| 440 | H | H | EtOOC-MS | 3-CF₃ | H | CH₃ | 2-CH₃ | H | 2 |
| 441 | H | H | EtOOC-MS | 3-CF₃ | H | —(CH₂)₃-(5) | — | H | 2 |
| 442 | H | H | EtOOC-MS | 3-CF₃ | H | H(NH)C | H | H | 2 |
| 443 | H | H | EtOOC-MS | 3-CF₃ | H | CH₃CH₂(NH)C | H | H | 2 |
| 444 | H | H | EtOOC-MS | 3-CF₃ | H | Ph(NH)C | H | H | 2 |
| 445 | H | H | EtOOC-MS | 3-CF₃ | H | C₄H₆N | H | H | 2 |
| 446 | H | H | EtOOC-MS | 3-CF₃ | H | C₅H₈N | H | H | 2 |
| 447 | H | H | EtOOC-MS | 3-CF₃ | H | C₆H₁₀N | H | H | 2 |
| 448 | H | H | EtOOC-MS | 3-CF₃ | H | C₄H₆NS | H | H | 2 |
| 449 | H | H | EtOOC-MS | 3-H₂NCO | H | CH₃ | H | H | 2 |
| 450 | H | H | EtOOC-MS | 3-H₂NCO | H | CH₃CH₂ | H | H | 2 |
| 451 | H | H | EtOOC-MS | 3-H₂NCO | H | CH₃(CH₃)CH | H | H | 2 |
| 452 | H | H | EtOOC-MS | 3-H₂NCO | H | CH₃(CH₂)₂CH₂ | H | H | 2 |
| 453 | H | H | EtOOC-MS | 3-H₂NCO | H | PhCH₂ | H | H | 2 |
| 454 | H | H | EtOOC-MS | 3-H₂NCO | H | Ph(CH₂)₂ | H | H | 2 |
| 455 | H | H | EtOOC-MS | 3-H₂NCO | H | Ph | H | H | 2 |
| 456 | H | H | EtOOC-MS | 3-H₂NCO | H | CH₃OCOCH₂ | H | H | 2 |
| 457 | H | H | EtOOC-MS | 3-H₂NCO | H | CH₃CO | H | H | 2 |
| 458 | H | H | EtOOC-MS | 3-H₂NCO | H | H₂NCO | H | H | 2 |
| 459 | H | H | EtOOC-MS | 3-H₂NCO | H | CH₃SO₂ | H | H | 2 |
| 460 | H | H | EtOOC-MS | 3-H₂NCO | H | 2-Pyr | H | H | 2 |
| 461 | H | H | EtOOC-MS | 3-H₂NCO | H | 3-Pyr | H | H | 2 |
| 462 | H | H | EtOOC-MS | 3-H₂NCO | H | 4-Pyr | H | H | 2 |
| 463 | H | H | EtOOC-MS | 3-H₂NCO | H | 2-Pyrm | H | H | 2 |
| 464 | H | H | EtOOC-MS | 3-H₂NCO | H | Pyr-3-CH₂ | H | H | 2 |
| 465 | H | H | EtOOC-MS | 3-H₂NCO | H | Pyr-4-CH₂ | H | H | 2 |
| 466 | H | H | EtOOC-MS | 3-H₂NCO | H | Pyr-2-(CH₂)₂ | H | H | 2 |
| 467 | H | H | EtOOC-MS | 3-H₂NCO | H | cPn | H | H | 2 |
| 468 | H | H | EtOOC-MS | 3-H₂NCO | H | CH₃ | 2-CH₃ | H | 2 |

TABLE 1-continued (1)

$$\text{H}_2\text{N}-\underset{\text{NH}}{\overset{}{\text{C}}}-\text{Ar}(R^1)-CH=C(R^2)-CH_2-N(R^3)-\text{Ar}(R^4,R^5)-O-\text{piperidine}(R^7,R^8)(N-R^6)$$

| No. | R¹ | R² | R³ | R⁴ | R⁵ | R⁶ | R⁷ | R⁸ | n |
|---|---|---|---|---|---|---|---|---|---|
| 469 | H | H | EtOOC-MS | 3-H₂NCO | H | —(CH₂)₃-(5) | — | H | 2 |
| 470 | H | H | EtOOC-MS | 3-H₂NCO | H | H(NH)C | H | H | 2 |
| 471 | H | H | EtOOC-MS | 3-H₂NCO | H | CH₃CH₂(NH)C | H | H | 2 |
| 472 | H | H | EtOOC-MS | 3-H₂NCO | H | Ph(NH)C | H | H | 2 |
| 473 | H | H | EtOOC-MS | 3-H₂NCO | H | C₄H₆N | H | H | 2 |
| 474 | H | H | EtOOC-MS | 3-H₂NCO | H | C₅H₈N | H | H | 2 |
| 475 | H | H | EtOOC-MS | 3-H₂NCO | H | C₆H₁₀N | H | H | 2 |
| 476 | H | H | EtOOC-MS | 3-H₂NCO | H | C₄H₆NS | H | H | 2 |
| 477 | H | H | EtOOC-MS | 3-F | H | CH₃ | H | H | 2 |
| 478 | H | H | EtOOC-MS | 3-F | H | CH₃CH₂ | H | H | 2 |
| 479 | H | H | EtOOC-MS | 3-F | H | CH₃(CH₃)CH | H | H | 2 |
| 480 | H | H | EtOOC-MS | 3-F | H | CH₃(CH₂)₂CH₂ | H | H | 2 |
| 481 | H | H | EtOOC-MS | 3-F | H | PhCH₂ | H | H | 2 |
| 482 | H | H | EtOOC-MS | 3-F | H | Ph(CH₂)₂ | H | H | 2 |
| 483 | H | H | EtOOC-MS | 3-F | H | Ph | H | H | 2 |
| 484 | H | H | EtOOC-MS | 3-F | H | CH₃OCOCH₂ | H | H | 2 |
| 485 | H | H | EtOOC-MS | 3-F | H | CH₃CO | H | H | 2 |
| 486 | H | H | EtOOC-MS | 3-F | H | H₂NCO | H | H | 2 |
| 487 | H | H | EtOOC-MS | 3-F | H | CH₃SO₂ | H | H | 2 |
| 488 | H | H | EtOOC-MS | 3-F | H | 2-Pyr | H | H | 2 |
| 489 | H | H | EtOOC-MS | 3-F | H | 3-Pyr | H | H | 2 |
| 490 | H | H | EtOOC-MS | 3-F | H | 4-Pyr | H | H | 2 |
| 491 | H | H | EtOOC-MS | 3-F | H | 2-Pyrm | H | H | 2 |
| 492 | H | H | EtOOC-MS | 3-F | H | Pyr-3-CH₂ | H | H | 2 |
| 493 | H | H | EtOOC-MS | 3-F | H | Pyr-4-CH₂ | H | H | 2 |
| 494 | H | H | EtOOC-MS | 3-F | H | Pyr-2-(CH₂)₂ | H | H | 2 |
| 495 | H | H | EtOOC-MS | 3-F | H | cPn | H | H | 2 |
| 496 | H | H | EtOOC-MS | 3-F | H | CH₃ | 2-CH₃ | H | 2 |
| 497 | H | H | EtOOC-MS | 3-F | H | —(CH₂)₃-(5) | — | H | 2 |
| 498 | H | H | EtOOC-MS | 3-F | H | H(NH)C | H | H | 2 |
| 499 | H | H | EtOOC-MS | 3-F | H | CH₃CH₂(NH)C | H | H | 2 |
| 500 | H | H | EtOOC-MS | 3-F | H | Ph(NH)C | H | H | 2 |
| 501 | H | H | EtOOC-MS | 3-F | H | C₄H₆N | H | H | 2 |
| 502 | H | H | EtOOC-MS | 3-F | H | C₅H₈N | H | H | 2 |
| 503 | H | H | EtOOC-MS | 3-F | H | C₆H₁₀N | H | H | 2 |
| 504 | H | H | EtOOC-MS | 3-F | H | C₄H₆NS | H | H | 2 |
| 505 | H | H | HOOC-MS | 3-Cl | H | CH₃ | H | H | 1 |
| 506 | H | H | HOOC-MS | 3-Cl | H | CH₃CH₂ | H | H | 1 |
| 507 | H | H | HOOC-MS | 3-Cl | H | CH₃(CH₃)CH | H | H | 1 |
| 508 | H | H | HOOC-MS | 3-Cl | H | CH₃(CH₂)₂CH₂ | H | H | 1 |
| 509 | H | H | HOOC-MS | 3-Cl | H | PhCH₂ | H | H | 1 |
| 510 | H | H | HOOC-MS | 3-Cl | H | Ph(CH₂)₂ | H | H | 1 |
| 511 | H | H | HOOC-MS | 3-Cl | H | Ph | H | H | 1 |
| 512 | H | H | HOOC-MS | 3-Cl | H | CH₃OCOCH₂ | H | H | 1 |
| 513 | H | H | HOOC-MS | 3-Cl | H | CH₃CO | H | H | 1 |
| 514 | H | H | HOOC-MS | 3-Cl | H | H₂NCO | H | H | 1 |
| 515 | H | H | HOOC-MS | 3-Cl | H | CH₃SO₂ | H | H | 1 |
| 516 | H | H | HOOC-MS | 3-Cl | H | 2-Pyr | H | H | 1 |
| 517 | H | H | HOOC-MS | 3-Cl | H | 3-Pyr | H | H | 1 |
| 518 | H | H | HOOC-MS | 3-Cl | H | 4-Pyr | H | H | 1 |
| 519 | H | H | HOOC-MS | 3-Cl | H | 2-Pyrm | H | H | 1 |
| 520 | H | H | HOOC-MS | 3-Cl | H | Pyr-3-CH₂ | H | H | 1 |
| 521 | H | H | HOOC-MS | 3-Cl | H | Pyr-4-CH₂ | H | H | 1 |
| 522 | H | H | HOOC-MS | 3-Cl | H | Pyr-2-(CH₂)₂ | H | H | 1 |
| 523 | H | H | HOOC-MS | 3-Cl | H | cPn | H | H | 1 |
| 524 | H | H | HOOC-MS | 3-Cl | H | CH₃ | 2-CH₃ | H | 1 |
| 525 | H | H | HOOC-MS | 3-Cl | H | —(CH₂)₃-(5) | — | H | 1 |
| 526 | H | H | HOOC-MS | 3-Cl | H | H(NH)C | H | H | 1 |
| 527 | H | H | HOOC-MS | 3-Cl | H | CH₃CH₂(NH)C | H | H | 1 |
| 528 | H | H | HOOC-MS | 3-Cl | H | Ph(NH)C | H | H | 1 |
| 529 | H | H | HOOC-MS | 3-Cl | H | C₄H₆N | H | H | 1 |
| 530 | H | H | HOOC-MS | 3-Cl | H | C₅H₈N | H | H | 1 |
| 531 | H | H | HOOC-MS | 3-Cl | H | C₆H₁₀N | H | H | 1 |
| 532 | H | H | HOOC-MS | 3-Cl | H | C₄H₆NS | H | H | 1 |
| 533 | H | H | HOOC-MS | 3-CH₃ | H | CH₃ | H | H | 1 |

TABLE 1-continued (1)

Structure: H$_2$N-C(=NH)-C$_6$H$_3$(R$^1$)-CH=C(R$^2$)-CH$_2$-N(R$^3$)-C$_6$H$_3$(R$^4$)(R$^5$)-O-[piperidine ring with (CH$_2$)$_n$, N-R$^6$, R$^7$, R$^8$]

| No. | R$^1$ | R$^2$ | R$^3$ | R$^4$ | R$^5$ | R$^6$ | R$^7$ | R$^8$ | n |
|---|---|---|---|---|---|---|---|---|---|
| 534 | H | H | HOOC-MS | 3-CH$_3$ | H | CH$_3$CH$_2$ | H | H | 1 |
| 535 | H | H | HOOC-MS | 3-CH$_3$ | H | CH$_3$(CH$_3$)CH | H | H | 1 |
| 536 | H | H | HOOC-MS | 3-CH$_3$ | H | CH$_3$(CH$_2$)$_2$CH$_2$ | H | H | 1 |
| 537 | H | H | HOOC-MS | 3-CH$_3$ | H | PhCH$_2$ | H | H | 1 |
| 538 | H | H | HOOC-MS | 3-CH$_3$ | H | Ph(CH$_2$)$_2$ | H | H | 1 |
| 539 | H | H | HOOC-MS | 3-CH$_3$ | H | Ph | H | H | 1 |
| 540 | H | H | HOOC-MS | 3-CH$_3$ | H | CH$_3$OCOCH$_2$ | H | H | 1 |
| 541 | H | H | HOOC-MS | 3-CH$_3$ | H | CH$_3$CO | H | H | 1 |
| 542 | H | H | HOOC-MS | 3-CH$_3$ | H | H$_2$NCO | H | H | 1 |
| 543 | H | H | HOOC-MS | 3-CH$_3$ | H | CH$_3$SO$_2$ | H | H | 1 |
| 544 | H | H | HOOC-MS | 3-CH$_3$ | H | 2-Pyr | H | H | 1 |
| 545 | H | H | HOOC-MS | 3-CH$_3$ | H | 3-Pyr | H | H | 1 |
| 546 | H | H | HOOC-MS | 3-CH$_3$ | H | 4-Pyr | H | H | 1 |
| 547 | H | H | HOOC-MS | 3-CH$_3$ | H | 2-Pyrm | H | H | 1 |
| 548 | H | H | HOOC-MS | 3-CH$_3$ | H | Pyr-3-CH$_2$ | H | H | 1 |
| 549 | H | H | HOOC-MS | 3-CH$_3$ | H | Pyr-4-CH$_2$ | H | H | 1 |
| 550 | H | H | HOOC-MS | 3-CH$_3$ | H | Pyr-2-(CH$_2$)$_2$ | H | H | 1 |
| 551 | H | H | HOOC-MS | 3-CH$_3$ | H | cPn | H | H | 1 |
| 552 | H | H | HOOC-MS | 3-CH$_3$ | H | CH$_3$ | 2-CH$_3$ | H | 1 |
| 553 | H | H | HOOC-MS | 3-CH$_3$ | H | —(CH$_2$)$_3$-(5) | — | H | 1 |
| 554 | H | H | HOOC-MS | 3-CH$_3$ | H | H(NH)C | H | H | 1 |
| 555 | H | H | HOOC-MS | 3-CH$_3$ | H | CH$_3$CH$_2$(NH)C | H | H | 1 |
| 556 | H | H | HOOC-MS | 3-CH$_3$ | H | Ph(NH)C | H | H | 1 |
| 557 | H | H | HOOC-MS | 3-CH$_3$ | H | C$_4$H$_6$N | H | H | 1 |
| 558 | H | H | HOOC-MS | 3-CH$_3$ | H | C$_5$H$_8$N | H | H | 1 |
| 559 | H | H | HOOC-MS | 3-CH$_3$ | H | C$_6$H$_{10}$N | H | H | 1 |
| 560 | H | H | HOOC-MS | 3-CH$_3$ | H | C$_4$H$_6$NS | H | H | 1 |
| 561 | H | H | HOOC-MS | H | H | CH$_3$ | H | H | 1 |
| 562 | H | H | HOOC-MS | H | H | CH$_3$CH$_2$ | H | H | 1 |
| 563 | H | H | HOOC-MS | H | H | CH$_3$(CH$_3$)CH | H | H | 1 |
| 564 | H | H | HOOC-MS | H | H | CH$_3$(CH$_2$)$_2$CH$_2$ | H | H | 1 |
| 565 | H | H | HOOC-MS | H | H | PhCH$_2$ | H | H | 1 |
| 566 | H | H | HOOC-MS | H | H | Ph(CH$_2$)$_2$ | H | H | 1 |
| 567 | H | H | HOOC-MS | H | H | Ph | H | H | 1 |
| 568 | H | H | HOOC-MS | H | H | CH$_3$OCOCH$_2$ | H | H | 1 |
| 569 | H | H | HOOC-MS | H | H | CH$_3$CO | H | H | 1 |
| 570 | H | H | HOOC-MS | H | H | H$_2$NCO | H | H | 1 |
| 571 | H | H | HOOC-MS | H | H | CH$_3$SO$_2$ | H | H | 1 |
| 572 | H | H | HOOC-MS | H | H | 2-Pyr | H | H | 1 |
| 573 | H | H | HOOC-MS | H | H | 3-Pyr | H | H | 1 |
| 574 | H | H | HOOC-MS | H | H | 4-Pyr | H | H | 1 |
| 575 | H | H | HOOC-MS | H | H | 2-Pyrm | H | H | 1 |
| 576 | H | H | HOOC-MS | H | H | Pyr-3-CH$_2$ | H | H | 1 |
| 577 | H | H | HOOC-MS | H | H | Pyr-4-CH$_2$ | H | H | 1 |
| 578 | H | H | HOOC-MS | H | H | Pyr-2-(CH$_2$)$_2$ | H | H | 1 |
| 579 | H | H | HOOC-MS | H | H | cPn | H | H | 1 |
| 580 | H | H | HOOC-MS | H | H | CH$_3$ | 2-CH$_3$ | H | 1 |
| 581 | H | H | HOOC-MS | H | H | —(CH$_2$)$_3$-(5) | — | H | 1 |
| 582 | H | H | HOOC-MS | H | H | H(NH)C | H | H | 1 |
| 583 | H | H | HOOC-MS | H | H | CH$_3$CH$_2$(NH)C | H | H | 1 |
| 584 | H | H | HOOC-MS | H | H | Ph(NH)C | H | H | 1 |
| 585 | H | H | HOOC-MS | H | H | C$_4$H$_6$N | H | H | 1 |
| 586 | H | H | HOOC-MS | H | H | C$_5$H$_8$N | H | H | 1 |
| 587 | H | H | HOOC-MS | H | H | C$_6$H$_{10}$N | H | H | 1 |
| 588 | H | H | HOOC-MS | H | H | C$_4$H$_6$NS | H | H | 1 |
| 589 | H | H | HOOC-MS | 3-CF$_3$ | H | CH$_3$ | H | H | 1 |
| 590 | H | H | HOOC-MS | 3-CF$_3$ | H | CH$_3$CH$_2$ | H | H | 1 |
| 591 | H | H | HOOC-MS | 3-CF$_3$ | H | CH$_3$(CH$_3$)CH | H | H | 1 |
| 592 | H | H | HOOC-MS | 3-CF$_3$ | H | CH$_3$(CH$_2$)$_2$CH$_2$ | H | H | 1 |
| 593 | H | H | HOOC-MS | 3-CF$_3$ | H | PhCH$_2$ | H | H | 1 |
| 594 | H | H | HOOC-MS | 3-CF$_3$ | H | Ph(CH$_2$)$_2$ | H | H | 1 |
| 595 | H | H | HOOC-MS | 3-CF$_3$ | H | Ph | H | H | 1 |
| 596 | H | H | HOOC-MS | 3-CF$_3$ | H | CH$_3$OCOCH$_2$ | H | H | 1 |
| 597 | H | H | HOOC-MS | 3-CF$_3$ | H | CH$_3$CO | H | H | 1 |
| 598 | H | H | HOOC-MS | 3-CF$_3$ | H | H$_2$NCO | H | H | 1 |

TABLE 1-continued (1)

$$\text{structure shown with substituents } R^1, R^2, R^3, R^4, R^5, R^6, R^7, R^8, n$$

| No. | R¹ | R² | R³ | R⁴ | R⁵ | R⁶ | R⁷ | R⁸ | n |
|---|---|---|---|---|---|---|---|---|---|
| 599 | H | H | HOOC-MS | 3-CF₃ | H | CH₃SO₂ | H | H | 1 |
| 600 | H | H | HOOC-MS | 3-CF₃ | H | 2-Pyr | H | H | 1 |
| 601 | H | H | HOOC-MS | 3-CF₃ | H | 3-Pyr | H | H | 1 |
| 602 | H | H | HOOC-MS | 3-CF₃ | H | 4-Pyr | H | H | 1 |
| 603 | H | H | HOOC-MS | 3-CF₃ | H | 2-Pyrm | H | H | 1 |
| 604 | H | H | HOOC-MS | 3-CF₃ | H | Pyr-3-CH₂ | H | H | 1 |
| 605 | H | H | HOOC-MS | 3-CF₃ | H | Pyr-4-CH₂ | H | H | 1 |
| 606 | H | H | HOOC-MS | 3-CF₃ | H | Pyr-2-(CH₂)₂ | H | H | 1 |
| 607 | H | H | HOOC-MS | 3-CF₃ | H | cPn | H | H | 1 |
| 608 | H | H | HOOC-MS | 3-CF₃ | H | CH₃ | 2-CH₃ | H | 1 |
| 609 | H | H | HOOC-MS | 3-CF₃ | H | —(CH₂)₃-(5) | — | H | 1 |
| 610 | H | H | HOOC-MS | 3-CF₃ | H | H(NH)C | H | H | 1 |
| 611 | H | H | HOOC-MS | 3-CF₃ | H | CH₃CH₂(NH)C | H | H | 1 |
| 612 | H | H | HOOC-MS | 3-CF₃ | H | Ph(NH)C | H | H | 1 |
| 613 | H | H | HOOC-MS | 3-CF₃ | H | C₄H₆N | H | H | 1 |
| 614 | H | H | HOOC-MS | 3-CF₃ | H | C₅H₈N | H | H | 1 |
| 615 | H | H | HOOC-MS | 3-CF₃ | H | C₆H₁₀N | H | H | 1 |
| 616 | H | H | HOOC-MS | 3-CF₃ | H | C₄H₆NS | H | H | 1 |
| 617 | H | H | HOOC-MS | 3-H₂NCO | H | CH₃ | H | H | 1 |
| 618 | H | H | HOOC-MS | 3-H₂NCO | H | CH₃CH₂ | H | H | 1 |
| 619 | H | H | HOOC-MS | 3-H₂NCO | H | CH₃(CH₃)CH | H | H | 1 |
| 620 | H | H | HOOC-MS | 3-H₂NCO | H | CH₃(CH₂)₂CH₂ | H | H | 1 |
| 621 | H | H | HOOC-MS | 3-H₂NCO | H | PhCH₂ | H | H | 1 |
| 622 | H | H | HOOC-MS | 3-H₂NCO | H | Ph(CH₂)₂ | H | H | 1 |
| 623 | H | H | HOOC-MS | 3-H₂NCO | H | Ph | H | H | 1 |
| 624 | H | H | HOOC-MS | 3-H₂NCO | H | CH₃OCOCH₂ | H | H | 1 |
| 625 | H | H | HOOC-MS | 3-H₂NCO | H | CH₃CO | H | H | 1 |
| 626 | H | H | HOOC-MS | 3-H₂NCO | H | H₂NCO | H | H | 1 |
| 627 | H | H | HOOC-MS | 3-H₂NCO | H | CH₃SO₂ | H | H | 1 |
| 628 | H | H | HOOC-MS | 3-H₂NCO | H | 2-Pyr | H | H | 1 |
| 629 | H | H | HOOC-MS | 3-H₂NCO | H | 3-Pyr | H | H | 1 |
| 630 | H | H | HOOC-MS | 3-H₂NCO | H | 4-Pyr | H | H | 1 |
| 631 | H | H | HOOC-MS | 3-H₂NCO | H | 2-Pyrm | H | H | 1 |
| 632 | H | H | HOOC-MS | 3-H₂NCO | H | Pyr-3-CH₂ | H | H | 1 |
| 633 | H | H | HOOC-MS | 3-H₂NCO | H | Pyr-4-CH₂ | H | H | 1 |
| 634 | H | H | HOOC-MS | 3-H₂NCO | H | Pyr-2-(CH₂)₂ | H | H | 1 |
| 635 | H | H | HOOC-MS | 3-H₂NCO | H | cPn | H | H | 1 |
| 636 | H | H | HOOC-MS | 3-H₂NCO | H | CH₃ | 2-CH₃ | H | 1 |
| 637 | H | H | HOOC-MS | 3-H₂NCO | H | —(CH₂)₃-(5) | — | H | 1 |
| 638 | H | H | HOOC-MS | 3-H₂NCO | H | H(NH)C | H | H | 1 |
| 639 | H | H | HOOC-MS | 3-H₂NCO | H | CH₃CH₂(NH)C | H | H | 1 |
| 640 | H | H | HOOC-MS | 3-H₂NCO | H | Ph(NH)C | H | H | 1 |
| 641 | H | H | HOOC-MS | 3-H₂NCO | H | C₄H₆N | H | H | 1 |
| 642 | H | H | HOOC-MS | 3-H₂NCO | H | C₅H₈N | H | H | 1 |
| 643 | H | H | HOOC-MS | 3-H₂NCO | H | C₆H₁₀N | H | H | 1 |
| 644 | H | H | HOOC-MS | 3-H₂NCO | H | C₄H₆NS | H | H | 1 |
| 645 | H | H | HOOC-MS | 3-F | H | CH₃ | H | H | 1 |
| 646 | H | H | HOOC-MS | 3-F | H | CH₃CH₂ | H | H | 1 |
| 647 | H | H | HOOC-MS | 3-F | H | CH₃(CH₃)CH | H | H | 1 |
| 648 | H | H | HOOC-MS | 3-F | H | CH₃(CH₂)₂CH₂ | H | H | 1 |
| 649 | H | H | HOOC-MS | 3-F | H | PhCH₂ | H | H | 1 |
| 650 | H | H | HOOC-MS | 3-F | H | Ph(CH₂)₂ | H | H | 1 |
| 651 | H | H | HOOC-MS | 3-F | H | Ph | H | H | 1 |
| 652 | H | H | HOOC-MS | 3-F | H | CH₃OCOCH₂ | H | H | 1 |
| 653 | H | H | HOOC-MS | 3-F | H | CH₃CO | H | H | 1 |
| 654 | H | H | HOOC-MS | 3-F | H | H₂NCO | H | H | 1 |
| 655 | H | H | HOOC-MS | 3-F | H | CH₃SO₂ | H | H | 1 |
| 656 | H | H | HOOC-MS | 3-F | H | 2-Pyr | H | H | 1 |
| 657 | H | H | HOOC-MS | 3-F | H | 3-Pyr | H | H | 1 |
| 658 | H | H | HOOC-MS | 3-F | H | 4-Pyr | H | H | 1 |
| 659 | H | H | HOOC-MS | 3-F | H | 2-Pyrm | H | H | 1 |
| 660 | H | H | HOOC-MS | 3-F | H | Pyr-3-CH₂ | H | H | 1 |
| 661 | H | H | HOOC-MS | 3-F | H | Pyr-4-CH₂ | H | H | 1 |
| 662 | H | H | HOOC-MS | 3-F | H | Pyr-2-(CH₂)₂ | H | H | 1 |
| 663 | H | H | HOOC-MS | 3-F | H | cPn | H | H | 1 |

TABLE 1-continued (1)

$$\text{structure with } R^1, R^2, R^3, R^4, R^5, R^6, R^7, R^8, n$$

| No. | R$^1$ | R$^2$ | R$^3$ | R$^4$ | R$^5$ | R$^6$ | R$^7$ | R$^8$ | n |
|---|---|---|---|---|---|---|---|---|---|
| 664 | H | H | HOOC-MS | 3-F | H | CH$_3$ | 2-CH$_3$ | H | 1 |
| 665 | H | H | HOOC-MS | 3-F | H | —(CH$_2$)$_3$-(5) | — | H | 1 |
| 666 | H | H | HOOC-MS | 3-F | H | H(NH)C | H | H | 1 |
| 667 | H | H | HOOC-MS | 3-F | H | CH$_3$CH$_2$(NH)C | H | H | 1 |
| 668 | H | H | HOOC-MS | 3-F | H | Ph(NH)C | H | H | 1 |
| 669 | H | H | HOOC-MS | 3-F | H | C$_4$H$_6$N | H | H | 1 |
| 670 | H | H | HOOC-MS | 3-F | H | C$_5$H$_8$N | H | H | 1 |
| 671 | H | H | HOOC-MS | 3-F | H | C$_6$H$_{10}$N | H | H | 1 |
| 672 | H | H | HOOC-MS | 3-F | H | C$_4$H$_6$NS | H | H | 1 |
| 673 | H | H | HOOC-MS | 3-Cl | H | CH$_3$ | H | H | 0 |
| 674 | H | H | HOOC-MS | 3-Cl | H | CH$_3$CH$_2$ | H | H | 0 |
| 675 | H | H | HOOC-MS | 3-Cl | H | CH$_3$(CH$_3$)CH | H | H | 0 |
| 676 | H | H | HOOC-MS | 3-Cl | H | CH$_3$(CH$_2$)$_2$CH$_2$ | H | H | 0 |
| 677 | H | H | HOOC-MS | 3-Cl | H | PhCH$_2$ | H | H | 0 |
| 678 | H | H | HOOC-MS | 3-Cl | H | Ph(CH$_2$)$_2$ | H | H | 0 |
| 679 | H | H | HOOC-MS | 3-Cl | H | Ph | H | H | 0 |
| 680 | H | H | HOOC-MS | 3-Cl | H | CH$_3$OCOCH$_2$ | H | H | 0 |
| 681 | H | H | HOOC-MS | 3-Cl | H | CH$_3$CO | H | H | 0 |
| 682 | H | H | HOOC-MS | 3-Cl | H | H$_2$NCO | H | H | 0 |
| 683 | H | H | HOOC-MS | 3-Cl | H | CH$_3$SO$_2$ | H | H | 0 |
| 684 | H | H | HOOC-MS | 3-Cl | H | 2-Pyr | H | H | 0 |
| 685 | H | H | HOOC-MS | 3-Cl | H | 3-Pyr | H | H | 0 |
| 686 | H | H | HOOC-MS | 3-Cl | H | 4-Pyr | H | H | 0 |
| 687 | H | H | HOOC-MS | 3-Cl | H | 2-Pyrm | H | H | 0 |
| 688 | H | H | HOOC-MS | 3-Cl | H | Pyr-3-CH$_2$ | H | H | 0 |
| 689 | H | H | HOOC-MS | 3-Cl | H | Pyr-4-CH$_2$ | H | H | 0 |
| 690 | H | H | HOOC-MS | 3-Cl | H | Pyr-2-(CH$_2$)$_2$ | H | H | 0 |
| 691 | H | H | HOOC-MS | 3-Cl | H | cPn | H | H | 0 |
| 692 | H | H | HOOC-MS | 3-Cl | H | CH$_3$ | 2-CH$_3$ | H | 0 |
| 693 | H | H | HOOC-MS | 3-Cl | H | —(CH$_2$)$_3$-(5) | — | H | 0 |
| 694 | H | H | HOOC-MS | 3-Cl | H | H(NH)C | H | H | 0 |
| 695 | H | H | HOOC-MS | 3-Cl | H | CH$_3$CH$_2$(NH)C | H | H | 0 |
| 696 | H | H | HOOC-MS | 3-Cl | H | Ph(NH)C | H | H | 0 |
| 697 | H | H | HOOC-MS | 3-Cl | H | C$_4$H$_6$N | H | H | 0 |
| 698 | H | H | HOOC-MS | 3-Cl | H | C$_5$H$_8$N | H | H | 0 |
| 699 | H | H | HOOC-MS | 3-Cl | H | C$_6$H$_{10}$N | H | H | 0 |
| 700 | H | H | HOOC-MS | 3-Cl | H | C$_4$H$_6$NS | H | H | 0 |
| 701 | H | H | HOOC-MS | 3-CH$_3$ | H | CH$_3$ | H | H | 0 |
| 702 | H | H | HOOC-MS | 3-CH$_3$ | H | CH$_3$CH$_2$ | H | H | 0 |
| 703 | H | H | HOOC-MS | 3-CH$_3$ | H | CH$_3$(CH$_3$)CH | H | H | 0 |
| 704 | H | H | HOOC-MS | 3-CH$_3$ | H | CH$_3$(CH$_2$)$_2$CH$_2$ | H | H | 0 |
| 705 | H | H | HOOC-MS | 3-CH$_3$ | H | PhCH$_2$ | H | H | 0 |
| 706 | H | H | HOOC-MS | 3-CH$_3$ | H | Ph(CH$_2$)$_2$ | H | H | 0 |
| 707 | H | H | HOOC-MS | 3-CH$_3$ | H | Ph | H | H | 0 |
| 708 | H | H | HOOC-MS | 3-CH$_3$ | H | CH$_3$OCOCH$_2$ | H | H | 0 |
| 709 | H | H | HOOC-MS | 3-CH$_3$ | H | CH$_3$CO | H | H | 0 |
| 710 | H | H | HOOC-MS | 3-CH$_3$ | H | H$_2$NCO | H | H | 0 |
| 711 | H | H | HOOC-MS | 3-CH$_3$ | H | CH$_3$SO$_2$ | H | H | 0 |
| 712 | H | H | HOOC-MS | 3-CH$_3$ | H | 2-Pyr | H | H | 0 |
| 713 | H | H | HOOC-MS | 3-CH$_3$ | H | 3-Pyr | H | H | 0 |
| 714 | H | H | HOOC-MS | 3-CH$_3$ | H | 4-Pyr | H | H | 0 |
| 715 | H | H | HOOC-MS | 3-CH$_3$ | H | 2-Pyrm | H | H | 0 |
| 716 | H | H | HOOC-MS | 3-CH$_3$ | H | Pyr-3-CH$_2$ | H | H | 0 |
| 717 | H | H | HOOC-MS | 3-CH$_3$ | H | Pyr-4-CH$_2$ | H | H | 0 |
| 718 | H | H | HOOC-MS | 3-CH$_3$ | H | Pyr-2-(CH$_2$)$_2$ | H | H | 0 |
| 719 | H | H | HOOC-MS | 3-CH$_3$ | H | cPn | H | H | 0 |
| 720 | H | H | HOOC-MS | 3-CH$_3$ | H | CH$_3$ | 2-CH$_3$ | H | 0 |
| 721 | H | H | HOOC-MS | 3-CH$_3$ | H | —(CH$_2$)$_3$-(5) | — | H | 0 |
| 722 | H | H | HOOC-MS | 3-CH$_3$ | H | H(NH)C | H | H | 0 |
| 723 | H | H | HOOC-MS | 3-CH$_3$ | H | CH$_3$CH$_2$(NH)C | H | H | 0 |
| 724 | H | H | HOOC-MS | 3-CH$_3$ | H | Ph(NH)C | H | H | 0 |
| 725 | H | H | HOOC-MS | 3-CH$_3$ | H | C$_4$H$_6$N | H | H | 0 |
| 726 | H | H | HOOC-MS | 3-CH$_3$ | H | C$_5$H$_8$N | H | H | 0 |
| 727 | H | H | HOOC-MS | 3-CH$_3$ | H | C$_6$H$_{10}$N | H | H | 0 |
| 728 | H | H | HOOC-MS | 3-CH$_3$ | H | C$_4$H$_6$NS | H | H | 0 |

TABLE 1-continued

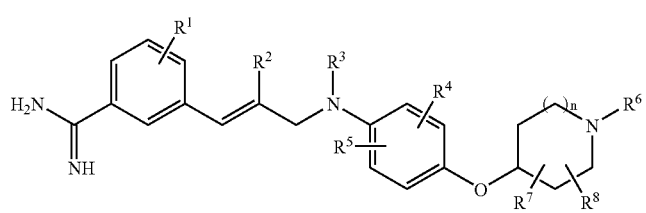

(1)

| No. | R¹ | R² | R³ | R⁴ | R⁵ | R⁶ | R⁷ | R⁸ | n |
|---|---|---|---|---|---|---|---|---|---|
| 729 | H | H | HOOC-MS | H | H | CH₃ | H | H | 0 |
| 730 | H | H | HOOC-MS | H | H | CH₃CH₂ | H | H | 0 |
| 731 | H | H | HOOC-MS | H | H | CH₃(CH₃)CH | H | H | 0 |
| 732 | H | H | HOOC-MS | H | H | CH₃(CH₂)₂CH₂ | H | H | 0 |
| 733 | H | H | HOOC-MS | H | H | PhCH₂ | H | H | 0 |
| 734 | H | H | HOOC-MS | H | H | Ph(CH₂)₂ | H | H | 0 |
| 735 | H | H | HOOC-MS | H | H | Ph | H | H | 0 |
| 736 | H | H | HOOC-MS | H | H | CH₃OCOCH₂ | H | H | 0 |
| 737 | H | H | HOOC-MS | H | H | CH₃CO | H | H | 0 |
| 738 | H | H | HOOC-MS | H | H | H₂NCO | H | H | 0 |
| 739 | H | H | HOOC-MS | H | H | CH₃SO₂ | H | H | 0 |
| 740 | H | H | HOOC-MS | H | H | 2-Pyr | H | H | 0 |
| 741 | H | H | HOOC-MS | H | H | 3-Pyr | H | H | 0 |
| 742 | H | H | HOOC-MS | H | H | 4-Pyr | H | H | 0 |
| 743 | H | H | HOOC-MS | H | H | 2-Pyrm | H | H | 0 |
| 744 | H | H | HOOC-MS | H | H | Pyr-3-CH₂ | H | H | 0 |
| 745 | H | H | HOOC-MS | H | H | Pyr-4-CH₂ | H | H | 0 |
| 746 | H | H | HOOC-MS | H | H | Pyr-2-(CH₂)₂ | H | H | 0 |
| 747 | H | H | HOOC-MS | H | H | cPn | H | H | 0 |
| 748 | H | H | HOOC-MS | H | H | CH₃ | 2-CH₃ | H | 0 |
| 759 | H | H | HOOC-MS | H | H | —(CH₂)₃-(5) | — | H | 0 |
| 750 | H | H | HOOC-MS | H | H | H(NH)C | H | H | 0 |
| 751 | H | H | HOOC-MS | H | H | CH₃CH₂(NH)C | H | H | 0 |
| 752 | H | H | HOOC-MS | H | H | Ph(NH)C | H | H | 0 |
| 753 | H | H | HOOC-MS | H | H | C₄H₆N | H | H | 0 |
| 754 | H | H | HOOC-MS | H | H | C₅H₈N | H | H | 0 |
| 755 | H | H | HOOC-MS | H | H | C₆H₁₀N | H | H | 0 |
| 756 | H | H | HOOC-MS | H | H | C₄H₆NS | H | H | 0 |
| 757 | H | H | HOOC-MS | 3-CF₃ | H | CH₃ | H | H | 0 |
| 758 | H | H | HOOC-MS | 3-CF₃ | H | CH₃CH₂ | H | H | 0 |
| 759 | H | H | HOOC-MS | 3-CF₃ | H | CH₃(CH₃)CH | H | H | 0 |
| 760 | H | H | HOOC-MS | 3-CF₃ | H | CH₃(CH₂)₂CH₂ | H | H | 0 |
| 761 | H | H | HOOC-MS | 3-CF₃ | H | PhCH₂ | H | H | 0 |
| 762 | H | H | HOOC-MS | 3-CF₃ | H | Ph(CH₂)₂ | H | H | 0 |
| 763 | H | H | HOOC-MS | 3-CF₃ | H | Ph | H | H | 0 |
| 764 | H | H | HOOC-MS | 3-CF₃ | H | CH₃OCOCH₂ | H | H | 0 |
| 765 | H | H | HOOC-MS | 3-CF₃ | H | CH₃CO | H | H | 0 |
| 766 | H | H | HOOC-MS | 3-CF₃ | H | H₂NCO | H | H | 0 |
| 767 | H | H | HOOC-MS | 3-CF₃ | H | CH₃SO₂ | H | H | 0 |
| 768 | H | H | HOOC-MS | 3-CF₃ | H | 2-Pyr | H | H | 0 |
| 769 | H | H | HOOC-MS | 3-CF₃ | H | 3-Pyr | H | H | 0 |
| 770 | H | H | HOOC-MS | 3-CF₃ | H | 4-Pyr | H | H | 0 |
| 771 | H | H | HOOC-MS | 3-CF₃ | H | 2-Pyrm | H | H | 0 |
| 772 | H | H | HOOC-MS | 3-CF₃ | H | Pyr-3-CH₂ | H | H | 0 |
| 773 | H | H | HOOC-MS | 3-CF₃ | H | Pyr-4-CH₂ | H | H | 0 |
| 774 | H | H | HOOC-MS | 3-CF₃ | H | Pyr-2-(CH₂)₂ | H | H | 0 |
| 775 | H | H | HOOC-MS | 3-CF₃ | H | cPn | H | H | 0 |
| 716 | H | H | HOOC-MS | 3-CF₃ | H | CH₃ | 2-CH₃ | H | 0 |
| 777 | H | H | HOOC-MS | 3-CF₃ | H | —(CH₂)₃-(5) | — | H | 0 |
| 778 | H | H | HOOC-MS | 3-CF₃ | H | H(NH)C | H | H | 0 |
| 779 | H | H | HOOC-MS | 3-CF₃ | H | CH₃CH₂(NH)C | H | H | 0 |
| 780 | H | H | HOOC-MS | 3-CF₃ | H | Ph(NH)C | H | H | 0 |
| 781 | H | H | HOOC-MS | 3-CF₃ | H | C₄H₆N | H | H | 0 |
| 782 | H | H | HOOC-MS | 3-CF₃ | H | C₅H₈N | H | H | 0 |
| 783 | H | H | HOOC-MS | 3-CF₃ | H | C₆H₁₀N | H | H | 0 |
| 784 | H | H | HOOC-MS | 3-CF₃ | H | C₄H₆NS | H | H | 0 |
| 785 | H | H | HOOC-MS | 3-H₂NCO | H | CH₃ | H | H | 0 |
| 786 | H | H | HOOC-MS | 3-H₂NCO | H | CH₃CH₂ | H | H | 0 |
| 787 | H | H | HOOC-MS | 3-H₂NCO | H | CH₃(CH₃)CH | H | H | 0 |
| 788 | H | H | HOOC-MS | 3-H₂NCO | H | CH₃(CH₂)₂CH₂ | H | H | 0 |
| 789 | H | H | HOOC-MS | 3-H₂NCO | H | PhCH₂ | H | H | 0 |
| 790 | H | H | HOOC-MS | 3-H₂NCO | H | Ph(CH₂)₂ | H | H | 0 |
| 791 | H | H | HOOC-MS | 3-H₂NCO | H | Ph | H | H | 0 |
| 792 | H | H | HOOC-MS | 3-H₂NCO | H | CH₃OCOCH₂ | H | H | 0 |
| 793 | H | H | HOOC-MS | 3-H₂NCO | H | CH₃CO | H | H | 0 |

TABLE 1-continued (1)

$$\text{structure shown with R}^1, R^2, R^3, R^4, R^5, R^6, R^7, R^8, n$$

| No. | R¹ | R² | R³ | R⁴ | R⁵ | R⁶ | R⁷ | R⁸ | n |
|-----|----|----|-----|------|----|------|------|----|---|
| 794 | H | H | HOOC-MS | 3-H₂NCO | H | H₂NCO | H | H | 0 |
| 795 | H | H | HOOC-MS | 3-H₂NCO | H | CH₃SO₂ | H | H | 0 |
| 796 | H | H | HOOC-MS | 3-H₂NCO | H | 2-Pyr | H | H | 0 |
| 797 | H | H | HOOC-MS | 3-H₂NCO | H | 3-Pyr | H | H | 0 |
| 798 | H | H | HOOC-MS | 3-H₂NCO | H | 4-Pyr | H | H | 0 |
| 799 | H | H | HOOC-MS | 3-H₂NCO | H | 2-Pyrm | H | H | 0 |
| 800 | H | H | HOOC-MS | 3-H₂NCO | H | Pyr-3-CH₂ | H | H | 0 |
| 801 | H | H | HOOC-MS | 3-H₂NCO | H | Pyr-4-CH₂ | H | H | 0 |
| 802 | H | H | HOOC-MS | 3-H₂NCO | H | Pyr-2-(CH₂)₂ | H | H | 0 |
| 803 | H | H | HOOC-MS | 3-H₂NCO | H | cPn | H | H | 0 |
| 804 | H | H | HOOC-MS | 3-H₂NCO | H | CH₃ | 2-CH₃ | H | 0 |
| 805 | H | H | HOOC-MS | 3-H₂NCO | H | —(CH₂)₃-(5) | — | H | 0 |
| 806 | H | H | HOOC-MS | 3-H₂NCO | H | H(NH)C | H | H | 0 |
| 807 | H | H | HOOC-MS | 3-H₂NCO | H | CH₃CH₂(NH)C | H | H | 0 |
| 808 | H | H | HOOC-MS | 3-H₂NCO | H | Ph(NH)C | H | H | 0 |
| 809 | H | H | HOOC-MS | 3-H₂NCO | H | C₄H₆N | H | H | 0 |
| 810 | H | H | HOOC-MS | 3-H₂NCO | H | C₅H₈N | H | H | 0 |
| 811 | H | H | HOOC-MS | 3-H₂NCO | H | C₆H₁₀N | H | H | 0 |
| 812 | H | H | HOOC-MS | 3-H₂NCO | H | C₄H₆NS | H | H | 0 |
| 813 | H | H | HOOC-MS | 3-F | H | CH₃ | H | H | 0 |
| 814 | H | H | HOOC-MS | 3-F | H | CH₃CH₂ | H | H | 0 |
| 815 | H | H | HOOC-MS | 3-F | H | CH₃(CH₃)CH | H | H | 0 |
| 816 | H | H | HOOC-MS | 3-F | H | CH₃(CH₂)₂CH₂ | H | H | 0 |
| 817 | H | H | HOOC-MS | 3-F | H | PhCH₂ | H | H | 0 |
| 818 | H | H | HOOC-MS | 3-F | H | Ph(CH₂)₂ | H | H | 0 |
| 819 | H | H | HOOC-MS | 3-F | H | Ph | H | H | 0 |
| 820 | H | H | HOOC-MS | 3-F | H | CH₃OCOCH₂ | H | H | 0 |
| 821 | H | H | HOOC-MS | 3-F | H | CH₃CO | H | H | 0 |
| 822 | H | H | HOOC-MS | 3-F | H | H₂NCO | H | H | 0 |
| 823 | H | H | HOOC-MS | 3-F | H | CH₃SO₂ | H | H | 0 |
| 824 | H | H | HOOC-MS | 3-F | H | 2-Pyr | H | H | 0 |
| 825 | H | H | HOOC-MS | 3-F | H | 3-Pyr | H | H | 0 |
| 826 | H | H | HOOC-MS | 3-F | H | 4-Pyr | H | H | 0 |
| 827 | H | H | HOOC-MS | 3-F | H | 2-Pyrm | H | H | 0 |
| 828 | H | H | HOOC-MS | 3-F | H | Pyr-3-CH₂ | H | H | 0 |
| 829 | H | H | HOOC-MS | 3-F | H | Pyr-4-CH₂ | H | H | 0 |
| 830 | H | H | HOOC-MS | 3-F | H | Pyr-2-(CH₂)₂ | H | H | 0 |
| 831 | H | H | HOOC-MS | 3-F | H | cPn | H | H | 0 |
| 832 | H | H | HOOC-MS | 3-F | H | CH₃ | 2-CH₃ | H | 0 |
| 833 | H | H | HOOC-MS | 3-F | H | —(CH₂)₃-(5) | — | H | 0 |
| 834 | H | H | HOOC-MS | 3-F | H | H(NH)C | H | H | 0 |
| 835 | H | H | HOOC-MS | 3-F | H | CH₃CH₂(NH)C | H | H | 0 |
| 836 | H | H | HOOC-MS | 3-F | H | Ph(NH)C | H | H | 0 |
| 837 | H | H | HOOC-MS | 3-F | H | C₄H₆N | H | H | 0 |
| 838 | H | H | HOOC-MS | 3-F | H | C₅H₈N | H | H | 0 |
| 839 | H | H | HOOC-MS | 3-F | H | C₆H₁₀N | H | H | 0 |
| 840 | H | H | HOOC-MS | 3-F | H | C₄H₆NS | H | H | 0 |
| 841 | H | H | HOOC-MS | 3-Cl | H | CH₃ | H | H | 2 |
| 842 | H | H | HOOC-MS | 3-Cl | H | CH₃CH₂ | H | H | 2 |
| 843 | H | H | HOOC-MS | 3-Cl | H | CH₃(CH₃)CH | H | H | 2 |
| 844 | H | H | HOOC-MS | 3-Cl | H | CH₃(CH₂)₂CH₂ | H | H | 2 |
| 845 | H | H | HOOC-MS | 3-Cl | H | PhCH₂ | H | H | 2 |
| 846 | H | H | HOOC-MS | 3-Cl | H | Ph(CH₂)₂ | H | H | 2 |
| 847 | H | H | HOOC-MS | 3-Cl | H | Ph | H | H | 2 |
| 848 | H | H | HOOC-MS | 3-Cl | H | CH₃OCOCH₂ | H | H | 2 |
| 849 | H | H | HOOC-MS | 3-Cl | H | CH₃CO | H | H | 2 |
| 850 | H | H | HOOC-MS | 3-Cl | H | H₂NCO | H | H | 2 |
| 851 | H | H | HOOC-MS | 3-Cl | H | CH₃SO₂ | H | H | 2 |
| 852 | H | H | HOOC-MS | 3-Cl | H | 2-Pyr | H | H | 2 |
| 853 | H | H | HOOC-MS | 3-Cl | H | 3-Pyr | H | H | 2 |
| 854 | H | H | HOOC-MS | 3-Cl | H | 4-Pyr | H | H | 2 |
| 855 | H | H | HOOC-MS | 3-Cl | H | 2-Pyrm | H | H | 2 |
| 856 | H | H | HOOC-MS | 3-Cl | H | Pyr-3-CH₂ | H | H | 2 |
| 857 | H | H | HOOC-MS | 3-Cl | H | Pyr-4-CH₂ | H | H | 2 |
| 858 | H | H | HOOC-MS | 3-Cl | H | Pyr-2-(CH₂)₂ | H | H | 2 |

TABLE 1-continued

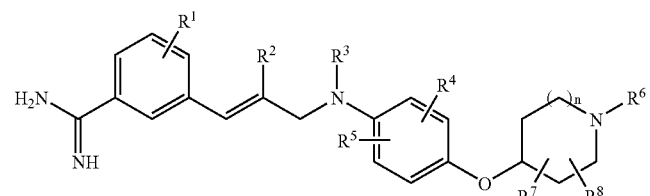

| No. | R$^1$ | R$^2$ | R$^3$ | R$^4$ | R$^5$ | R$^6$ | R$^7$ | R$^8$ | n |
|---|---|---|---|---|---|---|---|---|---|
| 859 | H | H | HOOC-MS | 3-Cl | H | cPn | H | H | 2 |
| 860 | H | H | HOOC-MS | 3-Cl | H | CH$_3$ | 2-CH$_3$ | H | 2 |
| 861 | H | H | HOOC-MS | 3-Cl | H | —(CH$_2$)$_3$-(5) | — | H | 2 |
| 862 | H | H | HOOC-MS | 3-Cl | H | H(NH)C | H | H | 2 |
| 863 | H | H | HOOC-MS | 3-Cl | H | CH$_3$CH$_2$(NH)C | H | H | 2 |
| 864 | H | H | HOOC-MS | 3-Cl | H | Ph(NH)C | H | H | 2 |
| 865 | H | H | HOOC-MS | 3-Cl | H | C$_4$H$_6$N | H | H | 2 |
| 866 | H | H | HOOC-MS | 3-Cl | H | C$_5$H$_8$N | H | H | 2 |
| 867 | H | H | HOOC-MS | 3-Cl | H | C$_6$H$_{10}$N | H | H | 2 |
| 868 | H | H | HOOC-MS | 3-Cl | H | C$_4$H$_6$NS | H | H | 2 |
| 869 | H | H | HOOC-MS | 3-CH$_3$ | H | CH$_3$ | H | H | 2 |
| 870 | H | H | HOOC-MS | 3-CH$_3$ | H | CH$_3$CH$_2$ | H | H | 2 |
| 871 | H | H | HOOC-MS | 3-CH$_3$ | H | CH$_3$(CH$_3$)CH | H | H | 2 |
| 872 | H | H | HOOC-MS | 3-CH$_3$ | H | CH$_3$(CH$_2$)$_2$CH$_2$ | H | H | 2 |
| 873 | H | H | HOOC-MS | 3-CH$_3$ | H | PhCH$_2$ | H | H | 2 |
| 874 | H | H | HOOC-MS | 3-CH$_3$ | H | Ph(CH$_2$)$_2$ | H | H | 2 |
| 875 | H | H | HOOC-MS | 3-CH$_3$ | H | Ph | H | H | 2 |
| 876 | H | H | HOOC-MS | 3-CH$_3$ | H | CH$_3$OCOCH$_2$ | H | H | 2 |
| 877 | H | H | HOOC-MS | 3-CH$_3$ | H | CH$_3$CO | H | H | 2 |
| 878 | H | H | HOOC-MS | 3-CH$_3$ | H | H$_2$NCO | H | H | 2 |
| 879 | H | H | HOOC-MS | 3-CH$_3$ | H | CH$_3$SO$_2$ | H | H | 2 |
| 880 | H | H | HOOC-MS | 3-CH$_3$ | H | 2-Pyr | H | H | 2 |
| 881 | H | H | HOOC-MS | 3-CH$_3$ | H | 3-Pyr | H | H | 2 |
| 882 | H | H | HOOC-MS | 3-CH$_3$ | H | 4-Pyr | H | H | 2 |
| 883 | H | H | HOOC-MS | 3-CH$_3$ | H | 2-Pyrm | H | H | 2 |
| 884 | H | H | HOOC-MS | 3-CH$_3$ | H | Pyr-3-CH$_2$ | H | H | 2 |
| 885 | H | H | HOOC-MS | 3-CH$_3$ | H | Pyr-4-CH$_2$ | H | H | 2 |
| 886 | H | H | HOOC-MS | 3-CH$_3$ | H | Pyr-2-(CH$_2$)$_2$ | H | H | 2 |
| 887 | H | H | HOOC-MS | 3-CH$_3$ | H | cPn | H | H | 2 |
| 888 | H | H | HOOC-MS | 3-CH$_3$ | H | CH$_3$ | 2-CH$_3$ | H | 2 |
| 889 | H | H | HOOC-MS | 3-CH$_3$ | H | —(CH$_2$)$_3$-(5) | — | H | 2 |
| 890 | H | H | HOOC-MS | 3-CH$_3$ | H | H(NH)C | H | H | 2 |
| 891 | H | H | HOOC-MS | 3-CH$_3$ | H | CH$_3$CH$_2$(NH)C | H | H | 2 |
| 892 | H | H | HOOC-MS | 3-CH$_3$ | H | Ph(NH)C | H | H | 2 |
| 893 | H | H | HOOC-MS | 3-CH$_3$ | H | C$_4$H$_6$N | H | H | 2 |
| 894 | H | H | HOOC-MS | 3-CH$_3$ | H | C$_5$H$_8$N | H | H | 2 |
| 895 | H | H | HOOC-MS | 3-CH$_3$ | H | C$_6$H$_{10}$N | H | H | 2 |
| 896 | H | H | HOOC-MS | 3-CH$_3$ | H | C$_4$H$_6$NS | H | H | 2 |
| 897 | H | H | HOOC-MS | H | H | CH$_3$ | H | H | 2 |
| 898 | H | H | HOOC-MS | H | H | CH$_3$CH$_2$ | H | H | 2 |
| 899 | H | H | HOOC-MS | H | H | CH$_3$(CH$_3$)CH | H | H | 2 |
| 900 | H | H | HOOC-MS | H | H | CH$_3$(CH$_2$)$_2$CH$_2$ | H | H | 2 |
| 901 | H | H | HOOC-MS | H | H | PhCH$_2$ | H | H | 2 |
| 902 | H | H | HOOC-MS | H | H | Ph(CH$_2$)$_2$ | H | H | 2 |
| 903 | H | H | HOOC-MS | H | H | Ph | H | H | 2 |
| 904 | H | H | HOOC-MS | H | H | CH$_3$OCOCH$_2$ | H | H | 2 |
| 905 | H | H | HOOC-MS | H | H | CH$_3$CO | H | H | 2 |
| 906 | H | H | HOOC-MS | H | H | H$_2$NCO | H | H | 2 |
| 907 | H | H | HOOC-MS | H | H | CH$_3$SO$_2$ | H | H | 2 |
| 908 | H | H | HOOC-MS | H | H | 2-Pyr | H | H | 2 |
| 909 | H | H | HOOC-MS | H | H | 3-Pyr | H | H | 2 |
| 910 | H | H | HOOC-MS | H | H | 4-Pyr | H | H | 2 |
| 911 | H | H | HOOC-MS | H | H | 2-Pyrm | H | H | 2 |
| 912 | H | H | HOOC-MS | H | H | Pyr-3-CH$_2$ | H | H | 2 |
| 913 | H | H | HOOC-MS | H | H | Pyr-4-CH$_2$ | H | H | 2 |
| 914 | H | H | HOOC-MS | H | H | Pyr-2-(CH$_2$)$_2$ | H | H | 2 |
| 915 | H | H | HOOC-MS | H | H | cPn | H | H | 2 |
| 916 | H | H | HOOC-MS | H | H | CH$_3$ | 2-CH$_3$ | H | 2 |
| 917 | H | H | HOOC-MS | H | H | —(CH$_2$)$_3$-(5) | — | H | 2 |
| 918 | H | H | HOOC-MS | H | H | H(NH)C | H | H | 2 |
| 919 | H | H | HOOC-MS | H | H | CH$_3$CH$_2$(NH)C | H | H | 2 |
| 920 | H | H | HOOC-MS | H | H | Ph(NH)C | H | H | 2 |
| 921 | H | H | HOOC-MS | H | H | C$_4$H$_6$N | H | H | 2 |
| 922 | H | H | HOOC-MS | H | H | C$_5$H$_8$N | H | H | 2 |
| 923 | H | H | HOOC-MS | H | H | C$_6$H$_{10}$N | H | H | 2 |

TABLE 1-continued (1)

| No. | R¹ | R² | R³ | R⁴ | R⁵ | R⁶ | R⁷ | R⁸ | n |
|---|---|---|---|---|---|---|---|---|---|
| 924 | H | H | HOOC-MS | H | H | C₄H₆NS | H | H | 2 |
| 925 | H | H | HOOC-MS | 3-CF₃ | H | CH₃ | H | H | 2 |
| 926 | H | H | HOOC-MS | 3-CF₃ | H | CH₃CH₂ | H | H | 2 |
| 927 | H | H | HOOC-MS | 3-CF₃ | H | CH₃(CH₃)CH | H | H | 2 |
| 928 | H | H | HOOC-MS | 3-CF₃ | H | CH₃(CH₂)₂CH₂ | H | H | 2 |
| 929 | H | H | HOOC-MS | 3-CF₃ | H | PhCH₂ | H | H | 2 |
| 930 | H | H | HOOC-MS | 3-CF₃ | H | Ph(CH₂)₂ | H | H | 2 |
| 931 | H | H | HOOC-MS | 3-CF₃ | H | Ph | H | H | 2 |
| 932 | H | H | HOOC-MS | 3-CF₃ | H | CH₃OCOCH₂ | H | H | 2 |
| 933 | H | H | HOOC-MS | 3-CF₃ | H | CH₃CO | H | H | 2 |
| 934 | H | H | HOOC-MS | 3-CF₃ | H | H₂NCO | H | H | 2 |
| 935 | H | H | HOOC-MS | 3-CF₃ | H | CH₃SO₂ | H | H | 2 |
| 936 | H | H | HOOC-MS | 3-CF₃ | H | 2-Pyr | H | H | 2 |
| 937 | H | H | HOOC-MS | 3-CF₃ | H | 3-Pyr | H | H | 2 |
| 938 | H | H | HOOC-MS | 3-CF₃ | H | 4-Pyr | H | H | 2 |
| 939 | H | H | HOOC-MS | 3-CF₃ | H | 2-Pyrm | H | H | 2 |
| 940 | H | H | HOOC-MS | 3-CF₃ | H | Pyr-3-CH₂ | H | H | 2 |
| 941 | H | H | HOOC-MS | 3-CF₃ | H | Pyr-4-CH₂ | H | H | 2 |
| 942 | H | H | HOOC-MS | 3-CF₃ | H | Pyr-2-(CH₂)₂ | H | H | 2 |
| 943 | H | H | HOOC-MS | 3-CF₃ | H | cPn | H | H | 2 |
| 944 | H | H | HOOC-MS | 3-CF₃ | H | CH₃ | 2-CH₃ | H | 2 |
| 945 | H | H | HOOC-MS | 3-CF₃ | H | —(CH₂)₃-(5) | — | H | 2 |
| 946 | H | H | HOOC-MS | 3-CF₃ | H | H(NH)C | H | H | 2 |
| 947 | H | H | HOOC-MS | 3-CF₃ | H | CH₃CH₂(NH)C | H | H | 2 |
| 948 | H | H | HOOC-MS | 3-CF₃ | H | Ph(NH)C | H | H | 2 |
| 949 | H | H | HOOC-MS | 3-CF₃ | H | C₄H₆N | H | H | 2 |
| 950 | H | H | HOOC-MS | 3-CF₃ | H | C₅H₈N | H | H | 2 |
| 951 | H | H | HOOC-MS | 3-CF₃ | H | C₆H₁₀N | H | H | 2 |
| 952 | H | H | HOOC-MS | 3-CF₃ | H | C₄H₆NS | H | H | 2 |
| 953 | H | H | HOOC-MS | 3-H₂NCO | H | CH₃ | H | H | 2 |
| 954 | H | H | HOOC-MS | 3-H₂NCO | H | CH₃CH₂ | H | H | 2 |
| 955 | H | H | HOOC-MS | 3-H₂NCO | H | CH₃(CH₃)CH | H | H | 2 |
| 956 | H | H | HOOC-MS | 3-H₂NCO | H | CH₃(CH₂)₂CH₂ | H | H | 2 |
| 957 | H | H | HOOC-MS | 3-H₂NCO | H | PhCH₂ | H | H | 2 |
| 958 | H | H | HOOC-MS | 3-H₂NCO | H | Ph(CH₂)₂ | H | H | 2 |
| 959 | H | H | HOOC-MS | 3-H₂NCO | H | Ph | H | H | 2 |
| 960 | H | H | HOOC-MS | 3-H₂NCO | H | CH₃OCOCH₂ | H | H | 2 |
| 961 | H | H | HOOC-MS | 3-H₂NCO | H | CH₃CO | H | H | 2 |
| 962 | H | H | HOOC-MS | 3-H₂NCO | H | H₂NCO | H | H | 2 |
| 963 | H | H | HOOC-MS | 3-H₂NCO | H | CH₃SO₂ | H | H | 2 |
| 964 | H | H | HOOC-MS | 3-H₂NCO | H | 2-Pyr | H | H | 2 |
| 965 | H | H | HOOC-MS | 3-H₂NCO | H | 3-Pyr | H | H | 2 |
| 966 | H | H | HOOC-MS | 3-H₂NCO | H | 4-Pyr | H | H | 2 |
| 967 | H | H | HOOC-MS | 3-H₂NCO | H | 2-Pyrm | H | H | 2 |
| 968 | H | H | HOOC-MS | 3-H₂NCO | H | Pyr-3-CH₂ | H | H | 2 |
| 969 | H | H | HOOC-MS | 3-H₂NCO | H | Pyr-4-CH₂ | H | H | 2 |
| 970 | H | H | HOOC-MS | 3-H₂NCO | H | Pyr-2-(CH₂)₂ | H | H | 2 |
| 971 | H | H | HOOC-MS | 3-H₂NCO | H | cPn | H | H | 2 |
| 972 | H | H | HOOC-MS | 3-H₂NCO | H | CH₃ | 2-CH₃ | H | 2 |
| 973 | H | H | HOOC-MS | 3-H₂NCO | H | —(CH₂)₃-(5) | — | H | 2 |
| 974 | H | H | HOOC-MS | 3-H₂NCO | H | H(NH)C | H | H | 2 |
| 975 | H | H | HOOC-MS | 3-H₂NCO | H | CH₃CH₂(NH)C | H | H | 2 |
| 976 | H | H | HOOC-MS | 3-H₂NCO | H | Ph(NH)C | H | H | 2 |
| 977 | H | H | HOOC-MS | 3-H₂NCO | H | C₄H₆N | H | H | 2 |
| 978 | H | H | HOOC-MS | 3-H₂NCO | H | C₅H₈N | H | H | 2 |
| 979 | H | H | HOOC-MS | 3-H₂NCO | H | C₆H₁₀N | H | H | 2 |
| 980 | H | H | HOOC-MS | 3-H₂NCO | H | C₄H₆NS | H | H | 2 |
| 981 | H | H | HOOC-MS | 3-F | H | CH₃ | H | H | 2 |
| 982 | H | H | HOOC-MS | 3-F | H | CH₃CH₂ | H | H | 2 |
| 983 | H | H | HOOC-MS | 3-F | H | CH₃(CH₃)CH | H | H | 2 |
| 984 | H | H | HOOC-MS | 3-F | H | CH₃(CH₂)₂CH₂ | H | H | 2 |
| 985 | H | H | HOOC-MS | 3-F | H | PhCH₂ | H | H | 2 |
| 986 | H | H | HOOC-MS | 3-F | H | Ph(CH₂)₂ | H | H | 2 |
| 987 | H | H | HOOC-MS | 3-F | H | Ph | H | H | 2 |
| 988 | H | H | HOOC-MS | 3-F | H | CH₃OCOCH₂ | H | H | 2 |

TABLE 1-continued (1)

| No. | R¹ | R² | R³ | R⁴ | R⁵ | R⁶ | R⁷ | R⁸ | n |
|---|---|---|---|---|---|---|---|---|---|
| 989 | H | H | HOOC-MS | 3-F | H | CH$_3$CO | H | H | 2 |
| 990 | H | H | HOOC-MS | 3-F | H | H$_2$NCO | H | H | 2 |
| 991 | H | H | HOOC-MS | 3-F | H | CH$_3$SO$_2$ | H | H | 2 |
| 992 | H | H | HOOC-MS | 3-F | H | 2-Pyr | H | H | 2 |
| 993 | H | H | HOOC-MS | 3-F | H | 3-Pyr | H | H | 2 |
| 994 | H | H | HOOC-MS | 3-F | H | 4-Pyr | H | H | 2 |
| 995 | H | H | HOOC-MS | 3-F | H | 2-Pyrm | H | H | 2 |
| 996 | H | H | HOOC-MS | 3-F | H | Pyr-3-CH$_2$ | H | H | 2 |
| 997 | H | H | HOOC-MS | 3-F | H | Pyr-4-CH$_2$ | H | H | 2 |
| 998 | H | H | HOOC-MS | 3-F | H | Pyr-2-(CH$_2$)$_2$ | H | H | 2 |
| 999 | H | H | HOOC-MS | 3-F | H | cPn | H | H | 2 |
| 1000 | H | H | HOOC-MS | 3-F | H | CH$_3$ | 2-CH$_3$ | H | 2 |
| 1001 | H | H | HOOC-MS | 3-F | H | —(CH$_2$)$_3$-(5) | — | H | 2 |
| 1002 | H | H | HOOC-MS | 3-F | H | H(NH)C | H | H | 2 |
| 1003 | H | H | HOOC-MS | 3-F | H | CH$_3$CH$_2$(NH)C | H | H | 2 |
| 1004 | H | H | HOOC-MS | 3-F | H | Ph(NH)C | H | H | 2 |
| 1005 | H | H | HOOC-MS | 3-F | H | C$_4$H$_6$N | H | H | 2 |
| 1006 | H | H | HOOC-MS | 3-F | H | C$_5$H$_8$N | H | H | 2 |
| 1007 | H | H | HOOC-MS | 3-F | H | C$_6$H$_{10}$N | H | H | 2 |
| 1008 | H | H | HOOC-MS | 3-F | H | C$_4$H$_6$NS | H | H | 2 |
| 1009 | H | H | EtOOC-MS | 3-Cl | H | C$_3$H$_4$NO | H | H | 1 |
| 1010 | H | H | EtOOC-MS | 3-CH$_3$ | H | C$_3$H$_4$NO | H | H | 1 |
| 1011 | H | H | EtOOC-MS | 3-H | H | C$_3$H$_4$NO | H | H | 1 |
| 1012 | H | H | EtOOC-MS | 3-CF$_3$ | H | C$_3$H$_4$NO | H | H | 1 |
| 1013 | H | H | EtOOC-MS | 3-H$_2$NCO | H | C$_3$H$_4$NO | H | H | 1 |
| 1014 | H | H | EtOOC-MS | 3-F | H | C$_3$H$_4$NO | H | H | 1 |
| 1015 | H | H | EtOOC-MS | 3-Cl | H | C$_3$H$_4$NO | H | H | 0 |
| 1016 | H | H | EtOOC-MS | 3-CH$_3$ | H | C$_3$H$_4$NO | H | H | 0 |
| 1017 | H | H | EtOOC-MS | 3-H | H | C$_3$H$_4$NO | H | H | 0 |
| 1018 | H | H | EtOOC-MS | 3-CF$_3$ | H | C$_3$H$_4$NO | H | H | 0 |
| 1019 | H | H | EtOOC-MS | 3-H$_2$NCO | H | C$_3$H$_4$NO | H | H | 0 |
| 1020 | H | H | EtOOC-MS | 3-F | H | C$_3$H$_4$NO | H | H | 0 |
| 1021 | H | H | EtOOC-MS | 3-Cl | H | C$_3$H$_4$NO | H | H | 2 |
| 1022 | H | H | EtOOC-MS | 3-CH$_3$ | H | C$_3$H$_4$NO | H | H | 2 |
| 1023 | H | H | EtOOC-MS | 3-H | H | C$_3$H$_4$NO | H | H | 2 |
| 1024 | H | H | EtOOC-MS | 3-CF$_3$ | H | C$_3$H$_4$NO | H | H | 2 |
| 1025 | H | H | EtOOC-MS | 3-H$_2$NCO | H | C$_3$H$_4$NO | H | H | 2 |
| 1026 | H | H | EtOOC-MS | 3-F | H | C$_3$H$_4$NO | H | H | 2 |
| 1027 | H | H | HOOC-MS | 3-Cl | H | C$_3$H$_4$NO | H | H | 1 |
| 1028 | H | H | HOOC-MS | 3-CH$_3$ | H | C$_3$H$_4$NO | H | H | 1 |
| 1029 | H | H | HOOC-MS | 3-H | H | C$_3$H$_4$NO | H | H | 1 |
| 1030 | H | H | HOOC-MS | 3-CF$_3$ | H | C$_3$H$_4$NO | H | H | 1 |
| 1031 | H | H | HOOC-MS | 3-H$_2$NCO | H | C$_3$H$_4$NO | H | H | 1 |
| 1032 | H | H | HOOC-MS | 3-F | H | C$_3$H$_4$NO | H | H | 1 |
| 1033 | H | H | HOOC-MS | 3-Cl | H | C$_3$H$_4$NO | H | H | 0 |
| 1034 | H | H | HOOC-MS | 3-CH$_3$ | H | C$_3$H$_4$NO | H | H | 0 |
| 1035 | H | H | HOOC-MS | 3-H | H | C$_3$H$_4$NO | H | H | 0 |
| 1036 | H | H | HOOC-MS | 3-CF$_3$ | H | C$_3$H$_4$NO | H | H | 0 |
| 1037 | H | H | HOOC-MS | 3-H$_2$NCO | H | C$_3$H$_4$NO | H | H | 0 |
| 1038 | H | H | HOOC-MS | 3-F | H | C$_3$H$_4$NO | H | H | 0 |
| 1039 | H | H | HOOC-MS | 3-Cl | H | C$_3$H$_4$NO | H | H | 2 |
| 1040 | H | H | HOOC-MS | 3-CH$_3$ | H | C$_3$H$_4$NO | H | H | 2 |
| 1041 | H | H | HOOC-MS | 3-H | H | C$_3$H$_4$NO | H | H | 2 |
| 1042 | H | H | HOOC-MS | 3-CF$_3$ | H | C$_3$H$_4$NO | H | H | 2 |
| 1043 | H | H | HOOC-MS | 3-H$_2$NCO | H | C$_3$H$_4$NO | H | H | 2 |
| 1044 | H | H | HOOC-MS | 3-F | H | C$_3$H$_4$NO | H | H | 2 |
| 1045 | H | H | EtOOC-MS | 3-Cl | H | C$_5$F$_4$N | H | H | 1 |
| 1046 | H | H | EtOOC-MS | 3-CH$_3$ | H | C$_5$F$_4$N | H | H | 1 |
| 1047 | H | H | EtOOC-MS | 3-H | H | C$_5$F$_4$N | H | H | 1 |
| 1048 | H | H | EtOOC-MS | 3-CF$_3$ | H | C$_5$F$_4$N | H | H | 1 |
| 1049 | H | H | EtOOC-MS | 3-H$_2$NCO | H | C$_5$F$_4$N | H | H | 1 |
| 1050 | H | H | EtOOC-MS | 3-F | H | C$_5$F$_4$N | H | H | 1 |
| 1051 | H | H | EtOOC-MS | 3-Cl | H | C$_5$F$_4$N | H | H | 0 |
| 1052 | H | H | EtOOC-MS | 3-CH$_3$ | H | C$_5$F$_4$N | H | H | 0 |
| 1053 | H | H | EtOOC-MS | 3-H | H | C$_5$F$_4$N | H | H | 0 |

TABLE 1-continued (1)

| No. | R¹ | R² | R³ | R⁴ | R⁵ | R⁶ | R⁷ | R⁸ | n |
|---|---|---|---|---|---|---|---|---|---|
| 1054 | H | H | EtOOC-MS | 3-CF₃ | H | C₅F₄N | H | H | 0 |
| 1055 | H | H | EtOOC-MS | 3-H₂NCO | H | C₅F₄N | H | H | 0 |
| 1056 | H | H | EtOOC-MS | 3-F | H | C₅F₄N | H | H | 0 |
| 1057 | H | H | EtOOC-MS | 3-Cl | H | C₅F₄N | H | H | 2 |
| 1058 | H | H | EtOOC-MS | 3-CH₃ | H | C₅F₄N | H | H | 2 |
| 1059 | H | H | EtOOC-MS | 3-H | H | C₅F₄N | H | H | 2 |
| 1060 | H | H | EtOOC-MS | 3-CF₃ | H | C₅F₄N | H | H | 2 |
| 1061 | H | H | EtOOC-MS | 3-H₂NCO | H | C₅F₄N | H | H | 2 |
| 1062 | H | H | EtOOC-MS | 3-F | H | C₅F₄N | H | H | 2 |
| 1063 | H | H | HOOC-MS | 3-Cl | H | C₅F₄N | H | H | 1 |
| 1064 | H | H | HOOC-MS | 3-CH₃ | H | C₅F₄N | H | H | 1 |
| 1065 | H | H | HOOC-MS | 3-H | H | C₅F₄N | H | H | 1 |
| 1066 | H | H | HOOC-MS | 3-CF₃ | H | C₅F₄N | H | H | 1 |
| 1067 | H | H | HOOC-MS | 3-H₂NCO | H | C₅F₄N | H | H | 1 |
| 1068 | H | H | HOOC-MS | 3-F | H | C₅F₄N | H | H | 1 |
| 1069 | H | H | HOOC-MS | 3-Cl | H | C₅F₄N | H | H | 0 |
| 1070 | H | H | HOOC-MS | 3-CH₃ | H | C₅F₄N | H | H | 0 |
| 1071 | H | H | HOOC-MS | 3-H | H | C₅F₄N | H | H | 0 |
| 1072 | H | H | HOOC-MS | 3-CF₃ | H | C₅F₄N | H | H | 0 |
| 1073 | H | H | HOOC-MS | 3-H₂NCO | H | C₅F₄N | H | H | 0 |
| 1074 | H | H | HOOC-MS | 3-F | H | C₅F₄N | H | H | 0 |
| 1075 | H | H | HOOC-MS | 3-Cl | H | C₅F₄N | H | H | 2 |
| 1076 | H | H | HOOC-MS | 3-CH₃ | H | C₅F₄N | H | H | 2 |
| 1077 | H | H | HOOC-MS | 3-H | H | C₅F₄N | H | H | 2 |
| 1078 | H | H | HOOC-MS | 3-CF₃ | H | C₅F₄N | H | H | 2 |
| 1079 | H | H | HOOC-MS | 3-H₂NCO | H | C₅F₄N | H | H | 2 |
| 1080 | H | H | HOOC-MS | 3-F | H | C₅F₄N | H | H | 2 |
| 1081 | H | H | EtOOC-MS | 3-Cl | H | H(CH₃CH₂N)C | H | H | 1 |
| 1082 | H | H | EtOOC-MS | 3-CH₃ | H | H(CH₃CH₂N)C | H | H | 1 |
| 1083 | H | H | EtOOC-MS | 3-H | H | H(CH₃CH₂N)C | H | H | 1 |
| 1084 | H | H | EtOOC-MS | 3-CF₃ | H | H(CH₃CH₂N)C | H | H | 1 |
| 1085 | H | H | EtOOC-MS | 3-H₂NCO | H | H(CH₃CH₂N)C | H | H | 1 |
| 1086 | H | H | EtOOC-MS | 3-F | H | H(CH₃CH₂N)C | H | H | 1 |
| 1087 | H | H | EtOOC-MS | 3-Cl | H | H(CH₃CH₂N)C | H | H | 0 |
| 1088 | H | H | EtOOC-MS | 3-CH₃ | H | H(CH₃CH₂N)C | H | H | 0 |
| 1089 | H | H | EtOOC-MS | 3-H | H | H(CH₃CH₂N)C | H | H | 0 |
| 1090 | H | H | EtOOC-MS | 3-CF₃ | H | H(CH₃CH₂N)C | H | H | 0 |
| 1091 | H | H | EtOOC-MS | 3-H₂NCO | H | H(CH₃CH₂N)C | H | H | 0 |
| 1092 | H | H | EtOOC-MS | 3-F | H | H(CH₃CH₂N)C | H | H | 0 |
| 1093 | H | H | EtOOC-MS | 3-Cl | H | H(CH₃CH₂N)C | H | H | 2 |
| 1094 | H | H | EtOOC-MS | 3-CH₃ | H | H(CH₃CH₂N)C | H | H | 2 |
| 1095 | H | H | EtOOC-MS | 3-H | H | H(CH₃CH₂N)C | H | H | 2 |
| 1096 | H | H | EtOOC-MS | 3-CF₃ | H | H(CH₃CH₂N)C | H | H | 2 |
| 1097 | H | H | EtOOC-MS | 3-H₂NCO | H | H(CH₃CH₂N)C | H | H | 2 |
| 1098 | H | H | EtOOC-MS | 3-F | H | H(CH₃CH₂N)C | H | H | 2 |
| 1099 | H | H | HOOC-MS | 3-Cl | H | H(CH₃CH₂N)C | H | H | 1 |
| 1100 | H | H | HOOC-MS | 3-CH₃ | H | H(CH₃CH₂N)C | H | H | 1 |
| 1101 | H | H | HOOC-MS | 3-H | H | H(CH₃CH₂N)C | H | H | 1 |
| 1102 | H | H | HOOC-MS | 3-CF₃ | H | H(CH₃CH₂N)C | H | H | 1 |
| 1103 | H | H | HOOC-MS | 3-H₂NCO | H | H(CH₃CH₂N)C | H | H | 1 |
| 1104 | H | H | HOOC-MS | 3-F | H | H(CH₃CH₂N)C | H | H | 1 |
| 1105 | H | H | HOOC-MS | 3-Cl | H | H(CH₃CH₂N)C | H | H | 0 |
| 1106 | H | H | HOOC-MS | 3-CH₃ | H | H(CH₃CH₂N)C | H | H | 0 |
| 1107 | H | H | HOOC-MS | 3-H | H | H(CH₃CH₂N)C | H | H | 0 |
| 1108 | H | H | HOOC-MS | 3-CF₃ | H | H(CH₃CH₂N)C | H | H | 0 |
| 1109 | H | H | HOOC-MS | 3-H₂NCO | H | H(CH₃CH₂N)C | H | H | 0 |
| 1110 | H | H | HOOC-MS | 3-F | H | H(CH₃CH₂N)C | H | H | 0 |
| 1111 | H | H | HOOC-MS | 3-Cl | H | H(CH₃CH₂N)C | H | H | 2 |
| 1112 | H | H | HOOC-MS | 3-CH₃ | H | H(CH₃CH₂N)C | H | H | 2 |
| 1113 | H | H | HOOC-MS | 3-H | H | H(CH₃CH₂N)C | H | H | 2 |
| 1114 | H | H | HOOC-MS | 3-CF₃ | H | H(CH₃CH₂N)C | H | H | 2 |
| 1115 | H | H | HOOC-MS | 3-H₂NCO | H | H(CH₃CH₂N)C | H | H | 2 |
| 1116 | H | H | HOOC-MS | 3-F | H | H(CH₃CH₂N)C | H | H | 2 |
| 1117 | H | H | EtOOC-MS | 3-Cl | H | CH₃ | —(CH₂)₂— | — | 1 |
| 1118 | H | H | EtOOC-MS | 3-CH₃ | H | CH₃ | —(CH₂)₂— | — | 1 |

TABLE 1-continued (1)

| No. | R¹ | R² | R³ | R⁴ | R⁵ | R⁶ | R⁷ | R⁸ | n |
|---|---|---|---|---|---|---|---|---|---|
| 1119 | H | H | EtOOC-MS | 3-H | H | CH₃ | —(CH₂)₂— | — | 1 |
| 1120 | H | H | EtOOC-MS | 3-CF₃ | H | CH₃ | —(CH₂)₂— | — | 1 |
| 1121 | H | H | EtOOC-MS | 3-H₂NCO | H | CH₃ | —(CH₂)₂— | — | 1 |
| 1122 | H | H | EtOOC-MS | 3-F | H | CH₃ | —(CH₂)₂— | — | 1 |
| 1123 | H | H | EtOOC-MS | 3-Cl | H | CH₃ | —(CH₂)₂— | — | 0 |
| 1124 | H | H | EtOOC-MS | 3-CH₃ | H | CH₃ | —(CH₂)₂— | — | 0 |
| 1125 | H | H | EtOOC-MS | 3-H | H | CH₃ | —(CH₂)₂— | — | 0 |
| 1126 | H | H | EtOOC-MS | 3-CF₃ | H | CH₃ | —(CH₂)₂— | — | 0 |
| 1127 | H | H | EtOOC-MS | 3-H₂NCO | H | CH₃ | —(CH₂)₂— | — | 0 |
| 1128 | H | H | EtOOC-MS | 3-F | H | CH₃ | —(CH₂)₂— | — | 0 |
| 1129 | H | H | EtOOC-MS | 3-Cl | H | CH₃ | —(CH₂)₂— | — | 2 |
| 1130 | H | H | EtOOC-MS | 3-CH₃ | H | CH₃ | —(CH₂)₂— | — | 2 |
| 1131 | H | H | EtOOC-MS | 3-H | H | CH₃ | —(CH₂)₂— | — | 2 |
| 1132 | H | H | EtOOC-MS | 3-CF₃ | H | CH₃ | —(CH₂)₂— | — | 2 |
| 1133 | H | H | EtOOC-MS | 3-H₂NCO | H | CH₃ | —(CH₂)₂— | — | 2 |
| 1134 | H | H | EtOOC-MS | 3-F | H | CH₃ | —(CH₂)₂— | — | 2 |
| 1135 | H | H | HOOC-MS | 3-Cl | H | CH₃ | —(CH₂)₂— | — | 1 |
| 1136 | H | H | HOOC-MS | 3-CH₃ | H | CH₃ | —(CH₂)₂— | — | 1 |
| 1137 | H | H | HOOC-MS | 3-H | H | CH₃ | —(CH₂)₂— | — | 1 |
| 1138 | H | H | HOOC-MS | 3-CF₃ | H | CH₃ | —(CH₂)₂— | — | 1 |
| 1139 | H | H | HOOC-MS | 3-H₂NCO | H | CH₃ | —(CH₂)₂— | — | 1 |
| 1140 | H | H | HOOC-MS | 3-F | H | CH₃ | —(CH₂)₂— | — | 1 |
| 1141 | H | H | HOOC-MS | 3-Cl | H | CH₃ | —(CH₂)₂— | — | 0 |
| 1142 | H | H | HOOC-MS | 3-CH₃ | H | CH₃ | —(CH₂)₂— | — | 0 |
| 1143 | H | H | HOOC-MS | 3-H | H | CH₃ | —(CH₂)₂— | — | 0 |
| 1144 | H | H | HOOC-MS | 3-CF₃ | H | CH₃ | —(CH₂)₂— | — | 0 |
| 1145 | H | H | HOOC-MS | 3-H₂NCO | H | CH₃ | —(CH₂)₂— | — | 0 |
| 1146 | H | H | HOOC-MS | 3-F | H | CH₃ | —(CH₂)₂— | — | 0 |
| 1147 | H | H | HOOC-MS | 3-Cl | H | CH₃ | —(CH₂)₂— | — | 2 |
| 1148 | H | H | HOOC-MS | 3-CH₃ | H | CH₃ | —(CH₂)₂— | — | 2 |
| 1149 | H | H | HOOC-MS | 3-H | H | CH₃ | —(CH₂)₂— | — | 2 |
| 1150 | H | H | HOOC-MS | 3-CF₃ | H | CH₃ | —(CH₂)₂— | — | 2 |
| 1151 | H | H | HOOC-MS | 3-H₂NCO | H | CH₃ | —(CH₂)₂— | — | 2 |
| 1152 | H | H | HOOC-MS | 3-F | H | CH₃ | —(CH₂)₂— | — | 2 |
| 1153 | H | H | EtOOC-MS | 3-Cl | H | C₈H₁₄N | H | H | 1 |
| 1154 | H | H | EtOOC-MS | 3-CH₃ | H | C₈H₁₄N | H | H | 1 |
| 1155 | H | H | EtOOC-MS | 3-H | H | C₈H₁₄N | H | H | 1 |
| 1156 | H | H | EtOOC-MS | 3-CF₃ | H | C₈H₁₄N | H | H | 1 |
| 1157 | H | H | EtOOC-MS | 3-H₂NCO | H | C₈H₁₄N | H | H | 1 |
| 1158 | H | H | EtOOC-MS | 3-F | H | C₈H₁₄N | H | H | 1 |
| 1159 | H | H | EtOOC-MS | 3-Cl | H | C₈H₁₄N | H | H | 0 |
| 1160 | H | H | EtOOC-MS | 3-CH₃ | H | C₈H₁₄N | H | H | 0 |
| 1161 | H | H | EtOOC-MS | 3-H | H | C₈H₁₄N | H | H | 0 |
| 1162 | H | H | EtOOC-MS | 3-CF₃ | H | C₈H₁₄N | H | H | 0 |
| 1163 | H | H | EtOOC-MS | 3-H₂NCO | H | C₈H₁₄N | H | H | 0 |
| 1164 | H | H | EtOOC-MS | 3-F | H | C₈H₁₄N | H | H | 0 |
| 1165 | H | H | EtOOC-MS | 3-Cl | H | C₈H₁₄N | H | H | 2 |
| 1166 | H | H | EtOOC-MS | 3-CH₃ | H | C₈H₁₄N | H | H | 2 |
| 1167 | H | H | EtOOC-MS | 3-H | H | C₈H₁₄N | H | H | 2 |
| 1168 | H | H | EtOOC-MS | 3-CF₃ | H | C₈H₁₄N | H | H | 2 |
| 1169 | H | H | EtOOC-MS | 3-H₂NCO | H | C₈H₁₄N | H | H | 2 |
| 1170 | H | H | EtOOC-MS | 3-F | H | C₈H₁₄N | H | H | 2 |
| 1171 | H | H | HOOC-MS | 3-Cl | H | C₈H₁₄N | H | H | 1 |
| 1172 | H | H | HOOC-MS | 3-CH₃ | H | C₈H₁₄N | H | H | 1 |
| 1173 | H | H | HOOC-MS | 3-H | H | C₈H₁₄N | H | H | 1 |
| 1174 | H | H | HOOC-MS | 3-CF₃ | H | C₈H₁₄N | H | H | 1 |
| 1175 | H | H | HOOC-MS | 3-H₂NCO | H | C₈H₁₄N | H | H | 1 |
| 1176 | H | H | HOOC-MS | 3-F | H | C₈H₁₄N | H | H | 1 |
| 1177 | H | H | HOOC-MS | 3-Cl | H | C₈H₁₄N | H | H | 0 |
| 1178 | H | H | HOOC-MS | 3-CH₃ | H | C₈H₁₄N | H | H | 0 |
| 1179 | H | H | HOOC-MS | 3-H | H | C₈H₁₄N | H | H | 0 |
| 1180 | H | H | HOOC-MS | 3-CF₃ | H | C₈H₁₄N | H | H | 0 |
| 1181 | H | H | HOOC-MS | 3-H₂NCO | H | C₈H₁₄N | H | H | 0 |
| 1182 | H | H | HOOC-MS | 3-F | H | C₈H₁₄N | H | H | 0 |
| 1183 | H | H | HOOC-MS | 3-Cl | H | C₈H₁₄N | H | H | 2 |

TABLE 1-continued (1)

$$\text{H}_2\text{N}-\text{C}(=\text{NH})-\text{C}_6\text{H}_3(\text{R}^1)-\text{CH}=\text{C}(\text{R}^2)-\text{CH}_2-\text{N}(\text{R}^3)-\text{C}_6\text{H}_3(\text{R}^4,\text{R}^5)-\text{O}-\text{C}_n\text{H}(\text{R}^7)(\text{R}^8)-\text{N}(\text{R}^6)$$

| No. | R¹ | R² | R³ | R⁴ | R⁵ | R⁶ | R⁷ | R⁸ | n |
|---|---|---|---|---|---|---|---|---|---|
| 1184 | H | H | HOOC-MS | 3-CH₃ | H | C₈H₁₄N | H | H | 2 |
| 1185 | H | H | HOOC-MS | 3-H | H | C₈H₁₄N | H | H | 2 |
| 1186 | H | H | HOOC-MS | 3-CF₃ | H | C₈H₁₄N | H | H | 2 |
| 1187 | H | H | HOOC-MS | 3-H₂NCO | H | C₈H₁₄N | H | H | 2 |
| 1188 | H | H | HOOC-MS | 3-F | H | C₈H₁₄N | H | H | 2 |
| 1189 | H | H | H₃CSO₂ | H | H | C₃H₄NO | H | H | 0 |
| 1190 | H | H | H₃CSO₂ | 3-F | H | C₃H₄NO | H | H | 0 |
| 1191 | H | H | H₃CSO₂ | 3-Cl | H | C₃H₄NO | H | H | 0 |
| 1192 | H | H | H₃CSO₂ | 3-CH₃ | H | C₃H₄NO | H | H | 0 |
| 1193 | H | H | H₃CSO₂ | 3-CF₃ | H | C₃H₄NO | H | H | 0 |
| 1194 | H | H | H₃CSO₂ | 3-H₂NCO | H | C₃H₄NO | H | H | 0 |
| 1195 | H | F | H₃CSO₂ | H | H | C₃H₄NO | H | H | 0 |
| 1196 | H | F | H₃CSO₂ | 3-F | H | C₃H₄NO | H | H | 0 |
| 1197 | H | F | H₃CSO₂ | 3-Cl | H | C₃H₄NO | H | H | 0 |
| 1198 | H | F | H₃CSO₂ | 3-CH₃ | H | C₃H₄NO | H | H | 0 |
| 1199 | H | F | H₃CSO₂ | 3-CF₃ | H | C₃H₄NO | H | H | 0 |
| 1200 | H | F | H₃CSO₂ | 3-H₂NCO | H | C₃H₄NO | H | H | 0 |
| 1201 | H | H | H₃CSO₂ | H | H | C₃H₄NO | H | H | 1 |
| 1202 | H | H | H₃CSO₂ | 2-F | H | C₃H₄NO | H | H | 1 |
| 1203 | H | H | H₃CSO₂ | 2-Cl | H | C₃H₄NO | H | H | 1 |
| 1204 | H | H | H₃CSO₂ | 2-CH₃ | H | C₃H₄NO | H | H | 1 |
| 1205 | H | H | H₃CSO₂ | 2-CF₃ | H | C₃H₄NO | H | H | 1 |
| 1206 | H | H | H₃CSO₂ | 2-H₂NCO | H | C₃H₄NO | H | H | 1 |
| 1207 | H | H | H₃CSO₂ | 3-F | H | C₃H₄NO | H | H | 1 |
| 1208 | H | H | H₃CSO₂ | 3-Cl | H | C₃H₄NO | H | H | 1 |
| 1209 | H | H | H₃CSO₂ | 3-CH₃ | H | C₃H₄NO | H | H | 1 |
| 1210 | H | H | H₃CSO₂ | 3-CF₃ | H | C₃H₄NO | H | H | 1 |
| 1211 | H | H | H₃CSO₂ | 3-H₂NCO | H | C₃H₄NO | H | H | 1 |
| 1212 | H | F | H₃CSO₂ | H | H | C₃H₄NO | H | H | 1 |
| 1213 | H | F | H₃CSO₂ | 3-F | H | C₃H₄NO | H | H | 1 |
| 1214 | H | F | H₃CSO₂ | 3-Cl | H | C₃H₄NO | H | H | 1 |
| 1215 | H | F | H₃CSO₂ | 3-CH₃ | H | C₃H₄NO | H | H | 1 |
| 1216 | H | F | H₃CSO₂ | 3-CF₃ | H | C₃H₄NO | H | H | 1 |
| 1217 | H | F | H₃CSO₂ | 3-H₂NCO | H | C₃H₄NO | H | H | 1 |
| 1218 | H | H | EtSO₂ | H | H | C₃H₄NO | H | H | 0 |
| 1219 | H | H | EtSO₂ | 3-F | H | C₃H₄NO | H | H | 0 |
| 1220 | H | H | EtSO₂ | 3-Cl | H | C₃H₄NO | H | H | 0 |
| 1221 | H | H | EtSO₂ | 3-CH₃ | H | C₃H₄NO | H | H | 0 |
| 1222 | H | H | EtSO₂ | 3-CF₃ | H | C₃H₄NO | H | H | 0 |
| 1223 | H | H | EtSO₂ | 3-H₂NCO | H | C₃H₄NO | H | H | 0 |
| 1224 | H | F | EtSO₂ | H | H | C₃H₄NO | H | H | 0 |
| 1225 | H | F | EtSO₂ | 3-F | H | C₃H₄NO | H | H | 0 |
| 1226 | H | F | EtSO₂ | 3-Cl | H | C₃H₄NO | H | H | 0 |
| 1227 | H | F | EtSO₂ | 3-CH₃ | H | C₃H₄NO | H | H | 0 |
| 1228 | H | F | EtSO₂ | 3-CF₃ | H | C₃H₄NO | H | H | 0 |
| 1229 | H | F | EtSO₂ | 3-H₂NCO | H | C₃H₄NO | H | H | 0 |
| 1230 | H | H | EtSO₂ | H | H | C₃H₄NO | H | H | 1 |
| 1231 | H | H | EtSO₂ | 2-F | H | C₃H₄NO | H | H | 1 |
| 1232 | H | H | EtSO₂ | 2-Cl | H | C₃H₄NO | H | H | 1 |
| 1233 | H | H | EtSO₂ | 2-CH₃ | H | C₃H₄NO | H | H | 1 |
| 1234 | H | H | EtSO₂ | 2-CF₃ | H | C₃H₄NO | H | H | 1 |
| 1235 | H | H | EtSO₂ | 2-H₂NCO | H | C₃H₄NO | H | H | 1 |
| 1236 | H | H | EtSO₂ | 3-F | H | C₃H₄NO | H | H | 1 |
| 1237 | H | H | EtSO₂ | 3-Cl | H | C₃H₄NO | H | H | 1 |
| 1238 | H | H | EtSO₂ | 3-CH₃ | H | C₃H₄NO | H | H | 1 |
| 1239 | H | H | EtSO₂ | 3-CF₃ | H | C₃H₄NO | H | H | 1 |
| 1240 | H | H | EtSO₂ | 3-H₂NCO | H | C₃H₄NO | H | H | 1 |
| 1241 | H | F | EtSO₂ | H | H | C₃H₄NO | H | H | 1 |
| 1242 | H | F | EtSO₂ | 3-F | H | C₃H₄NO | H | H | 1 |
| 1243 | H | F | EtSO₂ | 3-Cl | H | C₃H₄NO | H | H | 1 |
| 1244 | H | F | EtSO₂ | 3-CH₃ | H | C₃H₄NO | H | H | 1 |
| 1245 | H | F | EtSO₂ | 3-CF₃ | H | C₃H₄NO | H | H | 1 |
| 1246 | H | F | EtSO₂ | 3-H₂NCO | H | C₃H₄NO | H | H | 1 |
| 1247 | H | H | H₃CSO₂ | H | H | C₃H₄NS | H | H | 0 |
| 1248 | H | H | H₃CSO₂ | 3-F | H | C₃H₄NS | H | H | 0 |

TABLE 1-continued (1)

| No. | R¹ | R² | R³ | R⁴ | R⁵ | R⁶ | R⁷ | R⁸ | n |
|---|---|---|---|---|---|---|---|---|---|
| 1249 | H | H | H₃CSO₂ | 3-Cl | H | C₃H₄NS | H | H | 0 |
| 1250 | H | H | H₃CSO₂ | 3-CH₃ | H | C₃H₄NS | H | H | 0 |
| 1251 | H | H | H₃CSO₂ | 3-CF₃ | H | C₃H₄NS | H | H | 0 |
| 1252 | H | H | H₃CSO₂ | 3-H₂NCO | H | C₃H₄NS | H | H | 0 |
| 1253 | H | F | H₃CSO₂ | H | H | C₃H₄NS | H | H | 0 |
| 1254 | H | F | H₃CSO₂ | 3-F | H | C₃H₄NS | H | H | 0 |
| 1255 | H | F | H₃CSO₂ | 3-Cl | H | C₃H₄NS | H | H | 0 |
| 1256 | H | F | H₃CSO₂ | 3-CH₃ | H | C₃H₄NS | H | H | 0 |
| 1257 | H | F | H₃CSO₂ | 3-CF₃ | H | C₃H₄NS | H | H | 0 |
| 1258 | H | F | H₃CSO₂ | 3-H₂NCO | H | C₃H₄NS | H | H | 0 |
| 1259 | H | H | H₃CSO₂ | H | H | C₃H₄NS | H | H | 1 |
| 1260 | H | H | H₃CSO₂ | 2-F | H | C₃H₄NS | H | H | 1 |
| 1261 | H | H | H₃CSO₂ | 2-Cl | H | C₃H₄NS | H | H | 1 |
| 1262 | H | H | H₃CSO₂ | 2-CH₃ | H | C₃H₄NS | H | H | 1 |
| 1263 | H | H | H₃CSO₂ | 2-CF₃ | H | C₃H₄NS | H | H | 1 |
| 1264 | H | H | H₃CSO₂ | 2-H₂NCO | H | C₃H₄NS | H | H | 1 |
| 1265 | H | H | H₃CSO₂ | 3-F | H | C₃H₄NS | H | H | 1 |
| 1266 | H | H | H₃CSO₂ | 3-Cl | H | C₃H₄NS | H | H | 1 |
| 1267 | H | H | H₃CSO₂ | 3-CH₃ | H | C₃H₄NS | H | H | 1 |
| 1268 | H | H | H₃CSO₂ | 3-CF₃ | H | C₃H₄NS | H | H | 1 |
| 1269 | H | H | H₃CSO₂ | 3-H₂NCO | H | C₃H₄NS | H | H | 1 |
| 1270 | H | F | H₃CSO₂ | H | H | C₃H₄NS | H | H | 1 |
| 1271 | H | F | H₃CSO₂ | 3-F | H | C₃H₄NS | H | H | 1 |
| 1272 | H | F | H₃CSO₂ | 3-Cl | H | C₃H₄NS | H | H | 1 |
| 1273 | H | F | H₃CSO₂ | 3-CH₃ | H | C₃H₄NS | H | H | 1 |
| 1274 | H | F | H₃CSO₂ | 3-CF₃ | H | C₃H₄NS | H | H | 1 |
| 1275 | H | F | H₃CSO₂ | 3-H₂NCO | H | C₃H₄NS | H | H | 1 |
| 1276 | H | H | EtSO₂ | H | H | C₃H₄NS | H | H | 0 |
| 1277 | H | H | EtSO₂ | 3-F | H | C₃H₄NS | H | H | 0 |
| 1278 | H | H | EtSO₂ | 3-Cl | H | C₃H₄NS | H | H | 0 |
| 1279 | H | H | EtSO₂ | 3-CH₃ | H | C₃H₄NS | H | H | 0 |
| 1280 | H | H | EtSO₂ | 3-CF₃ | H | C₃H₄NS | H | H | 0 |
| 1281 | H | H | EtSO₂ | 3-H₂NCO | H | C₃H₄NS | H | H | 0 |
| 1282 | H | F | EtSO₂ | H | H | C₃H₄NS | H | H | 0 |
| 1283 | H | F | EtSO₂ | 3-F | H | C₃H₄NS | H | H | 0 |
| 1284 | H | F | EtSO₂ | 3-Cl | H | C₃H₄NS | H | H | 0 |
| 1285 | H | F | EtSO₂ | 3-CH₃ | H | C₃H₄NS | H | H | 0 |
| 1286 | H | F | EtSO₂ | 3-CF₃ | H | C₃H₄NS | H | H | 0 |
| 1287 | H | F | EtSO₂ | 3-H₂NCO | H | C₃H₄NS | H | H | 0 |
| 1288 | H | H | EtSO₂ | H | H | C₃H₄NS | H | H | 1 |
| 1289 | H | H | EtSO₂ | 2-F | H | C₃H₄NS | H | H | 1 |
| 1290 | H | H | EtSO₂ | 2-Cl | H | C₃H₄NS | H | H | 1 |
| 1291 | H | H | EtSO₂ | 2-CH₃ | H | C₃H₄NS | H | H | 1 |
| 1292 | H | H | EtSO₂ | 2-CF₃ | H | C₃H₄NS | H | H | 1 |
| 1293 | H | H | EtSO₂ | 2-H₂NCO | H | C₃H₄NS | H | H | 1 |
| 1294 | H | H | EtSO₂ | 3-F | H | C₃H₄NS | H | H | 1 |
| 1295 | H | H | EtSO₂ | 3-Cl | H | C₃H₄NS | H | H | 1 |
| 1296 | H | H | EtSO₂ | 3-CH₃ | H | C₃H₄NS | H | H | 1 |
| 1297 | H | H | EtSO₂ | 3-CF₃ | H | C₃H₄NS | H | H | 1 |
| 1298 | H | H | EtSO₂ | 3-H₂NCO | H | C₃H₄NS | H | H | 1 |
| 1299 | H | F | EtSO₂ | H | H | C₃H₄NS | H | H | 1 |
| 1300 | H | F | EtSO₂ | 3-F | H | C₃H₄NS | H | H | 1 |
| 1301 | H | F | EtSO₂ | 3-Cl | H | C₃H₄NS | H | H | 1 |
| 1302 | H | F | EtSO₂ | 3-CH₃ | H | C₃H₄NS | H | H | 1 |
| 1303 | H | F | EtSO₂ | 3-CF₃ | H | C₃H₄NS | H | H | 1 |
| 1304 | H | F | EtSO₂ | 3-H₂NCO | H | C₃H₄NS | H | H | 1 |
| 1305 | H | H | EtOOC-MS | H | H | C₃H₄NS | H | H | 0 |
| 1306 | H | H | EtOOC-MS | 3-F | H | C₃H₄NS | H | H | 0 |
| 1307 | H | H | EtOOC-MS | 3-Cl | H | C₃H₄NS | H | H | 0 |
| 1308 | H | H | EtOOC-MS | 3-CH₃ | H | C₃H₄NS | H | H | 0 |
| 1309 | H | H | EtOOC-MS | 3-CF₃ | H | C₃H₄NS | H | H | 0 |
| 1310 | H | H | EtOOC-MS | 3-H₂NCO | H | C₃H₄NS | H | H | 0 |
| 1311 | H | F | EtOOC-MS | H | H | C₃H₄NS | H | H | 0 |
| 1312 | H | F | EtOOC-MS | 3-F | H | C₃H₄NS | H | H | 0 |
| 1313 | H | F | EtOOC-MS | 3-Cl | H | C₃H₄NS | H | H | 0 |

TABLE 1-continued (1)

Structure: H₂N-C(=NH)-phenyl(R¹)-CH=C(R²)-CH₂-N(R³)-phenyl(R⁴,R⁵)-O-piperidine(R⁷,R⁸)(n)-N-R⁶

| No. | R¹ | R² | R³ | R⁴ | R⁵ | R⁶ | R⁷ | R⁸ | n |
|---|---|---|---|---|---|---|---|---|---|
| 1314 | H | F | EtOOC-MS | 3-CH₃ | H | C₃H₄NS | H | H | 0 |
| 1315 | H | F | EtOOC-MS | 3-CF₃ | H | C₃H₄NS | H | H | 0 |
| 1316 | H | F | EtOOC-MS | 3-H₂NCO | H | C₃H₄NS | H | H | 0 |
| 1317 | H | H | EtOOC-MS | H | H | C₃H₄NS | H | H | 1 |
| 1318 | H | H | EtOOC-MS | 2-F | H | C₃H₄NS | H | H | 1 |
| 1319 | H | H | EtOOC-MS | 2-Cl | H | C₃H₄NS | H | H | 1 |
| 1320 | H | H | EtOOC-MS | 2-CH₃ | H | C₃H₄NS | H | H | 1 |
| 1321 | H | H | EtOOC-MS | 2-CF₃ | H | C₃H₄NS | H | H | 1 |
| 1322 | H | H | EtOOC-MS | 2-H₂NCO | H | C₃H₄NS | H | H | 1 |
| 1323 | H | H | EtOOC-MS | 3-F | H | C₃H₄NS | H | H | 1 |
| 1324 | H | H | EtOOC-MS | 3-Cl | H | C₃H₄NS | H | H | 1 |
| 1325 | H | H | EtOOC-MS | 3-CH₃ | H | C₃H₄NS | H | H | 1 |
| 1326 | H | H | EtOOC-MS | 3-CF₃ | H | C₃H₄NS | H | H | 1 |
| 1327 | H | H | EtOOC-MS | 3-H₂NCO | H | C₃H₄NS | H | H | 1 |
| 1328 | H | F | EtOOC-MS | H | H | C₃H₄NS | H | H | 1 |
| 1329 | H | F | EtOOC-MS | 3-F | H | C₃H₄NS | H | H | 1 |
| 1330 | H | F | EtOOC-MS | 3-Cl | H | C₃H₄NS | H | H | 1 |
| 1331 | H | F | EtOOC-MS | 3-CH₃ | H | C₃H₄NS | H | H | 1 |
| 1332 | H | F | EtOOC-MS | 3-CF₃ | H | C₃H₄NS | H | H | 1 |
| 1333 | H | F | EtOOC-MS | 3-H₂NCO | H | C₃H₄NS | H | H | 1 |
| 1334 | H | H | HOOC-MS | H | H | C₃H₄NS | H | H | 0 |
| 1335 | H | H | HOOC-MS | 3-F | H | C₃H₄NS | H | H | 0 |
| 1336 | H | H | HOOC-MS | 3-Cl | H | C₃H₄NS | H | H | 0 |
| 1337 | H | H | HOOC-MS | 3-CH₃ | H | C₃H₄NS | H | H | 0 |
| 1338 | H | H | HOOC-MS | 3-CF₃ | H | C₃H₄NS | H | H | 0 |
| 1339 | H | H | HOOC-MS | 3-H₂NCO | H | C₃H₄NS | H | H | 0 |
| 1340 | H | F | HOOC-MS | H | H | C₃H₄NS | H | H | 0 |
| 1341 | H | F | HOOC-MS | 3-F | H | C₃H₄NS | H | H | 0 |
| 1342 | H | F | HOOC-MS | 3-Cl | H | C₃H₄NS | H | H | 0 |
| 1343 | H | F | HOOC-MS | 3-CH₃ | H | C₃H₄NS | H | H | 0 |
| 1344 | H | F | HOOC-MS | 3-CF₃ | H | C₃H₄NS | H | H | 0 |
| 1345 | H | F | HOOC-MS | 3-H₂NCO | H | C₃H₄NS | H | H | 0 |
| 1346 | H | H | HOOC-MS | H | H | C₃H₄NS | H | H | 1 |
| 1347 | H | H | HOOC-MS | 2-F | H | C₃H₄NS | H | H | 1 |
| 1348 | H | H | HOOC-MS | 2-Cl | H | C₃H₄NS | H | H | 1 |
| 1349 | H | H | HOOC-MS | 2-CH₃ | H | C₃H₄NS | H | H | 1 |
| 1350 | H | H | HOOC-MS | 2-CF₃ | H | C₃H₄NS | H | H | 1 |
| 1351 | H | H | HOOC-MS | 2-H₂NCO | H | C₃H₄NS | H | H | 1 |
| 1352 | H | H | HOOC-MS | 3-F | H | C₃H₄NS | H | H | 1 |
| 1353 | H | H | HOOC-MS | 3-Cl | H | C₃H₄NS | H | H | 1 |
| 1354 | H | H | HOOC-MS | 3-CH₃ | H | C₃H₄NS | H | H | 1 |
| 1355 | H | H | HOOC-MS | 3-CF₃ | H | C₃H₄NS | H | H | 1 |
| 1356 | H | H | HOOC-MS | 3-H₂NCO | H | C₃H₄NS | H | H | 1 |
| 1357 | H | F | HOOC-MS | H | H | C₃H₄NS | H | H | 1 |
| 1358 | H | F | HOOC-MS | 3-F | H | C₃H₄NS | H | H | 1 |
| 1359 | H | F | HOOC-MS | 3-Cl | H | C₃H₄NS | H | H | 1 |
| 1360 | H | F | HOOC-MS | 3-CH₃ | H | C₃H₄NS | H | H | 1 |
| 1361 | H | F | HOOC-MS | 3-CF₃ | H | C₃H₄NS | H | H | 1 |
| 1362 | H | F | HOOC-MS | 3-H₂NCO | H | C₃H₄NS | H | H | 1 |
| 1363 | H | H | H₃CSO₂ | H | H | C₄H₆N | H | H | 0 |
| 1364 | H | H | H₃CSO₂ | 2-F | H | C₄H₆N | H | H | 0 |
| 1365 | H | H | H₃CSO₂ | 2-Cl | H | C₄H₆N | H | H | 0 |
| 1366 | H | H | H₃CSO₂ | 2-CH₃ | H | C₄H₆N | H | H | 0 |
| 1367 | H | H | H₃CSO₂ | 2-CF₃ | H | C₄H₆N | H | H | 0 |
| 1368 | H | H | H₃CSO₂ | 2-H₂NCO | H | C₄H₆N | H | H | 0 |
| 1369 | H | H | H₃CSO₂ | 3-F | H | C₄H₆N | H | H | 0 |
| 1370 | H | H | H₃CSO₂ | 3-Cl | H | C₄H₆N | H | H | 0 |
| 1371 | H | H | H₃CSO₂ | 3-CH₃ | H | C₄H₆N | H | H | 0 |
| 1372 | H | H | H₃CSO₂ | 3-CF₃ | H | C₄H₆N | H | H | 0 |
| 1373 | H | H | H₃CSO₂ | 3-H₂NCO | H | C₄H₆N | H | H | 0 |
| 1374 | H | H | H₃CSO₂ | H | H | C₄H₆N | H | H | 1 |
| 1375 | H | H | H₃CSO₂ | 2-F | H | C₄H₆N | H | H | 1 |
| 1376 | H | H | H₃CSO₂ | 2-Cl | H | C₄H₆N | H | H | 1 |
| 1377 | H | H | H₃CSO₂ | 2-CH₃ | H | C₄H₆N | H | H | 1 |
| 1378 | H | H | H₃CSO₂ | 2-CF₃ | H | C₄H₆N | H | H | 1 |

TABLE 1-continued (1)

$H_2N-C(=NH)-$ phenyl(R$^1$)$-CR^2=CH-CH_2-N(R^3)-$ phenyl(R$^4$,R$^5$)$-O-$ piperidinyl(R$^7$,R$^8$,n)$-N-R^6$

| No. | R$^1$ | R$^2$ | R$^3$ | R$^4$ | R$^5$ | R$^6$ | R$^7$ | R$^8$ | n |
|---|---|---|---|---|---|---|---|---|---|
| 1379 | H | H | H$_3$CSO$_2$ | 2-H$_2$NCO | H | C$_4$H$_6$N | H | H | 1 |
| 1380 | H | H | H$_3$CSO$_2$ | 3-F | H | C$_4$H$_6$N | H | H | 1 |
| 1381 | H | H | H$_3$CSO$_2$ | 3-Cl | H | C$_4$H$_6$N | H | H | 1 |
| 1382 | H | H | H$_3$CSO$_2$ | 3-CH$_3$ | H | C$_4$H$_6$N | H | H | 1 |
| 1383 | H | H | H$_3$CSO$_2$ | 3-CF$_3$ | H | C$_4$H$_6$N | H | H | 1 |
| 1384 | H | H | H$_3$CSO$_2$ | 3-H$_2$NCO | H | C$_4$H$_6$N | H | H | 1 |
| 1385 | H | H | EtSO$_2$ | H | H | C$_4$H$_6$N | H | H | 0 |
| 1386 | H | H | EtSO$_2$ | 2-F | H | C$_4$H$_6$N | H | H | 0 |
| 1387 | H | H | EtSO$_2$ | 2-Cl | H | C$_4$H$_6$N | H | H | 0 |
| 1388 | H | H | EtSO$_2$ | 2-CH$_3$ | H | C$_4$H$_6$N | H | H | 0 |
| 1389 | H | H | EtSO$_2$ | 2-CF$_3$ | H | C$_4$H$_6$N | H | H | 0 |
| 1390 | H | H | EtSO$_2$ | 2-H$_2$NCO | H | C$_4$H$_6$N | H | H | 0 |
| 1391 | H | H | EtSO$_2$ | 3-F | H | C$_4$H$_6$N | H | H | 0 |
| 1392 | H | H | EtSO$_2$ | 3-Cl | H | C$_4$H$_6$N | H | H | 0 |
| 1393 | H | H | EtSO$_2$ | 3-CH$_3$ | H | C$_4$H$_6$N | H | H | 0 |
| 1394 | H | H | EtSO$_2$ | 3-CF$_3$ | H | C$_4$H$_6$N | H | H | 0 |
| 1395 | H | H | EtSO$_2$ | 3-H$_2$NCO | H | C$_4$H$_6$N | H | H | 0 |
| 1396 | H | H | EtSO$_2$ | H | H | C$_4$H$_6$N | H | H | 1 |
| 1397 | H | H | EtSO$_2$ | 2-F | H | C$_4$H$_6$N | H | H | 1 |
| 1398 | H | H | EtSO$_2$ | 2-Cl | H | C$_4$H$_6$N | H | H | 1 |
| 1399 | H | H | EtSO$_2$ | 2-CH$_3$ | H | C$_4$H$_6$N | H | H | 1 |
| 1400 | H | H | EtSO$_2$ | 2-CF$_3$ | H | C$_4$H$_6$N | H | H | 1 |
| 1401 | H | H | EtSO$_2$ | 2-H$_2$NCO | H | C$_4$H$_6$N | H | H | 1 |
| 1402 | H | H | EtSO$_2$ | 3-F | H | C$_4$H$_6$N | H | H | 1 |
| 1403 | H | H | EtSO$_2$ | 3-Cl | H | C$_4$H$_6$N | H | H | 1 |
| 1404 | H | H | EtSO$_2$ | 3-CH$_3$ | H | C$_4$H$_6$N | H | H | 1 |
| 1405 | H | H | EtSO$_2$ | 3-CF$_3$ | H | C$_4$H$_6$N | H | H | 1 |
| 1406 | H | H | EtSO$_2$ | 3-H$_2$NCO | H | C$_4$H$_6$N | H | H | 1 |
| 1407 | H | F | H$_3$CSO$_2$ | H | H | C$_4$H$_6$N | H | H | 0 |
| 1408 | H | F | H$_3$CSO$_2$ | 2-F | H | C$_4$H$_6$N | H | H | 0 |
| 1409 | H | F | H$_3$CSO$_2$ | 2-Cl | H | C$_4$H$_6$N | H | H | 0 |
| 1410 | H | F | H$_3$CSO$_2$ | 2-CH$_3$ | H | C$_4$H$_6$N | H | H | 0 |
| 1411 | H | F | H$_3$CSO$_2$ | 2-CF$_3$ | H | C$_4$H$_6$N | H | H | 0 |
| 1412 | H | F | H$_3$CSO$_2$ | 2-H$_2$NCO | H | C$_4$H$_6$N | H | H | 0 |
| 1413 | H | F | H$_3$CSO$_2$ | 3-F | H | C$_4$H$_6$N | H | H | 0 |
| 1414 | H | F | H$_3$CSO$_2$ | 3-Cl | H | C$_4$H$_6$N | H | H | 0 |
| 1415 | H | F | H$_3$CSO$_2$ | 3-CH$_3$ | H | C$_4$H$_6$N | H | H | 0 |
| 1416 | H | F | H$_3$CSO$_2$ | 3-CF$_3$ | H | C$_4$H$_6$N | H | H | 0 |
| 1417 | H | F | H$_3$CSO$_2$ | 3-H$_2$NCO | H | C$_4$H$_6$N | H | H | 0 |
| 1418 | H | F | H$_3$CSO$_2$ | H | H | C$_4$H$_6$N | H | H | 1 |
| 1419 | H | F | H$_3$CSO$_2$ | 2-F | H | C$_4$H$_6$N | H | H | 1 |
| 1420 | H | F | H$_3$CSO$_2$ | 2-Cl | H | C$_4$H$_6$N | H | H | 1 |
| 1421 | H | F | H$_3$CSO$_2$ | 2-CH$_3$ | H | C$_4$H$_6$N | H | H | 1 |
| 1422 | H | F | H$_3$CSO$_2$ | 2-CF$_3$ | H | C$_4$H$_6$N | H | H | 1 |
| 1423 | H | F | H$_3$CSO$_2$ | 2-H$_2$NCO | H | C$_4$H$_6$N | H | H | 1 |
| 1424 | H | F | H$_3$CSO$_2$ | 3-F | H | C$_4$H$_6$N | H | H | 1 |
| 1425 | H | F | H$_3$CSO$_2$ | 3-Cl | H | C$_4$H$_6$N | H | H | 1 |
| 1426 | H | F | H$_3$CSO$_2$ | 3-CH$_3$ | H | C$_4$H$_6$N | H | H | 1 |
| 1427 | H | F | H$_3$CSO$_2$ | 3-CF$_3$ | H | C$_4$H$_6$N | H | H | 1 |
| 1428 | H | F | H$_3$CSO$_2$ | 3-H$_2$NCO | H | C$_4$H$_6$N | H | H | 1 |
| 1429 | H | F | EtSO$_2$ | H | H | C$_4$H$_6$N | H | H | 0 |
| 1430 | H | F | EtSO$_2$ | 2-F | H | C$_4$H$_6$N | H | H | 0 |
| 1431 | H | F | EtSO$_2$ | 2-Cl | H | C$_4$H$_6$N | H | H | 0 |
| 1432 | H | F | EtSO$_2$ | 2-CH$_3$ | H | C$_4$H$_6$N | H | H | 0 |
| 1433 | H | F | EtSO$_2$ | 2-CF$_3$ | H | C$_4$H$_6$N | H | H | 0 |
| 1434 | H | F | EtSO$_2$ | 2-H$_2$NCO | H | C$_4$H$_6$N | H | H | 0 |
| 1435 | H | F | EtSO$_2$ | 3-F | H | C$_4$H$_6$N | H | H | 0 |
| 1436 | H | F | EtSO$_2$ | 3-Cl | H | C$_4$H$_6$N | H | H | 0 |
| 1437 | H | F | EtSO$_2$ | 3-CH$_3$ | H | C$_4$H$_6$N | H | H | 0 |
| 1438 | H | F | EtSO$_2$ | 3-CF$_3$ | H | C$_4$H$_6$N | H | H | 0 |
| 1439 | H | F | EtSO$_2$ | 3-H$_2$NCO | H | C$_4$H$_6$N | H | H | 0 |
| 1440 | H | F | EtSO$_2$ | H | H | C$_4$H$_6$N | H | H | 1 |
| 1441 | H | F | EtSO$_2$ | 2-F | H | C$_4$H$_6$N | H | H | 1 |
| 1442 | H | F | EtSO$_2$ | 2-Cl | H | C$_4$H$_6$N | H | H | 1 |
| 1443 | H | F | EtSO$_2$ | 2-CH$_3$ | H | C$_4$H$_6$N | H | H | 1 |

TABLE 1-continued (1)

| No. | R¹ | R² | R³ | R⁴ | R⁵ | R⁶ | R⁷ | R⁸ | n |
|---|---|---|---|---|---|---|---|---|---|
| 1444 | H | F | EtSO₂ | 2-CF₃ | H | C₄H₆N | H | H | 1 |
| 1445 | H | F | EtSO₂ | 2-H₂NCO | H | C₄H₆N | H | H | 1 |
| 1446 | H | F | EtSO₂ | 3-F | H | C₄H₆N | H | H | 1 |
| 1447 | H | F | EtSO₂ | 3-Cl | H | C₄H₆N | H | H | 1 |
| 1448 | H | F | EtSO₂ | 3-CH₃ | H | C₄H₆N | H | H | 1 |
| 1449 | H | F | EtSO₂ | 3-CF₃ | H | C₄H₆N | H | H | 1 |
| 1450 | H | F | EtSO₂ | 3-H₂NCO | H | C₄H₆N | H | H | 1 |
| 1451 | H | F | EtOOC-MS | H | H | C₄H₆N | H | H | 0 |
| 1452 | H | F | EtOOC-MS | 2-F | H | C₄H₆N | H | H | 0 |
| 1453 | H | F | EtOOC-MS | 2-Cl | H | C₄H₆N | H | H | 0 |
| 1454 | H | F | EtOOC-MS | 2-CH₃ | H | C₄H₆N | H | H | 0 |
| 1455 | H | F | EtOOC-MS | 2-CF₃ | H | C₄H₆N | H | H | 0 |
| 1456 | H | F | EtOOC-MS | 2-H₂NCO | H | C₄H₆N | H | H | 0 |
| 1457 | H | F | EtOOC-MS | 3-F | H | C₄H₆N | H | H | 0 |
| 1458 | H | F | EtOOC-MS | 3-Cl | H | C₄H₆N | H | H | 0 |
| 1459 | H | F | EtOOC-MS | 3-CH₃ | H | C₄H₆N | H | H | 0 |
| 1460 | H | F | EtOOC-MS | 3-CF₃ | H | C₄H₆N | H | H | 0 |
| 1461 | H | F | EtOOC-MS | 3-H₂NCO | H | C₄H₆N | H | H | 0 |
| 1462 | H | F | EtOOC-MS | H | H | C₄H₆N | H | H | 1 |
| 1463 | H | F | EtOOC-MS | 2-F | H | C₄H₆N | H | H | 1 |
| 1464 | H | F | EtOOC-MS | 2-Cl | H | C₄H₆N | H | H | 1 |
| 1465 | H | F | EtOOC-MS | 2-CH₃ | H | C₄H₆N | H | H | 1 |
| 1466 | H | F | EtOOC-MS | 2-CF₃ | H | C₄H₆N | H | H | 1 |
| 1467 | H | F | EtOOC-MS | 2-H₂NCO | H | C₄H₆N | H | H | 1 |
| 1468 | H | F | EtOOC-MS | 3-F | H | C₄H₆N | H | H | 1 |
| 1469 | H | F | EtOOC-MS | 3-Cl | H | C₄H₆N | H | H | 1 |
| 1470 | H | F | EtOOC-MS | 3-CH₃ | H | C₄H₆N | H | H | 1 |
| 1471 | H | F | EtOOC-MS | 3-CF₃ | H | C₄H₆N | H | H | 1 |
| 1472 | H | F | EtOOC-MS | 3-H₂NCO | H | C₄H₆N | H | H | 1 |
| 1473 | H | F | HOOC-MS | H | H | C₄H₆N | H | H | 0 |
| 1474 | H | F | HOOC-MS | 2-F | H | C₄H₆N | H | H | 0 |
| 1475 | H | F | HOOC-MS | 2-Cl | H | C₄H₆N | H | H | 0 |
| 1476 | H | F | HOOC-MS | 2-CH₃ | H | C₄H₆N | H | H | 0 |
| 1477 | H | F | HOOC-MS | 2-CF₃ | H | C₄H₆N | H | H | 0 |
| 1478 | H | F | HOOC-MS | 2-H₂NCO | H | C₄H₆N | H | H | 0 |
| 1479 | H | F | HOOC-MS | 3-F | H | C₄H₆N | H | H | 0 |
| 1480 | H | F | HOOC-MS | 3-Cl | H | C₄H₆N | H | H | 0 |
| 1481 | H | F | HOOC-MS | 3-CH₃ | H | C₄H₆N | H | H | 0 |
| 1482 | H | F | HOOC-MS | 3-CF₃ | H | C₄H₆N | H | H | 0 |
| 1483 | H | F | HOOC-MS | 3-H₂NCO | H | C₄H₆N | H | H | 0 |
| 1484 | H | F | HOOC-MS | H | H | C₄H₆N | H | H | 1 |
| 1485 | H | F | HOOC-MS | 2-F | H | C₄H₆N | H | H | 1 |
| 1486 | H | F | HOOC-MS | 2-Cl | H | C₄H₆N | H | H | 1 |
| 1487 | H | F | HOOC-MS | 2-CH₃ | H | C₄H₆N | H | H | 1 |
| 1488 | H | F | HOOC-MS | 2-CF₃ | H | C₄H₆N | H | H | 1 |
| 1489 | H | F | HOOC-MS | 2-H₂NCO | H | C₄H₆N | H | H | 1 |
| 1490 | H | F | HOOC-MS | 3-F | H | C₄H₆N | H | H | 1 |
| 1491 | H | F | HOOC-MS | 3-Cl | H | C₄H₆N | H | H | 1 |
| 1492 | H | F | HOOC-MS | 3-CH₃ | H | C₄H₆N | H | H | 1 |
| 1493 | H | F | HOOC-MS | 3-CF₃ | H | C₄H₆N | H | H | 1 |
| 1494 | H | F | HOOC-MS | 3-H₂NCO | H | C₄H₆N | H | H | 1 |

The preferred compounds in the above exemplification compounds are those of exemplification compound number of 14 (example 27), 21 (example 41), 22 (example 47), 23 (example 49), 25 (example 53), 26 (example 55), 53 (example 65), 54 (example 67), 81 (example 59), 82 (example 61), 85 (example 45), 109 (example 77), 110 (example 79), 137 (example 71), 138 (example 73), 507 (example 6), 518 (example 28), 523 (example 38), 525 (example 42), 526 (example 48), 527 (example 50), 529 (example 54), 530 (example 56), 557 (example 66), 558 (example 68), 585 (example 60), 586 (example 62), 589 (example 46), 613 (example 78), 614 (example 80), 641 (example 72), 642 (example 74), 1027 (example 89), 1029 (example 94), 1081 (example 86) and 1099 (example 87), and particularly preferred compounds include:

ethyl N-[3-(3-amidinophenyl)-2-(E)-propenyl]-N-[3-chloro-4-[1-(4-pyridyl)piperidin-4-yloxy]phenyl]sulfamoylacetate dihydrochloride (exemplification compound number 14, example 27), ethyl N-[3-(3-amidinophenyl)-2-(E)-propenyl]-N-[3-chloro-4-(1-formimidoylpiperidin-4-yloxy)phenyl]sulfamoylacetate dihydrochloride (exemplification compound number 22, example 47), ethyl N-[3-(3-amidinophenyl)-2-(E)-propenyl]-N-[3-chloro-4-[1-(1-iminopropyl)piperidin-4-yloxy]phenyl]sulfamoylacetate dihydrochloride (exemplification compound number 23, example 49), ethyl N-[3-(3-amidinophenyl)-2-(E)-propenyl]-N-[3-chloro-4-[1-(4,5-dihydro-3H-pyrrol-2-yl)piperidin-4-yloxy]phenyl]sulfamoylacetate dihydrochloride (exemplification compound number 25, example 53), ethyl N-[3-(3-amidinophenyl)-2-(E)-propenyl]-N-[4-[1-(4,5-dihydro-3H-pyrrol-2-yl)piperidin-4-yloxy]-3-methylphenyl]sulfamoylacetate dihydrochloride (exemplification compound number 53, example 65), ethyl N-[3-(3-amidinophenyl)-2-(E)-propenyl]-N-[4-[1-(4,5-dihydro-3H-pyrrol-2-yl)piperidin-4-yloxy]-3-trifluoromethylphenyl]sulfamoylacetate dihydrochloride (exemplification compound number 109, example 77), N-[3-(3-amidinophenyl)-2-(E)-propenyl]-N-[3-chloro-4-(1-isopropylpiperidin-4-yloxy)phenyl]sulfamoylacetic acid dihydrochloride (exemplification compound number 507, example 6), N-[3-(3-amidinophenyl)-2-(E)-propenyl]-N-[3-chloro-4-[1-(4-pyridyl)piperidin-4-yloxy]phenyl]sulfamoylacetic acid dihydrochloride (exemplification compound number 518, example 28), N-[3-(3-amidinophenyl)-2-(E)-propenyl]-N-[3-chloro-4-(1-cyclopentylpiperidin-4-yloxy)phenyl]sulfamoylacetic acid dihydrochloride (exemplification compound number 523, example 38), N-[3-(3-amidinophenyl)-2-(E)-propenyl]-N-[3-chloro-4-(indolizin-7-yloxy)phenyl]sulfamoylacetic acid dihydrochloride (exemplification compound number 525, example 42), N-[3-(3-amidinophenyl)-2-(E)-propenyl]-N-[3-chloro-4-(1-formimidoylpiperidin-4-yloxy)phenyl]sulfamoylacetic acid dihydrochloride (exemplification compound number 526, example 48), N-[3-(3-amidinophenyl)-2-(E)-propenyl]-N-[3-chloro-4-[1-(1-iminopropyl)piperidin-4-yloxy]phenyl]sulfamoylacetic acid dihydrochloride (exemplification compound number 527, example 50), N-[3-(3-amidinophenyl)-2-(E)-propenyl]-N-[3-chloro-4-[1-(4,5-dihydro-3H-pyrrol-2-yl)piperidin-4-yloxy]phenyl]sulfamoylacetic acid dihydrochloride (exemplification compound number 529, example 54), N-[3-(3-amidinophenyl)-2-(E)-propenyl]-N-[4-[1-(4,5-dihydro-3H-pyrrol-2-yl)piperidin-4-yloxy]-3-methylphenyl]sulfamoylacetic acid dihydrochloride (exemplification compound number 557, example 66), N-[3-(3-amidinophenyl)-2-(E)-propenyl]-N-[4-[1-(4,5-dihydro-3H-pyrrol-2-yl)piperidin-4-yloxy]phenyl]sulfamoylacetic acid dihydrochloride (exemplification compound number 585, example 60), N-[3-(3-amidinophenyl)-2-(E)-propenyl]-N-[4-(1-methylpiperidin-4-yloxy)-3-trifluoromethylphenyl]sulfamoylacetic acid dihydrochloride (exemplification compound number 589, example 46), N-[3-(3-amidinophenyl)-2-(E)-propenyl]-N-[4-[1-(4,5-dihydro-3H-pyrrol-2-yl)piperidin-4-yloxy]-3-trifluoromethylphenyl]sulfamoylacetic acid dihydrochloride (exemplification compound number 613, example 78), N-[3-(3-amidinophenyl)-2-(E)-propenyl]-N-[3-carbamoyl-4-[1-(4,5-dihydro-3H-pyrrol-2-yl)piperidin-4-yloxy]phenyl]sulfamoylacetic acid dihydrochloride (exemplification compound number 641, example 72), N-[3-(3-amidinophenyl)-2-(E)-propenyl]-N-[3-chloro-4-[1-(4,5-dihydrooxazol-2-yl)piperidin-4-yloxy]phenyl]sulfamoylacetic acid dihydrochloride (exemplification compound number 1027, example 89), N-[3-(3-amidinophenyl)-2-(E)-propenyl]-N-[4-[1-(4,5-dihydrooxazol-2-yl)piperidin-4-yloxy]phenyl]sulfamoylacetic acid dihydrochloride (exemplification compound number 1029, example 94), and N-[3-(3-amidinophenyl)-2-(E)-propenyl]-N-[3-chloro-4-[1-(N-ethylformimidoyl)piperidin-4-yloxy]phenyl]sulfamoylacetic acid dihydrochloride (exemplification compound number 1099, example 87).

The compound (1) of the present invention can be prepared by the following methods.

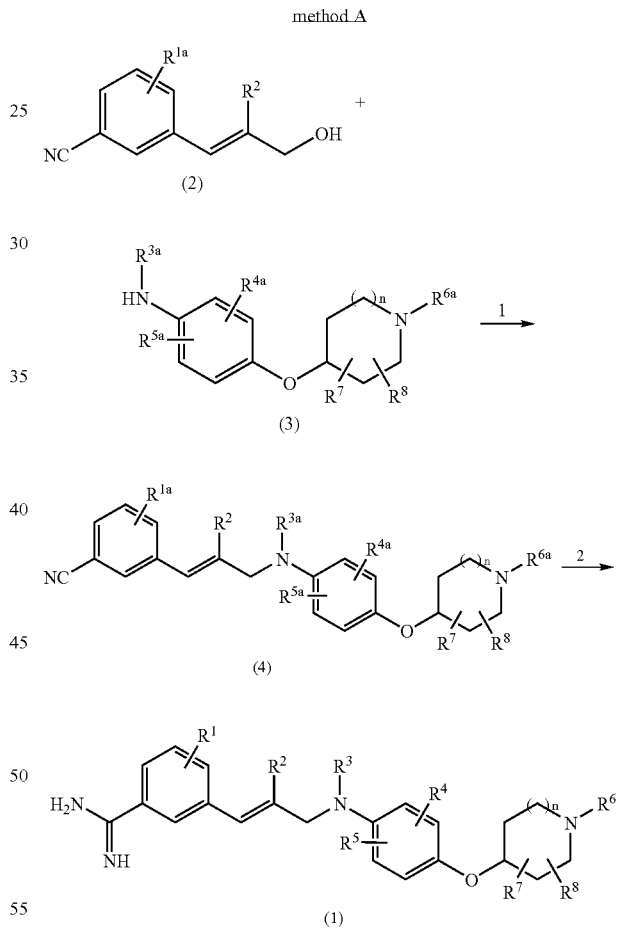

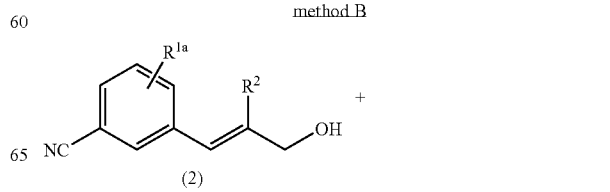

-continued
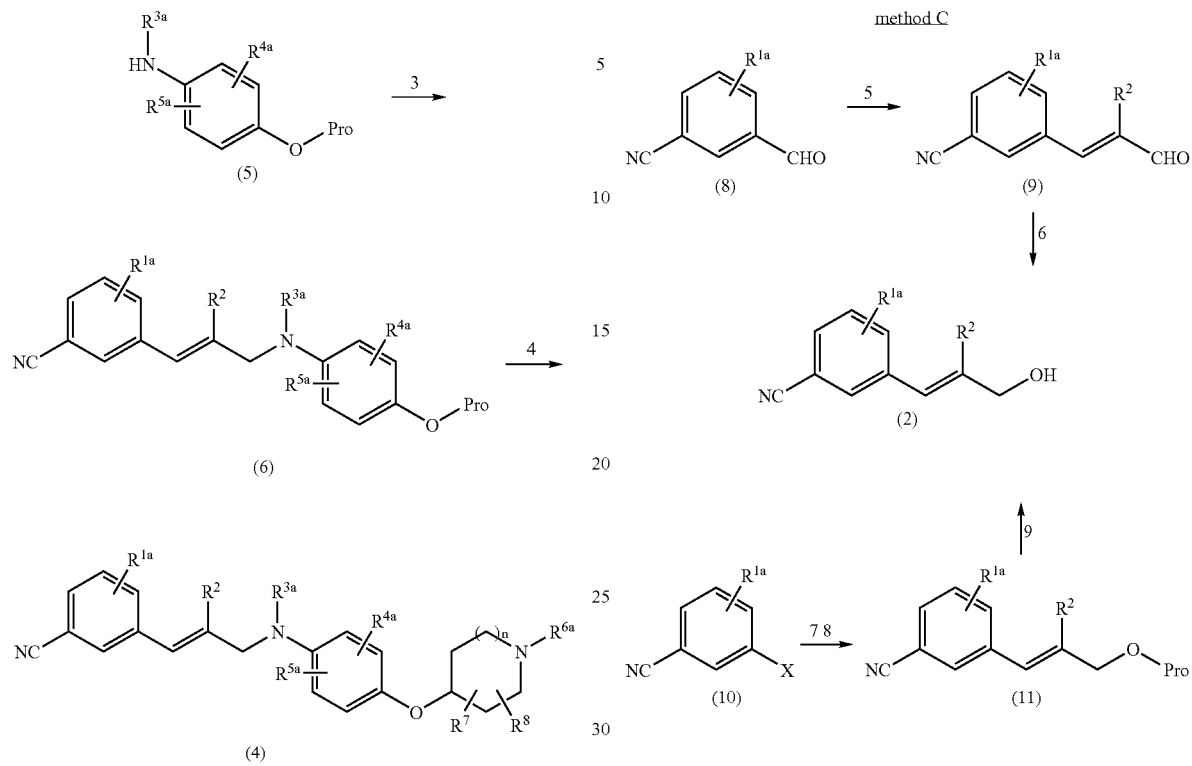
method C
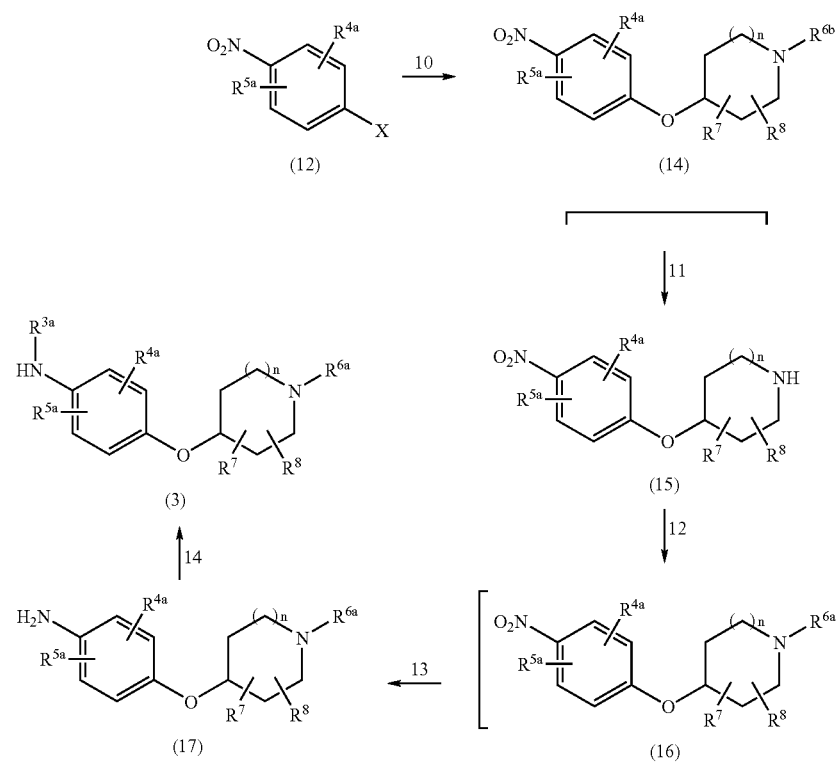
method D

In the above reaction schemes $R^1$, $R^2$, $R^3$, $R^4$, $R^5$, $R^6$, $R^7$, $R^8$ and n are as defined hereinbefore. $R^{1a}$ represents a protected $R^1$ group or a group having a protected substituent on $R^1$; $R^{3a}$ represents a protected $R^3$ group or a group having a protected substituent on $R^3$; $R^{4a}$ represents a protected $R^4$ group or a group having a protected substituent on $R^4$; $R^{5a}$ represents a protected $R^5$ group or a group having a protected substituent on $R^5$; and $R^{6a}$ represents a protected $R^6$ group or a group having a protected substituent on $R^6$. $R^{6b}$ represents $R^{6a}$ or an amino protecting group. Pro represents a hydroxyl protecting group. X represents a halogen atom or a hydroxyl group.

Method A is a process for the preparation of a compound (1) of the present invention.

(Step 1)

This step is a process for the preparation of a compound of general formula (4), which process is accomplished by a coupling reaction of a compound of general formula (2) with a compound of general formula (3) in the presence of a phosphine compound and an azo compound in an inert solvent.

There is no particular limitation on the solvent employed in Step 1 provided that it has no adverse effect on the reaction and it dissolves the starting materials at least to some extent. Such a solvent includes an aliphatic hydrocarbon such as hexane, heptane, ligroin or petroleum ether; an aromatic hydrocarbon such as benzene, toluene or xylene; a halogenated hydrocarbon such as dichloromethane, chloroform, carbon tetrachloride, dichloroethane, chlorobenzene or dichlorobenzene; or an ether such as diethyl ether, diisopropyl ether, tetrahydrofuran, dioxane, dimethoxyethane or di(ethylene glycol)dimethyl ether; preferably a halogenated hydrocarbon (dichloromethane) or an ether (particularly diethyl ether or tetrahydrofuran).

The phosphine compound employed in Step 1 includes, for example, a tri $C_1$–$C_6$ alkylphosphine such as trimethylphosphine, triethylphosphine, tripropylphosphine, tributylphosphine, tripentylphosphine, trihexylphosphine or the like; a tri $C_6$–$C_{10}$ arylphosphine such as triphenylphosphine, triindenylphosphine, trinaphthylphosphine or the like; or a tri $C_6$–$C_{10}$ arylphosphine wherein said aryl group may optionally be substituted with a $C_1$-$C_4$ alkyl group such as tolyldiphenylphosphine, tritolylphosphine, trimesitylphosphine, tributylphenylphosphine, tri-6-ethyl-2-naphthylphosphine or the like; preferably a tri $C_1$–$C_6$ alkylphosphine (particularly trimethylphosphine, triethylphosphine, tripropylphosphine or tributylphosphine) or a tri $C_6$–$C_{10}$ arylphosphine (particularly triphenylphosphine, triindenylphosphine or trinaphthylphosphine) and more preferably tributylphosphine or triphenylphosphine.

The azo compound employed in Step 1 includes, for example, azodicarbonyldipiperidine or a di $C_1$–$C_4$ alkyl azodicarboxylate such as dimethyl azodicarboxylate, diethyl azodicarboxylate, dipropyl azodicarboxylate or dibutyl azodicarboxylate; preferably azodicarbonyldipiperidine, dimethyl azodicarboxylate or diethyl azodicarboxylate.

The reaction temperature of Step 1 varies depending on the starting materials and reagents. It is usually in the range between −50° C. and 100° C., and preferably between 0° C. and 60° C.

The reaction time of Step 1 varies depending on the starting materials, reagents and the reaction temperature. It is usually in the range from 5 minutes to 24 hours and preferably from 10 minutes to 6 hours.

After the reaction, the desired compound of Step 1 can be isolated from the reaction mixture by a conventional procedure. For example, if insoluble material is present in the reaction mixture, the reaction mixture is filtered and the filtrate is concentrated to afford a residue. Or after the reaction, the reaction mixture is concentrated, then the residue is partitioned between water and a solvent immiscible with water such as benzene, ether, ethyl acetate or the like. The organic layer is washed with water, dried over anhydrous magnesium sulfate or the like and concentrated to give the desired product. If necessary, the product can be further purified by a conventional technique such as recrystallization, reprecipitation, chromatography or the like.

(Step 2)

This step is a process for the preparation of a compound of general formula (1), which process is accomplished by the following essential reaction:

reaction (a): conversion of a cyano group to an amidino group, and, if necessary, by an appropriate combination of the following optional reactions:

reaction (b): deprotection of a protected amino group, reaction (c): introduction of a desired substituent at an amino group, reaction (d): hydrolysis of an ester, and reaction (e): deprotection of a protected hydroxyl group.

The essential reaction (a), which is the conversion of a cyano group to an amidino group, can be accomplished by a conventional procedure known to those skilled in the art, for example, (1) by reaction of a starting material with an alcohol in the presence of an acid in the presence or absence of an inert solvent (preferably in the presence of an inert solvent), followed by ammonolysis of the product (an iminoether compound) or (2) by a reaction of a starting material with hydroxylamine in the presence or absence of a base in an inert solvent, followed by hydrolysis of the product (an amidoxime compound).

The reaction (a) (1) is a two step reaction and the first step reaction is the reaction of a nitrile group with an alcohol in the presence of an acid to afford an imino ether compound.

There is no particular limitation on the solvent employed in the first step of reaction (a)(1) provided that it has no adverse effect on the reaction and it dissolves the starting materials at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; an ester such as methyl acetate or ethyl acetate; a nitro compound such as nitromethane; an amide such as formamide, N,N-dimethylformamide, N,N-dimethylacetamide or N-methyl-2-pyrrolidinone; a sulfoxide such as dimethyl sulfoxide or sulfolane; or a mixture thereof; preferably an aromatic hydrocarbon (particularly benzene) or a halogenated hydrocarbon (particularly dichloromethane) and more preferably a halogenated hydrocarbon (particularly dichloromethane).

The reaction can also be carried out in an excess of the alcohol (for example methanol, ethanol, propanol, 2-propanol, butanol or isobutanol; preferably methanol or ethanol) as a solvent and a reagent and the reaction is usually conducted in an alcohol provided that there is no obstacle.

The acid employed in the first step of reaction (a)(1) includes, for example, a mineral acid such as hydrogen chloride, hydrochloric acid, hydrobromic acid, hydroiodic acid, nitric acid, perchloric acid, sulfuric acid or phosphoric acid; a sulfonic acid such as methanesulfonic acid, trifluoromethanesulfonic acid, ethanesulfonic acid, benzenesulfonic acid or p-toluenesulfonic acid; or a Lewis acid such as boron trifluoride, aluminum chloride, iron (III) chloride, zinc chloride or mercuric (II) chloride; preferably a mineral acid or a Lewis acid and more preferably hydrogen chloride.

The reaction temperature of the first step of reaction (a)(1) varies depending on the starting materials and reagents. It is usually in the range between $-10°$ C. and $100°$ C., and preferably between $0°$ C. and $50°$ C.

The reaction time of the first step of reaction (a)(1) varies depending on the starting materials, reagents and the reaction temperature. It is usually in the range from 10 minutes to 48 hours and preferably from 1 hour to 15 hours.

After the reaction the desired compound of the first step of reaction (a)(1) can be isolated from the reaction mixture by a conventional procedure (for example concentration of the reaction mixture). The product of reaction (a)(1) can be used in the next reaction without further isolation or purification.

The second step of reaction (a)(1) is an ammonolysis reaction of the iminoether compound obtained from the first step, which reaction is usually carried out in the presence of ammonium ion in an inert solvent.

There is no particular limitation on the solvent employed in the second step of reaction (a)(1) provided that it has no adverse effect on the reaction and it dissolves the starting materials at least to some extent. Such a solvent includes, for example an alcohol such as methanol, ethanol, propanol, 2-propanol, butanol or isobutanol; water; or a mixture of an alcohol and water. Preferred solvents are methanol, ethanol, water, aqueous methanol or aqueous ethanol, and particularly preferred solvents are aqueous methanol or aqueous ethanol.

The ammonium ion source in the second step of reaction (a)(1) includes, for example, aqueous ammonium solution, ammonium chloride, ammonium carbonate or a mixture thereof, preferably ammonium chloride.

The pH in the second step of reaction (a)(1) is in the range between neutral and weak basic. It is preferably adjusted between 7 and 9 by using aqueous ammonium solution and hydrochloric acid.

The reaction temperature of the second step of reaction (a)(1) varies depending on the starting materials and reagents. It is usually in the range between $-10°$ C. and $100°$ C., and preferably between $0°$ C. and $50°$ C.

The reaction time of the second step of reaction (a)(1) varies depending on the starting materials, reagents and the reaction temperature. It is usually in the range from 10 minutes to 48 hours and preferably from 1 hour to 15 hours.

After the reaction, the desired compound of the second step of reaction (a)(1) can be isolated from the reaction mixture by a conventional procedure. For example the reaction mixture is concentrated to afford the desired compound or the reaction mixture is partitioned between water and a solvent immiscible with water such as benzene, ether, ethyl acetate or the like; the organic layer is washed with water, dried over anhydrous magnesium sulfate or the like and concentrated to give the desired product. If necessary, the product can be further purified by a conventional technique such as recrystallization, reprecipitation, chromatography or the like.

The reaction (a) (2) is a two step reaction and the first step reaction is reaction of a nitrile group with a hydroxylamine in an inert solvent, if necessary in the presence of a base to afford an amidoxime compound.

There is no particular limitation on the solvent employed in the first step of reaction (a)(2) provided that it has no adverse effect on the reaction and it dissolves the starting materials at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; a nitro compound such as nitromethane; a nitrile such as acetonitrile or isobutyronitrile; an alcohol such as methanol, ethanol, propanol, 2-propanol, butanol or isobutanol; an amide such as formamide, N,N-dimethylformamide, N,N-dimethylacetamide or N-methyl-2-pyrrolidinone; a sulfoxide such as dimethyl sulfoxide or sulfolane; or water; preferably an alcohol (particularly methanol or ethanol).

The source of hydroxylamine employed in the first step of reaction (a)(2) includes an aqueous solution or an organic solution of hydroxylamine, or an acid addition salt of hydroxylamine.

There is no particular limitation on the base employed in the first step of reaction (a)(2) provided that when an acid addition salt of hydroxylamine is employed, it can neutralize said acid addition salt (when a solution of hydroxylamine is used, a base is not always used) and includes, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal acetate such as sodium acetate; an alkali metal hydroxide such as sodium hydroxide, potassium hydroxide or lithium hydroxide; an alkali metal alkoxide such as sodium methoxide, sodium ethoxide, potassium t-butoxide or lithium methoxide; or an organic base such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU), preferably an alkali metal carbonate (particularly sodium carbonate) or an alkali metal alkoxide (particularly potassium t-butoxide).

The reaction temperature of the first step of reaction (a)(2) varies depending on the starting materials and reagents. It is usually in the range between $0°$ C. and $150°$ C., and preferably between $50°$ C. and $100°$ C.

The reaction time of the first step of reaction (a)(2) varies depending on the starting materials, reagents and the reaction temperature. It is usually in the range from 1 hour to 24 hours and preferably from 5 hours to 12 hours.

After the reaction, the desired compound of the first step of reaction (a)(2) can be isolated from the reaction mixture by a conventional procedure (for example concentration of the reaction mixture). The product can be used next reaction without isolation and purification.

The second step of reaction (a)(2) is hydrogenolysis of the amidoxime compound obtained from the first step of reaction of (a)(2).

Before the hydrogenolysis the hydroxyl group is modified by addition of a removable group, which is usually an acetyl group and the acetylation reaction is carried out by using acetic anhydride in acetic acid, if necessary in a solvent.

There is no particular limitation on the solvent for the acetylation provided that it has no adverse effect on the reaction and it dissolves the starting materials at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; a nitro compound such as nitromethane; or nitrile such as acetonitrile or isobutyronitrile, preferably a halogenated hydrocarbon (particularly dichloromethane) or an ether (particularly tetrahydrofuran).

The reaction temperature of the acetylation varies depending on the starting materials and reagents. It is usually in the range between 0° C. and 150° C., and preferably between 10° C. and 50° C.

The reaction time of the acetylation varies depending on the starting materials, reagents and the reaction temperature. It is usually in the range from 1 hour to 24 hours and preferably from 5 hours to 12 hours.

After the reaction the desired compound of the acetylation can be isolated from the reaction mixture by a conventional procedure (for example concentration of the reaction mixture). The product can be used next reaction without further isolation or purification.

The hydrogenolysis of the amidoxime compound (deacetoxylation of the acetylated hydroxyl group) is usually conducted in the same solvent as that of the first step of reaction (a)(2) (acetylation). However, if necessary, the solvent of the first step of reaction (a)(2) (acetylation) is distilled off, the residue is dissolved in another solvent and then the hydrogenolysis (deacetoxylation) is conducted.

There is no particular limitation on the solvent for the hydrogenolysis provided that it has no adverse effect on the reaction and it dissolves the starting materials at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; a nitro compound such as nitromethane; a nitrile such as acetonitrile or isobutyronitrile; an alcohol such as methanol, ethanol, propanol, 2-propanol, butanol or isobutanol; an amide such as formamide, N,N-dimethylformamide, N,N-dimethylacetamide or N-methyl-2-pyrrolidinone; a sulfoxide such as dimethyl sulfoxide or sulfolane; a carboxylic acid such as formic acid or acetic acid; water; or a mixture thereof, preferably an alcohol (particularly methanol or ethanol), acetic acid or a mixture thereof.

There is no particular limitation on the catalyst of the catalytic reduction provided that it is usually used in catalytic reductions. Such a catalyst includes, for example, palladium black, palladium-charcoal, palladium hydroxide, palladium hydroxide-charcoal, Raney nickel, rhodium-aluminum oxide, palladium-barium sulfate, platinum oxide or platinum black; preferably palladium-charcoal.

The reaction temperature of the second step of reaction (a) (2) varies depending on the starting materials and reagents. It is usually in the range between −10° C. and 100° C., and preferably between 0° C. and 80° C.

The reaction time of the second step of reaction (a) (2) varies depending on the starting materials, reagents and the reaction temperature. It is usually in the range from 1 hour to 24 hours and preferably from 5 hours to 12 hours.

After the reaction, the desired compound of the second step of reaction (a) (2) can be isolated from the reaction mixture by a conventional procedure. For example the reaction mixture is filtered in order to remove the catalyst, followed by concentration of the filtrate to afford the desired compound or the filtrate is partitioned between water and a solvent immiscible with water such as benzene, ether, ethyl acetate or the like; the organic layer is washed with water, dried over anhydrous magnesium sulfate or the like and concentrated to give the desired product. If necessary, the product thus obtained can be further purified by a conventional technique such as recrystallization, reprecipitation, chromatography or the like.

The "deprotection of a protected amino group" as an optional reaction (b) of Step 2 is carried out according to a conventional procedure known to those skilled in the art as follows.

When the amino-protecting group is a formyl, acetyl, benzoyl, methoxycarbonyl, ethoxycarbonyl, t-butoxycarbonyl, 2-trimethylsilylethoxycarbonyl, 2-bromo-t-butoxycarbonyl, 2,2-dibromo-t-butoxycarbonyl, vinyloxycarbonyl, benzyloxycarbonyl, (1-phenyl)benzyloxycarbonyl, 9-anthrylmethyloxycarbonyl, p-methoxybenzyloxycarbonyl or p-nitrobenzyloxycarbonyl group, said protecting group can be removed by treatment of the compound having said protecting group with an acid in an inert solvent or in an aqueous solvent. In this reaction the desired product can be obtained as an acid addition salt.

The acid employed in this process includes, for example, hydrochloric acid, sulfuric acid, phosphoric acid, hydrobromic acid or trifluoroacetic acid; preferably hydrochloric acid, sulfuric acid, hydrobromic acid or trifluoroacetic acid.

There is no particular limitation on the solvent for this deprotection reaction provided that it has no adverse effect on the reaction and it dissolves the starting materials at least to some extent. Such a solvent includes, for example, an aliphatic hydrocarbon such as hexane, heptane, ligroin or petroleum ether; an aromatic hydrocarbon such as benzene, toluene or xylene; a halogenated hydrocarbon such as dichloromethane, chloroform, carbon tetrachloride, dichloroethane, chlorobenzene or dichlorobenzene; an ether such as diethyl ether, diisopropyl ether, tetrahydrofuran, dioxane; dimethoxyethane or di(ethylene glycol)dimethyl ether; an ester such as methyl acetate or ethyl acetate; an alcohol such as methanol, ethanol, propanol, 2-propanol or butanol; an amide such as formamide, N,N-dimethylformamide, N,N-dimethylacetamide or hexamethylphosphoric triamide; a sulfoxide such as dimethyl sulfoxide or sulfolane; an aliphatic acid such as formic acid or acetic acid; water; or a mixture thereof, preferably a halogenated hydrocarbon, an ether, an alcohol, an aliphatic acid or a mixture thereof and more preferably a halogenated hydrocarbon (particularly dichloromethane), an ether (particularly tetrahydrofuran or dioxane), an aliphatic acid (particularly acetic acid), or an alcohol (particularly methanol or ethanol), water or a mixture thereof.

The reaction temperature of the deprotection reaction varies depending on the starting materials, solvent and acid employed. It is usually in the range between −10° C. and 150° C., and preferably between 0° C. and 100° C.

The reaction time of the deprotection reaction varies depending on the starting materials, solvent and acid employed. It is usually in the range from 5 minutes to 48 hours and preferably from 10 minutes to 15 hours.

After the reaction, a desired compound of (b) process of step 2 can be isolated from the reaction mixture by a conventional procedure. For example the reaction mixture is filtered to afford the desired compound as a precipitate; if necessary the reaction mixture is neutralized, and the neutralized mixture is concentrated to dryness to afford the desired compound; or water is added to the reaction mixture, if necessary the aqueous mixture is neutralized, the aqueous or neutralized mixture is extracted with a solvent immiscible with water such as benzene, ether, ethyl acetate or the like, the organic layer is washed with water, dried over anhydrous magnesium sulfate or the like and concentrated to give the desired product. If necessary, the product thus obtained can be further purified by a conventional technique such as recrystallization, reprecipitation, chromatography or the like.

When the amino protecting group is an alkanoyl, arylcarbonyl, alkoxycarbonyl, alkenyloxycarbonyl, aryldicarbonyl, aralkyl or aralkyloxycarbonyl group, said protecting group can be removed by treatment of the compound having said protecting group with a base in an inert solvent or an aqueous solvent.

The base employed in this step includes, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; an alkali metal alkoxide such as sodium methoxide, sodium ethoxide, potassium t-butoxide or lithium methoxide; an alkali metal mercaptan such as sodium methylmercaptan or sodium ethylmercaptan or an organic base such as hydrazine, methylamine, dimethylamine, ethylamine, triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU), preferably an alkali metal carbonate (particularly sodium carbonate or potassium carbonate), an alkali metal hydroxide (particularly sodium hydroxide or potassium hydroxide), an alkali metal alkoxide (particularly sodium methoxide, sodium ethoxide or potassium t-butoxide) or an organic base (particularly hydrazine or methylamine).

There is no particular limitation on the solvent for this deprotection reaction provided that it has no adverse effect on the reaction and it dissolves the starting materials at least to some extent. Such a solvent includes, for example, an aliphatic hydrocarbon such as hexane, heptane, ligroin or petroleum ether; an aromatic hydrocarbon such as benzene, toluene or xylene; a halogenated hydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol or butanol; an amide such as formamide, N,N-dimethylformamide, N,N-dimethylacetamide or hexamethylphosphoric triamde; a sulfoxide such as dimethyl sulfoxide or sulfolane; water or a mixture of water and the organic solvent indicated hereinbefore, preferably a halogenated hydrocarbon, an ether, an alcohol or a mixture of water and the organic solvent indicated hereinbefore and more preferably an ether (particularly tetrahydrofuran or dioxane), an alcohol (particularly methanol or ethanol) or a mixture of water and the solvent indicated hereinbefore.

The reaction temperature of the deprotection reaction varies depending on the starting materials, solvent and base employed. It is usually in the range between −10° C. and 50° C., and preferably between −5° C. and 10° C.

The reaction time of the deprotection reaction varies depending on the starting materials, solvent and base employed. It is usually in the range from 5 minutes to 20 hours and preferably from 10 minutes to 3 hours.

After the reaction, the desired compound of the deprotection reaction can be isolated from the reaction mixture by a conventional procedure. For example the precipitate in the reaction mixture is filtered to afford the desired compound; if necessary after the reaction mixture is neutralized with an acid, the neutralized mixture is concentrated to afford the desired compound; water is added to the reaction mixture, the pH of the mixture is adjusted to afford the desired compound as a precipitate; or the pH-adjusted aqueous mixture is extracted with a solvent immiscible with water such as benzene, ether, ethyl acetate or the like, the organic layer is washed with water, the organic layer is dried over anhydrous magnesium sulfate or the like and then the organic layer is concentrated to afford the desired compound. If necessary, the product thus obtained can be further purified by a conventional technique such as recrystallization, reprecipitation, chromatography or the like.

When the amino protecting group is a t-butoxycarbonyl group, said protecting group can be removed by treatment of the compound having said protecting group with a silyl compound or a Lewis acid in an inert solvent.

The silyl compound employed in this reaction includes, for example, trimethylsilyl chloride, trimethylsilyl iodide or trimethylsilyl trifluoromethanesulfonate. The Lewis acid employed in this reaction includes, for example, aluminum chloride or the like.

There is no particular limitation on the solvent for this deprotection reaction provided that it has no adverse effect on the reaction and it dissolves the starting materials at least to some extent. Such a solvent includes, for example, a halogenated hydrocarbon such as dichloromethane, chloroform or carbon tetrachloride; an ether such as diethyl ether, tetrahydrofuran or dioxane; or a nitrile such as acetonitrile, preferably a halogenated hydrocarbon (particularly dichloromethane or chloroform) or a nitrile (particularly acetonitrile).

The reaction temperature of the deprotection reaction varies depending on the starting materials, reagents and solvent employed. It is usually in the range between −20° C. and 100° C., and preferably between 0° C. and 50° C.

The reaction time of the deprotection reaction varies depending on the starting materials, reagents and solvent employed. It is usually in the range from 10 minutes to 10 hours and preferably from 30 minutes to 3 hours.

After the reaction, the desired compound of the deprotection reaction can be isolated from the reaction mixture by a conventional procedure. For example the reaction mixture is concentrated, to the residue is added water, the aqueous mixture is basified, followed by filteration to afford the desired product or the aqueous mixture is extracted with a solvent immiscible with water such as benzene, ether, ethyl acetate or the like, the organic layer is washed with water, dried over anhydrous magnesium sulfate or the like and concentrated to give the desired product. If necessary, the product thus obtained can be further purified by a conventional technique such as recrystallization, reprecipitation, chromatography or the like.

When the amino protecting group is an allyloxycarbonyl group, the protecting group can be removed by the same procedure as that of an aralkyl group or the like, for example catalytic reduction, that is, by treatment of the compound having said protecting group with palladium and triphenylphosphine or nickel tetracarbonyl.

When the amino protecting group is an aralkyl or $C_7$–$C_{11}$ aralkyloxycarbonyl group, said protecting group can usually be removed by treatment of the compound having said protecting group with a reduction reagent (preferably catalytic reduction in the presence of a catalyst) or with an oxidizing reagent in an inert solvent.

There is no particular limitation on the solvent for the catalytic reduction provided that it has no adverse effect on the reaction. Such a solvent includes, for example, an aliphatic hydrocarbon such as hexane or cyclohexane; an aromatic hydrocarbon such as benzene, toluene or xylene; an ether such as diethyl ether, tetrahydrofuran or dioxane; an ester such as ethyl acetate or propyl acetate; an alcohol such as methanol, ethanol or 2-propanol; an aliphatic acid such as formic acid or acetic acid; or a mixture of water and the solvent indicated hereinbefore, preferably an aliphatic hydrocarbon, an aromatic hydrocarbon, an ether, an ester, an alcohol, an aliphatic acid or a mixture of water and the solvent indicated hereinbefore, and more preferably an alcohol (particularly methanol or ethanol), an aliphatic acid (particularly formic acid or acetic acid) or a mixture of water and the solvent indicated hereinbefore.

There is no particular limitation on the catalyst for the catalytic reduction provided that it can usually be used in catalytic reduction. Such a catalyst includes, for example, palladium-charcoal, Raney nickel, rhodium-aluminum oxide, or palladium-barium sulfate; preferably palladium-charcoal or Raney nickel.

There is no particular limitation on the hydrogen pressure in the catalytic reduction. The pressure is usually in the range between 1 and 10 atmospheric pressure, preferably 1 atmospheric pressure.

The reaction temperature of the catalytic reduction varies depending on the starting materials, solvent, reducing agent employed and the like and is usually in the range between 0° C. and 100° C., and preferably between 10° C. and 50° C.

The reaction time of the catalytic reduction varies depending on the starting materials, solvent, reducing agent employed, the reaction temperature and the like and is usually in the range from 15 minutes to 24 hours; and preferably from 30 minutes to 12 hours.

After the reaction the desired compound of the catalytic reduction can be isolated from the reaction mixture by a conventional procedure. For example the reaction mixture is filtered in order to remove the catalyst in the reaction mixture, the filtrate is concentrated to afford the desired compound; water is added to the reaction mixture, the aqueous mixture is basified and then the basified mixture is filtered to afford the desired compound as a precipitate; or the resulting mixture is extracted with a solvent immiscible with water such as benzene, ether, ethyl acetate or the like, the organic layer is washed with water, dried over anhydrous magnesium sulfate or the like and concentrated to give the desired product. If necessary, the product thus obtained can be further purified by a conventional technique such as recrystallization, reprecipitation, chromatography or the like.

There is no particular limitation on the solvent for this deprotection reaction with an oxidizing agent provided that it has no adverse effect on the reaction. Such a solvent includes, for example, a ketone such as acetone; a halogenated hydrocarbon such as dichloromethane, chloroform or carbon tetrachloride; a nitrile such as acetonitrile; an ether such as diethyl ether, tetrahydrofuran or dioxane; an amide such as N,N-dimethylformamide, N,N-dimethylacetamide or hexamethylphosphoric triamide; a sulfoxide such as dimethyl sulfoxide; or a mixture of water and the organic solvent indicated hereinbefore, preferably a ketone, a halogenated hydrocarbon, a nitrile, an ether, an amide, a sulfoxide or a mixture of water and the organic solvent indicated hereinbefore and more preferably a ketone (particularly acetone), a halogenated hydrocarbon (particularly dichloromethane), a nitrile (particularly acetonitrile), an amide (particularly hexamethylphosphoric triamide), a sulfoxide (particularly dimethyl sulfoxide) or a mixture of water and the organic solvent indicated hereinbefore.

The oxidizing agent employed in the deprotection reaction includes, for example, potassium persulfate, sodium persulfate, ceric ammonium nitrate (CAN) or 2,3-dichloro-5,6-dicyano-p-benzoquinone (DDQ), and preferably CAN or DDQ.

The reaction temperature of the oxidative deprotection reaction varies depending on the starting material, solvent and oxidizing reagent employed. It is usually in the range between 0° C. and 150° C., and preferably between 10° C. and 50° C.

The reaction time of the oxidative deprotection reaction varies depending on the starting material, solvent and oxidizing reagent employed. It is usually in the range from 15 minutes to 24 hours and preferably from 30 minutes to 12 hours.

After the reaction, the desired compound of the oxidative deprotection reaction can be isolated from the reaction mixture by a conventional procedure. For example the reaction mixture is filtered in order to remove the oxidizing reagent in the reaction mixture, the filtrate is concentrated to afford the desired product; water is added to the reaction mixture, the aqueous mixture is basified and then the basified mixture is filtered to afford the desired compound as a precipitate; or the resulting mixture is extracted with a solvent immiscible with water such as benzene, ether, ethyl acetate or the like, the organic layer is washed with water, dried over anhydrous magnesium sulfate or the like and concentrated to give the desired product. If necessary, the product thus obtained can be further purified by a conventional technique such as recrystallization, reprecipitation, chromatography or the like.

The optional reaction (c) is a process for "introduction of a desired substituent at an amino group", which process is accomplished by reaction of the starting material with a reagent of formula $R^6$-Xa (wherein Xa is a halogen atom (particularly a fluorine or chlorine atom) or an alkoxy group (particularly a methoxy or ethoxy group)) in an inert solvent in the presence or absence of a base.

There is no particular limitation on the solvent employed in the reaction (c) provided that it has no adverse effect on the reaction and it dissolves the starting materials at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; a nitro compound such as nitromethane; a nitrile such as acetonitrile or isobutyronitrile; an alcohol such as methanol, ethanol, propanol, 2-propanol, butanol or isobutanol; an amide such as formamide, N,N-dimethylformamide, N,N-dimethylacetamide or N-methyl-2-pyrrolidinone; or a sulfoxide such as dimethyl sulfoxide or sulfolane; preferably an alcohol (particularly ethanol).

The base employed in the reaction (c) includes, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydroxide such as sodium hydroxide, potassium hydroxide or lithium hydroxide; or an organic base such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU), preferably an alkali metal carbonate (particularly sodium carbonate or potassium carbonate) or an organic base (particularly triethylamine).

The reaction temperature of the reaction (c) varies depending on the starting materials, reagents and the like. It is usually in the range between −10° C. and 100° C., and preferably between 0° C. and 50° C.

The reaction time of the reaction (c) varies depending on the starting materials, reagents and the reaction temperature. It is usually in the range from 1 hour to 48 hours and preferably from 5 hours to 15 hours.

After the reaction, the desired compound of the reaction (c) can be isolated from the reaction mixture by a conventional procedure. For example the reaction mixture is concentrated to afford the desired compound or the reaction mixture is partitioned between water and a solvent immiscible with water such as benzene, ether, ethyl acetate or the like, the organic layer is washed with water, dried over anhydrous magnesium sulfate or the like and concentrated to give the desired product. If necessary, the product thus obtained can be further purified by a conventional technique such as recrystallization, reprecipitation, chromatography or the like.

The optional reaction (d) is a process for "hydrolysis of an ester", which process is accomplished by hydrolysis of the starting material with an acid or base in the presence or absence of a solvent according to a conventional procedure known to those skilled in the art, preferably by hydrolysis of said compound with an acid.

There is no particular limitation on the solvent employed in the reaction (d) provided that it has no adverse effect on the reaction and it dissolves the starting materials at least to some extent. Such a solvent includes, for example, an alcohol such as methanol, ethanol, propanol, 2-propanol, butanol or isobutanol; or a mixture of water and the alcohol indicated hereinbefore; preferably aqueous methanol or aqueous ethanol.

The acid employed in the reaction (d) includes, for example, a mineral acid such as hydrochloric acid, hydrobromic acid, hydroiodic acid, nitric acid, perchloric acid, sulfuric acid or phosphoric acid; a sulfonic acid such as methanesulfonic acid, trifluoromethanesulfonic acid, ethanesulfonic acid, benzenesulfonic acid or p-toluenesulfonic acid; or a carboxylic acid such as fumaric acid, succinic acid, citric acid, tartaric acid, oxalic acid, maleic acid or the like; preferably a mineral acid (particularly hydrochloric acid).

The base employed in the reaction (d) includes, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydroxide such as sodium hydroxide, potassium hydroxide or lithium hydroxide; preferably sodium hydroxide.

The reaction temperature of the reaction (d) varies depending on the starting materials, reagents employed and the like. When an acid is used, it is usually in the range between 0° C. and 150° C., and preferably between 50° C. and 100° C. When a base is used, it is usually in the range between −10° C. and 50° C., and preferably between −5° C. and 10° C.

The reaction time of the reaction (d) varies depending on the starting materials, reagents employed and the temperature. When an acid is used, it is usually in the range from 30 minutes to 48 hours and preferably from 3 hours to 10 hours. When a base is used, it is usually in the range from 5 minutes to 10 hours and preferably from 10 minutes to 3 hours.

After the reaction, the desired compound of the reaction (d) can be isolated from the reaction mixture by a conventional procedure. For example the reaction mixture is concentrated to afford the desired compound; or the reaction mixture is acidified by using an acid (for example hydrochloric acid) and the acidified mixture is filtered to afford the desired product as a precipitate; or the acidified mixture is partitioned between water and a solvent immiscible with water such as benzene, ether, ethyl acetate or the like, the organic layer is washed with water, dried over anhydrous magnesium sulfate or the like and concentrated to give the desired product. In addition carbon dioxide can be passed through the aqueous reaction mixture or sodium carbonate or potassium carbonate is added to the aqueous reaction mixture to afford a carbonate salt of the desired compound. If necessary, the product thus obtained can be further purified by a conventional technique such as recrystallization, reprecipitation, chromatography or the like.

The optional reaction (e) is a process for "deprotection of a protected hydroxyl group", which process is accomplished according to a procedure described by T. W. Greene & P. G. M. Wuts in Protective Groups in Organic Synthesis, $3^{rd}$ edition, John Wiley & Sons, Inc.

When the hydroxyl protecting group is a formyl, acetyl, benzoyl, tetrahydropyran-2-yl, 3-bromotetrahydropyran-2-yl, 4-methoxytetrahydropyran-4-yl, tetrahydrothiopyran-2-yl, 4-methoxytetrahydrothiopyran-4-yl, tetrahydrofuran-2-yl, tetrahydrothiofuran-2-yl, methoxymethyl, 1,1-dimethyl-1-methoxymethyl, ethoxymethyl, propoxymethyl, isopropoxymethyl, butoxymethyl, t-butoxymethyl, 2-methoxyethoxymethyl, 2,2,2-trichloroethoxymethyl, bis(2-chloroethoxy)methyl, 1-ethoxyethyl, 1-(isopropoxy)ethyl, methoxycarbonyl, ethoxycarbonyl, t-butoxycarbonyl, 2-trimethylsilylethoxycarbonyl, 2-bromo-t-butoxycarbonyl, 2,2-dibromo-t-butoxycarbonyl, vinyloxycarbonyl, benzyloxycarbonyl, (1-phenyl)benzyloxycarbonyl, 9-anthrylmethyloxycarbonyl, p-methoxybenzyloxycarbonyl, or p-nitrobenzyloxycarbonyl group, such a protecting group can be removed by treatment of a compound having said protecting group with an acid in an inert solvent or an aqueous solvent.

The acid employed in the reaction (e) is, for example, hydrochloric acid, sulfuric acid, phosphoric acid, hyrobromic acid or trifluoroacetic acid, preferably hydrochloric acid, sulfuric acid, hyrobromic acid or trifluoroacetic acid.

There is no particular limitation on the solvent employed in the reaction (e) provided that it has no adverse effects on the reaction and it dissolves the starting materials at least to some extent. Such a solvent includes, for example, an aliphatic hydrocarbon such as hexane, heptane, ligroin or petroleum ether; an aromatic hydrocarbon such as benzene, toluene or xylene; a halogenated hydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an ester such as methyl acetate or ethyl acetate; an alcohol such as methanol, ethanol, propanol, 2-propanol or butanol; an amide such as formamide, N,N-dimethylformamide, N,N-dimethylacetamide or hexamethylphosphoric triamide; a sulfoxide such as dimethyl sulfoxide or sulfolane; an aliphatic acid such as formic acid or acetic acid, water or a mixture of water and an organic solvent indicated hereinbefore, preferably a halogenated hydrocarbon, an ether, an ester, an alcohol, an aliphatic acid or a mixture of water and an organic solvent indicated hereinbefore and more preferably a halogenated hydrocarbon (particularly dichloromethane), an ether (particularly tetrahydrofuran or dioxane), an ester (particularly ethyl acetate), an aliphatic acid (particularly acetic acid), water or a mixture of water and an organic solvent indicated hereinbefore.

The reaction temperature of the reaction (e) varies depending on the starting materials, solvents and acid employed. It is usually in the range between −10° C. and 150° C., preferably between 0° C. and 60° C.

The reaction time of the reaction (e) varies depending on the starting material, solvent and acid employed. It is usually in the range from 5 minutes to 20 hours, preferably from 10 minutes to 12 hours.

After the reaction, the desired compound of the reaction (e) can be isolated from the reaction mixture by a conventional procedure. For example the reaction mixture, if necessary is neutralized, is concentrated to afford the desired compound; or the reaction mixture is partitioned between water and a solvent immiscible with water such as benzene, ether, ethyl acetate or the like, the organic layer is washed with water, dried over anhydrous magnesium sulfate or the like and concentrated to give the desired product. If necessary, the product thus obtained can be further purified by a conventional technique such as recrystallization, reprecipitation, chromatography or the like.

When the hydroxyl protecting group is an alkanoyl, carboxylated alkanoyl, haloalkanoyl, alkoxyalkanoyl, unsaturated alkanoyl, arylcarbonyl, haloarylcarbonyl, alkylated arylcarbonyl, carboxylated arylcarbonyl, nitrated arylcarbonyl, alkoxycarbonylated arylcarbonyl or an arylated arylcarbonyl, such a protecting group can be removed by treatment of a compound having said protecting group with a base in an inert solvent or an aqueous solvent.

The base employed in the reaction (e) includes, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; an alkali metal alkoxide such as sodium methoxide, sodium ethoxide, potassium t-butoxide or lithium methoxide; an alkali metal mercaptan such as sodium methylmercaptan or sodium ethylmercaptan or an organic base such as hydrazine, methylamine, dimethylamine, ethylamine, triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU), preferably an alkali metal carbonate (particularly sodium carbonate or potassium carbonate), an alkali metal hydroxide (particularly sodium hydroxide or potassium hydroxide), an alkali metal alkoxide (particularly sodium methoxide, sodium ethoxide or potassium t-butoxide) or an organic base (particularly hydrazine or methylamine).

There is no particular limitation on the solvent employed in the reaction (e) provided that it has no adverse effect on the reaction and it dissolves the starting material at least to some extent. Such a solvent includes, for example, an aliphatic hydrocarbon such as hexane, heptane, ligroin or petroleum ether; an aromatic hydrocarbon such as benzene, toluene or xylene; a halogenated hydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol or butanol; an amide such as formamide, N,N-dimethylformamide, N,N-dimethylacetamide or hexamethylphosphoric triamide; a sulfoxide such as dimethyl sulfoxide or sulfolane; or a mixture of water and the solvent indicated hereinbefore, preferably a halogenated hydrocarbon, an ether, an alcohol, or a mixture of water and a solvent indicated hereinbefore and more preferably an ether (particularly tetrahydrofuran or dioxane), an alcohol (particularly methanol or ethanol), or a mixture of water and the solvent indicated hereinbefore.

The reaction temperature of the reaction (e) varies depending on the starting materials, solvents and base employed. It is usually in the range between −10° C. and 150° C., and preferably between 0° C. and 50° C.

The reaction time of the reaction (e) varies depending on the starting material, solvent and base employed. It is usually in the range from 50 minutes to 20 hours and preferably from 10 minutes to 5 hours.

After the reaction, the desired compound of the reaction (e) can be isolated from the reaction mixture by a conventional procedure. For example the reaction mixture is concentrated to afford the desired compound; then the reaction mixture is partitioned between water and a solvent immiscible with water such as benzene, ether, ethyl acetate or the like, the organic layer is washed with water, dried over anhydrous magnesium sulfate or the like and concentrated to give the desired product. If necessary, the product thus obtained can be further purified by a conventional technique such as recrystallization, reprecipitation, chromatography or the like.

When the hydroxyl protecting group is an aralkyl or aralkyloxycarbonyl group, such a group can preferably be removed by treatment of the compound having said protecting group with a reducing reagent (preferably catalytic reduction in the presence of a catalyst) or an oxidizing reagent in an inert solvent.

There is no particular limitation on the solvent for the catalytic reductive deprotection reaction provided that it has no adverse effect on the reaction. Such a solvent includes, for example, an aliphatic hydrocarbon such as hexane or cyclohexane; an aromatic hydrocarbon such as benzene, toluene or xylene; an ether such as diethyl ether, tetrahydrofuran or dioxane; an ester such as ethyl acetate or propyl acetate; an alcohol such as methanol, ethanol or 2-propanol; an aliphatic acid such as formic acid or acetic acid; or a mixture of water and the organic solvent indicated hereinbefore, preferably an aliphatic hydrocarbon, an aromatic hydrocarbon, an ether, an ester, an alcohol, an aliphatic acid or a mixture of water and an organic solvent indicated hereinbefore, and more preferably an alcohol (particularly methanol or ethanol), an aliphatic acid (particularly formic acid or acetic acid) or a mixture of water and the organic solvent indicated hereinbefore.

There is no particular limitation on the catalyst for the catalytic reduction provided that it can usually be used in catalytic reduction. Such a catalyst includes, for example, palladium-charcoal, Raney nickel, rhodium-aluminum oxide, or palladium-barium sulfate and preferably palladium-charcoal or Raney nickel.

There is no particular limitation on the pressure of hydrogen in the catalytic reduction. The pressure is usually in the range between 1 and 10 atmospheric pressure and preferably 1 atmospheric pressure.

The reaction temperature of the catalytic reduction varies depending on the starting materials, solvents, reducing agent employed and the like. It is usually in the range between 0° C. and 100° C., and preferably between 10° C. and 50° C.

The reaction time of the catalytic reduction varies depending on the starting materials, solvents, reducing agent employed, the reaction temperature and the like. It is usually in the range from 15 minutes to 10 hours and preferably from 30 minutes to 3 hours.

After the reaction, the desired compound of the catalytic reduction can be isolated from the reaction mixture by a conventional procedure. For example the reaction mixture is filtered in order to remove the catalyst in the reaction mixture, the filtrate is concentrated, the residue is partitioned between water and a solvent immiscible with water such as benzene, ether, ethyl acetate or the like, the organic layer is washed with water, dried over anhydrous magnesium sulfate or the like and concentrated to give the desired product. If necessary, the product thus obtained can be further purified by a conventional technique such as recrystallization, reprecipitation, chromatography or the like.

There is no particular limitation on the solvent for the deprotection reaction with an oxidizing agent provided that it has no adverse effect on the reaction. Such a solvent includes, for example, a ketone such as acetone; a halogenated hydrocarbon such as dichloromethane, chloroform or carbon tetrachloride; a nitrile such as acetonitrile; an ether such as diethyl ether, tetrahydrofuran or dioxane; an amide such as N,N-dimethylformamide, N,N-dimethylacetamide or hexamethylphosphoric triamide; a sulfoxide such as dimethyl sulfoxide; or a mixture of water and the organic solvent indicated hereinbefore, preferably a ketone, a halogenated hydrocarbon, a nitrile, an ether, an amide, a sulfoxide or a mixture of water and an organic solvent indicated hereinbefore and more preferably a ketone (particularly acetone), a halogenated hydrocarbon (particularly dichloromethane), a nitrile (particularly acetonitrile), an amide (particularly hexamethylphosphoric triamide), a sulfoxide (particularly dimethyl sulfoxide) or a mixture of water and the organic solvent indicated hereinbefore.

The oxidizing agent employed in the deprotection reaction includes, for example, potassium persulfate, sodium persulfate, ceric ammonium nitrate (CAN) or 2,3-dichloro-5,6-dicyano-p-benzoquinone (DDQ), and preferably CAN or DDQ.

The reaction temperature of the oxidative deprotection reaction varies depending on the starting materials, solvent and oxidizing reagent employed and the like. It is usually in the range between 0° C. and 150° C., and preferably between 10° C. and 50° C.

The reaction time of the oxidative deprotection reaction varies depending on the starting materials, solvent and oxidizing reagent employed and the like. It is usually in the range from 15 minutes to 24 hours and preferably from 30 minutes to 5 hours.

After the reaction, the desired compound of the oxidative deprotection reaction can be isolated from the reaction mixture by a conventional procedure. For example the reaction mixture is filtered in order to remove the oxidizing reagent in the reaction mixture, the filtrate is concentrated, the residue is partitioned between water and a solvent immiscible with water such as benzene, ether, ethyl acetate or the like, the organic layer is washed with water, dried over anhydrous magnesium sulfate or the like and concentrated to give the desired product. If necessary, the product thus obtained can be further purified by a conventional technique such as recrystallization, reprecipitation, chromatography or the like.

When the hydroxyl protecting group is a silyl group, such a protecting group can usually be removed by a reaction of a compound having said protecting group with a compound which forms a fluoride ion, in an inert solvent.

There is no particular limitation on the solvent employed in the deprotection of a silyl group provided that it has no adverse effect on the reaction and it dissolves the starting material at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether, preferably an ether (particularly tetrahydrofuran).

The compound, which forms a fluoride anion and is employed in the deprotection reaction, includes, for example, tetrabutylammonium fluoride, hydrofluoric acid, hydrofluoric acid-pyridine or potassium fluoride and preferably tetrabutylammonium fluoride.

The reaction temperature of the deprotection varies depending on the starting materials, reagents employed and the like. It is usually in the range between −50° C. and 100° C., and preferably between −10° C. and 50° C.

The reaction time of the deprotection varies depending on the starting materials, reagents employed and the temperature. It is usually in the range from 5 minutes to 12 hours and preferably from 10 minutes to 1 hour.

After the reaction, the desired compound of the deprotection reaction of a silyl group can be isolated from the reaction mixture by a conventional procedure. For example the reaction mixture is partitioned between water and a solvent immiscible with water such as benzene, ether, ethyl acetate or the like, the organic layer is washed with water, dried over anhydrous magnesium sulfate or the like and concentrated to give the desired product. If necessary, the product thus obtained can be further purified by a conventional technique such as recrystallization, reprecipitation, chromatography or the like.

Method B is a Process for Preparation of a Compound of General Formula (4)

(Step 3)

Step 3 is a process for the preparation of a compound of general formula (6), which process can be accomplished by a coupling reaction between a compound of general formula (2) and a compound of general formula (5) in the presence of a phosphine compound and an azo compound in an inert solvent.

Step 3 can be carried out by the same procedure as that described in Step 1.

(Step 4)

Step 4 is a process for the preparation of a compound of general formula (4), which process can be accomplished by deprotection of a protected hydroxyl group [reaction (a)], and by coupling a reaction between the product from reaction (a) and a compound of general formula (7) [wherein $R^{6a}$, $R^7$, $R^8$ and n are as defined hereinbefore, reaction (b)].

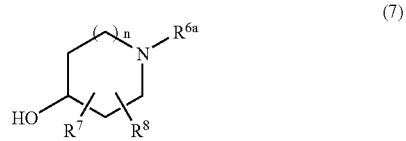

(7)

The reaction (a) can be carried out by the same procedure as that described in reaction (e) of Step 2, and reaction (b) can be conducted by the same procedure as that described in Step 1.

Method C is a process for the preparation of a compound of general formula (2).

(Step 5)

Step 5 is a process for the preparation of a compound of general formula (9), which process can be accomplished by reaction of a compound of general formula (8) with a compound of formula $(Ph)_3PCR^2CHO$ (wherein Ph represents a phenyl group and $R^2$ is as defined hereinbefore) in an inert solvent.

There is no particular limitation on the solvent employed in Step 5 provided that it has no adverse effect on the reaction and it dissolves the starting materials at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; or a nitrile such as acetonitrile, propionitrile or butyronitrile and preferably an aromatic hydrocarbon (particularly benzene or toluene).

The reaction temperature of Step 5 varies depending on the starting materials, reagents employed and the like. It is usually in the range between 0° C. and 150° C., and preferably between 30° C. and 100° C.

The reaction time of Step 5 varies depending on the starting materials, reagents employed and the temperature. It is usually in the range from 10 minutes to 10 hours and preferably from 30 minutes to 5 hours.

After the reaction, the desired compound of Step 5 can be isolated from the reaction mixture by a conventional procedure. For example the reaction mixture is concentrated to give the desired product. If necessary, the product thus obtained can be further purified by a conventional technique such as recrystallization, reprecipitation, chromatography or the like.

(Step 6)

Step 6 is a process for the preparation of a compound of formula (2), which process can be accomplished by reduction of a compound of formula (9) with a reducing agent in an inert solvent.

There is no particular limitation on the solvent employed in Step 6 provided that it has no adverse effect on the reaction and it dissolves the starting materials at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol, butanol or isobutanol; or a mixture thereof.

When the reducing reagent is an aluminum hydride compound or diborane, the solvent employed in Step 6 includes an aliphatic hydrocarbon (particularly hexane or cyclohexane), an aromatic hydrocarbon (particularly benzene, toluene or xylene), or an ether (particularly diethyl ether, tetrahydrofuran or dioxane). When the reducing agent is sodium borohydride, the solvent employed in Step 6 is an alcohol (particularly methanol or ethanol) or a mixture of an alcohol and a halogenated hydrocarbon (particularly a mixture of ethanol and dichloromethane).

The reducing reagent employed in Step 6 includes an aluminum hydride compound such as lithium aluminum hydride, diisobutylaluminum hydride or the like; sodium borohydride or diborane and preferably sodium borohydride. In addition when sodium borohydride is used as a reducing agent, cerium chloride can be used as a catalyst.

The reaction temperature of Step 6 varies depending on the starting materials, reagents employed and the like. It is usually in the range between −78° C. and 100° C., and preferably between 0° C. and 50° C.

The reaction time of Step 6 varies depending on the starting materials, reagents employed and the temperature. It is usually in the range from 10 minutes to 12 hours and preferably from 30 minutes to 5 hours.

After the reaction, the desired compound of Step 6 can be isolated from the reaction mixture by a conventional procedure. For example the reaction mixture is concentrated, the residue is partitioned between water and a solvent immiscible with water such as benzene, ether, ethyl acetate or the like. The organic layer is washed with water, dried over anhydrous magnesium sulfate or the like and concentrated to give the desired product. If necessary, the product thus obtained can be further purified by a conventional technique such as recrystallization, reprecipitation or chromatography.

(Step 7 and Step 8)

Step 7 and Step 8 are a process for the preparation of a compound of general formula (11), which process can be accomplished by reaction of compound of formula $HCCCH_2O$-Pro (wherein Pro is as defined hereinbefore) with catecholborane in the presence or absence of an inert solvent (preferably in the absence of an inert solvent (Step 7)), and by reaction of the compound obtained from Step 7 with a compound of general formula (10) in the presence of a base and a palladium catalyst in an inert solvent (Step 8).

There is no particular limitation on the solvent employed in Step 7 provided that it has no adverse effect on the reaction and it dissolves the starting materials at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; or an ether such as diethyl ether, diisopropyl ether, tetrahydrofuran, dioxane, dimethoxyethane or di(ethylene glycol)dimethyl ether; and preferably an aliphatic hydrocarbon (particularly hexane or petroleum ether) or an aromatic hydrocarbon (particularly toluene).

The reaction temperature of Step 7 varies depending on the starting materials, reagents employed and the like. It is usually in the range between −10° C. and 100° C., and preferably between 30° C. and 80° C.

The reaction time of Step 7 varies depending on the starting materials, reagents employed and the temperature. It is usually in the range from 10 minutes to 10 hours and preferably from 30 minutes to 5 hours.

After the reaction, the desired compound of Step 7 can be isolated from the reaction mixture by a conventional procedure. For example the reaction mixture is concentrated to afford the desired product. In addition the crude product of Step 7 can be used in Step 8 without purification.

There is no particular limitation on the solvent employed in Step 8 provided that it has no adverse effect on the reaction and it dissolves the starting materials at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol, butanol or isobutanol; or a mixture thereof; and preferably an aromatic hydrocarbon (particularly toluene).

The palladium catalyst employed in Step 8 includes, for example, a palladium phosphine complex such as tetrakis(triphenylphosphine)palladium, palladium chloride bis (triphenylphosphine) complex, palladium chloride bis (diphenylphosphinoferrocene) complex, palladium acetate bis (triphenylphosphine) and the like; or tris(dibenzylideneacetone)dipalladium chloroform complex, bis(dibenzylideneacetone)palladium, palladium acetate, or π-allylpalladium chloride dimer; preferably tetrakis(triphenylphosphine)palladium, palladium chloride bis(triphenylphosphine) complex or palladium chloride bis(diphenylphosphinoferrocene) complex and more preferably tetrakis(triphenylphosphine) palladium.

The base employed in Step 8 includes, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal alkoxide such as sodium methoxide, sodium ethoxide, potassium t-butoxide or lithium methoxide; or an organic base such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2] octane (DABCO) or 1,8-diazabicyclo[5.4.0]undec-7-ene (DBU), and preferably an alkali metal alkoxide (particularly sodium ethoxide).

The reaction temperature of Step 8 varies depending on the starting materials, reagents and the like. It is usually in the range between 0° C. and 150° C., and preferably between 50° C. and 120° C.

The reaction time of Step 8 varies depending on the starting materials, reagents employed and reaction temperature. It is usually in the range from 10 minutes to 10 hours and preferably from 30 minutes to 5 hours.

After the reaction, the desired compound of Step 8 can be isolated from the reaction mixture by a conventional procedure. For example the reaction mixture is partitioned between water and a solvent immiscible with water such as benzene, ether, ethyl acetate or the like. The organic layer is washed with water, dried over anhydrous magnesium sulfate or the like and concentrated to give the desired product. If necessary, the product thus obtained can be further purified by a conventional technique such as recrystallization, reprecipitation or chromatography.

(Step 9)

Step 9 is a process for the preparation of a compound of formula (2), which process can be accomplished by deprotection of a protected hydroxyl group in the compound of formula (11). Step 9 can be carried out by the same procedure as that described in reaction (e) of Step 2.

(Step 10)

Step 10 is a process for the preparation of a compound of general formula (14).

When X in general formula (12) represents a leaving group, Step 10 can be accomplished by the reaction of a compound of formula (12) with a compound of general formula (13) (wherein $R^{6b}$, $R^7$, $R^8$ and n are as defined hereinbefore) in the presence of a base in an inert solvent [reaction (a)], or

(13)

when X in general formula (12) represents a hydroxyl group, Step 10 can be accomplished by a dehydrative coupling reaction of a compound of formula (12) with a compound of general formula (13) in the presence of a phosphine compound and an azo compound in an inert solvent [reaction (b)]. In addition, reaction (b) can be carried out by the same procedure as that described in Step 1.

Reaction (a):

There is no particular limitation on the solvent employed in the reaction (a) provided that it has no adverse effect on the reaction and it dissolves the starting materials at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a nitro compound such as nitromethane; a nitrile such as acetonitrile or isobutyronitrile; an amide such as formamide, N,N-dimethylformamide, N,N-dimethylacetamide or N-methyl-2-pyrrolidinone; a sulfoxide such as dimethyl sulfoxide or sulfolane; and preferably an amide (particularly N,N-dimethylformamide or N,N-dimethylacetamide).

The base employed in the reaction (a) includes, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal acetate such as sodium acetate; an alkali metal hydride such as lithium hydride, sodium hydride or potassium hydride; an alkali metal hydroxide such as sodium hydroxide, potassium hydroxide or lithium hydroxide; an alkali metal alkoxide such as sodium methoxide, sodium ethoxide, potassium t-butoxide or lithium methoxide; or an organic base such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8-diazabicyclo[5.4.0]undec-7-ene (DBU); an alkyl lithium compound such as methyl lithium, ethyl lithium or butyl lithium; a lithium amide compound such as lithium diisopropylamide or lithium dicyclohexylamide; and preferably an alkali metal hydride (particularly lithium hydride or sodium hydride), an alkali metal alkoxide (particularly sodium methoxide) or an alkyl lithium compound (particularly butyl lithium).

The reaction temperature of reaction (a) varies depending on the starting materials, reagents employed and the like. It is usually in the range between −10° C. and 100° C., and preferably between −5° C. and 50° C.

The reaction time of reaction (a) varies depending on the starting materials, reagents employed and the temperature. It is usually in the range from 5 minutes to 24 hours and preferably from 10 minutes to 12 hours.

After the reaction, the desired compound of reaction (a) can be isolated from the reaction mixture by a conventional procedure. For example the reaction mixture is partitioned between water and a solvent immiscible with water such as benzene, ether, ethyl acetate or the like. The organic layer is washed with water, dried over anhydrous magnesium sulfate or the like and concentrated to give the desired product. If necessary, the product thus obtained can be further purified by a conventional technique such as recrystallization, reprecipitation or chromatography.

(Step 11)

Step 11 is a process for the preparation of a compound of general formula (15), which process is carried out when $R^{6b}$ in a compound of general formula (17) is different from $R^{6a}$. Deprotection of the protected amino group can be accomplished by a similar procedure to that described in reaction (b) of Step 2. In addition, when $R^{6b}$ and $R^{6a}$ in a compound of general formula (17) are same groups, Step 11 can be omitted.

(Step 12)

Step 12 is a process for the preparation of a compound of general formula (16), which process can be carried out by following reactions (1), (2) or (3):

Reaction (1): reaction of compound of general formula (15) with a reagent of formula $R^6$-Xa [wherein Xa is a halogen atom (particularly a chlorine atom or a bromine atom) or an alkoxy group (particularly a methoxy group or an ethoxy group)) in the presence of a base in an inert solvent.

Reaction (2): reaction of a compound of general formula (15) with a reagent of formula $R^6$-Xa (wherein Xa is a halogen atom (particularly a chlorine atom or a bromine atom) or a trifluoromethanesulfonyloxy group) in the presence of a palladium catalyst, phosphine compound and base in an inert solvent.

Reaction (3): reaction of a compound of general formula (15) with an acyclic ketone having from 1 to 6 carbon atoms or a cyclic ketone having from 3 to 8 carbon atoms in the presence of acetic acid and sodium cyanoborohydride or sodium triacetoxyborohydride in an inert solvent.

In addition when Step 11 is omitted, Step 12 can be also omitted.

The reaction (1) can be accomplished by a similar procedure to that described in reaction (c) of Step 2.

There is no particular limitation on the solvent employed in reaction (2) provided that it has no adverse effect on the reaction and it dissolves the starting materials at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol, butanol or isobutanol; or a mixture thereof; and preferably an aromatic hydrocarbon (particularly toluene).

The palladium catalyst employed in reaction (2) includes, for example, a palladium phosphine complex such as tetrakis(triphenylphosphine)palladium, palladium chloride bis(triphenylphosphine) complex, palladium chloride bis(diphenylphosphinoferrocene) complex, palladium acetate bis (triphenylphosphine) and the like; or tris(dibenzylideneacetone)dipalladium, bis(dibenzylideneacetone)palladium, palladium acetate, or π-allylpalladium chloride dimer; and preferably palladium acetate or tris(dibenzylideneacetone)palladium.

The phosphine compound employed in reaction (2) includes, for example, a tri $C_1$–$C_6$ alkylphosphine such as trimethylphosphine, triethylphosphine, tripropylphosphine, tributylphosphine, tri-t-butylphosphine, tripentylphosphine, trihexylphosphine and the like; a tri $C_6$–$C_{10}$ arylphosphine such as triphenylphosphine, triindenylphosphine, trinaphthylphosphine and the like; or a tri $C_6$–$C_{10}$ arylphosphine wherein said aryl group may optionally be substituted with a $C_1$–$C_4$ alkyl group such as tolyldiphenylphosphine, tritolylphosphine, trimesitylphosphine, tributylphenylphosphine, tri-6-ethyl-2-naphthylphosphine and the like; 2-(di-t-butylphosphino)biphenyl, 2-(dicyclohexylphosphino)biphenyl, 2-(dicyclohexylphosphino)-2'-(N,N-dimethylamino)biphenyl and the like; and preferably tri-t-butylphosphine, 2-(di-t-butylphosphino)biphenyl, 2-(dicyclohexylphosphino)biphenyl, or 2-(dicyclohexylphosphino)-2'-(N,N-dimethylamino)biphenyl.

The base employed in reaction (2) includes, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal alkoxide such as sodium methoxide, sodium ethoxide, sodium t-butoxide, potassium t-butoxide or lithium methoxide; or an organic base such as triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO) or 1,8- diazabicyclo[5.4.0]undec-7-ene (DBU), preferably an alkali metal alkoxide (particularly sodium t-butoxide).

The reaction temperature of reaction (2) varies depending on the starting materials, reagents employed and the like. It is usually in the range between 0° C. and 150° C., and preferably between 50° C. and 100° C.

The reaction time of reaction (2) varies depending on the starting materials, reagents employed and the temperature. It is usually in the range from 30 minutes to 24 hours and preferably from 1 to 5 hours.

After the reaction, the desired compound of reaction (2) can be isolated from the reaction mixture by a conventional procedure. For example the reaction mixture is concentrated to give the desired product. If necessary, the product thus obtained can be further purified by a conventional technique such as recrystallization, reprecipitation or chromatography.

The acyclic ketone having from 1 to 6 carbon atoms employed in reaction (3) includes formaldehyde, acetaldehyde, propan-1-one, propan-2-one (acetone), butan-2-one, petan-2-one, hexan-2-one and the like and is preferably acetone. The cyclic ketone having from 3 to 8 carbon atoms employed in reaction (3) includes cyclopropanone, cyclobutanone, cyclopentanone, cyclohexanone, cycloheptanone and cyclooctanone and is preferably cyclopentanone.

There is no particular limitation on the solvent employed in reaction (3) provided that it has no adverse effect on the reaction and it dissolves the starting materials at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol, butanol or isobutanol; an amide such as formamide, N,N-dimethylformamide, N,N-dimethylacetamide or N-methyl-2-pyrrolidinone; a sulfoxide such as dimethyl sulfoxide or sulfolane; or a mixture thereof and preferably a halogenated hydrocarbon (particularly dichloromethane), an alcohol (particularly methanol or ethanol) or a mixture thereof (particularly a mixture of dichloromethane and methanol).

The reaction temperature of reaction (3) varies depending on the starting materials, reagents employed and the like. It is usually in the range between −10° C. and 150° C., and preferably between 0° C. and 100° C.

The reaction time of reaction (3) varies depending on the starting materials, reagents employed and the temperature. It is usually in the range from 10 minutes to 24 hours and preferably from 1 hour to 12 hours.

After the reaction, the desired compound of reaction (3) can be isolated from the reaction mixture by a conventional procedure. For example the reaction mixture is partitioned between water and a solvent immiscible with water such as benzene, ether, ethyl acetate or the like. The organic layer is washed with water, dried over anhydrous magnesium sulfate or the like and concentrated to give the desired product. If necessary, the product thus obtained can be further purified by a conventional technique such as recrystallization, reprecipitation or chromatography.

In addition when the Step 11 is omitted, the step 12 can be also omitted (Step 13)

Step 13 is a process for the preparation of a compound of formula (17), which process can be accomplished by reduction of a compound of formula (14) or (16) as follows:

reaction (1): the reduction reaction is carried out by using catalytic reduction under an atmosphere of hydrogen at from 1 to 5 atmospheric pressure (preferably 1 atmospheric pressure) in an inert solvent; or reaction (2): the reduction reaction is carried out according to a conventional procedure for reduction of a nitro group to an amino group, which procedure is known to those skilled in the art, such as stirring the compound in the presence of a metal powder in acetic acid.

There is no particular limitation on the solvent employed in the catalytic reduction provided that it has no adverse effect on the reaction and it dissolves the starting materials at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, propanol, 2-propanol, butanol or isobutanol; or a mixture thereof and preferably an alcohol (particularly methanol) or a mixture of an ether and an alcohol (particularly a mixture of tetrahydrofuran and methanol or ethanol).

There is no particular limitation on the catalyst of the catalytic reduction provided that it is usually used in catalytic reduction. Such a catalyst includes, for example, palladium black, palladium-charcoal, palladium hydroxide, palladium hydroxide-charcoal, Raney nickel, rhodium-aluminum oxide, palladium-barium sulfate, platinum oxide or platinum black; preferably palladium-charcoal.

The reaction temperature of the catalytic reduction varies depending on the starting materials, reagents employed and the like. It is usually in the range between −10° C. and 100° C., and preferably between 0° C. and 50° C.

The reaction time of the catalytic reduction varies depending on the starting materials, reagents employed and the temperature. It is usually in the range from 10 minutes to 10 hours and preferably from 30 minutes to 6 hours.

After the reaction, the desired compound of the catalytic reduction can be isolated from the reaction mixture by a conventional procedure. For example the reaction mixture is filtered and the filtrate is concentrated to give the desired product. If necessary, the product thus obtained can be further purified by a conventional technique such as recrystallization, reprecipitation or chromatography.

The solvent employed in the reduction using a metal powder includes acetic acid, aqueous hydrochloric acid, water, an alcohol or a mixture of water and an organic solvent and preferably acetic acid.

The metal powder employed in the reduction includes, for example, zinc powder, tin powder, or iron powder and preferably zinc powder or tin powder.

The reaction temperature of the reduction varies depending on the starting materials, reagents employed and the like. It is usually in the range between −10° C. and 100° C., and preferably between 0° C. and 50° C.

The reaction time of the reduction varies depending on the starting materials, reagents employed and the temperature. It is usually in the range from 10 minutes to 10 hours and preferably from 30 minutes to 3 hours.

After the reaction, the desired compound of the reduction can be isolated from the reaction mixture by a conventional procedure. For example the reaction mixture is filtered and the filtrate is concentrated to give the desired product. If necessary, the product thus obtained can be further purified by a conventional technique such as recrystallization, reprecipitation or chromatography.

(Step 14)

Step 14 is a process for the preparation of a compound of general formula (3), which process can be accomplished by the reaction of a compound of formula (17) with a compound of general formula $R^{3a}$-Xa (wherein $R^{3a}$ is as defined hereinbefore and Xa represents a leaving group) in the presence or absence of a base (preferably in the presence of a base) in an inert solvent.

There is no particular limitation on the solvent employed in Step 14 provided that it has no adverse effect on the reaction and it dissolves the starting materials at least to some extent. Such a solvent includes, for example, an aliphatic hydrocarbon such as hexane, cyclohexane, heptane, ligroin or petroleum ether; an aromatic hydrocarbon such as benzene, toluene or xylene; a halogenated hydrocarbon such as dichloromethane, chloroform, carbon tetrachloride, 1,2-dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone or methyl ethyl ketone; a nitro compound such as nitromethane; a nitrile compound such as acetonitrile or isobutyronitrile; an amide such as formamide, N,N-dimethylformamide, N,N-dimethylacetamide or N-methyl-2-pyrrolidinone; or a sulfoxide such as dimethyl sulfoxide or sulfolane; and preferably a halogenated hydrocarbon (particularly dichloromethane), an ether (particularly diethyl ether or tetrahydrofuran) or an amide (particularly N,N-dimethylformamide).

The base employed in Step 14 includes, for example, an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; an alkali metal alkoxide such as sodium methoxide, sodium ethoxide, potassium t-butoxide or lithium methoxide; or an organic base such as methylamine, dimethylamine, ethylamine, triethylamine, tributylamine, diisopropylethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo [2.2.2]octane (DABCO) or 1,8-diazabicyclo [5.4.0]undec-7-ene (DBU), preferably an alkali metal carbonate (particularly sodium carbonate or potassium carbonate), an alkali metal hydrogencarbonate (particularly sodium hydrgencarbonate or potassium hydrgencarbonate), or an alkali metal hydride (particularly lithium hydride or sodium hydride).

The reaction temperature of Step 14 varies depending on the starting materials, reagents employed and the like. It is usually in the range between −10° C. and 100° C., and preferably between 0° C. and 50° C.

The reaction time of Step 14 varies depending on the starting materials, reagents employed and the temperature. It is usually in the range from 10 minutes to 24 hours and preferably from 1 hour to 12 hours.

After the reaction, the desired compound of Step 14 can be isolated from the reaction mixture by a conventional procedure. For example the reaction mixture is partitioned between water and a solvent immiscible with water such as benzene, ether, ethyl acetate or the like. The organic layer is washed with water, dried over anhydrous magnesium sulfate or the like and concentrated to give the desired product. If necessary, the product thus obtained can be further purified by a conventional technique such as recrystallization, reprecipitation or chromatography.

The starting materials of formulae (5), (7), (8) and (12) are know compounds or can be easily prepared according to procedures known to those skilled in the art [for example, *Bioorg. Med. Chem. Lett.*, 8, 277 (1998), *Tetrahedron letters*, 37, 6439 (1996) and the like].

EXAMPLES

The present invention will further be exemplified by Examples and Formulation examples, however, the scope of the present invention is not limited by these Examples.

In addition, NMR spectra were determined by using tetramethylsilane as an internal standard. Values of δ are represented as ppm unit and coupling constants are represented as Hz unit, which are approximated by 0.5 Hz unit. The coupling patterns are abbreviated as follows:

d: doublet,
dd: double doublet,
ddd: double double doublet,
dt: double triplet,
t: triplet,
q: quartet,
m: multiplet,
s: singlet,
bs: broad or collapsed singlet-like observed signal.

Example 1

Ethyl N-[3-(3-amidinophenyl)-2-(E)-propenyl]-N-[3-chloro-4-(1-methylpiperidin-4-yloxy)phenyl]sulfamoylacetate dihydrochloride (Exemplification Compound Number 1)

Hydrogen chloride was bubbled through a solution of ethyl N-[3-chloro-4-(1-methylpiperidin-4-yloxy)phenyl]-N-[3-(3-cyanophenyl)-2-(E)-propenyl]sulfamoylacetate (938 mg) obtained in reference example 7 in a mixture of dichloromethane (30 ml) and ethanol (15 ml) under ice-cooling, and the resulting mixture was stirred at room temperature for 5 hours under sealed conditions and then evaporated in vacuo. Subsequently, to a solution of the residue obtained in ethanol (20 ml) were added successively an aqueous ammonium chloride solution (prepared by dissolving 189 mg in 10 ml of water) and a 28% ammonia solution (0.35 ml), and the resulting mixture was stirred at room temperature overnight. After stirring, to the reaction mixture was added a 4N solution of hydrogen chloride in dioxane and the resulting mixture was evaporated in vacuo. The residue obtained was purified by preparative HPLC (YMC-Pack ODS-A; YMC, eluent: 22% acetonitrile/water). The amorphous solid obtained was dissolved in 1N hydrochloric acid, and the resulting mixture was evaporated to dryness in vacuo. The residue obtained was dissolved in water and then lyophilized to afford the title compound (841 mg, yield: 77%) as a colorless amorphous solid.

$^1$H NMR (500 MHz, DMSO-$d_6$) δ ppm: 1.22 (3H, t, J=7.0), 1.90–2.08 (2H, m), 2.14–2.26 (2H, m), 2.74 (3H, m), 3.00–3.10 (2H, m), 3.32 (1H, m), 3.40–3.50 (1H, m), 4.19 (2H, q, J=7.0), 4.41 (2H, s), 4.47 (2H, d, J=6.0), 4.62 and 4.87 (total 1H, each m), 6.44 (1H, dt, J=16.0, 6.0), 6.58 (1H, d, J=16.0), 7.31 (1H, t, J=9.0), 7.41 (1H, m), 7.55 (1H, t, J=8.0), 7.60 (1H, m), 7.69 (1H, d, J=8.0), 7.73 (1H, d, J=8.0), 7.89 (1H, s);

IR (KBr, cm$^{-1}$): 1737, 1675, 1352, 1156.

Example 2

N-[3-(3-Amidinophenyl)-2-(E)-propenyl]-N-[3-chloro-4-(1-methylpiperidin-4-yloxy)phenyl]sulfamoylacetic acid dihydrochloride (Exemplification Compound Number 505)

Ethyl N-[3-(3-amidinophenyl)-2-(E)-propenyl]-N-[3-chloro-4-(1-methylpiperidin-4-yloxy)phenyl]sulfamoylacetate dihydrochloride (435 mg) obtained in example 1 was dissolved in 3N hydrochloric acid (20 ml) and the resulting mixture was stirred at 60° C. for 6.5 hours. After cooling to room temperature, the reaction mixture was evaporated in vacuo. The residue obtained was purified by preparative HPLC (YMC-Pack ODS-A; YMC, eluent: 13% acetonitrile/water). The amorphous solid obtained was dissolved in 1N hydrochloric acid (1.00 ml) and the resulting mixture was evaporated to dryness in vacuo. The residue obtained was dissolved in water and then lyophilized to afford the title compound (243 mg, yield: 59%) as a colorless amorphous solid.

$^1$H NMR (500 MHz, DMSO-d$_6$) δ ppm: 1.94 and 2.03 (total 2H, each m), 2.19 (2H, m), 2.74 (3H, m), 3.00–3.10 (2H, m), 3.30–3.50 (2H, m), 4.28 (2H, s), 4.47 (2H, d, J=6.0), 4.61 and 4.87 (total 1H, each m), 6.44 (1H, dt, J=16.0, 6.0), 6.58 (1H, d, J=16.0), 7.31 (1H, m), 7.41 (1H, m), 7.55 (1H, t, J=8.0), 7.60 (1H, m), 7.69 (1H, d, J=8.0), 7.73 (1H, d, J=8.0), 7.88 (1H, s);

IR (KBr, cm$^{-1}$): 1732, 1676, 1348, 1155.

Example 3

Ethyl N-[3-(3-amidinophenyl)-2-(E)-propenyl]-N-[3-chloro-4-(1-ethylpiperidin-4-yloxy)phenyl]sulfamoylacetate dihydrochloride (Exemplification Compound Number 2)

Hydrogen chloride was bubbled through a solution of ethyl N-[3-chloro-4-(1-ethylpiperidin-4-yloxy)phenyl]-N-[3-(3-cyanophenyl)-2-(E)-propenyl]sulfamoylacetate (1240 mg) obtained in reference example 13 in a mixture of dichloromethane (30 ml) and ethanol (15 ml) under ice-cooling, and the resulting mixture was stirred at room temperature for 7 hours under sealed conditions and then evaporated in vacuo. Subsequently, to a solution of the residue obtained in ethanol (20 ml) were added successively an aqueous ammonium chloride solution (prepared by dissolving 243 mg in 10 ml of water) and a 28% ammonia solution (0.41 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 22% acetonitrile/water). The amorphous solid obtained was dissolved in 1N hydrochloric acid, and the resulting mixture was evaporated to dryness in vacuo. The residue obtained was dissolved in water and then lyophilized to afford the title compound (807 mg, yield: 56%) as a colorless amorphous solid.

$^1$H NMR (500 MHz, DMSO-d$_6$) δ ppm: 1.22 (3H, t, J=7.0), 1.26 (3H, t, J=7.0), 1.92–2.08 (2H, m), 2.21 (2H, m), 2.99 (2H, m), 3.09 (2H, m), 3.36 and 3.50 (total 2H, each m), 4.19 (2H, q, J=7.0), 4.41 (2H, s), 4.47 (2H, d, J=6.0), 4.64 and 4.90 (total 1H, each m), 6.44 (1H, dt, J=16.0, 6.0), 6.58 (1H, d, J=16.0), 7.31 (1H, m), 7.41 (1H, m), 7.55 (1H, t, J=8.0), 7.60 (1H, m), 7.68 (1H, d, J=8.0), 7.73 (1H, d, J=8.0), 7.88 (1H, s);

IR (KBr, cm$^{-1}$): 1738, 1675, 1353, 1155.

Example 4

N-[3-(3-Amidinophenyl)-2-(E)-propenyl]-N-[3-chloro-4-(1-ethylpiperidin-4-yloxy)phenyl]sulfamoylacetic acid dihydrochloride (Exemplification Compound Number 506)

Ethyl N-[3-(3-amidinophenyl)-2-(E)-propenyl]-N-[3-chloro-4-(1-ethylpiperidin-4-yloxy)phenyl]sulfamoylacetate dihydrochloride (400 mg) obtained in example 3 was dissolved in 3N hydrochloric acid (20 ml) and the resulting mixture was stirred at 60° C. for 4 hours. After cooling to room temperature, the reaction mixture was evaporated in vacuo. The residue obtained was purified by preparative HPLC (YMC-Pack ODS-A; YMC, eluent: 15% acetonitrile/water). The amorphous solid obtained was dissolved in 1N hydrochloric acid (1.00 ml) and the resulting mixture was evaporated to dryness in vacuo. The residue obtained was dissolved in water and then lyophilized to afford the title compound (324 mg, yield: 85%) as a colorless amorphous solid.

$^1$H NMR (500 MHz, DMSO-d$_6$) δ ppm: 1.24 (3H, t, J=7.5), 1.98 (2H, m), 2.18 (2H, m), 3.05 (2H, m), 3.00–3.50 (4H, m), 4.15 (2H, s), 4.48 (2H, d, J=6.0), 4.75 (1H, m), 6.44 (1H, dt, J=16.0, 6.0), 6.57 (1H, d, J=16.0), 7.29 (1H, d, J=9.0), 7.43 (1H, dd, J=9.0, 2.5), 7.54 (1H, t, J=8.0), 7.62 (1H, d, J=2.5), 7.68 (1H, d, J=8.0), 7.72 (1H, d, J=8.0), 7.88 (1H, s);

IR (KBr, cm$^{-1}$): 1731, 1676, 1348, 1154.

Example 5

Ethyl N-[3-(3-amidinophenyl)-2-(E)-propenyl]-N-[3-chloro-4-(1-isopropylpiperidin-4-yloxy)phenyl]sulfamoylacetate dihydrochloride (Exemplification Compound Number 3)

Hydrogen chloride was bubbled through a solution of ethyl N-[3-chloro-4-(1-isopropylpiperidin-4-yloxy)phenyl]-N-[3-(3-cyanophenyl)-2-(E)-propenyl]sulfamoylacetate (1171 mg) obtained in reference example 17 in a mixture of dichloromethane (30 ml) and ethanol (15 ml) under ice-cooling, and the resulting mixture was stirred at room temperature for 7 hours under sealed conditions and then evaporated in vacuo. Subsequently, to a solution of the residue obtained in ethanol (20 ml) were added successively an aqueous ammonium chloride solution (prepared by dissolving 224 mg in 10 ml of water) and a 28% ammonia solution (0.42 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 25% acetonitrile/water). The amorphous solid obtained was dissolved in 1N hydrochloric acid, and the resulting mixture was evaporated to dryness in vacuo. The residue obtained was dissolved in water and then lyophilized to afford the title compound (904 mg, yield: 67%) as a colorless amorphous solid.

$^1$H NMR (500 MHz, DMSO-d$_6$) δ ppm: 1.23 (3H, t, J=7.0), 1.28 (6H, m), 2.00–2.12 (2H, m), 2.18–2.36 (2H, m), 3.07 (2H, m), 3.22–3.52 (3H, m), 4.19 (2H, q, J=7.0), 4.42 (2H, m), 4.47 (2H, d, J=6.0), 4.66 and 4.95 (total 1H, each m), 6.44 (1H, dt, J=16.0, 6.0), 6.58 (1H, d, J=16.0), 7.31 (1H, m), 7.41 (1H, m), 7.55 (1H, t, J=8.0), 7.60 (1H, m), 7.68 (1H, d, J=8.0), 7.73 (1H, d, J=8.0), 7.88 (1H, s);

IR (KBr, cm$^{-1}$) 1738, 1675, 1353, 1156.

Example 6

N-[3-(3-Amidinophenyl)-2-(E)-propenyl]-N-[3-chloro-4-(1-isopropylpiperidin-4-yloxy)phenyl]sulfamoylacetic acid dihydrochloride (Exemplification Compound Number 507)

Ethyl N-[3-(3-amidinophenyl)-2-(E)-propenyl]-N-[3-chloro-4-(1-isopropylpiperidin-4-yloxy)phenyl]sulfamoylacetate dihydrochloride (615 mg) obtained in example 5 was dissolved in 3N hydrochloric acid (20 ml) and the resulting mixture was stirred at 60° C. for 4 hours. After cooling to room temperature, the reaction mixture was evaporated in vacuo. The residue obtained was purified by preparative HPLC (YMC-Pack ODS-A; YMC, eluent: 17% acetonitrile/water). The amorphous solid obtained was dissolved in 1N hydrochloric acid (1.00 ml) and the resulting mixture was evaporated to dryness in vacuo. The residue obtained was dissolved in water and then lyophilized to afford the title compound (433 mg, yield: 74%) as a colorless amorphous solid.

$^1$H NMR (500 MHz, DMSO-d$_6$) δ ppm: 1.22 (6H, d, J=6.5), 1.97 (2H, m), 2.18 (2H, m), 2.90–3.40 (5H, m), 3.99 (2H, s), 4.48 (2H, d, J=6.0), 4.75 (1H, m), 6.44 (1H, dt, J=16.0, 6.0), 6.55 (1H, d, J=16.0), 7.27 (1H, d, J=9.0), 7.46 (1H, dd, J=9.0, 2.5), 7.54 (1H, t, J=8.0), 7.65 (1H, d, J=2.5), 7.67 (1H, d, J=8.0), 7.71 (1H, d, J=8.0), 7.87 (1H, s);

IR (KBr, cm$^{-1}$) 1677, 1344, 1151.

Example 7

Ethyl N-[3-(3-amidinophenyl)-2-(E)-propenyl]-N-[4-(1-butylpiperidin-4-yloxy)-3-chlorophenyl]sulfamoylacetate dihydrochloride (Exemplification Compound Number 4)

Hydrogen chloride was bubbled through a solution of ethyl N-[4-(1-butylpiperidin-4-yloxy)-3-chlorophenyl]-N-[3-(3-cyanophenyl)-2-(E)-propenyl]sulfamoylacetate (1177 mg) obtained in reference example 21 in a mixture of dichloromethane (30 ml) and ethanol (15 ml) under ice-cooling, and the resulting mixture was stirred at room temperature for 6 hours under sealed conditions and then evaporated in vacuo. Subsequently, to a solution of the residue obtained in ethanol (20 ml) were added successively an aqueous ammonium chloride solution (prepared by dissolving 219 mg in 10 ml of water) and a 28% ammonia solution (0.41 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 27% acetonitrile/water). The amorphous solid obtained was dissolved in 1N hydrochloric acid, and the resulting mixture was evaporated to dryness in vacuo. The residue obtained was dissolved in water and then lyophilized to afford the title compound (742 mg, yield: 55%) as a colorless amorphous solid.

$^1$H NMR (500 MHz, DMSO-d$_6$) δ ppm: 0.93 (3H, t, J=7.5), 1.23 (3H, t, J=7.0), 1.32 (2H, m), 1.67 (2H, m), 1.90–2.08 (2H, m), 2.15–2.28 (2H, m), 2.95–3.10 (4H, m), 3.35–3.58 (2H, m), 4.19 (2H, q, J=7.0), 4.41 (2H, s), 4.47 (2H, d, J=6.0), 4.63 and 4.88 (total 1H, each m), 6.43 (1H, dt, J=16.0, 6.0), 6.58 (1H, d, J=16.0), 7.31 (1H, m), 7.41 (1H, m), 7.55 (1H, t, J=8.0), 7.60 (1H, m), 7.67 (1H, d, J=8.0), 7.73 (1H, d, J=8.0), 7.87 (1H, s);

IR (KBr, cm$^{-1}$): 1738, 1675, 1353, 1156.

Example 8

N-[3-(3-Amidinophenyl)-2-(E)-propenyl-N-[4-(1-butylpiperidin-4-yloxy)-3-chlorophenyl]sulfamoylacetic acid dihydrochloride (Exemplification Compound Number 508)

Ethyl N-[3-(3-amidinophenyl)-2-(E)-propenyl]-N-[4-(1-butylpiperidin-4-yloxy)-3-chlorophenyl]sulfamoylacetate dihydrochloride (600 mg) obtained in example 7 was dissolved in 3N hydrochloric acid (20 ml) and the resulting mixture was stirred at 60° C. for 4.5 hours. After cooling to room temperature, the reaction mixture was evaporated in vacuo. The residue obtained was purified by preparative HPLC (YMC-Pack ODS-A; YMC, eluent: 20% acetonitrile/water). The amorphous solid obtained was dissolved in 1N hydrochloric acid (1.00 ml) and the resulting mixture was evaporated to dryness in vacuo. The residue obtained was dissolved in water and then lyophilized to afford the title compound (450 mg, yield: 78%) as a colorless amorphous solid.

$^1$H NMR (500 MHz, DMSO-d$_6$) δ ppm: 0.90 (3H, t, J=7.5), 1.31 (2H, m), 1.61 (2H, m), 1.92 (2H, m), 2.13 (2H, m), 2.87 (2H, m), 2.90–3.20 (4H, m), 4.03 (2H, s), 4.48 (2H, d, J=6.0), 4.70 (1H, m), 6.44 (1H, dt, J=16.0, 6.0), 6.56 (1H, d, J=16.0), 7.27 (1H, d, J=9.0), 7.45 (1H, dd, J=9.0, 2.5), 7.54 (1H, t, J=8.0), 7.64 (1H, d, J=2.5), 7.67 (1H, d, J=8.0), 7.71 (1H, d, J=8.0), 7.86 (1H, s);

IR (KBr, cm$^{-1}$) 1676, 1347, 1153.

Example 9

Ethyl N-[3-(3-amidinophenyl)-2-(E)-propenyl]-N-[4-(1-benzylpiperidin-4-yloxy)-3-chlorophenyl]sulfamoylacetate dihydrochloride (Exemplification Compound Number 5)

Hydrogen chloride was bubbled through a solution of ethyl N-[4-(1-benzylpiperidin-4-yloxy)-3-chlorophenyl]-N-[3-(3-cyanophenyl)-2-(E)-propenyl]sulfamoylacetate (1531 mg) obtained in reference example 25 in a mixture of dichloromethane (30 ml) and ethanol (15 ml) under ice-cooling, and the resulting mixture was stirred at room temperature for 5 hours under sealed conditions and then evaporated in vacuo. Subsequently, to a solution of the residue obtained in ethanol (20 ml) were added successively an aqueous ammonium chloride solution (prepared by dissolving 233 mg in 10 ml of water) and a 28% ammonia solution (0.40 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 30% acetonitrile/water). The amorphous solid obtained was dissolved in 1N hydrochloric acid, and the resulting mixture was evaporated to dryness in vacuo. The residue obtained was dissolved in water and then lyophilized to afford the title compound (931 mg, yield: 53%) as a colorless amorphous solid.

$^1$H NMR (500 MHz, DMSO-d$_6$) δ ppm: 1.22 (3H, t, J=7.0), 1.94–2.05 (2H, m), 2.16–2.28 (2H, m), 3.01 (2H, m), 3.24–3.44 (2H, m), 4.18 (2H, q, J=7.0), 4.31 (2H, m), 4.40 (2H, s), 4.46 (2H, d, J=6.0), 4.59 and 4.88 (total 1H, each m), 6.42 (1H, dt, J=16.0, 6.0), 6.57 (1H, d, J=16.0), 7.27 (1H, d, J=9.0), 7.31 (1H, d, J=9.0), 7.38 (1H, m), 7.43–7.51 (3H, m), 7.52–7.59 (2H, m), 7.60–7.66 (2H, m), 7.67 (1H, d, J=8.0), 7.72 (1H, d, J=8.0), 7.87 (1H, s);

IR (KBr, cm$^{-1}$): 1738, 1675, 1353, 1155.

Example 10

N-[3-(3-Amidinophenyl)-2-(E)-propenyl]-N-[4-(1-benzylpiperidin-4-yloxy)-3-chlorophenyl]sulfamoylacetic acid dihydrochloride (Exemplification Compound Number 509)

Ethyl N-[3-(3-amidinophenyl)-2-(E)-propenyl]-N-[4-(1-benzylpiperidin-4-yloxy)-3-chlorophenyl]sulfamoylacetate dihydrochloride (731 mg) obtained in example 9 was dissolved in 3N hydrochloric acid (30 ml) and the resulting mixture was stirred at 60° C. for 6.5 hours. After cooling to room temperature, the reaction mixture was evaporated in vacuo. The residue obtained was purified by preparative HPLC (YMC-Pack ODS-A; YMC, eluent: 20% acetonitrile/water). The amorphous solid obtained was dissolved in 1N hydrochloric acid (1.00 ml) and the resulting mixture was evaporated to dryness in vacuo. The residue obtained was dissolved in water and then lyophilized to afford the title compound (547 mg, yield: 87%) as a colorless amorphous solid.

$^1$H NMR (500 MHz, DMSO-$d_6$) δ ppm: 1.90–2.08 (2H, m), 2.12–2.26 (2H, m), 2.92–3.02 (2H, m), 3.20–3.50 (2H, m), 4.20–4.38 (2H, m), 4.25 (2H, s), 4.46 (2H, d, J=6.0), 4.61 and 4.83 (total 1H, each m), 6.42 (1H, dt, J=16.0, 6.0), 6.56 (1H, d, J=16.0), 7.27 (1H, d, J=9.0), 7.39 (1H, dd, J=9.0, 2.5), 7.40–7.50 (3H, m), 7.54 (1H, t, J=8.0), 7.55–7.65 (3H, m), 7.66 (1H, d, J=8.0), 7.72 (1H, d, J=8.0), 7.85 (1H, s);

IR (KBr, cm$^{-1}$): 1732, 1675, 1349, 1154.

Example 11

Ethyl N-[3-(3-amidinophenyl)-2-(E)-propenyl]-N-[3-chloro-4-(1-phenethyl)piperidin-4-yloxy)phenyl]sulfamoylacetate dihydrochloride (Exemplification Compound Number 6)

Hydrogen chloride was bubbled through a solution of ethyl N-[3-chloro-4-(1-phenethylpiperidin-4-yloxy)phenyl]-N-[3-(3-cyanophenyl)-2-(E)-propenyl]sulfamoylacetate (1013 mg) obtained in reference example 29 in a mixture of dichloromethane (30 ml) and ethanol (15 ml) under ice-cooling, and the resulting mixture was stirred at room temperature for 6 hours under sealed conditions and then evaporated in vacuo. Subsequently, to a solution of the residue obtained in ethanol (20 ml) were added successively an aqueous ammonium chloride solution (prepared by dissolving 174 mg in 10 ml of water) and a 28% ammonia solution (0.33 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 30% acetonitrile/water). The amorphous solid obtained was dissolved in 1N hydrochloric acid, and the resulting mixture was evaporated to dryness in vacuo. The residue obtained was dissolved in water and then lyophilized to afford the title compound (788 mg, yield: 68%) as a colorless amorphous solid.

$^1$H NMR (500 MHz, DMSO-$d_6$) δ ppm: 1.22 (3H, t, J=7.0), 1.96–2.12 (2H, m), 2.19–2.32 (2H, m), 3.02–3.18 (4H, m), 3.24–3.40 (2H, m), 3.49 and 3.62 (total 2H, each m), 4.19 (2H, q, J=7.0), 4.42 (2H, s), 4.47 (2H, d, J=6.0), 4.65 and 4.91 (total 1H, each m), 6.44 (1H, dt, J=16.0, 6.0), 6.58 (1H, d, J=16.0), 7.22–7.38 (6H, m), 7.41 (1H, m), 7.55 (1H, t, J=8.0), 7.60 (1H, m), 7.68 (1H, d, J=8.0), 7.73 (1H, d, J=8.0), 7.88 (1H, s);

IR (KBr, cm$^{-1}$): 1738, 1675, 1353, 1156.

Example 12

N-[3-(3-Amidinophenyl)-2-(E)-propenyl]-N-[3-chloro-4-(1-phenethylpiperidin-4-yloxy)phenyl]sulfamoylacetic acid dihydrochloride (Exemplification Compound Number 510)

Ethyl N-[3-(3-amidinophenyl)-2-(E)-propenyl]-N-[3-chloro-4-(1-phenethylpiperidin-4-yloxy)phenyl]sulfamoylacetate dihydrochloride (588 mg) obtained in example 11 was dissolved in 3N hydrochloric acid (30 ml) and the resulting mixture was stirred at 60° C. for 6.5 hours. After cooling to room temperature, the reaction mixture was evaporated in vacuo. The residue obtained was purified by preparative HPLC (YMC-Pack ODS-A; YMC, eluent: 25% acetonitrile/water). The amorphous solid obtained was dissolved in 1N hydrochloric acid (1.00 ml) and the resulting mixture was evaporated to dryness in vacuo. The residue obtained was dissolved in water and then lyophilized to afford the title compound (405 mg, yield: 72%) as a colorless amorphous solid.

$^1$H NMR (500 MHz, DMSO-$d_6$) δ ppm: 2.02 (2H, m), 2.18–2.28 (2H, m), 3.07 (4H, m), 3.20–3.50 (4H, m), 4.26 (2H, s), 4.47 (2H, d, J=6.0), 4.84 (1H, m), 6.44 (1H, dt, J=16.0, 6.0), 6.58 (1H, d, J=16.0), 7.22–7.39 (6H, m), 7.42 (1H, dd, J=9.0, 2.5), 7.55 (1H, t, J=8.0), 7.60 (1H, d, J=2.5), 7.67 (1H, d, J=8.0), 7.73 (1H, d, J=8.0), 7.87 (1H, s);

IR (KBr, cm$^{-1}$): 1732, 1675, 1349, 1154.

Example 13

Ethyl N-[3-(3-amidinophenyl)-2-(E)-propenyl]-N-[3-chloro-4-(1-phenylpiperidin-4-yloxy)phenyl]sulfamoylacetate dihydrochloride (Exemplification Compound Number 7)

Hydrogen chloride was bubbled through a solution of ethyl N-[3-chloro-4-(1-phenylpiperidin-4-yloxy)phenyl]-N-[3-(3-cyanophenyl)-2-(E)-propenyl]sulfamoylacetate (1440 mg) obtained in reference example 33 in a mixture of dichloromethane (18 ml) and ethanol (18 ml) under ice-cooling, and the resulting mixture was stirred at room temperature for 5 hours under sealed conditions and then evaporated in vacuo. Subsequently, to a solution of the residue obtained in ethanol (30 ml) were added successively an aqueous ammonium chloride solution (prepared by dissolving 233 mg in 10 ml of water) and a 28% ammonia solution (0.49 ml), and the resulting mixture was stirred at room temperature overnight and then evaporated in vacuo. The residue obtained was purified by preparative HPLC (YMC-Pack ODS-A; YMC, eluent: 60% acetonitrile/water) to obtain an amorphous solid (924 mg). Subsequently, to a solution of this solid (254 mg) in ethanol (6 ml) was added a 4N solution of hydrogen chloride in dioxane (0.31 ml) and the resulting mixture was evaporated in vacuo. The residue obtained was dissolved in water and then lyophilized to afford the title compound (278 mg, yield: 61%) as a colorless amorphous solid.

$^1$H NMR (400 MHz, DMSO-$d_6$) δ ppm: 1.23 (3H, t, J=7.0), 1.93–2.14 (2H, m), 2.16–2.37 (2H, m), 3.17–3.94 (4H, m), 4.19 (2H, q, J=7.0), 4.42 (2H, s), 4.48 (2H, d, J=6.0), 4.85 (1H, m), 6.45 (1H, dt, J=16.0, 6.0), 6.59 (1H, d, J=16.0), 7.21 (1H, m), 7.28–7.64 (4H, m), 7.34 (1H, d, J=9.0), 7.42 (1H, dd, J=9.0, 2.5), 7.55 (1H, t, J=8.0), 7.61 (1H, d, J=2.5), 7.69 (1H, d, J=8.0), 7.74 (1H, d, J=8.0), 7.89 (1H, s);

IR (KBr, cm$^{-1}$): 1738, 1675, 1353, 1156.

Example 14

N-[3-(3-Amidinophenyl)-2-(E)-propenyl]-N-[3-chloro-4-(1-phenylpiperidin-4-yloxy)phenyl]sulfamoylacetic acid dihydrochloride (Exemplification Compound Number 511)

Ethyl N-[3-(3-amidinophenyl)-2-(E)-propenyl]-N-[3-chloro-4-(1-phenylpiperidin-4-yloxy)phenyl]sulfamoylacetate (676 mg) obtained in example 13 was dissolved in a mixture of 3N hydrochloric acid (9 ml) and dioxane (3 ml) and the resulting mixture was stirred at 80° C. for 6 hours. After cooling to room temperature, the reaction mixture was evaporated in vacuo. The residue obtained was purified by preparative HPLC (YMC-Pack ODS-A; YMC, eluent: 40% acetonitrile/water). The amorphous solid obtained was dissolved in 1N hydrochloric acid (10 ml) and the resulting mixture was evaporated to dryness in vacuo. The residue obtained was dissolved in water and then lyophilized to afford the title compound (385 mg, yield: 53%) as a colorless amorphous solid.

$^1$H NMR (400 MHz, DMSO-d$_6$) δ ppm: 1.88–2.08 (2H, m), 2.10–2.32 (2H, m), 3.04–3.91 (4H, m), 4.28 (2H, s), 4.47 (2H, d, J=6.0), 4.82 (1H, m), 6.44 (1H, dt, J=16.0, 6.0), 6.58 (1H, d, J=16.0), 7.11 (1H, m), 7.26–7.49 (4H, m), 7.32 (1H, d, J=9.0), 7.42 (1H, dd, J=9.0, 2.5), 7.55 (1H, t, J=8.0), 7.60 (1H, d, J=2.5), 7.68 (1H, d, J=8.0), 7.74 (1H, d, J=8.0), 7.88 (1H, s);

IR (KBr, cm$^{-1}$): 1733, 1676, 1349, 1155.

Example 15

Ethyl N-[3-(3-amidinophenyl)-2-(E)-propenyl]-N-[3-chloro-4-(1-methoxycarbonylmethylpiperidin-4-yloxy)phenyl]sulfamoylacetate dihydrochloride (Exemplification Compound Number 8)

Hydrogen chloride was bubbled through a solution of ethyl N-[3-chloro-4-(1-methoxycarbonylmethylpiperidin-4-yloxy)phenyl]-N-[3-(3-cyanophenyl)-2-(E)-propenyl]sulfamoylacetate (1700 mg) obtained in reference example 37 in a mixture of dichloromethane (30 ml) and ethanol (15 ml) under ice-cooling, and the resulting mixture was stirred at room temperature for 7 hours under sealed conditions and then evaporated in vacuo. Subsequently, to a solution of the residue obtained in ethanol (20 ml) were added successively an aqueous ammonium chloride solution (prepared by dissolving 227 mg in 10 ml of water) and a 28% ammonia solution (0.42 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 35% acetonitrile/water). The amorphous solid obtained was dissolved in 1N hydrochloric acid, and the resulting mixture was evaporated to dryness in vacuo. The residue obtained was dissolved in water and then lyophilized to afford the title compound (950 mg, yield: 48%) as a colorless amorphous solid.

$^1$H NMR (500 MHz, DMSO-d$_6$) δ ppm: 1.22 (3H, t, J=7.0), 1.84–2.32 (4H, m), 2.90–3.68 (4H, m), 3.76 (3H, s), 4.19 (2H, q, J=7.0), 4.30 (2H, m), 4.41 (2H, s), 4.47 (2H, d, J=6.0), 4.63 and 4.84 (total 1H, each m), 6.43 (1H, dt, J=16.0, 6.0), 6.58 (1H, d, J=16.0), 7.30 (1H, m), 7.40 (1H, m), 7.55 (1H, t, J=8.0), 7.59 (1H, m), 7.68 (1H, d, J=8.0), 7.73 (1H, d, J=8.0), 7.87 (1H, s);

IR (KBr, cm$^{-1}$): 1742, 1675, 1353, 1156.

Example 16

N-[3-(3-Amidinophenyl)-2-(E)-propenyl]-N-[4-(1-carboxymethylpiperidin-4-yloxy)-3-chlorophenyl]sulfamoylacetic acid dihydrochloride (Exemplification Compound Number 512)

Ethyl N-[3-(3-amidinophenyl)-2-(E)-propenyl]-N-[3-chloro-4-(1-methoxycarbonylmethylpiperidin-4-yloxy)phenyl]sulfamoylacetate dihydrochloride (810 mg) obtained in example 15 was dissolved in 3N hydrochloric acid (30 ml) and the resulting mixture was stirred at 60° C. for 15 hours. After cooling to room temperature, the reaction mixture was evaporated in vacuo. The residue obtained was purified by preparative HPLC (YMC-Pack ODS-A; YMC, eluent: 15% acetonitrile/water). The amorphous solid obtained was dissolved in 1N hydrochloric acid and the resulting mixture was evaporated to dryness in vacuo. The residue obtained was dissolved in water and then lyophilized to afford the title compound (581 mg, yield: 76%) as a colorless amorphous solid.

$^1$H NMR (400 MHz, DMSO-d$_6$) δ ppm: 1.91–2.07 (2H, m), 2.14–2.28 (2H, m), 3.00–3.90 (4H, m), 4.16 (2H, s), 4.28 (2H, s), 4.47 (2H, d, J=6.0), 4.65 and 4.84 (total 1H, each m), 6.45 (1H, dt, J=16.0, 6.0), 6.57 (1H, d, J=16.0), 7.32 (1H, m), 7.42 (1H, dd, J=9.0, 2.5), 7.54 (1H, t, J=8.0), 7.60 (1H, d, J=2.5), 7.72 (2H, m), 7.91 (1H, s);

IR (KBr, cm$^{-1}$): 1737, 1676, 1348, 1155.

Example 17

Ethyl N-[4-(1-acetylpiperidin-4-yloxy)-3-chlorophenyl]-N-[3-(3-amidinophenyl)-2-(E)-propenyl]sulfamoylacetate hydrochloride (Exemplification Compound Number 9)

Hydrogen chloride was bubbled through a solution of ethyl N-[4-(1-acetylpiperidin-4-yloxy)-3-chlorophenyl]-N-[3-(3-cyanophenyl)-2-(E)-propenyl]sulfamoylacetate (733 mg) obtained in reference example 39 in a mixture of dichloromethane (30 ml) and ethanol (15 ml) under ice-cooling, and the resulting mixture was stirred at room temperature for 5 hours under sealed conditions and then evaporated in vacuo. Subsequently, to a solution of the residue obtained in ethanol (20 ml) were added successively an aqueous ammonium chloride solution (prepared by dissolving 175 mg in 10 ml of water) and a 28% ammonia solution (0.22 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 35% acetonitrile/water). The amorphous solid obtained was dissolved in 1N hydrochloric acid, and the resulting mixture was evaporated to dryness in vacuo. The residue obtained was dissolved in water and then lyophilized to afford the title compound (488 mg, yield: 64%) as a colorless amorphous solid.

$^1$H NMR (400 MHz, DMSO-d$_6$) δ ppm: 1.23 (3H, t, J=7.0), 1.55 (1H, m), 1.65 (1H, m), 1.84 (1H, m), 1.93 (1H, m), 2.01 (3H, s), 3.28–3.44 (2H, m), 3.56–3.72 (2H, m), 4.19 (2H, q, J=7.0), 4.41 (2H, s), 4.46 (2H, d, J=6.0), 4.75 (1H, m), 6.43 (1H, dt, J=16.0, 6.0), 6.58 (1H, d, J=16.0), 7.29 (1H, d, J=9.0), 7.38 (1H, dd, J=9.0, 2.5), 7.55 (1H, t, J=8.0), 7.57 (1H, d, J=2.5), 7.67 (1H, d, J=8.0), 7.73 (1H, d, J=8.0), 7.86 (1H, s);

IR (KBr, cm$^{-1}$): 1739, 1677, 1354, 1157.

Example 18

N-[4-(1-Acetylpiperidin-4-yloxy)-3-chlorophenyl]-N-[3-(3-amidinophenyl)-2-(E)-propenyl]sulfamoylacetic acid hydrochloride (Exemplification Compound Number 513)

Ethyl N-[4-(1-acetylpiperidin-4-yloxy)-3-chlorophenyl]-N-[3-(3-amidinophenyl)-2-(E)-propenyl]sulfamoylacetate hydrochloride (352 mg) obtained in example 17 was dissolved in 3N hydrochloric acid (20 ml) and the resulting mixture was stirred at 60° C. for 6 hours. After cooling to room temperature, the reaction mixture was evaporated in vacuo. The residue obtained was purified by preparative HPLC (YMC-Pack ODS-A; YMC, eluent: 25% acetonitrile/water). The amorphous solid obtained was dissolved in 1N hydrochloric acid (0.50 ml), and the resulting mixture was evaporated to dryness in vacuo to afford the title compound (109 mg, yield: 32%) as a colorless amorphous solid.

$^1$H NMR (500 MHz, DMSO-$d_6$) δ ppm: 1.54 (1H, m), 1.65 (1H, m), 1.83 (1H, m), 1.92 (1H, m), 2.00 (3H, s), 3.30–3.70 (4H, m), 3.83 (2H, s), 4.48 (2H, d, J=6.0), 4.71 (1H, m), 6.44 (1H, dt, J=16.0, 6.0), 6.53 (1H, d, J=16.0), 7.26 (1H, d, J=9.0), 7.48 (1H, dd, J=9.0, 2.5), 7.52 (1H, t, J=8.0), 7.66 (1H, d, J=8.0), 7.68 (1H, d, J=2.5), 7.71 (1H, d, J=8.0), 7.85 (1H, s);

IR (KBr, cm$^{-1}$): 1682, 1345, 1152.

Example 19

Ethyl N-[3-(3-amidinophenyl)-2-(E)-propenyl]-N-[4-(1-carbamoylpiperidin-4-yloxy)-3-chlorophenyl]sulfamoylacetate hydrochloride (Exemplification Compound Number 10)

Hydrogen chloride was bubbled through a solution of ethyl N-[4-(1-carbamoylpiperidin-4-yloxy)-3-chlorophenyl]-N-[3-(3-cyanophenyl)-2-(E)-propenyl]sulfamoylacetate (1015 mg) obtained in reference example 43 in a mixture of dichloromethane (30 ml) and ethanol (15 ml) under ice-cooling, and the resulting mixture was stirred at room temperature for 6 hours under sealed conditions and then evaporated in vacuo. Subsequently, to a solution of the residue obtained in ethanol (20 ml) were added successively an aqueous ammonium chloride solution (prepared by dissolving 194 mg in 10 ml of water) and a 28% ammonia solution (0.36 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 30% acetonitrile/water). The amorphous solid obtained was dissolved in 1N hydrochloric acid, and the resulting mixture was evaporated to dryness in vacuo. The residue obtained was dissolved in water and then lyophilized to afford the title compound (737 mg, yield: 66%) as a colorless amorphous solid.

$^1$H NMR (500 MHz, DMSO-$d_6$) δ ppm: 1.23 (3H, t, J=7.0), 1.46–1.58 (2H, m), 1.80–1.89 (2H, m), 3.15–3.24 (2H, m), 3.49–3.60 (2H, m), 4.19 (2H, q, J=7.0), 4.41 (2H, s), 4.46 (2H, d, J=6.0), 4.68 (1H, m), 6.43 (1H, dt, J=16.0, 6.0), 6.58 (1H, d, J=16.0), 7.28 (1H, d, J=9.0), 7.38 (1H, dd, J=9.0, 2.5), 7.55 (1H, t, J=8.0), 7.57 (1H, d, J=2.5), 7.68 (1H, d, J=8.0), 7.73 (1H, d, J=8.0), 7.87 (1H, s);

IR (KBr, cm$^{-1}$): 1738, 1675, 1352, 1156.

Example 20

N-[3-(3-Amidinophenyl)-2-(E)-propenyl]-N-[4-(1-carbamoylpiperidin-4-yloxy)-3-chlorophenyl]sulfamoylacetic acid hydrochloride (Exemplification Compound Number 514)

Ethyl N-[3-(3-amidinophenyl)-2-(E)-propenyl]-N-[4-(1-carbamoylpiperidin-4-yloxy)-3-chlorophenyl]sulfamoylacetate hydrochloride (600 mg) obtained in example 19 was dissolved in 3N hydrochloric acid (20 ml) and the resulting mixture was stirred at 60° C. for 5 hours. After cooling to room temperature, the reaction mixture was evaporated in vacuo. The residue obtained was purified by preparative HPLC (YMC-Pack ODS-A; YMC, eluent: 20% acetonitrile/water). The amorphous solid obtained was dissolved in 1N hydrochloric acid and the resulting mixture was evaporated to dryness in vacuo. The residue obtained was suspended in water containing dioxane (one drop) and then lyophilized to afford the title compound (466 mg, yield: 81%) as a colorless amorphous solid.

$^1$H NMR (500 MHz, DMSO-$d_6$) δ ppm: 1.48–1.58 (2H, m), 1.80–1.90 (2H, m), 3.14–3.24 (2H, m), 3.50–3.60 (2H, m), 4.27 (2H, s), 4.46 (2H, d, J=6.0), 4.67 (1H, m), 6.43 (1H, dt, J=16.0, 6.0), 6.58 (1H, d, J=16.0), 7.27 (1H, d, J=9.0), 7.38 (1H, dd, J=9.0, 2.5), 7.55 (1H, t, J=8.0), 7.57 (1H, d, J=2.5), 7.67 (1H, d, J=8.0), 7.73 (1H, d, J=8.0), 7.86 (1H, s);

IR (KBr, cm$^{-1}$): 1676, 1348, 1155.

Example 21

Ethyl N-[3-(3-amidinophenyl)-2-(E)-propenyl]-N-[3-chloro-4-(1-methanesulfonylpiperidin-4-yloxy)phenyl]sulfamoylacetate hydrochloride (Exemplification Compound Number 11)

Hydrogen chloride was bubbled through a solution of ethyl N-[3-chloro-4-(1-methanesulfonylpiperidin-4-yloxy)phenyl]-N-[3-(3-cyanophenyl)-2-(E)-propenyl]sulfamoylacetate (835 mg) obtained in reference example 47 in a mixture of dichloromethane (30 ml) and ethanol (15 ml) under ice-cooling, and the resulting mixture was stirred at room temperature for 6 hours under sealed conditions and then evaporated in vacuo. Subsequently, to a solution of the residue obtained in ethanol (20 ml) were added successively an aqueous ammonium chloride solution (prepared by dissolving 150 mg in 10 ml of water) and a 28% ammonia solution (0.19 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 40% acetonitrile/water). The amorphous solid obtained was dissolved in 1N hydrochloric acid, and the resulting mixture was evaporated to dryness in vacuo. The residue obtained was dissolved in water and then lyophilized to afford the title compound (685 mg, yield: 75%) as a colorless amorphous solid.

$^1$H NMR (500 MHz, DMSO-$d_6$) δ ppm: 1.23 (3H, t, J=7.0), 1.72–1.82 (2H, m), 1.93–2.03 (2H, m), 2.89 (3H, s), 3.12–3.22 (2H, m), 3.24–3.40 (2H, m), 4.19 (2H, q, J=7.0), 4.41 (2H, s), 4.47 (2H, d, J=6.0), 4.70 (1H, m), 6.43 (1H, dt, J=16.0, 6.0), 6.58 (1H, d, J=16.0), 7.28 (1H, d, J=9.0), 7.39 (1H, dd, J=9.0, 2.5), 7.55 (1H, t, J=8.0), 7.58 (1H, d, J=2.5), 7.67 (1H, d, J=8.0), 7.73 (1H, d, J=8.0), 7.85 (1H, s);

IR (KBr, cm$^{-1}$): 1739, 1677, 1346, 1156.

Example 22

N-[3-(3-Amidinophenyl)-2-(E)-propenyl]-N-[3-chloro-4-(1-methanesulfonylpiperidin-4-yloxy)phenyl]sulfamoylacetic acid hydrochloride (Exemplification Compound Number 515)

Ethyl N-[3-(3-amidinophenyl)-2-(E)-propenyl]-N-[3-chloro-4-(1-methanesulfonylpiperidin-4-yloxy)phenyl]sulfamoylacetate hydrochloride (502 mg) obtained in example 21 was dissolved in a mixture of 3N hydrochloric acid (20 ml) and dioxane (5 ml), and the resulting mixture was stirred at 60° C. for 5 hours. After cooling to room temperature, the reaction mixture was evaporated in vacuo. The residue obtained was purified by preparative HPLC (YMC-Pack ODS-A; YMC, eluent: 25~50% acetonitrile/water). The amorphous solid obtained was dissolved in 1N hydrochloric acid, and the resulting mixture was evaporated to dryness in vacuo to afford the title compound (346 mg, yield: 72%) as a colorless amorphous solid.

$^1$H NMR (500 MHz, DMSO-$d_6$) δ ppm: 1.72–1.82 (2H, m), 1.93–2.03 (2H, m), 2.89 (3H, s), 3.12–3.20 (2H, m), 3.23–3.40 (2H, m), 4.04 (2H, s), 4.48 (2H, d, J=6.0), 4.68 (1H, m), 6.44 (1H, dt, J=16.0, 6.0), 6.56 (1H, d, J=16.0), 7.26 (1H, d, J=9.0), 7.44 (1H, dd, J=9.0, 2.5), 7.54 (1H, t, J=8.0), 7.63 (1H, d, J=2.5), 7.67 (1H, d, J=8.0), 7.72 (1H, d, J=8.0), 7.86 (1H, s);

IR (KBr, cm$^{-1}$): 1679, 1344, 1155.

Example 23

Ethyl N-[3-(3-amidinophenyl)-2-(E)-propenyl]-N-[3-chloro-4–1-(2-pyridyl)piperidin-4-yloxy]phenyl]sulfamoylacetate dihydrochloride (Exemplification Compound Number 12)

Hydrogen chloride was bubbled through a solution of ethyl N-[3-chloro-4-[1-(2-pyridyl)piperidin-4-yloxy]phenyl]-N-[3-(3-cyanophenyl)-2-(E)-propenyl]sulfamoylacetate (1095 mg) obtained in reference example 51 in a mixture of dichloromethane (30 ml) and ethanol (15 ml) under ice-cooling, and the resulting mixture was stirred at room temperature for 6 hours under sealed conditions and then evaporated in vacuo. Subsequently, to a solution of the residue obtained in ethanol (20 ml) were added successively an aqueous ammonium chloride solution (prepared by dissolving 197 mg in 10 ml of water) and a 28% ammonia solution (0.37 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 50% acetonitrile/water). The amorphous solid obtained was dissolved in 1N hydrochloric acid, and the resulting mixture was evaporated to dryness in vacuo. The residue obtained was dissolved in water and then lyophilized to afford the title compound (533 mg, yield: 42%) as a colorless amorphous solid.

$^1$H NMR (500 MHz, DMSO-$d_6$) δ ppm: 1.23 (3H, t, J=7.0), 1.72–1.84 (2H, m), 2.01–2.13 (2H, m), 3.68–3.79 (2H, m), 3.88–3.99 (2H, m), 4.20 (2H, q, J=7.0), 4.43 (2H, s), 4.48 (2H, d, J=6.0), 4.85 (1H, m), 6.45 (1H, dt, J=16.0, 6.0), 6.59 (1H, d, J=16.0), 6.92 (1H, m), 7.35 (1H, d, J=9.0), 7.32–7.44 (1H, m), 7.4 dd (1H, d, J=9.0, 2.5), 7.55 (1H, t, J=8.0), 7.59 (1H, d, J=2.5), 7.70 (1H, d, J=8.0), 7.74 (1H, d, J=8.0), 7.90 (1H, s), 7.96 (1H, m), 8.02 (1H, d, J=4.5);

IR (KBr, cm$^{-1}$): 1738, 1674, 1353, 1155.

Example 24

N-[3-(3-Amidinophenyl)-2-(E)-propenyl]-N-[3-chloro-4-[1-(2-pyridyl)piperidin-4-yloxy]phenyl]sulfamoylacetic acid dihydrochloride (Exemplification Compound Number 516)

Ethyl N-[3-(3-amidinophenyl)-2-(E)-propenyl]-N-[3-chloro-4-[1-(2-pyridyl)piperidin-4-yloxy]phenyl]sulfamoylacetate dihydrochloride (533 mg) obtained in example 23 was dissolved in 3N hydrochloric acid (30 ml) and the resulting mixture was stirred at 60° C. for 6 hours. After cooling to room temperature, the reaction mixture was evaporated in vacuo. The residue obtained was purified by preparative HPLC (YMC-Pack ODS-A; YMC, eluent: 30~50% acetonitrile/water). The amorphous solid obtained was dissolved in 1N hydrochloric acid and the resulting mixture was evaporated to dryness in vacuo. The residue obtained was dissolved in water and then lyophilized to afford the title compound (427 mg, yield: 84%) as a colorless amorphous solid.

$^1$H NMR (500 MHz, DMSO-$d_6$) δ ppm: 1.71–1.82 (2H, m), 2.01–2.12 (2H, m), 3.63–3.75 (2H, m), 3.85–3.97 (2H, m), 4.28 (2H, s), 4.47 (2H, d, J=6.0), 4.84 (1H, m), 6.44 (1H, dt, J=16.0, 6.0), 6.58 (1H, d, J=16.0), 6.89 (1H, m), 7.33 (1H, d, J=9.0), 7.30–7.40 (1H, m), 7.41 (1H, dd, J=9.0, 2.5), 7.55 (1H, t, J=8.0), 7.59 (1H, d, J=2.5), 7.68 (1H, d, J=8.0), 7.73 (1H, d, J=8.0), 7.88 (1H, s), 7.93 (1H, m), 8.02 (1H, J=6.0);

IR (KBr, cm$^{-1}$): 1733, 1676, 1349, 1155.

Example 25

Ethyl N-[3-(3-amidinophenyl)-2-(E)-propenyl]-N-[3-chloro-4-[1-(3-pyridyl)piperidin-4-yloxy]phenyl]sulfamoylacetate dihydrochloride (Exemplification Compound Number 13)

Hydrogen chloride was bubbled through a solution of ethyl N-[3-chloro-4-[1-(3-pyridyl)piperidin-4-yloxy]phenyl]-N-[3-(3-cyanophenyl)-2-(E)-propenyl]sulfamoylacetate (490 mg) obtained in reference example 55 in a mixture of dichloromethane (15 ml) and ethanol (15 ml) under ice-cooling, and the resulting mixture was stirred at room temperature overnight under sealed conditions and then evaporated in vacuo. Subsequently, to a solution of the residue obtained in ethanol (9 ml) were added successively an aqueous ammonium chloride solution (prepared by dissolving 79 mg in 3 ml of water) and a 28% ammonia solution (0.17 ml), and the resulting mixture was stirred at room temperature overnight and then evaporated in vacuo. The residue obtained was purified by preparative HPLC (YMC-Pack ODS-A; YMC, eluent: 40% acetonitrile/water) to obtain an amorphous solid (306 mg). Subsequently, to a solution of this solid (44 mg) in ethanol (4 ml) was added a 4N solution of hydrogen chloride in dioxane (0.05 ml) and the resulting mixture was evaporated in vacuo. The residue obtained was dissolved in water and then lyophilized to afford the title compound (47 mg, yield: 58%) as a colorless amorphous solid.

$^1$H NMR (400 MHz, DMSO-$d_6$) δ ppm: 1.23 (3H, t, J=7.0), 1.69–1.82 (2H, m), 1.96–2.08 (2H, m), 3.42 (2H, m), 3.66 (2H, m), 4.19 (2H, q, J=7.0), 4.43 (2H, s), 4.47 (2H, d, J=6.0), 4.80 (1H, m), 6.45 (1H, dt, J=16.0, 6.0), 6.59 (1H, d, J=16.0), 7.33 (1H, d, J=9.0), 7.41 (1H, dd, J=9.0, 2.5), 7.55 (1H, t, J=8.0), 7.59 (1H, d, J=2.5), 7.69 (1H, d, J=8.0), 7.74 (1H, d, J=8.0), 7.75 (1H, dd, J=9.0, 5.0), 7.89 (1H, s), 8.03 (1H, dd, J=9.0, 2.5), 8.15 (1H, d, J=5.0), 8.48 (1H, d, J=2.5);

IR (KBr, cm$^{-1}$): 1737, 1675, 1352, 1155.

Example 26

N-[3-(3-Amidinophenyl)-2-(E)-propenyl]-N-[3-chloro-4-[1-(3-pyridyl)piperidin-4-yloxy]phenyl]sulfamoylacetic acid dihydrochloride (Exemplification Compound Number 517)

Ethyl N-[3-(3-amidinophenyl)-2-(E)-propenyl]-N-[3-chloro-4-[1-(3-pyridyl)piperidin-4-yloxy]phenyl]sulfamoylacetate (247 mg) obtained in example 25 was dissolved in 3N hydrochloric acid (12 ml) and the resulting mixture was stirred at 60° C. for 4 hours. After cooling to room temperature, the reaction mixture was evaporated in vacuo. The residue obtained was purified by preparative HPLC (YMC-Pack ODS-A; YMC, eluent: 27% acetonitrile/water). The amorphous solid obtained was dissolved in 1N hydrochloric acid (10 ml) and the resulting mixture was evaporated to dryness in vacuo. The residue obtained was dissolved in water and then lyophilized to afford the title compound (427 mg, yield: 84%) as a colorless amorphous solid.

$^1$H NMR (400 MHz, DMSO-d$_6$) δ ppm: 1.69–1.81 (2H, m), 1.97–2.08 (2H, m), 3.42 (2H, m), 3.67 (2H, m), 4.29 (2H, s), 4.47 (2H, d, J=6.0), 4.80 (1H, m), 6.45 (1H, dt, J=16.0, 6.0), 6.58 (1H, d, J=16.0), 7.33 (1H, d, J=9.0), 7.41 (1H, dd, J=9.0, 2.5), 7.55 (1H, t, J=8.0), 7.59 (1H, d, J=2.5), 7.69 (1H, d, J=8.0), 7.74 (1H, d, J=8.0), 7.77 (1H, dd, J=9.0, 5.5), 7.89 (1H, s), 8.04 (1H, dd, J=9.0, 2.0), 8.15 (1H, d, J=5.5), 8.48 (1H, d, J=2.0);

IR (KBr, cm$^{-1}$): 1731, 1675, 1348, 1154.

Example 27

Ethyl N-[3-(3-amidinophenyl)-2-(E)-propenyl]-N-[3-chloro-4-[1-(4-pyridyl)piperidin-4-yloxy]phenyl]sulfamoylacetate dihydrochloride (Exemplification Compound Number 14)

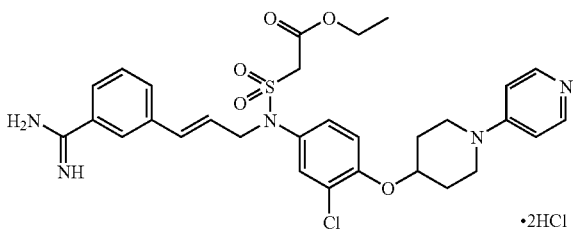

Hydrogen chloride was bubbled through a solution of ethyl N-[3-chloro-4-[1-(4-pyridyl)piperidin-4-yloxy]phenyl]-N-[3-(3-cyanophenyl)-2-(E)-propenyl]sulfamoylacetate (637 mg) obtained in reference example 59 in a mixture of dichloromethane (30 ml) and ethanol (15 ml) under ice-cooling, and the resulting mixture was stirred at room temperature for 5.5 hours under sealed conditions and then evaporated in vacuo. Subsequently, to a solution of the residue obtained in ethanol (20 ml) were added successively an aqueous ammonium chloride solution (prepared by dissolving 115 mg in 10 ml of water) and a 28% ammonia solution (0.21 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 27% acetonitrile/water). The amorphous solid obtained was dissolved in 1N hydrochloric acid, and the resulting mixture was evaporated to dryness in vacuo. The residue obtained was dissolved in water and then lyophilized to afford the title compound (456 mg, yield: 62%) as a colorless amorphous solid.

$^1$H NMR (500 MHz, DMSO-d$_6$) δ ppm: 1.23 (3H, t, J=7.0), 1.72–1.82 (2H, m), 2.00–2.10 (2H, m), 3.71 (2H, m), 3.86 (2H, m), 4.19 (2H, q, J=7.0), 4.42 (2H, s), 4.48 (2H, d, J=6.0), 4.87 (1H, m), 6.44 (1H, dt, J=16.0, 6.0), 6.59 (1H, d, J=16.0), 7.23 (2H, J=7.5), 7.34 (1H, d, J=9.0), 7.41 (1H, dd, J=9.0, 2.5), 7.55 (1H, t, J=8.0), 7.59 (1H, d, J=2.5), 7.68 (1H, d, J=8.0), 7.74 (1H, d, J=8.0), 7.88 (1H, s), 8.24 (2H, d, J=7.5);

IR (KBr, cm$^{-1}$): 1738, 1675, 1352, 1155.

Example 28

N-[3-(3-Amidinophenyl)-2-(E)-propenyl]-N-[3-chloro-4-[1-(4-pyridyl)piperidin-4-yloxy]phenyl]sulfamoylacetic acid dihydrochloride (Exemplification Compound Number 518)

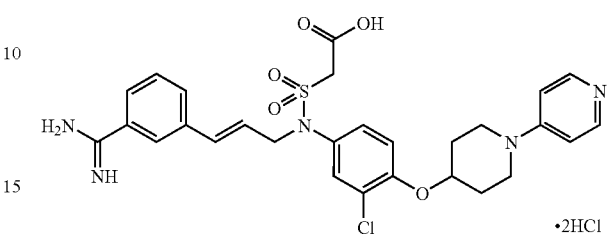

Ethyl N-[3-(3-amidinophenyl)-2-(E)-propenyl]-N-[3-chloro-4-[1-(4-pyridyl)piperidin-4-yloxy]phenyl]sulfamoylacetate dihydrochloride (315 mg) obtained in example 27 was dissolved in 3N hydrochloric acid (20 ml) and the resulting mixture was stirred at 60° C. for 8 hours. After cooling to room temperature, the reaction mixture was evaporated in vacuo. The residue obtained was purified by preparative HPLC (YMC-Pack ODS-A; YMC, eluent: 20% acetonitrile/water). The amorphous solid obtained was dissolved in 1N hydrochloric acid (0.50 ml) and the resulting mixture was evaporated to dryness in vacuo. The residue obtained was dissolved in water and then lyophilized to afford the title compound (286 mg, yield: 95%) as a colorless amorphous solid.

$^1$H NMR (500 MHz, DMSO-d$_6$) δ ppm: 1.70–1.80 (2H, m), 1.99–2.09 (2H, m), 3.69 (2H, m), 3.85 (2H, m), 4.26 (2H, s), 4.47 (2H, d, J=6.0), 4.86 (1H, m), 6.45 (1H, dt, J=16.0, 6.0), 6.58 (1H, d, J=16.0), 7.22 (2H, d, J=7.5), 7.33 (1H, d, J=9.0), 7.42 (1H, dd, J=9.0, 2.5), 7.55 (1H, t, J=8.0), 7.59 (1H, d, J=2.5), 7.69 (1H, d, J=8.0), 7.73 (1H, d, J=8.0), 7.89 (1H, s), 8.24 (2H, d, J=7.5);

IR (KBr, cm$^{-1}$): 1731, 1675, 1347, 1154.

Example 29

Ethyl N-[3-(3-amidinophenyl)-2-(E)-propenyl]-N-[3-chloro-4-[1-(2-pyrimidyl)piperidin-4-yloxy]phenyl]sulfamoylacetate dihydrochloride (Exemplification Compound Number 15)

Hydrogen chloride was bubbled through a solution of ethyl N-[3-chloro-4-[1-(2-pyrimidyl)piperidin-4-yloxy]phenyl]-N-[3-(3-cyanophenyl)-2-(E)-propenyl]sulfamoylacetate (1590 mg) obtained in reference example 63 in a mixture of dichloromethane (30 ml) and ethanol (15 ml) under ice-cooling, and the resulting mixture was stirred at room temperature for 7 hours under sealed conditions and then evaporated in vacuo. Subsequently, to a solution of the residue obtained in ethanol (20 ml) were added successively an aqueous ammonium chloride solution (prepared by dissolving 285 mg in 10 ml of water) and a 28% ammonia solution (0.53 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 27% acetonitrile/water). The amorphous solid obtained was dissolved in 1N hydrochloric acid, and the resulting mixture was evaporated to dryness in vacuo. The residue obtained was dissolved in water and then lyophilized to afford the title compound (1280 mg, yield: 70%) as a colorless amorphous solid.

$^1$H NMR (500 MHz, DMSO-d$_6$) δ ppm: 1.23 (3H, t, J=7.0), 1.58–1.68 (2H, m), 1.89–1.99 (2H, m), 3.68 (2H, m), 4.04 (2H, m), 4.19 (2H, q, J=7.0), 4.41 (2H, s), 4.47 (2H, d, J=6.0), 4.80 (1H, m), 6.43 (1H, dt, J=16.0, 6.0), 6.59 (1H, d, J=16.0), 6.63 (1H, t, J=4.5), 7.31 (1H, d, J=9.0), 7.39 (1H, dd, J=9.0, 2.5), 7.55 (1H, t, J=8.0), 7.57 (1H, d, J=2.5), 7.67 (1H, d, J=8.0), 7.74 (1H, d, J=8.0), 7.86 (1H, s), 8.36 (2H, d, J=4.5);

IR (KBr, cm$^{-1}$): 1740, 1676, 1348, 1151.

Example 30

N-[3-(3-Amidinophenyl)-2-(E)-propenyl]-N-[3-chloro-4-[1-(2-pyrimidyl)piperidin-4-yloxy]phenyl]sulfamoylacetic acid dihydrochloride (Exemplification Compound Number 519)

Ethyl N-[3-(3-amidinophenyl)-2-(E)-propenyl]-N-[3-chloro-4-[1-(2-pyrimidyl)piperidin-4-yloxy]phenyl]sulfamoylacetate dihydrochloride (800 mg) obtained in example 29 was dissolved in 3N hydrochloric acid (40 ml) and the resulting mixture was stirred at 60° C. for 9 hours. After cooling to room temperature, the reaction mixture was evaporated in vacuo. The residue obtained was purified by preparative HPLC (YMC-Pack ODS-A; YMC, eluent: 35~50% acetonitrile/water). The amorphous solid obtained was dissolved in 1N hydrochloric acid and the resulting mixture was evaporated to dryness in vacuo. The residue obtained was dissolved in water and then lyophilized to afford the title compound (673 mg, yield: 88%) as a colorless amorphous solid.

$^1$H NMR (500 MHz, DMSO-d$_6$) δ ppm: 1.60–1.70 (2H, m), 1.90–2.00 (2H, m), 3.60–3.80 (2H, m), 4.00–4.10 (2H, m), 4.28 (2H, s), 4.47 (2H, d, J=6.0), 4.81 (1H, m), 6.44 (1H, dt, J=16.0, 6.0), 6.58 (1H, d, J=16.0), 6.68 (1H, t, J=5.0), 7.31 (1H, d, J=9.0), 7.40 (1H, dd, J=9.0, 2.5), 7.55 (1H, t, J=8.0), 7.58 (1H, d, J=2.5), 7.69 (1H, d, J=8.0), 7.73 (1H, d, J=8.0), 7.89 (1H, s), 8.40 (2H, J=5.0);

IR (KBr, cm$^{-1}$): 1732, 1675, 1345, 1154.

Example 31

Ethyl N-[3-(3-amidinophenyl)-2-(E)-propenyl]-N-[3-chloro-4-[1-(3-pyridylmethyl)piperidin-4-yloxy]phenyl]sulfamoylacetate trihydrochloride (Exemplification Compound Number 16)

Hydrogen chloride was bubbled through a solution of ethyl N-[3-chloro-4-[1-(3-pyridylmethyl)piperidin-4-yloxy]phenyl]-N-[3-(3-cyanophenyl)-2-(E)-propenyl]sulfamoylacetate (945 mg) obtained in reference example 67 in a mixture of dichloromethane (30 ml) and ethanol (15 ml) under ice-cooling, and the resulting mixture was stirred at room temperature for 6.5 hours under sealed conditions and then evaporated in vacuo. Subsequently, to a solution of the residue obtained in ethanol (20 ml) were added successively an aqueous ammonium chloride solution (prepared by dissolving 166 mg in 10 ml of water) and a 28% ammonia solution (0.31 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 25% acetonitrile/water). The amorphous solid obtained was dissolved in 1N hydrochloric acid, and the resulting mixture was evaporated to dryness in vacuo. The residue obtained was dissolved in water and then lyophilized to afford the title compound (328 mg, yield: 29%) as a colorless amorphous solid.

$^1$H NMR (500 MHz, DMSO-d$_6$) δ ppm: 1.22 (3H, t, J=7.0), 1.96–2.09 (2H, m), 2.18–2.31 (2H, m), 3.07 (2H, m), 3.33 and 3.46 (total 2H, each m), 4.19 (2H, q, J=7.0), 4.41 (2H, s), 4.42–4.52 (2H, m), 4.46 (2H, d, J=6.0), 4.62 and 4.89 (total 1H, each m), 6.43 (1H, dt, J=16.0, 6.0), 6.57 (1H, d, J=16.0), 7.30 (1H, m), 7.40 (1H, m), 7.55 (1H, t, J=8.0), 7.58 (1H, s), 7.68 (1H, d, J=8.0), 7.72 (1H, d, J=8.0), 7.75 (1H, m), 7.87 (1H, s), 8.36–8.48 (1H, m), 8.79 (1H, d, J=4.5), 8.96 (1H, m);

IR (KBr, cm$^{-1}$): 1736, 1674, 1350, 1154.

Example 32

N-[3-(3-Amidinophenyl)-2-(E)-propenyl]-N-[3-chloro-4-[1-(3-pyridylmethyl)piperidin-4-yloxy]phenyl]sulfamoylacetic acid trihydrochloride (Exemplification Compound Number 520)

Ethyl N-[3-(3-amidinophenyl)-2-(E)-propenyl]-N-[3-chloro-4-[1-(3 -pyridylmethyl)piperidin-4-yloxy]phenyl]sulfamoylacetate trihydrochloride (175 mg) obtained in example 31 was dissolved in 3N hydrochloric acid (10 ml) and the resulting mixture was stirred at 60° C. for 8 hours. After cooling to room temperature, the reaction mixture was evaporated in vacuo. The residue obtained was purified by preparative HPLC (YMC-Pack ODS-A; YMC, eluent: 15~20% acetonitrile/water). The amorphous solid obtained was dissolved in 1N hydrochloric acid and the resulting mixture was evaporated to dryness in vacuo. The residue obtained was dissolved in water and then lyophilized to afford the title compound (74 mg, yield: 44%) as a colorless amorphous solid.

$^1$H NMR (500 MHz, DMSO-d$_6$) δ ppm: 1.97–2.12 (2H, m), 2.17–2.34 (2H, m), 3.00–3.17 (2H, m), 3.33 and 3.46 (total 2H, each m), 4.27 (2H, s), 4.47 (2H, d, J=6.0), 4.48–4.56 (2H, m), 4.62 and 4.90 (total 1H, each m), 6.44 (1H, dt, J=16.0, 6.0), 6.57 (1H, d, J=16.0), 7.30 (1H, m), 7.36–7.45 (1H, m), 7.54 (1H, t, J=8.0), 7.58 (1H, s), 7.69 (1H, d, J=8.0), 7.72 (1H, d, J=8.0), 7.83–7.93 (2H, m), 8.60 (1H, m), 8.86 (1H, d, J=5.0), 9.06 (1H, m);

IR (KBr, cm$^{-1}$) 1731, 1675, 1347, 1155.

Example 33

Ethyl N-[3-(3-amidinophenyl)-2-(E)-propenyl]-N-[3-chloro-4-[1-(4-pyridylmethyl)piperidin-4-yloxy]phenyl]sulfamoylacetate trihydrochloride (Exemplification Compound Number 17)

Hydrogen chloride was bubbled through a solution of ethyl N-[3-chloro-4-[1-(4-pyridylmethyl)piperidin-4-yloxy]phenyl]-N-[3-(3-cyanophenyl)-2-(E)-propenyl]sulfamoylacetate (971 mg) obtained in reference example 72 in a mixture of dichloromethane (30 ml) and ethanol (15 ml) under ice-cooling, and the resulting mixture was stirred at room temperature for 7 hours under sealed conditions and then evaporated in vacuo. Subsequently, to a solution of the residue obtained in ethanol (20 ml) were added successively an aqueous ammonium chloride solution (prepared by dissolving 171 mg in 10 ml of water) and a 28% ammonia solution (0.32 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 10~35% acetonitrile/water). The amorphous solid obtained was dissolved in 1N hydrochloric acid, and the resulting mixture was evaporated to dryness in vacuo. The residue obtained was dissolved in water and then lyophilized to afford the title compound (580 mg, yield: 49%) as a colorless amorphous solid.

$^1$H NMR (500 MHz, DMSO-d$_6$) δ ppm: 1.22 (3H, t, J=7.0), 1.98–2.16 (2H, m), 2.16–2.40. (2H, m), 3.07 (2H, m), 3.32 and 3.44 (total 2H, each m), 4.19 (2H, q, J=7.0), 4.41 (2H, s), 4.46 (2H, d, J=6.0), 4.44–4.56 (2H, m), 4.62 and 4.90 (total 1H, each m), 6.43 (1H, dt, J=16.0, 6.0), 6.57 (1H, d, J=16.0), 7.30 (1H, m), 7.40 (1H, m), 7.54 (1H, t, J=8.0), 7.58 (1H, s), 7.68 (1H, d, J=8.0), 7.72 (1H, d, J=8.0), 7.88 (1H, s), 8.00 (2H, m), 8.82 (2H, m);

IR (KBr, cm$^{-1}$): 1737, 1675, 1351, 1155.

Example 34

N-[3-(3-Amidinophenyl)-2-(E)-propenyl]-N-[3-chloro-4-[1-(4-pyridylmethyl)piperidin-4-yloxy]phenyl]sulfamoylacetic acid trihydrochloride (Exemplification Compound Number 521)

Ethyl N-[3-(3-amidinophenyl)-2-(E)-propenyl]-N-[3-chloro-4-[1-(4-pyridylmethyl)piperidin-4-yloxy]phenyl]sulfamoylacetate trihydrochloride (440 mg) obtained in example 33 was dissolved in 3N hydrochloric acid (10 ml) and the resulting mixture was stirred at 60° C. for 2 hours. After cooling to room temperature, the reaction mixture was evaporated in vacuo. The residue obtained was purified by preparative HPLC (YMC-Pack ODS-A; YMC, eluent: 10~20% acetonitrile/water). The amorphous solid obtained was dissolved in 1N hydrochloric acid and the resulting mixture was evaporated to dryness in vacuo. The residue obtained was dissolved in water and then lyophilized to afford the title compound (155 mg, yield: 37%) as a colorless amorphous solid.

$^1$H NMR (500 MHz, DMSO-d$_6$) δ ppm: 1.97–2.16 (2H, m), 2.16–2.40 (2H, m), 3.10 (2H, m), 3.32 and 3.44 (total 2H, each m), 4.28 (2H, s), 4.47 (2H, d, J=6.0), 4.56 (2H, m), 4.61 and 4.90 (total 1H, each m), 6.44 (1H, dt, J=16.0, 6.0), 6.57 (1H, d, J=16.0), 7.31 (1H, m), 7.41 (1H, m), 7.54 (1H, t, J=8.0), 7.59 (1H, s), 7.71 (2H, m), 7.90 (1H, s), 8.18 (2H, m), 8.91 (2H, m);

IR (KBr, cm$^{-1}$): 1731, 1675, 1347, 1154.

Example 35

Ethyl N-[3-(3-amidinophenyl)-2-(E)-propenyl]-N-[3-chloro-4-[1-[2-(2-pyridyl)ethyl]piperidin-4-yloxy]phenyl]sulfamoylacetate trihydrochloride (Exemplification Compound Number 18)

Hydrogen chloride was bubbled through a solution of ethyl N-[3-chloro-4-[1-[2-(2-pyridyl)ethyl]piperidin-4-yloxy]-N-[3-(3-cyanophenyl)-2-(E)-propenyl]sulfamoylacetate (1727 mg) obtained in reference example 77 in a mixture of dichloromethane (30 ml) and ethanol (15 ml) under ice-cooling, and the resulting mixture was stirred at room temperature for 6.5 hours under sealed conditions and then evaporated in vacuo. Subsequently, to a solution of the residue obtained in ethanol (20 ml) were added successively an aqueous ammonium chloride solution (prepared by dissolving 296 mg in 10 ml of water) and a 28% ammonia solution (0.72 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 25~30% acetonitrile/water). The amorphous solid obtained was dissolved in 1N hydrochloric acid, and the resulting mixture was evaporated to dryness in vacuo. The residue obtained was dissolved in water and then lyophilized to afford the title compound (944 mg, yield: 45%) as a colorless amorphous solid.

$^1$H NMR (500 MHz, DMSO-d$_6$) δ ppm: 1.23 (3H, t, J=7.0), 2.00–2.12 (2H, m), 2.21–2.33 (2H, m), 3.10–3.70 (4H, m), 3.48–3.60 (4H, m), 4.19 (2H, q, J=7.0), 4.42 (2H, s), 4.48 (2H, d, J=6.0), 4.82 (1H, m), 6.44 (1H, dt, J=16.0, 6.0), 6.58 (1H, d, J=16.0), 7.33 (1H, d, J=9.0), 7.42 (1H, dd, J=9.0, 2.5), 7.55 (1H, t, J=8.0), 7.60 (1H, d, J=2.5), 7.67–7.75 (1H, m), 7.70 (1H, d, J=8.0), 7.73 (1H, d, J=8.0), 7.80 (1H, m), 7.90 (1H, s), 8.26 (1H, m), 8.73 (1H, d, J=5.0);

IR (KBr, cm$^{-1}$) 1736, 1674, 1350, 1154.

Example 36

N-[3-(3-Amidinophenyl)-2-(E)-propenyl]-N-[3-chloro-4-[1-[2-(2-pyridyl)ethyl]piperidin-4-yloxy]phenyl]sulfamoylacetic acid trihydrochloride (Exemplification Compound Number 522)

Ethyl N-[3-(3-amidinophenyl)-2-(E)-propenyl]-N-[3-chloro-4-[1-[2-(2-pyridyl)ethyl]piperidin-4-yloxy]phenyl]sulfamoylacetate trihydrochloride (400 mg) obtained in example 35 was dissolved in 3N hydrochloric acid (20 ml) and the resulting mixture was stirred at 60° C. for 4.5 hours. After cooling to room temperature, the reaction mixture was evaporated in vacuo. The residue obtained was purified by preparative HPLC (YMC-Pack ODS-A; YMC, eluent: 17% acetonitrile/water). The amorphous solid obtained was dissolved in 1N hydrochloric acid and the resulting mixture was evaporated to dryness in vacuo. The residue obtained was dissolved in water and then lyophilized to afford the title compound (201 mg, yield: 52%) as a colorless amorphous solid.

$^1$H NMR (500 MHz, DMSO-d$_6$) δ ppm: 2.00–2.12 (2H, m), 2.20–2.32 (2H, m), 3.20–3.60 (4H, m), 3.39–3.48 (2H, m), 3.50–3.59 (2H, m), 4.28 (2H, s), 4.47 (2H, d, J=6.0), 4.81 (1H, m), 6.45 (1H, dt, J=16.0, 6.0), 6.58 (1H, d, J=16.0), 7.32 (1H, d, J=9.0), 7.42 (1H, dd, J=9.0, 2.5), 7.50–7.58 (1H, m), 7.55 (1H, t, J=8.0), 7.58–7.66 (1H, m), 7.60 (1H, d, J=2.5), 7.69 (1H, d, J=8.0), 7.73 (1H, d, J=8.0), 7.89 (1H, s), 8.07 (1H, m), 8.65 (1H, d, J=4.5);

IR (KBr, cm$^{-1}$): 1730, 1675, 1347, 1154.

Example 37

Ethyl N-[3-(3-amidinophenyl)-2-(E)-propenyl]-N-[3-chloro-4-(1-cyclopentylpiperidin-4-yloxy)phenyl]sulfamoylacetate dihydrochloride (Exemplification Compound Number 19)

Hydrogen chloride was bubbled through a solution of ethyl N-[3-chloro-4-(1-cyclopentylpiperidin-4-yloxy)phenyl]-N-[3-(3-cyanophenyl)-2-(E)-propenyl]sulfamoylacetate (1.30 g) obtained in reference example 81 in a mixture of dichloromethane (30 ml) and ethanol (15 ml) under ice-cooling, and the resulting mixture was stirred at room temperature for 6 hours under sealed conditions and then evaporated in vacuo. Subsequently, to a solution of the residue obtained in ethanol (20 ml) were added successively an aqueous ammonium chloride solution (prepared by dissolving 0.24 g in 10 ml of water) and a 28% ammonia solution (0.45 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 25% acetonitrile/water). The amorphous solid obtained was dissolved in 1N hydrochloric acid, and the resulting mixture was evaporated to dryness in vacuo. The residue obtained was dissolved in water and then lyophilized to afford the title compound (1.20 g, yield: 80%) as a colorless amorphous solid.

$^1$H NMR (500 MHz, DMSO-d$_6$) δ ppm: 1.23 (3H, t, J=7.0), 1.47–1.60 (2H, m), 1.64–1.76 (2H, m), 1.76–1.90 (2H, m), 1.94–2.12 (4H, m), 2.16–2.36 (2H, m), 3.02 (2H, m), 3.32–3.55 (3H, m), 4.19 (2H, q, J=7.0), 4.42 (2H, s), 4.48 (2H, d, J=6.0), 4.68 and 4.92 (total 1H, each m), 6.45 (1H, dt, J=16.0, 6.0), 6.58 (1H, d, J=16.0), 7.32 (1H, m), 7.42 (1H, m), 7.55 (1H, t, J=8.0), 7.60 (1H, m), 7.68–7.76 (2H, m), 7.92 (1H, s);

IR (KBr, cm$^{-1}$): 1739, 1674, 1354, 1156.

Example 38

N-[3-(3-Amidinophenyl)-2-(E)-propenyl]-N-[3-chloro-4-(1-cyclopentylpiperidin-4-yloxy)phenyl]sulfamoylacetic acid dihydrochloride (Exemplification Compound Number 523)

Ethyl N-[3-(3-amidinophenyl)-2-(E)-propenyl]-N-[3-chloro-4-(1-cyclopentylpiperidin-4-yloxy)phenyl]sulfamoylacetate dihydrochloride (790 mg) obtained in example 37 was dissolved in 3N hydrochloric acid (20 ml) and the resulting mixture was stirred at 60° C. for 4.5 hours. After cooling to room temperature, the reaction mixture was evaporated in vacuo. The residue obtained was purified by preparative HPLC YMC-Pack ODS-A; YMC, eluent: 20% acetonitrile/water). The amorphous solid obtained was dissolved in 1N hydrochloric acid and the resulting mixture was evaporated to dryness in vacuo. The residue obtained was dissolved in water and then lyophilized to afford the title compound (522 mg, yield: 69%) as a colorless amorphous solid.

$^1$H NMR (500 MHz, DMSO-d$_6$) δ ppm: 1.48–1.63 (2H, m), 1.63–1.76 (2H, m), 1.76–1.88 (2H, m), 1.93–2.10 (4H, m), 2.15–2.35 (2H, m), 2.91–3.13 (2H, m), 3.20–3.59 (3H, m), 4.26 (2H, s), 4.47 (2H, d, J=6.0), 4.66 and 4.91 (total 1H, each m), 6.45 (1H, dt, J=16.0, 6.0), 6.58 (1H, d, J=16.0), 7.31 (1H, d, J=9.0), 7.42 (1H, dd, J=9.0, 2.5), 7.55 (1H, t, J=8.0), 7.61 (1H, d, J=2.5), 7.69 (1H, d, J=8.0), 7.73 (1H, d, J=8.0), 7.90 (1H, s);

IR (KBr, cm$^{-1}$): 1732, 1676, 1348, 1155.

Example 39

Ethyl N-[3-(3-amidinophenyl)-2-(E)-propenyl]-N-[3-chloro-4-(1,2-dimethylpiperidin-4-yloxy)phenyl]sulfamoylacetate dihydrochloride (Exemplification Compound Number 20)

Hydrogen chloride was bubbled through a solution of ethyl N-[3-chloro-4-(1,2-dimethylpiperidin-4-yloxy)phenyl]-N-[3-(3-cyanophenyl)-2-(E)-propenyl]sulfamoylacetate (1100 mg) obtained in reference example 89 in a mixture of dichloromethane (20 ml) and ethanol (20 ml) under ice-cooling, and the resulting mixture was stirred at room temperature for 4 hours under sealed conditions and then evaporated in vacuo. Subsequently, to a solution of the residue obtained in ethanol (25 ml) were added successively an aqueous ammonium chloride solution (prepared by dissolving 240 mg in 5 ml of water) and a 28% ammonia solution (0.54 ml), and the resulting mixture was stirred at room temperature overnight and then evaporated in vacuo. The residue obtained was purified by preparative HPLC (YMC-Pack ODS-A; YMC, eluent: 25% acetonitrile/water). Subsequently, to a solution of the amorphous solid obtained in ethanol (5 ml) was added a 4N solution of hydrogen chloride in dioxane (0.40 ml), and the resulting mixture was evaporated in vacuo to afford the title compound (420 mg, yield: 33%) as a colorless amorphous solid.

$^1$H NMR (500 MHz, DMSO-d$_6$) δ ppm: 1.23 (3H, t, J=7.0), 1.33 (3H, d, J=6.5), 1.70–1.85 (1H, m), 1.85–2.00 (1H, m), 2.20–2.35 (2H, m), 2.75 (3H, s), 3.05–3.15 (1H, m), 3.25–3.35 (1H, m), 3.45–3.55 (1H, m), 4.19 (2H, q, J=7.0), 4.41 (2H, s), 4.47 (2H, d, J=6.0), 4.65 (1H, m), 6.43 (1H, dt, J=16.0, 6.0), 6.58 (1H, d, J=16.0), 7.33 (1H, d, J=9.0), 7.40 (1H, dd, J=9.0, 2.5), 7.55 (1H, t, J=8.0), 7.59 (1H, d, J=2.5), 7.68 (1H, d, J=8.0), 7.73 (1H, d, J=8.0), 7.87 (1H, s);

IR (KBr, cm$^{-1}$): 1738, 1675.

Example 40

N-[3-(3-Amidinophenyl)-2-(E)-propenyl]-N-[3-chloro-4-(1,2-dimethylpiperidin-4-yloxy)phenyl]sulfamoylacetic acid dihydrochloride (Exemplification Compound Number 524)

Ethyl N-[3-(3-amidinophenyl)-2-(E)-propenyl]-N-[3-chloro-4-(1,2-dimethylpiperidin-4-yloxy)phenyl]sulfamoylacetate dihydrochloride (260 mg) obtained in example 39 was dissolved in 3N hydrochloric acid (20 ml) and the resulting mixture was stirred at 60° C. for 4 hours. After cooling to room temperature, the reaction mixture was evaporated in vacuo. The residue obtained was purified by preparative HPLC (YMC-Pack ODS-A; YMC, eluent: 15% acetonitrile/water). The amorphous solid obtained was dissolved in 1N hydrochloric acid, and the resulting mixture was evaporated to dryness in vacuo to afford the title compound (220 mg, yield: 89%) as a colorless amorphous solid.

$^1$H NMR (500 MHz, DMSO-d$_6$) δ ppm: 1.33 (3H, d, J=6.5), 1.70–1.80 (1H, m), 1.85–1.95 (1H, m), 2.20–2.35 (2H, m), 2.76 (3H, s), 3.05–3.15 (1H, m), 3.20–3.35 (1H, m), 3.45–3.60 (1H, m), 4.28 (2H, s), 4.47 (2H, d, J=6.0), 4.64 (1H, m), 6.43 (1H, dt, J=16.0, 6.0), 6.58 (1H, d, J=16.0), 7.33 (1H, d, J=9.0), 7.41 (1H, dd, J=9.0, 2.5), 7.55 (1H, t, J=8.0), 7.59 (1H, d, J=2.5), 7.68 (1H, d, J=8.0), 7.73 (1H, d, J=8.0), 7.86 (1H, s);

IR (KBr, cm$^{-1}$): 1733, 1676.

Example 41

Ethyl N-[3-(3-amidinophenyl)-2-(E)-propenyl]-N-[3-chloro-4-(indolizin-7-yloxy)phenyl]sulfamoylacetate dihydrochloride (Exemplification Compound Number 21)

Hydrogen chloride was bubbled through a solution of ethyl N-[3-chloro-4-(indolizin-7-yloxy)phenyl]-N-[3-(3-cyanophenyl)-2-(E)-propenyl]sulfamoylacetate (600 mg) obtained in reference example 95 in a mixture of dichloromethane (20 ml) and ethanol (20 ml) under ice-cooling, and the resulting mixture was stirred at room temperature for 3 hours under sealed conditions and then evaporated in vacuo. Subsequently, to a solution of the residue obtained in ethanol (25 ml) were added successively an aqueous ammonium chloride solution (prepared by dissolving 130 mg in 5 ml of water) and a 28% ammonia solution (0.29 ml), and the resulting mixture was stirred at room temperature overnight and then evaporated in vacuo. The residue obtained was purified by preparative HPLC (YMC-Pack ODS-A; YMC, eluent: 20% acetonitrile/water). To a solution of the amorphous solid obtained in ethanol (5 ml) was added a 4N solution of hydrogen chloride in dioxane (0.20 ml), and the resulting mixture was evaporated to dryness in vacuo to afford the title compound (140 mg, yield: 20%) as a yellow amorphous solid.

¹H NMR (500 MHz, DMSO-d₆) δ ppm: 1.23 (3H, t, J=7.0), 1.60–2.35 (8H, m), 3.00–3.10 (2H, m), 3.25–3.35 (1H, m), 3.45–3.55 (2H, m), 4.19 (2H, q, J=7.0), 4.41 (2H, s), 4.47 (2H, d, J=6.0), 4.98 (1H, m), 6.43 (1H, dt, J=16.0, 6.0), 6.58 (1H, d, J=16.0), 7.30–7.35 (1H, m), 7.40–7.45 (1H, m), 7.55 (1H, t, J=8.0), 7.55–7.65 (1H, m), 7.68 (1H, d, J=8.0), 7.73 (1H, d, J=8.0), 7.87 (1H, s);

IR (KBr, cm⁻¹): 1738, 1675.

Example 42

N-[3-(3-Amidinophenyl)-2-(E)-propenyl]-N-[3-chloro-4-(indolizin-7-yloxy)phenyl]sulfamoylacetic acid dihydrochloride (Exemplification Compound Number 525)

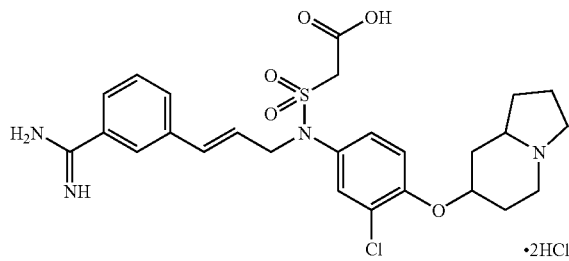

Ethyl N-[3-(3-amidinophenyl)-2-(E)-propenyl]-N-[3-chloro-4-(indolizin-7-yloxy)phenyl]sulfamoylacetate dihydrochloride (130 mg) obtained in example 41 was dissolved in 3N hydrochloric acid (15 ml) and the resulting mixture was stirred at 60° C. for 3 hours. After cooling to room temperature, the reaction mixture was evaporated in vacuo. The residue obtained was purified by preparative HPLC (YMC-Pack ODS-A; YMC, eluent: 15% acetonitrile/water). The amorphous solid obtained was dissolved in 1N hydrochloric acid, and the resulting mixture was evaporated to dryness in vacuo to afford the title compound (110 mg; yield: 88%) as a colorless amorphous solid.

¹H NMR (500 MHz, DMSO-d₆) δ ppm: 1.60–2.35 (8H, m), 2.95–3.10 (2H, m), 3.15–3.50 (3H, m), 4.28 (2H, s), 4.47 (2H, d, J=6.0), 4.99 (1H, m), 6.44 (1H, dt, J=16.0, 6.0), 6.58 (1H, d, J=16.0), 7.30–7.35 (1H, m), 7.40–7.45 (1H, m), 7.55 (1H, t, J=8.0), 7.55–7.6.5 (1H, m), 7.69 (1H, d, J=8.0), 7.73 (1H, d, J=8.0), 7.89 (1H, s);

IR (KBr, cm⁻¹): 1734, 1675.

Example 43

Ethyl N-[3-(3-amidinophenyl)-2-(E)-propenyl]-N-[4-(1-methylpiperidin-4-yloxy)phenyl]sulfamoylacetate dihydrochloride (Exemplification Compound Number 57)

Hydrogen chloride was bubbled through a solution of ethyl N-[3-(3-cyanophenyl)-2-(E)-propenyl]-N-[4-(1-methylpiperidin-4-yloxy)phenyl]sulfamoylacetate (570 mg) obtained in reference example 99 in a mixture of dichloromethane (20 ml) and ethanol (20 ml) under ice-cooling, and the resulting mixture was stirred at room temperature for 4 hours under sealed conditions and then evaporated in vacuo. Subsequently, to a solution of the residue obtained in ethanol (20 ml) were added successively an aqueous ammonium chloride solution (prepared by dissolving 140 mg in 5 ml of water) and a 28% ammonia solution (0.31 ml), and the resulting mixture was stirred at room temperature overnight and then evaporated in vacuo. The residue obtained was purified by preparative HPLC (YMC-Pack ODS-A; YMC, eluent: 17.5% acetonitrile/water). Subsequently, to a solution of the amorphous solid obtained in ethanol (10 ml) was added a 4N solution of hydrogen chloride in dioxane (0.22 ml), and the resulting mixture was evaporated to dryness in vacuo to afford the title compound (150 mg, yield: 22%) as a pale yellow amorphous solid.

¹H NMR (500 MHz, DMSO-d₆) δ ppm: 1.23 (3H, t, J=7.0), 1.85–2.05 (2H, m), 2.05–2.25 (2H, m), 2.73 (3H, s), 3.00–3.15 (2H, m), 3.20–3.30 (1H, m), 3.40–3.50 (1H, m), 4.20 (2H, q, J=7.0), 4.34 (2H, s), 4.44 (2H, d, J=6.0), 4.50–4.60 and 4.70–4.80 (total 1H, each m), 6.43 (1H, dt, J=16.0, 6.0), 6.55 (1H, d, J=16.0), 7.00–7.10 (2H, m), 7.35–7.45 (2H, m), 7.54 (1H, t, J=8.0), 7.68 (1H, d, J=8.0), 7.71 (1H, d, J=8.0), 7.88 (1H, s);

IR (KBr, cm⁻¹): 1738, 1674.

Example 44

N-[3-(3-Amidinophenyl)-2-(E)-propenyl]-N-[4-(1-methylpiperidin-4-yloxy)phenyl]sulfamoylacetic acid dihydrochloride (Exemplification Compound Number 561)

Ethyl N-[3-(3-amidinophenyl)-2-(E)-propenyl]-N-[4-(1-methylpiperidin-4-yloxy)phenyl]sulfamoylacetate dihydrochloride (250 mg) obtained in example 43 was dissolved in 3N hydrochloric acid (30 ml) and the resulting mixture was stirred at 60° C. for 3 hours. After cooling to room temperature, the reaction mixture was evaporated in vacuo. The residue obtained was purified by preparative HPLC (YMC-Pack ODS-A; YMC, eluent: 10% acetonitrile/water). The amorphous solid obtained was dissolved in 1N hydrochloric acid, and the resulting mixture was evaporated to dryness in vacuo to afford the title compound (160 mg, yield: 58%) as a colorless amorphous solid.

¹H NMR (500 MHz, DMSO-d₆) δ ppm: 1.80–1.95 (1H, m), 1.95–2.05 (1H, m), 2.05–2.25 (2H, m), 2.70–2.80 (3H, m), 3.00–3.15 (2H, m), 3.20–3.30 (1H, m), 3.40–3.50 (1H, m), 4.20 (2H, s), 4.45 (2H, d, J=6.0), 4.53 and 4.74 (total 1H, each m), 6.44 (1H, dt, J=16.0, 6.0), 6.55 (1H, d, J=16.0), 7.02 (1H, d, J=9.0), 7.05 (1H, d, J=9.0), 7.39 (1H, d, J=9.0), 7.41 (1H, d, J=9.0), 7.54 (1H, t, J=8.0), 7.68 (1H, d, J=8.0), 7.71 (1H, d, J=8.0), 7.87 (1H, s);

IR (KBr, cm⁻¹) 1733, 1676.

Example 45

Ethyl N-[3-(3-amidinophenyl)-2-(E)-propenyl]-N-[4-(1-methylpiperidin-4-yloxy)-3-trifluoromethylphenyl]sulfamoylacetate dihydrochloride (Exemplification Compound Number 85)

Hydrogen chloride was bubbled through a solution of ethyl N-[3-(3-cyanophenyl)-2-(E)-propenyl]-N-[4-(1-methylpiperidin-4-yloxy)-3-trifluoromethylphenyl]sulfamoylacetate (1298 mg) obtained in reference example 104 in a mixture of dichloromethane (30 ml) and ethanol (15 ml) under ice-cooling, and the resulting mixture was stirred at room temperature for 6.5 hours under sealed conditions and then evaporated in vacuo. Subsequently, to a solution of the residue obtained in ethanol (20 ml) were added successively an aqueous ammonium chloride solution (prepared by dissolving 246 mg in 10 ml of water) and a 28% ammonia solution (0.32 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 25% acetonitrile/water). The amorphous solid obtained was dissolved in 1N hydrochloric acid, and the resulting mixture was evaporated to dryness in vacuo to afford the title compound (1115 mg, yield: 74%) as a colorless amorphous solid.

$^1$H NMR (500 MHz, DMSO-$d_6$) δ ppm: 1.22 (3H, t, J=7.0), 1.91 and 2.06 (total 2H, each m), 2.17–2.27 (2H, m), 2.73 (3H, m), 2.87 and 3.50 (total 2H, each m), 3.37 and 3.44 (total 2H, each m), 4.19 (2H, q, J=7.0), 4.45 (2H, m), 4.50 (2H, d, J=6.0), 4.74 and 5.00 (total 1H, each m), 6.45 (1H, dt, J=16.0, 6.0), 6.58 (1H, d, J=16.0), 7.39 and 7.45 (total 1H, each d, J=10.0), 7.55 (1H, t, J=8.0), 7.65–7.74 (4H, m), 7.89 (1H, s);

IR (KBr, cm$^{-1}$): 1739, 1676, 1353, 1155.

Example 46

N-[3-(3-Amidinophenyl)-2-(E)-propenyl]-N-[4–1-methylpiperidin-4-yloxy)-3-trifluoromethylphenyl]sulfamoylacetic acid dihydrochloride (Exemplification Compound Number 589)

Ethyl N-[3-(3-amidinophenyl)-2-(E)-propenyl]-N-[4-(1-methylpiperidin-4-yloxy)-3-trifluoromethylphenyl]sulfamoylacetate dihydrochloride (803 mg) obtained in example 45 was dissolved in 3N hydrochloric acid (20 ml) and the resulting mixture was stirred at 60° C. for 8 hours. After cooling to room temperature, the reaction mixture was evaporated in vacuo. The residue obtained was purified by preparative HPLC (YMC-Pack ODS-A; YMC, eluent: 17% acetonitrile/water). The amorphous solid obtained was dissolved in 1N hydrochloric acid and the resulting mixture was evaporated to dryness in vacuo. The residue obtained was dissolved in water and then lyophilized to afford the title compound (607 mg, yield: 79%) as a colorless amorphous solid.

$^1$H NMR (500 MHz, CD$_3$OD) δ ppm: 1.93 and 2.17 (total 2H, each m), 2.28 and 2.39 (total 2H, each m), 2.90 (3H, m), 3.10–3.25 (2H, m), 3.47 and 3.60 (total 2H, each m), 4.12 (2H, s), 4.55 (2H, d, J=6.5), 5.00 (1H, m), 6.43 (1H, dt, J=16.0, 6.5), 6.57 (1H, d, J=16.0), 7.30 and 7.36 (total 1H, each m), 7.54 (1H, t, J=8.0), 7.65 (1H, d, J=8.0), 7.71 (1H, d, J=8.0), 7.72–7.80 (2H, m), 7.80 (1H, s);

IR (KBr, cm$^{-1}$): 1733, 1676, 1350, 1154.

Example 47

Ethyl N-[3-(3-amidinophenyl)-2-(E)-propenyl]-N-[3-chloro-4-[(1-formimidoylpiperidin-4-yloxy)phenyl]sulfamoylacetate dihydrochloride (Exemplification Compound Number 22)

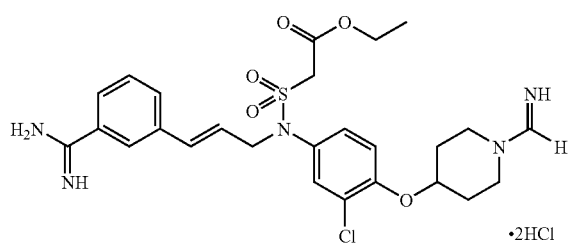

·2HCl (a) Ethyl N-[3-(3-amidinophenyl)-2-(E)-propenyl]-N-[3-chloro-4-(piperidin-4-yloxy)phenyl]sulfamoylacetate dihydrochloride Hydrogen chloride was bubbled through a solution of ethyl N-[4-(1-t-butoxycarbonylpiperidin-4-yloxy)-3-chlorophenyl]-N-[3-(3-cyanophenyl)-2-(E)-propenyl]sulfamoylacetate (1200 mg) obtained in reference example 70 in a mixture of dichloromethane (30 ml) and ethanol (20 ml) under ice-cooling, and the resulting mixture was stirred at room temperature for 6 hours under sealed conditions and then evaporated in vacuo. Subsequently, to a solution of the residue obtained in ethanol (20 ml) were added successively an aqueous ammonium chloride solution (prepared by dissolving 208 mg in 10 ml of water) and a 28% ammonia solution (0.40 ml), and the resulting mixture was stirred at room temperature overnight. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 20% acetonitrile/water). Subsequently, to a solution of the amorphous solid obtained in methanol (20 ml) was added a 4N solution of hydrogen chloride in dioxane (0.50 ml), and the resulting mixture was evaporated to dryness in vacuo. The residue obtained was dissolved in water and then lyophilized to afford the title compound (662 mg, yield: 56%) as a pale yellow amorphous solid.

$^1$H NMR (500 MHz, DMSO-$d_6$) δ ppm: 1.23 (3H, t, J=7.0), 1.88 (2H, m), 2.10 (2H, m), 3.08 (2H, m), 3.17 (2H, m), 4.19 (2H, q, J=7.0), 4.41 (2H, s), 4.47 (2H, d, J=6.5), 4.78 (1H, m), 6.44 (1H, dt, J=16.0, 6.5), 6.57 (1H, d, J=16.0), 7.30 (1H, d, J=9.5), 7.41 (1H, dd, J=9.5, 2.5), 7.55 (1H, t, J=8.0), 7.59 (1H, d, J=2.5), 7.69 (1H, d, J=8.0), 7.73 (1H, d, J=8.0), 7.88 (1H, s);

IR (KBr, cm$^{-1}$): 1737, 1675.

(b) Ethyl N-[3-(3-amidinophenyl)-2-(E)-propenyl]-N-[3-chloro-4-(1-formimidoylpiperidin-4-yloxy)phenyl]sulfamoylacetate dihydrochloride To a solution of ethyl N-[3-(3-amidinophenyl)-2-(E)-propenyl]-N-[3-chloro-4-(piperidin-4-yloxy)phenyl]sulfamoylacetate dihydrochloride (0.79 g) obtained in example 47(a) in ethanol (25 ml) were added successively ethyl formimidate hydrochloride (0.29 g) and triethylamine (0.72 ml) at room temperature and the resulting mixture was allowed to stand at room temperature for 16 hours. To the reaction mixture was added a 4N solution of hydrogen chloride in dioxane (10 ml) and the resulting mixture was evaporated in vacuo. The residue obtained was purified by preparative HPLC (YMC-Pack ODS-A; YMC, eluent: 20% acetonitrile/water). Subsequently, to a solution of the amorphous solid obtained in ethanol (10 ml) was added a 4N solution of hydrogen chloride in dioxane (2 ml), and the resulting mixture was evaporated to dryness in vacuo. The residue obtained was dissolved in water and then lyophilized to afford the title compound (0.50 g, yield: 61%) as a colorless amorphous solid.

$^1$H NMR (500 MHz, DMSO-$d_6$) δ ppm: 1.23 (3H, t, J=7.0), 1.73–1.87 (2H, m), 1.99–2.10 (2H, m), 3.57–3.68 (2H, m), 3.71–3.78 (2H, m), 4.19 (2H, q, J=7.0), 4.42 (2H, s), 4.47 (2H, d, J=6.0), 4.81–4.86 (1H, m), 6.45 (1H, dt, J=16.0, 6.0), 6.58 (1H, d, J=16.0), 7.33 (1H; d, J=9.0), 7.41 (1H, dd, J=9.0, 2.5), 7.55 (1H, t, J=8.0), 7.60 (1H, d, J=2.5), 7.69–7.75 (2H, m), 7.90 (1H, s), 7.99 (1H, dd, J≦15.0, 7.0);

IR (KBr, cm$^{-1}$): 1737, 1702, 1675, 1351, 1155.

Example 48

N-13-(3-Amidinophenyl)-2-(E)-propenyl]-N-[3-chloro-4-(1-formimidoylpiperidin-4-yloxy]phenyl]sulfamoylacetic acid dihydrochloride (Exemplification Compound Number 526)

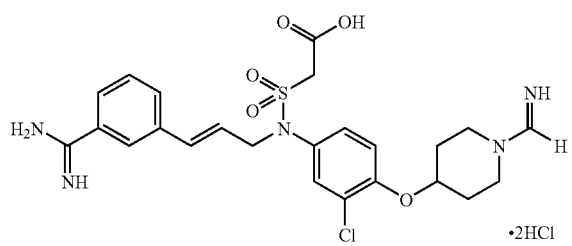

Ethyl N-[3-(3-amidinophenyl)-2-(E)-propenyl]-N-[3-chloro-4-(1-formimidoylpiperidin-4-yloxy)phenyl]sulfamoylacetate dihydrochloride (0.35 g) obtained in example 47(b) was dissolved in 3N hydrochloric acid (15 ml) and the resulting mixture was stirred at 60° C. for 4.5 hours. After cooling to room temperature, the reaction mixture was evaporated in vacuo. The residue obtained was purified by preparative HPLC (YMC-Pack ODS-A; YMC, eluent: 15% acetonitrile/water). The amorphous solid obtained was dissolved in 1N hydrochloric acid (3 ml) and the resulting mixture was evaporated to dryness in vacuo. The residue obtained was dissolved in water and then lyophilized to afford the title compound (0.17 g, yield: 52%) as a colorless amorphous solid.

$^1$H NMR (400 MHz, DMSO-$d_6$) δ ppm: 1.73–1.87 (2H, m), 1.98–2.11 (2H, m), 3.57–3.79 (4H, m), 4.28 (2H, s), 4.47 (2H, d, J=6.0), 4.79–4.86 (1H, m), 6.44 (1H, dt, J=16.0, 6.0), 6.58 (1H, d, J=16.0), 7.32 (1H, d, J=9.0), 7.42 (1H, dd, J=9.0, 2.5), 7.55 (1H, t, J=8.0), 7.59 (1H, d, J=2.5), 7.70 (1H, d, J=8.0), 7.73 (1H, d, J=8.0), 7.89 (1H, s), 7.99 (1H, dd, J=15.0, 7.0);

IR (KBr, cm$^{-1}$): 1731, 1703, 1675, 1347, 1154.

Example 49

Ethyl N-[3-(3-amidinophenyl)-2-(E)-propenyl]-N-[3-chloro-4-[1-(1-iminopropyl)piperidin-4-yloxy]phenyl-1 sulfamoylacetate dihydrochloride (Exemplification Compound Number 23)

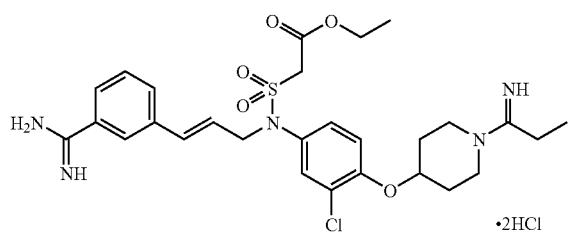

To a solution of ethyl N-[3-(3-amidinophenyl)-2-(E)-propenyl]-N-[3-chloro-4-(piperidin-4-yloxy)phenyl]sulfamoylacetate dihydrochloride (0.77 g) obtained in example 47(a) in ethanol (25 ml) were added successively ethyl propionimidate hydrochloride (0.54 g), which was prepared from propionitrile according to the method described in *J. Amer. Chem. Soc.*, 98, 567 (1976), and triethylamine (0.88 ml) at room temperature and the resulting mixture was allowed to stand at room temperature for 22 hours. Because of the slow progress of the reaction, ethyl propionimidate hydrochloride (0.18 g) and triethylamine (0.35 ml) were furthermore added successively and the resulting mixture was stirred at room temperature for 4.5 hours. After stirring, to the reaction mixture was added a 4N solution of hydrogen chloride in dioxane (10 ml) and the resulting mixture was evaporated in vacuo. The residue obtained was purified by preparative HPLC (YMC-Pack ODS-A; YMC, eluent: 25% acetonitrile/water). Subsequently, to a solution of the amorphous solid obtained in ethanol (10 ml) was added a 4N solution of hydrogen chloride in dioxane (2 ml), and the resulting mixture was evaporated to dryness in vacuo. The residue obtained was dissolved in water and then lyophilized to afford the title compound (0.57 g, yield: 67%) as a colorless amorphous solid.

$^1$H NMR (400 MHz, DMSO-$d_6$) δ ppm: 1.15 (3H, t, J=7.5), 1.23 (3H, t, J=7.0), 1.74–1.83 (2H, m), 2.01–2.10 (2H, m), 2.61 (2H, q, J=7.5), 3.58–3.77 (4H, m), 4.19 (2H, q, J=7.0), 4.42 (2H, s), 4.47 (2H, d, J=5.5), 4.80–4.89 (1H, m), 6.45 (1H, dt, J=15.5, 5.5), 6.58 (1H, d, J=15.5), 7.33 (1H, d, J=9.0), 7.41 (1H, dd, J=9.0, 2.5), 7.55 (1H, t, J=8.0), 7.59 (1H, d, J=2.5), 7.69–7.74 (2H, m), 7.90 (1H, s);

IR (KBr, cm$^{-1}$) 1738, 1671, 1619, 1352, 1157.

Example 50

N-[3-(3-Amidinophenyl)-2-(E)-propenyl]-N-[3-chloro-4-[1-(1-iminopropyl)piperidin-4-yloxy]phenyl]sulfamoylacetic acid dihydrochloride (Exemplification Compound Number 527)

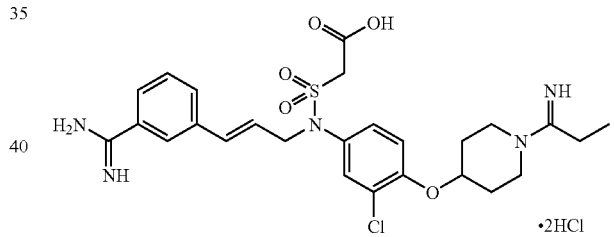

Ethyl N-[3-(3-amidinophenyl)-2-(E)-propenyl]-N-[3-chloro-4-[1-(1-iminopropyl)piperidin-4-yloxy]phenyl]sulfamoylacetate dihydrochloride (0.42 g) obtained in example 49 was dissolved in 3N hydrochloric acid (15 ml) and the resulting mixture was stirred at 60° C. for 6.5 hours. After cooling to room temperature, the reaction mixture was evaporated in vacuo. The residue obtained was purified by preparative HPLC (YMC-Pack ODS-A; YMC, eluent: 18% acetonitrile/water). The amorphous solid obtained was dissolved in 1N hydrochloric acid (3 ml) and the resulting mixture was evaporated to dryness in vacuo. The residue obtained was dissolved in water and then lyophilized to afford the title compound (0.37 g, yield: 93%) as a colorless amorphous solid.

$^1$H NMR (400 MHz, DMSO-$d_6$) δ ppm: 1.15 (3H, t, J=7.5), 1.71–1.87 (2H, m), 2.00–2.12 (2H, m), 2.63 (2H, q, J=7.5), 3.59–3.81 (4H, m), 4.30 (2H, s), 4.48 (2H, d, J=5.5), 4.81–4.88 (1H, m), 6.46 (1H, dt, J=16.0, 5.5), 6.58 (1H, d, J=16.0), 7.34 (1H, d, J=9.0), 7.43 (1H, dd, J=9.0, 2.5), 7.55 (1H, t, J=8.0), 7.60 (1H, d, J=2.5), 7.70–7.76 (2H, m), 7.94 (1H, s);

IR (KBr, cm$^{-1}$): 1734, 1671, 1620, 1349, 1156.

Example 51

Ethyl N-[3-(3-amidinophenyl)-2-(E)-propenyl]-N-[4-(1-iminophenylmethylpiperidin-4-yloxy)-3-chlorophenyl]sulfamoylacetate dihydrochloride (Exemplification Compound Number 24)

To a solution of ethyl N-[3-(3-amidinophenyl)-2-(E)-propenyl]-N-[3-chloro-4-(piperidin-4-yloxy)phenyl]sulfamoylacetate dihydrochloride (0.69 g) obtained in example 47(a) in ethanol (20 ml) were added successively ethyl benzimidate hydrochloride (0.63 g) and triethylamine (0.94 ml) at room temperature, and the resulting mixture was stirred at 60° C. for 2.5 hours, and then allowed to stand at room temperature for 16.5 hours. Furthermore, the resulting mixture was stirred at 60° C. for 11.5 hours and then allowed to stand at room temperature for 60.5 hours, successively. To the reaction mixture was added 4N solution of hydrogen chloride in dioxane (5 ml), and the resulting mixture was evaporated in vacuo. The residue obtained was purified by preparative HPLC (YMC-Pack ODS-A; YMC, eluent: 25% acetonitrile/water). Subsequently, to a solution of the amorphous solid obtained in ethanol (5 ml) was added a 4N solution of hydrogen chloride in dioxane (2 ml), and the resulting mixture was evaporated to dryness in vacuo to afford the title compound (0.36 g, yield: 45%) as a colorless amorphous solid.

$^1$H NMR (500 MHz, DMSO-d$_6$) δ ppm: 1.22 (3H, t, J=7.0), 1.73–1.81 (1H, m), 1.90–2.03 (2H, m), 2.17–2.24 (1H, m), 3.30–3.51 (2H, m), 3.78–3.86 (1H, m), 3.89–3.95 (1H, m), 4.18 (2H, q, J=7.0), 4.41 (2H, s), 4.47 (1H, d, J=6.0), 4.83–4.88 (1H, m), 6.43 (1H, dt, J=16.0, 6.0), 6.58 (1H, d, J=16.0), 7.33 (1H, d, J=9.0), 7.40 (1H, dd, J=9.0, 2.5), 7.53–7.73 (9H, m), 7.88 (1H, s);

IR (KBr, cm$^{-1}$): 1738, 1671, 1605, 1353, 1156.

Example 52

N-[3-(3-Amidinophenyl)-2-(E)-propenyl]-N-[4-(1-iminophenylmethylpiperidin-4-yloxy)-3-chlorophenyl]sulfamoylacetic acid dihydrochloride (Exemplification Compound Number 528)

Ethyl N-[3-(3-amidinophenyl)-2-(E)-propenyl]-N-[4-(1-iminophenylmethylpiperidin-4-yloxy)-3-chlorophenyl]sulfamoylacetate dihydrochloride (0.25 g) obtained in example 51 was dissolved in 3N hydrochloric acid (12 ml) and the resulting mixture was stirred at 60° C. for 3 hours. After cooling to room temperature, the reaction mixture was evaporated in vacuo. The residue obtained was purified by preparative HPLC (YMC-Pack ODS-A; YMC, eluent: 20% acetonitrile/water). The amorphous solid obtained was dissolved in 1N hydrochloric acid (3 ml) and the resulting mixture was evaporated to dryness in vacuo. The residue obtained was dissolved in water and then lyophilized to afford the title compound (0.21 g, yield: 89%) as a colorless amorphous solid.

$^1$H NMR (500 MHz, DMSO-d$_6$) δ ppm: 1.70–1.78 (1H, m), 1.88–2.02 (2H, m), 2.14–2.22 (1H, m), 3.28–3.50 (2H, m), 3.83–3.90 (1H, m), 3.91–4.01 (1H, m), 4.27 (2H, s), 4.45 (2H, d, J=5.0), 4.82–4.89 (1H, m), 6.44 (1H, dt, J=16.0, 5.0), 6.56 (1H, d, J=16.0), 7.32 (1H, d, J=9.0), 7.40 (1H, dd, J=9.0, 2.5), 7.51–7.71 (9H, m), 7.90 (1H, s);

IR (KBr, cm$^{-1}$): 1733, 1673, 1605, 1349, 1155.

Example 53

Ethyl N-[3-(3-amidinophenyl)-2-(E)-propenyl]-N-[3-chloro-4-[1-(4,5-dihydro-3H-pyrrol-2-yl)piperidin-4-yloxy]phenyl]sulfamoylacetate dihydrochloride (Exemplification Compound Number 25)

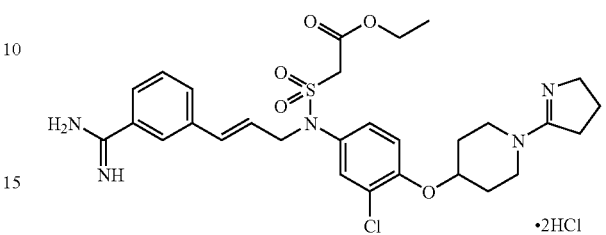

To a solution of ethyl N-[3-(3-amidinophenyl)-2-(E)-propenyl]-N-[3-chloro-4-(piperidin-4-yloxy)phenyl]sulfamoylacetate dihydrochloride (0.75 g) obtained in example 47(a) in ethanol (25 ml) were added successively 5-methoxy-3,4-dihydro-2H-pyrrole (0.25 g), which was prepared from 2-pyrrolidinone according to the method described in Org. Prep. Proced. Int., 24, 147 (1992), and triethylamine (0.69 ml) at room temperature, and the resulting mixture was stirred at room temperature for 10 hours and then allowed to stand at room temperature for 84 hours. To the reaction mixture was added a 4N solution of hydrogen chloride in dioxane (10 ml) and the resulting mixture was evaporated in vacuo. The residue obtained was purified by preparative HPLC (YMC-Pack ODS-A; YMC, eluent: 25% acetonitrile/water). Subsequently, to a solution of the amorphous solid obtained in ethanol (10 ml) was added a 4N solution of hydrogen chloride in dioxane (2 ml), and the resulting mixture was evaporated to dryness in vacuo. The residue obtained was dissolved in water and then lyophilized to afford the title compound (0.52 g, yield: 62%) as a colorless amorphous solid.

$^1$H NMR (400 MHz, DMSO-d$_6$) δ ppm: 1.23 (3H, t, J=7.0), 1.75–1.86 (2H, m), 2.02–2.14 (4H, m), 2.97 (2H, t, J=8.0), 3.50–3.91 (6H, m), 4.19 (2H, q, J=7.0), 4.42 (2H, s), 4.47 (2H, d, J=6.0), 4.81–4.87 (1H, m), 6.45 (1H, dt, J=16.0, 6.0), 6.58 (1H, d, J=16.0), 7.34 (1H, d, J=9.0), 7.41 (1H, dd, J=9.0, 2.5), 7.55 (1H, t, J=8.0), 7.59 (1H, d, J=2.5), 7.70–7.74 (2H, m), 7.91 (1H, s);

IR (KBr, cm$^{-1}$): 1738, 1672, 1352, 1156.

Example 54

N-[3-(3-Amidinophenyl)-2-(E)-propenyl]-N-[3-chloro-4-[1-(4,5-dihydro-3H-pyrrol-2-yl)piperidin-4-yloxy]phenyl]sulfamoylacetic acid dihydrochloride (Exemplification Compound Number 529)

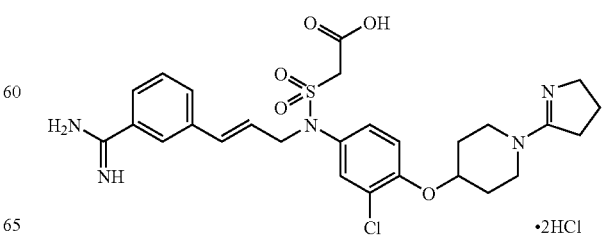

Ethyl N-[3-(3-amidinophenyl)-2-(E)-propenyl]-N-[3-chloro-4-[1-(4,5-dihydro-3H-pyrrol-2-yl)piperidin-4-yloxy]phenyl]sulfamoylacetate dihydrochloride (0.36 g) obtained in example 53 was dissolved in 3N hydrochloric acid (15 ml) and the resulting mixture was stirred at 60° C. for 6 hours. After cooling to room temperature, the reaction mixture was evaporated in vacuo. The residue obtained was purified by preparative HPLC (YMC-Pack ODS-A; YMC, eluent: 15~18% acetonitrile/water). The amorphous solid obtained was dissolved in 1N hydrochloric acid (3 ml) and the resulting mixture was evaporated to dryness in vacuo. The residue obtained was dissolved in water and then lyophilized to afford the title compound (0.32 g, yield: 90%) as a colorless amorphous solid.

$^1$H NMR (400 MHz, DMSO-d$_6$) δ ppm: 1.73–1.88 (2H, m), 2.00–2.14 (4H, m), 2.97 (2H, t, J=8.0), 3.50–3.88 (6H, m), 4.30 (2H, s), 4.47 (2H, d, J=5.5), 4.81–4.88 (1H, m), 6.46 (1H, dt, J=16.0, 5.5), 6.58 (1H, d, J=16.0), 7.34 (1H, d, J=9.0), 7.42 (1H, dd, J=9.0, 2.5), 7.55 (1H, t, J=8.0), 7.59 (1H, d, J=2.5), 7.71–7.76 (2H, m), 7.93 (1H, s);

IR (KBr, cm$^{-1}$): 1734, 1672, 1350, 1155.

Example 55

Ethyl N-[3-(3-amidinophenyl)-2-(E)-propenyl]-N-[3-chloro-4-[1-(2,3,4,5-tetrahydropyridin-6-yl)piperidin-4-yloxy]phenyl]sulfamoylacetate dihydrochloride (Exemplification Compound Number 26)

To a solution of ethyl N-[3-(3-amidinophenyl)-2-(E)-propenyl]-N-[3-chloro-4-(piperidin-4-yloxy)phenyl]sulfamoylacetate dihydrochloride (0.81 g) obtained in example 47(a) in ethanol (20 ml) were added successively 6-ethoxy-2,3,4,5-tetrahydropyridine (0.33 g), which was prepared from piperidin-2-one according to the method described in *Org. Prep. Proced. Int.*, 24, 147 (1992), and triethylamine (0.74 ml) at room temperature, and the resulting mixture was stirred at 35° C. for 3.5 hours, allowed to stand at room temperature for 11 hours, and stirred furthermore at 45° C. for 24 hours successively. After stirring, to the reaction mixture was added a 4N solution of hydrogen chloride in dioxane (5 ml) and the resulting mixture was evaporated in vacuo. The residue obtained was purified by preparative HPLC (YMC-Pack ODS-A; YMC, eluent: 23% acetonitrile/water). Subsequently, to a solution of the amorphous solid obtained in ethanol (5 ml) was added a 4N solution of hydrogen chloride in dioxane (1 ml), and the resulting mixture was evaporated to dryness in vacuo. The residue obtained was dissolved in water and then lyophilized to afford the title compound (0.21 g, yield: 23%) as a colorless amorphous solid.

$^1$H NMR (400 MHz, DMSO-d$_6$) δ ppm: 1.22 (3H, t, J=7.0), 1.65–1.80 (6H, m), 2.00–2.09 (2H, m), 2.66–2.72 (2H, m), 3.30–3.36 (2H, m), 3.49–3.75 (4H, m), 4.19 (2H, q, J=7.0), 4.42 (2H, s), 4.47 (2H, d, J=5.5), 4.81–4.87 (1H, m), 6.44 (1H, dt, J=16.0, 5.5), 6.58 (1H, d, J=16.0), 7.33 (1H, d, J=9.0), 7.41 (1H, dd, J=9.0, 2.5), 7.53–7.59 (2H, m), 7.69–7.74 (2H, m), 7.90 (1H, s);

IR (KBr, cm$^{-1}$): 1738, 1674, 1637, 1354, 1155.

Example 56

N-[3-(3-Amidinophenyl)-2-(E)-propenyl]-N-[3-chloro-4-[1-(2,3,4,5-tetrahydropyridin-6-yl)piperidin-4-yloxy]phenyl]sulfamoylacetic acid dihydrochloride (Exemplification Compound Number 530)

Ethyl N-[3-(3-amidinophenyl)-2-(E)-propenyl]-N-[3-chloro-4-[1-(2,3,4,5-tetrahydropyridin-6-yl)piperidin-4-yloxy]phenyl]sulfamoylacetate dihydrochloride (0.28 g) obtained in example 55 was dissolved in 3N hydrochloric acid (12 ml) and the resulting mixture was stirred at 60° C. for 5 hours. After cooling to room temperature, the reaction mixture was evaporated in vacuo. The residue obtained was purified by preparative HPLC (YMC-Pack ODS-A; YMC, eluent: 18% acetonitrile/water). The amorphous solid obtained was dissolved in 1N hydrochloric acid (3 ml) and the resulting mixture was evaporated to dryness in vacuo. The residue obtained was dissolved in water and then lyophilized to afford the title compound (0.19 g, yield: 71%) as a colorless amorphous solid.

$^1$H NMR (400 MHz, DMSO-d$_6$) δ ppm: 1.64–1.81 (6H, m), 1.99–2.08 (2H, m), 2.67–2.72 (2H, m), 3.30–3.37 (2H, m), 3.55–3.78 (4H, m), 4.28 (2H, s), 4.47 (2H, d, J=6.0), 4.80–4.87 (1H, m), 6.44 (1H, dt, J=16.0, 6.0), 6.58 (1H, d, J=16.0), 7.32 (1H, d, J=9.0), 7.41 (1H, dd, J=9.0, 2.5), 7.53–7.59 (2H, m), 7.67–7.74 (2H, m), 7.88 (1H, s);

IR (KBr, cm$^{-1}$): 1734, 1675, 1637, 1352, 1156.

Example 57

Ethyl N-[3-(3-amidinophenyl)-2-(E)-propenyl]-N-[3-chloro-4-[1-(3,4,5,6-tetrahydro-2H-azepin-7-yl)piperidin-4-yloxy]phenyl]sulfamoylacetate dihydrochloride (Exemplification Compound Number 27)

To a solution of ethyl N-[3-(3-amidinophenyl)-2-(E)-propenyl]-N-[3-chloro-4-(piperidin-4-yloxy)phenyl]sulfamoylacetate dihydrochloride (0.75 g) obtained in example 47(a) in ethanol (25 ml) were added successively 7-methoxy-3,4,5,6-tetrahydro-2H-azepine (0.39 g) and triethylamine (0.85 ml) at room temperature, and the resulting mixture was stirred at room temperature for 7 hours and then allowed to stand at room temperature for 15 hours. Because of the slow progress of the reaction, 7-methoxy-3,4,5,6-tetrahydro-2H-azepine (0.22 g) and triethylamine (0.51 ml) were furthermore added successively, and the resulting mixture was stirred at 45° C. for 12 hours, allowed to stand at room temperature for 11 hours and then furthermore stirred at 45° C. for 10 hours. After stirring, to the reaction mixture was added a 4N solution of hydrogen chloride in dioxane (5 ml) and the resulting mixture was evaporated in vacuo. The residue obtained was purified by preparative HPLC (YMC-Pack ODS-A; YMC, eluent: 25% acetonitrile/water). Subsequently, to a solution of the amorphous solid obtained in ethanol (5 ml) was added a 4N solution of hydrogen chloride in dioxane (2 ml), and the resulting mixture was evaporated to dryness in vacuo. The residue obtained was dissolved in water and then lyophilized to afford the title compound (0.30 g, yield: 35%) as a colorless amorphous solid.

$^1$H NMR (400 MHz, DMSO-d$_6$) δ ppm: 1.21 (3H, t, J=7.0), 1.52–1.63 (4H, m), 1.68–1.81 (4H, m), 2.04–2.10 (2H, m), 2.84–2.88 (2H, m), 3.36–3.42 (2H, m), 3.62–3.91 (4H, m), 4.18 (2H, q, J=7.0), 4.41 (2H, s), 4.46 (2H, d, J=6.0), 4.81–4.87 (1H, m), 6.44 (1H, dt, J=16.0, 6.0), 6.57 (1H, d, J=16.0), 7.32 (1H, d, J=9.0), 7.40 (1H, dd, J=9.0, 2.5), 7.52–7.59 (2H, m), 7.66–7.74 (2H, m), 7.88 (1H, s);

IR (KBr, cm$^{-1}$): 1738, 1674, 1628, 1353, 1156.

Example 58

N-[3-(3-Amidinophenyl)-2-(E)-propenyl]-N-[3-chloro-4-[1-(3,4,5,6-tetrahydro-2H-azepin-7-yl)piperidin-4-yloxy]phenyl]sulfamoylacetic acid dihydrochloride (Exemplification Compound Number 531)

Ethyl N-[3-(3-amidinophenyl)-2-(E)-propenyl]-N-[3-chloro-4-[1-(3,4,5,6-tetrahydro-2H-azepin-7-yl)piperidin-4-yloxy]phenyl]sulfamoylacetate dihydrochloride (0.24 g) obtained in example 57 was dissolved in 3N hydrochloric acid (10 ml) and the resulting mixture was stirred at 60° C. for 6 hours. After cooling to room temperature, the reaction mixture was evaporated in vacuo. The residue obtained was purified by preparative HPLC (YMC-Pack ODS-A; YMC, eluent: 18% acetonitrile/water). The amorphous solid obtained was dissolved in 1N hydrochloric acid (3 ml) and the resulting mixture was evaporated to dryness in vacuo. The residue obtained was dissolved in water and then lyophilized to afford the title compound (0.18 g, yield: 76%) as a colorless amorphous solid.

$^1$H NMR (400 MHz, DMSO-$d_6$) δ ppm: 1.52–1.62 (4H, m), 1.67–1.82 (4H, m), 2.00–2.09 (2H, m), 2.84–2.88 (2H, m), 3.43–3.49 (2H, m), 3.63–3.91 (4H, m), 4.27 (2H, s), 4.46 (2H, d, J=5.5), 4.80–4.86 (1H, m), 6.44 (1H, dt, J=16.0, 5.5), 6.57 (1H, d, J=16.0), 7.32 (1H, d, J=9.0), 7.40 (1H, dd, J=9.0, 2.5), 7.51–7.61 (2H, m), 7.68–7.75 (2H, m), 7.89 (1H, s);

IR (KBr, cm$^{-1}$): 1734, 1675, 1628, 1351, 1156.

Example 59

Ethyl N-[3-(3-amidinophenyl)-2-(E)-propenyl]-N-[4-[1-(4,5-dihydro-3H-pyrrol-2-yl)piperidin-4-yloxy]phenyl]sulfamoylacetate dihydrochloride (Exemplification Compound Number 81)

(a) Ethyl N-[3-(3-amidinophenyl)-2-(E)-propenyl]-N-[4-(piperidin-4-yloxy)phenyl]sulfamoylacetate dihydrochloride Hydrogen chloride was bubbled through a solution of ethyl N-[4-(1-t-butoxycarbonylpiperidin-4-yloxy)phenyl]-N-[3-(3-cyanophenyl)-2-(E)-propenyl]sulfamoylacetate (1.46 g) obtained in reference example 108 in a mixture of dichloromethane (50 ml) and ethanol (25 ml) for 1 hour under ice-cooling, and the resulting mixture was stirred at room temperature for 8 hours under sealed conditions and then evaporated in vacuo. Subsequently, to a solution of the residue obtained in ethanol (40 ml) were added successively an aqueous ammonium chloride solution (prepared by dissolving 0.30 g in 15 ml of water) and a 28% ammonia solution (0.58 ml), and the resulting mixture was allowed to stand at room temperature for 12 hours. To the reaction mixture was added a 4N solution of hydrogen chloride in dioxane and the resulting mixture was evaporated in vacuo. The residue obtained was purified by preparative HPLC (YMC-Pack ODS-A; YMC, eluent: 15% acetonitrile/water) to afford the title compound (0.98 g, yield: 68%) as a pale yellow amorphous solid.

$^1$H NMR (500 MHz, DMSO-$d_6$) δ ppm: 1.23 (3H, t, J=7.0), 1.83 (2H, m), 2.10 (2H, m), 3.05 (2H, m), 3.19 (2H, m), 4.20 (2H, q, J=7.0), 4.34 (2H, s), 4.45 (2H, d, J=6.0), 4.66 (1H, m), 6.45 (1H, dt, J=16.0, 6.0), 6.55 (1H, d, J=16.0), 7.04 (2H, d, J=8.5), 7.39 (2H, d, J=8.5), 7.55 (1H, t, J=8.0), 7.69 (1H, d, J=8.0), 7.72 (1H, d, J=8.0), 7.89 (1H, s);

IR (KBr, cm$^{-1}$): 1737, 1675.

(b) Ethyl N-[3-(3-amidinophenyl)-2-(E)-propenyl]-N-[4-[1-(4,5-dihydro-3H-pyrrol-2-yl)piperidin-4-yloxy]phenyl]sulfamoylacetate dihydrochloride To a solution of ethyl N-[3-(3-amidinophenyl)-2-(E)-propenyl]-N-[4-(piperidin-4-yloxy)phenyl]sulfamoylacetate dihydrochloride (0.52 g) obtained in example 59(a) in ethanol (5 ml) were added successively 5-methoxy-3,4-dihydro-2H-pyrrole (0.26 g), which was prepared from 2-pyrrolidi-none according to the method described in Org. Prep. Proced. Int., 24, 147 (1992), and triethylamine (0.60 ml) at room temperature, and the resulting mixture was stirred at room temperature for 29 hours and then evaporated in vacuo. The residue obtained was purified by preparative HPLC (YMC-Pack ODS-A; YMC, eluent: 25% acetonitrile/water). Subsequently, to a solution of the amorphous solid obtained in ethanol (40 ml) was added a 4N solution of hydrogen chloride in dioxane (0.75 ml), and the resulting mixture was evaporated to dryness in vacuo. The residue obtained was dissolved in water and then lyophilized to afford the title compound (0.43 g, yield: 77%) as a colorless amorphous solid.

$^1$H NMR (400 MHz, DMSO-$d_6$) δ ppm: 1.23 (3H, t, J=7.0), 1.68–1.80 (2H, m), 2.00–2.14 (4H, m), 2.96 (2H, t, J=8.0), 3.46–3.87 (6H, m), 4.20 (2H, q, J=7.0), 4.34 (2H, s), 4.45 (2H, d, J=6.0), 4.67–4.73 (1H, m), 6.44 (1H, dt, J=16.0, 6.0), 6.55 (1H, d, J=16.0), 7.04 (2H, d, J=9.0), 7.39 (2H, d, J=9.0), 7.55 (1H, t, J=8.0), 7.68–7.73 (2H, m), 7.88 (1H, s);

IR (KBr, cm$^{-1}$): 1738, 1671, 1349, 1157.

Example 60

N-[3-(3-Amidinophenyl)-2-(E)-propenyl]-N-[4-[1-(4,5-dihydro-3H-pyrrol-2-yl)piperidin-4-yloxy]phenyl]sulfamoylacetic acid dihydrochloride (Exemplification Compound Number 585)

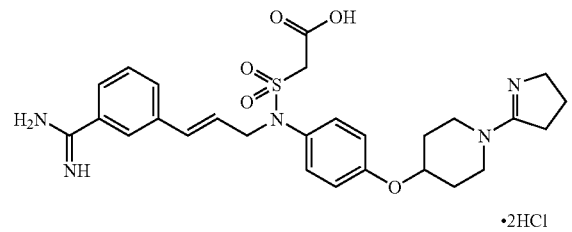

Ethyl N-[3-(3-amidinophenyl)-2-(E)-propenyl]-N-[4-[1-(4,5-dihydro-3H-pyrrol-2-yl)piperidin-4-yloxy]phenyl]sulfamoylacetate dihydrochloride (0.38 g) obtained in example 59(b) was dissolved in 3N hydrochloric acid (10 ml) and the resulting mixture was stirred at 60° C. for 4 hours. After cooling to room temperature, the reaction mixture was evaporated in vacuo. The residue obtained was purified by preparative HPLC (YMC-Pack ODS-A; YMC, eluent: 15% acetonitrile/water). The amorphous solid obtained was dissolved in 1N hydrochloric acid (3 ml) and the resulting mixture was evaporated to dryness in vacuo. The residue obtained was dissolved in water and then lyophilized to afford the title compound (0.21 g, yield: 59%) as a colorless amorphous solid.

$^1$H NMR (400 MHz, DMSO-$d_6$) δ ppm: 1.68–1.80 (2H, m), 2.00–2.13 (4H, m), 2.96 (2H, t, J=8.0), 3.46–3.72 (5H, m), 3.83–3.92 (1H, m), 4.20 (2H, s), 4.45 (2H, d, J=5.5), 4.67–4.73 (1H, m), 6.45 (1H, dt, J=16.0, 5.5), 6.54 (1H, d, J=16.0), 7.04 (2H, d, J=9.0), 7.39 (2H, d, J=9.0), 7.54 (1H, t, J=8.0), 7.71(2H, d, J=8.0), 7.90 (1H, s);

IR (KBr, cm$^{-1}$): 1733, 1672, 1347, 1155.

Example 61

Ethyl N-[3-(3-amidinophenyl)-2-(E)-propenyl]-N-[4-[1-(2,3,4,5-tetrahydropyridin-6-yl)piperidin-4-yloxy]phenyl]sulfamoylacetate dihydrochloride (Exemplification Compound Number 82)

To a solution of ethyl N-[3-(3-amidinophenyl)-2-(E)-propenyl]-N-[4-(piperidin-4-yloxy)phenyl]sulfamoylacetate dihydrochloride (0.50 g) obtained in example 59(a) in ethanol (5 ml) were added successively 6-ethoxy-2,3,4,5-tetrahydropyridine (0.31 g), which was prepared from piperidin-2-one according to the method described in Org. Prep. Proced. Int., 24, 147 (1992), and triethylamine (0.60 ml) at room temperature, and the resulting mixture was stirred at room temperature for 4 days and then evaporated in vacuo. The residue obtained was purified by preparative HPLC (YMC-Pack ODS-A; YMC, eluent: 25% acetonitrile/water). Subsequently, to a solution of the amorphous solid obtained in ethanol (25 ml) was added a 4N solution of hydrogen chloride in dioxane (2 ml), and the resulting mixture was evaporated to dryness in vacuo. The residue obtained was dissolved in water and then lyophilized to afford the title compound (0.27 g, yield: 47%) as a colorless amorphous solid.

$^1$H NMR (400 MHz, DMSO-$d_6$) δ ppm: 1.23 (3H, t, J=7.0), 1.65–1.78 (6H, m), 1.99–2.07 (2H, m), 2.68–2.72 (2H, m), 3.29–3.36 (2H, m), 3.44–3.55 (2H, m), 3.70–3.90 (2H, m), 4.20 (2H, q, J=7.0), 4.34 (2H, s), 4.44 (2H, d, J=5.5), 4.68–4.74 (1H, m), 6.44 (1H, dt, J=16.0, 5.5), 6.55 (1H, d, J=16.0), 7.03 (2H, d, J=9.0), 7.39 (2H, d, J=9.0), 7.55 (1H, t, J=7.7), 7.68–7.73 (2H, m), 7.88 (1H, s);

IR (KBr, cm$^{-1}$): 1738, 1674, 1637, 1351, 1157.

Example 62

N-[3-(3-Amidinophenyl)-2-(E)-propenyl]-N-[4-[1-(2,3,4,5-tetrahydropyridin-6-yl)piperidin-4-yloxy]phenyl]sulfamoylacetic acid dihydrochloride (Exemplification Compound Number 586)

Ethyl N-[3-(3-amidinophenyl)-2-(E)-propenyl]-N-[4-[1-(2,3,4,5-tetrahydropyridin-6-yl)piperidin-4-yloxy]phenyl]sulfamoylacetate dihydrochloride (0.76 g) obtained in example 61 was dissolved in 3N hydrochloric acid (15 ml) and the resulting mixture was stirred at 60° C. for 6 hours. After cooling to room temperature, the reaction mixture was evaporated in vacuo. The residue obtained was purified by preparative HPLC (YMC-Pack ODS-A; YMC, eluent: 20% acetonitrile/water). The amorphous solid obtained was dissolved in 1N hydrochloric acid (5 ml) and the resulting mixture was evaporated to dryness in vacuo. The residue obtained was dissolved in water and then lyophilized to afford the title compound (0.60 g, yield: 83%) as a colorless amorphous solid.

$^1$H NMR (400 MHz, DMSO-$d_6$) δ ppm: 1.65–1.78 (6H, m), 2.00–2.07 (2H, m), 2.68–2.71 (2H, m), 3.30–3.55 (4H, m), 3.70–3.87 (2H, m), 4.21 (2H, s), 4.45 (2H, d, J=5.5), 4.67–4.73 (1H, m), 6.45 (1H, dt, J=16.0, 6.0), 6.55 (1H, d, J=16.0), 7.03 (2H, d, J=9.0), 7.39 (2H, d, J=9.0), 7.54 (1H, t, J=8.0), 7.67–7.73 (2H, m), 7.87 (1H, s);

IR (KBr, cm$^{-1}$): 1734, 1674, 1637, 1348, 1156.

Example 63

Ethyl N-[3-(3-amidinophenyl)-2-(E)-propenyl]-N-[4-[1-(3,4,5,6-tetrahydro-2H-azepin-7-yl)piperidin-4-yloxy]phenyl]sulfamoylacetate dihydrochloride (Exemplification Compound Number 83)

To a solution of ethyl N-[3-(3-amidinophenyl)-2-(E)-propenyl]-N-[4-(piperidin-4-yloxy)phenyl]sulfamoylacetate dihydrochloride (0.51 g) obtained in example 59(a) in ethanol (5 ml) were added successively 7-methoxy-3,4,5,6-tetrahydro-2H-azepine (0.34 g) and triethylamine (0.60 ml) at room temperature, and the resulting mixture was stirred at room temperature for 18 hours and then evaporated in vacuo. The residue obtained was purified by preparative HPLC (YMC-Pack ODS-A; YMC, eluent: 25% acetonitrile/water). Subsequently, to a solution of the amorphous solid obtained in ethanol (5 ml) was added a 4N solution of hydrogen chloride in dioxane (1 ml), and the resulting mixture was evaporated to dryness in vacuo. The residue obtained was dissolved in water and then lyophilized to afford the title compound (0.14 g, yield: 24%) as a colorless amorphous solid.

$^1$H NMR (400 MHz, DMSO-$d_6$) δ ppm: 1.23 (3H, t, J=7.0), 1.46–1.76 (8H, m), 2.01–2.10 (2H, m), 2.86–2.89 (2H, m), 3.45–3.50 (2H, m), 3.57–3.70 (2H, m), 3.85–3.97 (2H, m), 4.20 (2H, q, J=7.0), 4.34 (2H, s), 4.45 (2H, d, J=6.0), 4.70–4.76 (1H, m), 6.45 (1H, dt, J=16.0, 6.0), 6.55 (1H, d, J=16.0), 7.39 (2H, d, J=9.0), 7.54 (2H, d, J=9.0), 7.54 (1H, t, J=8.0 Hz), 7.69–7.73 (2H, m), 7.90 (1H, s);

IR (KBr, cm$^{-1}$): 1737, 1674, 1629, 1351, 1158.

Example 64

N-[3-(3-Amidinophenyl)-2-(E)-propenyl]-N-[4-[1-(3,4,5,6-tetrahydro-2H-azepin-7-yl)piperidin-4-yloxy]phenyl]sulfamoylacetic acid dihydrochloride (Exemplification Compound Number 587)

Ethyl N-[3-(3-amidinophenyl)-2-(E)-propenyl]-N-[4-[1-(3,4,5,6-tetrahydro-2H-azepin-7-yl)piperidin-4-yloxy]phenyl]sulfamoylacetate dihydrochloride (0.96 g) obtained in example 63 was dissolved in 3N hydrochloric acid (25 ml) and the resulting mixture was stirred at 60° C. for 6 hours. After cooling to room temperature, the reaction mixture was evaporated in vacuo. The residue obtained was purified by preparative HPLC (YMC-Pack ODS-A; YMC, eluent: 20% acetonitrile/water). The amorphous solid obtained was dissolved in 1N hydrochloric acid (5 ml) and the resulting mixture was evaporated to dryness in vacuo. The residue obtained was dissolved in water and then lyophilized to afford the title compound (0.54 g, yield: 59%) as a colorless amorphous solid.

$^1$H NMR (400 MHz, DMSO-$d_6$) δ ppm: 1.53–1.64 (4H, m), 1.68–1.77 (4H, m), 2.02–2.10 (2H, m), 2.86–2.88 (2H, m), 3.45–3.50 (2H, m), 3.56–3.70 (2H, m), 3.78–3.97 (2H, m), 4.21 (2H, s), 4.45 (2H, d, J=6.0), 4.69–4.75 (1H, m), 6.45 (1H, dt, J=16.0, 6.0), 6.55 (1H, d, J=16.0), 7.04 (2H, d, J=9.0), 7.40 (2H, d, J=9.0), 7.54 (1H, t, J=7.5), 7.69–7.72 (2H, m), 7.90 (1H, s);

IR (KBr, cm$^{-1}$): 1733, 1677, 1629, 1344, 1154.

Example 65

Ethyl N-[3-(3-amidinophenyl)-2-(E)-propenyl]-N-[4-[1-(4,5-dihydro-3H-pyrrol-2-yl)piperidin-4-yloxy]-3-methylphenyl]sulfamoylacetate dihydrochloride (Exemplification Compound Number 53)

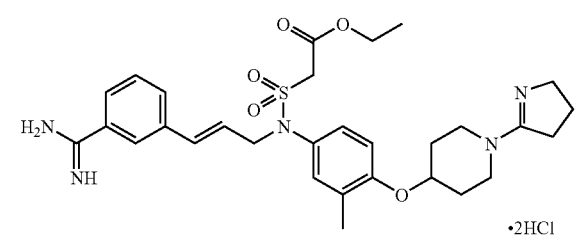

(a) Ethyl N-[3-(3-amidinophenyl)-2-(E)-propenyl]-N-[3-methyl-4-(piperidin-4-yloxy)phenyl]sulfamoylacetate dihydrochloride Hydrogen chloride was bubbled through a solution of ethyl N-[4-(1-t-butoxycarbonylpiperidin-4-yloxy)-3-methylphenyl]-N-[3-(3-cyanophenyl)-2-(E)-propenyl]sulfamoylacetate (1.90 g) obtained in reference example 112 in a mixture of dichloromethane (40 ml) and ethanol (40 ml) under ice-cooling, and the resulting mixture was stirred at room temperature for 5 hours under sealed conditions and then evaporated in vacuo. Subsequently, to a solution of the residue obtained in ethanol (45 ml) were added successively an aqueous ammonium chloride solution (prepared by dissolving 0.34 g in 15 ml of water) and a 28% ammonia solution (0.64 ml), and the resulting mixture was allowed to stand at room temperature for 13 hours. After standing, to the reaction mixture was added a 4N solution of hydrogen chloride in dioxane and the resulting mixture was evaporated in vacuo. The residue obtained was purified by preparative HPLC (YMC-Pack ODS-A; YMC, eluent: 20% acetonitrile/water). Subsequently, to a solution of the amorphous solid obtained in methanol (20 ml) was added a 4N solution of hydrogen chloride in ethyl acetate (1 ml), and the resulting mixture was evaporated to dryness in vacuo to afford the title compound (1.36 g, yield: 73%) as a colorless amorphous solid.

$^1$H NMR (400 MHz, DMSO-$d_6$) δ ppm: 1.23 (3H, t, J=7.0), 1.87 (2H, m), 2.10 (2H, m), 2.17 (3H, s), 3.07 (2H, m), 3.17 (2H, m), 4.20 (2H, q, J=7.0), 4.33 (2H, s), 4.44 (2H, d, J=6.0), 4.65 (1H, m), 6.44 (1H, dt, J=16.0, 6.0), 6.56 (1H, d, J=16.0), 7.05 (1H, d, J=9.0), 7.24 (1H, dd, J=9.0, 2.5), 7.29 (1H, d, J=2.5), 7.54 (1H, t, J=8.0), 7.71 (2H, m), 7.90 (1H, s);

IR (KBr, cm$^{-1}$): 1738, 1675.

(b) Ethyl N-[3-(3-amidinophenyl)-2-(E)-propenyl]-N-[4-[1-(4,5-dihydro-3H-pyrrol-2-yl)piperidin-4-yloxy]-3-methylphenyl]sulfamoylacetate dihydrochloride To a solution of ethyl N-[3-(3-amidinophenyl)-2-(E)-propenyl]-N-[3-methyl-4-(piperidin-4-yloxy)phenyl]sulfamoylacetate (700 mg) obtained in example 65(a) in ethanol (15 ml) were added successively 5-methoxy-3,4-dihydro-2H-pyrrole (405 mg), which was prepared from 2-pyrrolidinone according to the method described in Org. Prep. Proced. Int., 24, 147 (1992), and triethylamine (0.57 ml) at room temperature, and the resulting mixture was stirred at room temperature overnight and then evaporated in vacuo. The residue obtained was purified by preparative HPLC (YMC-Pack ODS-A; YMC; eluent: 22% acetonitrile/water) to afford an amorphous solid (565 mg). Subsequently, to a solution of the amorphous solid obtained (151 mg) in ethanol (4 ml) was added a 4N solution of hydrogen chloride in dioxane (2 ml), and the resulting mixture was evaporated to dryness in vacuo. The residue obtained was dissolved in water and then lyophilized to afford the title compound (157 mg, yield: 66%) as a colorless amorphous solid.

$^1$H NMR (400 MHz, DMSO-$d_6$) δ ppm: 1.23 (3H, t, J=7.0), 1.72–1.85 (2H, m), 1.98–2.14 (4H, m), 2.16 (3H, s), 2.96 (2H, t, J=8.0), 3.46–3.81 (6H, m), 4.20 (2H, q, J=7.0), 4.33 (2H, s), 4.44 (2H, d, J=6.0), 4.73 (1H, m), 6.44 (1H, dt, J=16.0, 6.0), 6.57 (1H, d, J=16.0), 7.07 (1H, d, J=9.0), 7.24 (1H, dd, J=9.0, 2.5), 7.29 (1H, d, J=2.5), 7.55 (1H, t, J=8.0), 7.69 (1H, d, J=8.0), 7.72 (1H, d, J=8.0), 7.89 (1H, s);

IR (KBr, cm$^{-1}$): 1738, 1671, 1350, 1157.

Example 66

N-[3-(3-Amidinophenyl)-2-(E)-propenyl]-N-[4-[1-(4,5-dihydro-3H-pyrrol-2-yl)piperidin-4-yloxy-]-3-methylphenyl]sulfamoylacetic acid dihydrochloride (Exemplification Compound Number 557)

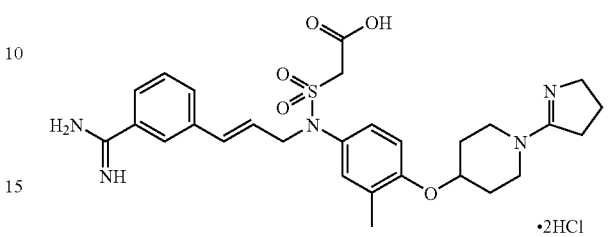

•2HCl

Ethyl N-[3-(3-amidinophenyl)-2-(E)-propenyl]-N-[4-[1-(4,5-dihydro-3H-pyrrol-2-yl)piperidin-4-yloxy]-3-methylphenyl]sulfamoylacetate (409 mg) obtained in example 65(b) was dissolved in 4N hydrochloric acid (12 ml) and the resulting mixture was stirred at 70° C. for 2 hours. After cooling to room temperature, the reaction mixture was evaporated in vacuo. The residue obtained was purified by preparative HPLC (YMC-Pack ODS-A; YMC, eluent: 17% acetonitrile/water). The amorphous solid obtained was dissolved in 1N hydrochloric acid (10 ml) and the resulting mixture was evaporated to dryness in vacuo. The residue obtained was dissolved in water and then lyophilized to afford the title compound (266 mg, yield: 60%) as a colorless amorphous solid.

$^1$H NMR (400 MHz, DMSO-$d_6$) δ ppm: 1.72–1.86 (2H, m), 1.97–2.14 (4H, m), 2.16 (3H, s), 2.96 (2H, m), 3.47–3.80 (5H, m), 3.72–3.82 (1H, m), 4.19 (2H, s), 4.44 (2H, d, J=6.0), 4.72 (1H, m), 6.44 (1H, dt, J=16.0, 6.0), 6.56 (1H, d, J=16.0), 7.06 (1H, d, J=8.5), 7.25 (1H, dd, J=8.5, 2.5), 7.29 (1H, d, J=2.5), 7.55 (1H, t, J=8.0), 7.69 (1H, d, J=8.0), 7.72 (1H, d, J=8.0), 7.89 (1H, s);

IR (KBr, cm$^{-1}$): 1733, 1672, 1347, 1155.

Example 67

Ethyl N-[3-(3-amidinophenyl)-2-(E)-propenyl]-N-[3-methyl-4-[1-(2,3,4,5-tetrahydropyridin-6-yl)piperidin-4-yloxy]phenyl]sulfamoylacetate dihydrochloride (Exemplification Compound Number 54)

To a solution of ethyl N-[3-(3-amidinophenyl)-2-(E)-propenyl]-N-[3-methyl-4-(piperidin-4-yloxy)phenyl]sulfamoylacetate (730 mg) obtained in example 65(a) in ethanol (15 ml) were added successively 6-ethoxy-2,3,4,5-tetrahydropyridine (482 mg), which was prepared from piperidin-2-one according to the method described in Org. Prep. Proced. Int., 24, 147 (1992), and triethylamine (0.59 ml) at room temperature, and the resulting mixture was stirred at room temperature for 2 days and then evaporated in vacuo. The residue obtained was purified by preparative HPLC (YMC-Pack ODS-A; YMC, eluent: 28% acetonitrile/water). Subsequently, to a solution of the amorphous solid obtained in ethanol (6 ml) was added a 4N solution of hydrogen chloride in dioxane (0.39 ml), and the resulting mixture was evaporated to dryness in vacuo. The residue obtained was dissolved in water and then lyophilized to afford the title compound (331 mg, yield: 36%) as a colorless amorphous solid.

$^1$H NMR (400 MHz, DMSO-$d_6$) δ ppm: 1.23 (3H, t, J=7.0), 1.64–1.70 (6H, m), 1.96–2.08 (2H, m), 2.16 (3H, s), 2.70 (2H, t, J=6.0), 3.25–3.37 (2H, m), 3.46–3.83 (4H, m), 4.20 (2H, q, J=7.0), 4.33 (2H, s), 4.44 (2H, d, J=6.0), 4.73 (1H, m), 6.44 (1H, dt, J=16.0, 6.0), 6.57 (1H, d, J=16.0), 7.06 (1H, d, J=9.0), 7.24 (1H, dd, J=9.0, 2.5), 7.29 (1H, d, J=2.5), 7.55 (1H, t, J=8.0), 7.70 (1H, d, J=8.0), 7.72 (1H, d, J=8.0), 7.90 (1H, s);

IR (KBr, cm$^{-1}$): 1738, 1674, 1637, 1351, 1157.

Example 68

N-[3-(3-Amidinophenyl)-2-(E)-propenyl]-N-[3-methyl-4-(2,3,4,5-tetrahydropyridin-6-yl)piperidin-4-yloxy]phenyl] sulfamoylacetic acid dihydrochloride (Exemplification Compound Number 558)

Ethyl N-[3-(3-amidinophenyl)-2-(E)-propenyl]-N-[3-methyl-4-[1-(2,3,4,5-tetrahydropyridin-6-yl)piperidin-4-yloxy]phenyl]sulfamoylacetate dihydrochloride (265 mg) obtained in example 67 was dissolved in 3N hydrochloric acid (10 ml) and the resulting mixture was stirred at 60° C. for 5 hours. After cooling to room temperature, the reaction mixture was evaporated in vacuo. The residue obtained was purified by preparative HPLC (YMC-Pack ODS-A; YMC, eluent: 20% acetonitrile/water). The amorphous solid obtained was dissolved in 1N hydrochloric acid (8 ml) and the resulting mixture was evaporated to dryness in vacuo. The residue obtained was dissolved in water and then lyophilized to afford the title compound (236 mg, yield: 93%) as a colorless amorphous solid.

$^1$H NMR (400 MHz, DMSO-d$_6$) δ ppm: 1.64–1.82 (6H, m), 1.96–2.08 (2H, m), 2.16 (3H, s), 2.70 (2H, m), 3.33 (2H, m), 3.46–3.83 (4H, m), 4.21 (2H, s), 4.44 (2H, d, J=6.0), 4.73 (1H, m), 6.44 (1H, dt, J=16.0, 6.0), 6.56 (1H, d, J=16.0), 7.05 (1H, d, J=8.5), 7.25 (1H, dd, J=8.5, 2.5), 7.29 (1H, d, J=2.5), 7.55 (1H, t, J=8.0), 7.69 (1H, d, J=8.0), 7.72 (1H, d, J=8.0), 7.89 (1H, s);

IR (KBr, cm$^{-1}$): 1733, 1676, 1637, 1347, 1156.

Example 69

Ethyl N-[3-(3-amidinophenyl)-2-(E)-propenyl]-N-[3-methyl-4-[1-(3,4,5,6-tetrahydro-2H-azepin-7-yl)piperidin-4-yloxy]phenyl]sulfamoylacetate dihydrochloride (Exemplification Compound Number 55)

To a solution of ethyl N-[3-(3-amidinophenyl)-2-(E)-propenyl]-N-[3-methyl-4-(piperidin-4-yloxy)phenyl]sulfamoylacetate (640 mg) obtained in example 65(a) in ethanol (12 ml) were added successively 7-methoxy-3,4,5,6-tetrahydro-2H-azepine (348 mg) and triethylamine (0.26 ml) at room temperature and the resulting mixture was stirred at room temperature for 2.5 days and then evaporated in vacuo. The residue obtained was purified by preparative HPLC (YMC-Pack ODS-A; YMC, eluent: 20% acetonitrile/water). Subsequently, to a solution of the amorphous solid obtained in ethanol (5 ml) was added a 4N solution of hydrogen chloride in dioxane (0.42 ml), and the resulting mixture was evaporated to dryness in vacuo. The residue obtained was dissolved in water and then lyophilized to afford the title compound (336 mg, yield: 40%) as a colorless amorphous solid.

$^1$H NMR (400 MHz, DMSO-d$_6$) δ ppm: 1.23 (3H, t, J=7.0), 1.52–1.64 (4H, m), 1.68–1.82 (4H, m), 1.98–2.09 (2H, m), 2.17 (3H, s), 2.87 (2H, m), 3.48 (2H, m), 3.65–3.75 (2H, m), 3.77–3.88 (2H, m), 4.19 (2H, q, J=7.0), 4.33 (2H, s), 4.44 (2H, d, J=6.0), 4.74 (1H, m), 6.44 (1H, dt, J=16.0, 6.0), 6.57 (1H, d, J=16.0), 7.06 (1H, d, J=8.5), 7.25 (1H, dd, J=8.5, 2.5), 7.28 (1H, d, J=2.5), 7.55 (1H, t, J=8.0), 7.69 (1H, d, J=8.0), 7.72 (1H, d, J=8.0), 7.89 (1H, s);

IR (KBr, cm$^{-1}$): 1738, 1675, 1628, 1351, 1157.

Example 70

N-[3-(3-Amidinophenyl)-2-(E)-propenyl]-N-[3-methyl-4-[1-(3,4,5,6-tetrahydro-2H-azepin-7-yl)piperidin-4-yloxy]phenyl]sulfamoylacetic acid dihydrochloride (Exemplification Compound Number 559)

Ethyl N-[3-(3-amidinophenyl)-2-(E)-propenyl]-N-[3-methyl-4-[1-(3,4,5,6-tetrahydro-2H-azepin-7-yl)piperidin-4-yloxy]phenyl]sulfamoylacetate dihydrochloride (335 mg) obtained in example 69 was dissolved in 3N hydrochloric acid (10 ml) and the resulting mixture was stirred at 60° C. for 5 hours. After cooling to room temperature, the reaction mixture was evaporated in vacuo. The residue obtained was purified by preparative HPLC (YMC-Pack ODS-A; YMC, eluent: 20% acetonitrile/water). The amorphous solid obtained was dissolved in 1N hydrochloric acid (10 ml) and the resulting mixture was evaporated to dryness in vacuo. The residue obtained was dissolved in water and then lyophilized to afford the title compound (258 mg, yield: 80%) as a colorless amorphous solid.

$^1$H NMR (400 MHz, DMSO-d$_6$) δ ppm: 1.53–1.65 (4H, m), 1.68–1.84 (4H, m), 1.98–2.10 (2H, m), 2.16 (3H, s), 2.88 (2H, m), 3.44–3.53 (2H, m), 3.62–3.93 (4H, m), 4.19 (2H, s), 4.40 (2H, d, J=6.0), 4.74 (1H, m), 6.44 (1H, dt, J=16.0, 6.0), 6.56 (1H, d, J=16.0), 7.05 (1H, d, J=9.0), 7.26 (1H, dd, J=9.0, 2.5), 7.29 (1H, d, J=2.5), 7.55 (1H, t, J=8.0), 7.69 (1H, d, J=8.0), 7.72 (1H, d, J=8.0), 7.89 (1H, s);

IR (KBr, cm$^{-1}$): 1732, 1676, 1628, 1348, 1156.

Example 71

Ethyl N-[3-(3-amidinophenyl)-2-(E)-propenyl]-N-[3-carbamoyl-4-[1-(4,5-dihydro-3H-pyrrol-2-yl)piperidin-4-yloxy]phenyl]sulfamoylacetate dihydrochloride (Exemplification Compound Number 137)

(a) Ethyl N-[3-(3-amidinophenyl)-2-(E)-propenyl]-N-[3-carbamoyl-4-(piperidin-4-yloxy)phenyl]sulfamoylacetate dihydrochloride Hydrogen chloride was bubbled through a solution of ethyl N-[4-(1-t-butoxycarbonylpiperidin-4-yloxy)-3-carbamoylphenyl]-N-[3-(3-cyanophenyl)-2-(E)-propenyl]sulfamoylacetate (2.40 g) obtained in reference example 119 in a mixture of dichloromethane (20 ml) and ethanol (20 ml) for 2.5 hours under ice-cooling, and the resulting mixture was stirred at room temperature for 6 hours under sealed conditions and then evaporated in vacuo. Subsequently, to a solution of the residue obtained in ethanol (20 ml) were added successively an aqueous ammonium chloride solution (prepared by dissolving 0.50 g in 5 ml of water) and a 28% ammonia solution (1.10 ml), and the resulting mixture was allowed to stand at room temperature for 13 hours and evaporated in vacuo. The residue obtained was purified by preparative HPLC (YMC-Pack ODS-A; YMC, eluent: 15% acetonitrile/water). Subsequently to a solution of the amorphous solid obtained in ethanol (20 ml) was added a 4N solution of hydrogen chloride in ethyl acetate (0.90 ml), and the resulting mixture was evaporated to dryness in vacuo to afford the title compound (0.60 g, yield: 25%) as a colorless amorphous solid.

$^1$H NMR (500 MHz, DMSO-d$_6$) δ ppm: 1.23 (3H, t, J=7.0), 1.85–2.00 (2H, m), 2.05–2.20 (2H, m), 3.00–3.10 (2H, m), 3.15–3.25 (2H, m), 4.20 (2H, q, J=7.0), 4.38 (2H, s), 4.47 (2H, d, J=6.0), 4.80 (1H, m), 6.45 (1H, dt, J=16.0, 6.0), 6.57 (1H, d, J=16.0), 7.24 (1H, m), 7.50 (1H, m), 7.54 (1H, m), 7.65–7.75 (3H, m), 7.90 (1H, m);

IR (KBr, cm$^{-1}$): 1736, 1671, 1658.

(b) Ethyl N-[3-(3-amidinophenyl)-2-(E)-propenyl]-N-[3-carbamoyl-4-[1-(4,5-dihydro-3H-pyrrol-2-yl)piperidin-4-yloxy]phenyl]sulfamoylacetate dihydrochloride To a solution of ethyl N-[3-(3-amidinophenyl)-2-(E)-propenyl]-N-[3-carbamoyl-4-(piperidin-4-yloxy)phenyl]sulfamoylacetate (500 mg) obtained in example 71(a) in ethanol (15 ml) were added successively 5-methoxy-3,4-dihydro-2H-pyrrole (340 mg), which was prepared from 2-pyrrolidinone according to the method described in *Org. Prep. Proced. Int.*, 24, 147 (1992), and triethylamine (0.77 ml) at room temperature, and the resulting mixture was stirred at room temperature overnight and then evaporated in vacuo. The residue obtained was purified by preparative HPLC (YMC-Pack ODS-A; YMC, eluent: 15% acetonitrile/water). Subsequently, to a solution of the amorphous solid obtained in ethanol (5 ml) was added a 4N solution of hydrogen chloride in dioxane (0.50 ml), and the resulting mixture was evaporated to dryness in vacuo to afford the title compound (420 mg, yield: 67%) as a colorless amorphous solid.

$^1$H NMR (500 MHz, DMSO-$d_6$) δ ppm: 1.23 (3H, t, J=7.0), 1.80–1.95 (2H, m), 2.00–2.15 (4H, m), 2.96 (2H, m), 3.45–3.55 (1H, m), 3.55–3.65 (1H, m), 3.61 (2H, m), 3.65–3.75 (1H, m), 3.75–3.85 (1H, m), 4.20 (2H, q, J=7.0), 4.37 (2H, s), 4.47 (2H, d, J=6.0), 4.86 (1H, m), 6.44 (1H, dt, J=16.0, 6.0), 6.58 (1H, d, J=16.0), 7.28 (1H, d, J=9.0), 7.51 (1H, dd, J=9.0, 2.5), 7.55 (1H, t, J=8.0), 7.68 (1H, d, J=8.0), 7.72 (1H, d, J=8.0), 7.77 (1H, d, J=2.5), 7.87 (1H, s);

IR (KBr, cm$^{-1}$): 1737, 1670.

Example 72

N-[3-(3-Amidinophenyl)-2-(E)-propenyl]-N-[3-carbamoyl-4-[1-(4,5-dihydro-3H-pyrrol-2-yl)piperidin-4-yloxy]phenyl]sulfamoylacetic acid dihydrochloride (Exemplification Compound Number 641)

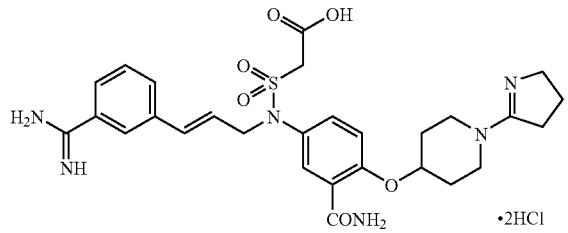

Ethyl N-[3-(3-amidinophenyl)-2-(E)-propenyl]-N-[3-carbamoyl-4-[1-(4,5-dihydro-3H-pyrrol-2-yl)piperidin-4-yloxy]phenyl]sulfamoylacetate dihydrochloride (380 mg) obtained in example 71(b) was dissolved in 3N hydrochloric acid (12 ml) and the resulting mixture was stirred at 60° C. for 3 hours. After cooling to room temperature, the reaction mixture was evaporated in vacuo. The residue obtained was purified by a preparative HPLC (YMC-Pack ODS-A; YMC, eluent: 13% acetonitrile/water). The amorphous solid obtained was dissolved in a mixture of 1N hydrochloric acid (1.2 ml) and water (5 ml), and the resulting mixture was evaporated to dryness in vacuo to afford the title compound (240 mg, yield: 65%) as a colorless amorphous solid.

$^1$H NMR (500 MHz, DMSO-$d_6$) δ ppm: 1.80–1.95 (2H, m), 2.00–2.15 (4H, m), 2.96 (2H, m), 3.45–3.55 (1H, m), 3.55–3.65 (1H, m), 3.61 (2H, m), 3.65–3.75 (1H, m), 3.75–3.85 (1H, m), 4.24 (2H, s), 4.47 (2H, d, J=6.0), 4.85 (1H, m), 6.44 (1H, dt, J=16.0, 6.0), 6.57 (1H, d, J=16.0), 7.28 (1H, d, J=9.0), 7.52 (1H, dd, J=9.0, 2.5), 7.55 (1H, t, J=8.0), 7.67 (1H, d, J=8.0), 7.72 (1H, d, J=8.0), 7.77 (1H, d, J=2.5), 7.86 (1H, s);

IR (KBr, cm$^{-1}$) 1731, 1670.

Example 73

Ethyl N-[3-(3-amidinophenyl)-2-(E)-propenyl]-N-[3-carbamoyl-4-[1-(2,3,4,5-tetrahydropyridin-6-yl)piperidin-4-yloxy]phenyl]sulfamoylacetate dihydrochloride (Exemplification Compound Number 138)

To a solution of ethyl N-[3-(3-amidinophenyl)-2-(E)-propenyl]-N-[3-carbamoyl-4-(piperidin-4-yloxy)phenyl]sulfamoylacetate (500 mg) obtained in example 71(a) in ethanol (15 ml) were added successively 6-ethoxy-2,3,4,5-tetrahydropyridine (360 mg), which was prepared from piperidin-2-one according to the method described in *Org. Prep. Proced. Int.*, 24, 147 (1992), and triethylamine (0.77 ml) at room temperature, and the resulting mixture was stirred at room temperature overnight. Because of the slow progress of the reaction, 6-ethoxy-2,3,4,5-tetrahydropyridine (630 mg) and triethylamine (0.77 ml) were added successively and the resulting mixture was stirred at room temperature for one day, and at the end of this time, 6-ethoxy-2,3,4,5-tetrahydropyridine (320 mg) and triethylamine (0.35 ml) were furthermore added successively and the resulting mixture was stirred at room temperature for one day and then evaporated in vacuo. The residue obtained was purified by preparative HPLC (YMC-Pack ODS-A; YMC, eluent: 15% acetonitrile/water). Subsequently, to a solution of the amorphous solid obtained in ethanol (6 ml) was added a 4N solution of hydrogen chloride in dioxane (0.25 ml), and the resulting mixture was evaporated to dryness in vacuo to afford the title compound (200 mg, yield: 31%) as a colorless amorphous solid.

$^1$H NMR (500 MHz, DMSO-$d_6$) δ ppm: 1.24 (3H, t, J=7.0), 1.65–1.90 (6H, m), 2.00–2.10 (2H, m), 2.70 (2H, m), 3.34 (2H, m), 3.40–3.60 (2H, m), 3.70–3.85 (2H, m), 4.21 (2H, q, J=7.0), 4.37 (2H, s), 4.48 (2H, d, J=6.0), 4.87 (1H, m), 6.44 (1H, dt, J=16.0, 6.0), 6.59 (1H, d, J=16.0), 7.28 (1H, d, J=9.0), 7.52 (1H, dd, J=9.0, 3.0), 7.56 (1H, t, J=8.0), 7.68 (1H, d, J=8.0), 7.73 (1H, d, J=8.0), 7.78 (1H, d, J=3.0), 7.86 (1H, s);

IR (KBr, cm$^{-1}$): 1737, 1673.

Example 74

N-[3-(3-Amidinophenyl)-2-(E)-propenyl]-N-[3-carbamoyl-4-[1-(2,3,4,5-tetrahydropyridin-6-yl)piperidin-4-yloxy]phenyl]sulfamoylacetic acid dihydrochloride (Exemplification Compound Number 642)

Ethyl N-[3-(3-amidinophenyl)-2-(E)-propenyl]-N-[3-carbamoyl-4-[1-(2,3,4,5-tetrahydropyridin-6-yl)piperidin-4-yloxy]phenyl]sulfamoylacetate dihydrochloride (200 mg) obtained in example 73 was dissolved in 3N hydrochloric acid (20 ml) and the resulting mixture was stirred at 60° C. for 3 hours. After cooling to room temperature, the reaction mixture was evaporated in vacuo. The residue obtained was purified by preparative HPLC (YMC-Pack ODS-A; YMC, eluent: 13% acetonitrile/water). The amorphous solid obtained was dissolved in 1N hydrochloric acid (0.9 ml) and the resulting mixture was evaporated to dryness in vacuo to afford the title compound (137 g, yield: 71%) as a colorless amorphous solid.

$^1$H NMR (500 MHz, DMSO-$d_6$) δ ppm: 1.65–1.90 (6H, m), 2.00–2.10 (2H, m), 2.69 (2H, m), 3.34 (2H, m), 3.40–3.60 (2H, m), 3.70–3.85 (2H, m), 4.24 (2H, s), 4.47

(2H, d, J=6.0), 4.86 (1H, m), 6.44 (1H, dt, J=16.0, 6.0), 6.57 (1H, d, J=16.0), 7.27 (1H, d, J=9.0), 7.52 (1H, dd, J=9.0, 3.0), 7.55 (1H, t, J=8.0), 7.67 (1H, d, J=8.0), 7.72 (1H, d, J=8.0), 7.77 (1H, d, J=3.0), 7.86 (1H, s);

IR (KBr, cm$^{-1}$): 1731, 1674.

Example 75

Ethyl N-[3-(3-amidinophenyl)-2-(E)-propenyl]-N-[3-carbamoyl-4-[1-(3,4,5,6-tetrahydro-2H-azepin-7-yl)piperidin-4-yloxy]phenyl]sulfamoylacetate dihydrochloride (Exemplification Compound Number 139)

To a solution of ethyl N-[3-(3-amidinophenyl)-2-(E)-propenyl]-N-[3-carbamoyl-4-(piperidin-4-yloxy)phenyl] sulfamoylacetate (400 mg) obtained in example 71(a) in ethanol (10 ml) were added successively 7-methoxy-3,4,5,6-tetrahydro-2H-azepine (280 mg) and triethylamine (0.31 ml) at room temperature and the resulting mixture was stirred at room temperature overnight. Because of the slow progress of the reaction, 7-methoxy-3,4,5,6-tetrahydro-2H-azepine (280 mg) and triethylamine (0.31 ml) were furthermore added successively, and the resulting mixture was stirred at 40° C. for 12 hours and allowed to stand at room temperature overnight. The reaction mixture was then evaporated in vacuo. The residue obtained was purified by preparative HPLC (YMC-Pack ODS-A; YMC, eluent: 20% acetonitrile/water). Subsequently, to a solution of the amorphous solid obtained in ethanol (5 ml) was added a 4N solution of hydrogen chloride in dioxane (0.20 ml), and the resulting mixture was evaporated to dryness in vacuo to afford the title compound (140 mg, yield: 26%) as a colorless amorphous solid.

$^1$H NMR (500 MHz, DMSO-d$_6$) δ ppm: 1.24 (3H, t, J=7.0), 1.50–1.65 (4H, m), 1.70–1.75 (2H, m), 1.80–1.90 (2H, m), 2.05–2.15 (2H, m), 2.85–2.90 (2H, m), 3.45–3.50 (2H, m), 3.55–3.65 (1H, m), 3.65–3.75 (1H, m), 3.75–3.85 (1H, m), 3.85–3.95 (1H, m), 4.20 (2H, q, J=7.0), 4.37 (2H, s), 4.47 (2H, d, J=6.0), 4.86 (1H, m), 6.44 (1H, dt, J=16.0, 6.0), 6.58 (1H, d, J=16.0), 7.28 (1H, d, J=9.0), 7.51 (1H, dd, J=9.0, 2.5), 7.55 (1H, t, J=8.0), 7.67 (1H, d, J=8.0), 7.72 (1H, d, J=8.0), 7.78 (1H, d, J=2.5), 7.86 (1H, s);

IR (KBr, cm$^{-1}$) 1737, 1672.

Example 76

N-[3-(3-Amidinophenyl)-2-(E)-propenyl]-N-[3-carbamoyl-4-[1-(3,4,5,6-tetrahydro-2H-azepin-7-yl)piperidin-4-yloxy]phenyl]sulfamoylacetic acid dihydrochloride (Exemplification Compound Number 643)

Ethyl N-[3-(3-amidinophenyl)-2-(E)-propenyl]-N-[3-carbamoyl-4-[1-(3,4,5,6-tetrahydro-2H-azepin-7-yl)piperidin-4-yloxy]phenyl]sulfamoylacetate dihydrochloride (130 mg) obtained in example 75 was dissolved in 3N hydrochloric acid (10 ml) and the resulting mixture was stirred at 60° C. for 2 hours. After cooling to room temperature, the reaction mixture was evaporated in vacuo. The residue obtained was purified by preparative HPLC (YMC-Pack ODS-A; YMC, eluent: 12% acetonitrile/water). The amorphous solid obtained was dissolved in a mixture of 1N hydrochloric acid (0.25 ml) and water (5 ml), and the resulting mixture was evaporated to dryness in vacuo to afford the title compound (50 mg, yield: 40%) as a colorless amorphous solid.

$^1$H NMR (500 MHz, DMSO-d$_6$) δ ppm: 1.55–1.65 (4H, m), 1.70–1.75 (2H, m), 1.80–1.90 (2H, m), 2.05–2.15 (2H, m), 2.85–2.90 (2H, m), 3.45–3.50 (2H, m), 3.55–3.65 (1H, m), 3.65–3.75 (1H, m), 3.80–3.90 (1H, m), 3.90–4.00 (1H, m), 4.24 (2H, s), 4.47 (2H, d, J=6.0), 4.86 (1H, m), 6.45 (1H, dt, J=16.0, 6.0), 6.57 (1H, d, J=16.0), 7.27 (1H, d, J=9.0), 7.51 (1H, dd, J=9.0, 2.5), 7.54 (1H, t, J=8.0), 7.68 (1H, d, J=8.0), 7.72 (1H, d, J=8.0), 7.77 (1H, d, J=2.5), 7.88 (1H, s);

IR (KBr, cm$^{-1}$): 1732, 1674.

Example 77

Ethyl N-[3-(3-amidinophenyl)-2-(E)-propenyl]-N-[4-[1-(4,5-dihydro-3H-pyrrol-2-yl)piperidin-4-yloxy]-3-trifluoromethylphenyl]sulfamoylacetate dihydrochloride (Exemplification Compound Number 109)

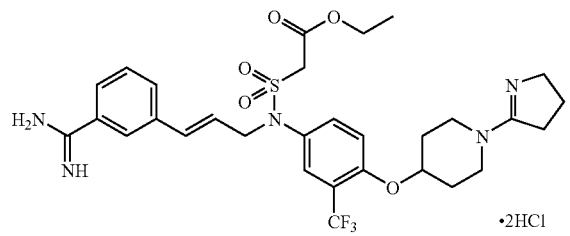

(a) Ethyl N-[3-(3-amidinophenyl)-2-(E)-propenyl]-N-[4-(piperidin-4-yloxy)-3-trifluoromethylphenyl]sulfamoylacetate dihydrochloride Hydrogen chloride was bubbled through a solution of ethyl N-[4-(1-t-butoxycarbonylpiperidin-4-yloxy)-3-trifluoromethylphenyl]-N-[3-(3-cyanophenyl)-2-(E)-propenyl]sulfamoylacetate (2.06 g) obtained in reference example 122 in a mixture of dichloromethane (50 ml) and ethanol (25 ml) under ice-cooling, and the resulting mixture was stirred at room temperature for 6 hours under sealed conditions and then evaporated in vacuo. Subsequently, to a solution of the residue obtained in ethanol (45 ml) were added successively an aqueous ammonium chloride solution (prepared by dissolving 0.34 g in 15 ml of water) and a 28% ammonia solution (0.63 ml), and the resulting mixture was allowed to stand at room temperature for 12 hours. After standing, to the reaction mixture was added a 4N solution of hydrogen chloride in dioxane (2.5 ml) and the resulting mixture was evaporated in vacuo. The residue obtained was purified by preparative HPLC (YMC-Pack ODS-A; YMC, eluent: 25% acetonitrile/water). Subsequently, to a solution of the amorphous solid obtained in methanol (20 ml) was added a 4N solution of hydrogen chloride in dioxane (0.5 ml), and the resulting mixture was evaporated to dryness in vacuo to afford the title compound (1.21 g, yield: 60%) as a colorless amorphous solid.

$^1$H NMR (500 MHz, DMSO-d$_6$) δ ppm: 1.22 (3H, t, J=7.0), 1.87 (2H, m), 2.08 (2H, m), 3.11 (2H, m), 3.33 (2H, m), 4.18 (2H, q, J=7.0), 4.44 (2H, s), 4.50 (2H, d, J=6.5), 4.89 (1H, m), 6.44 (1H, dt, J=16.0, 6.5), 6.57 (1H, d, J=16.0), 7.39 (1H, d, J=9.0), 7.55 (1H, t, J=8.0), 7.66–7.73 (4H, m), 7.85 (1H, s);

IR (KBr, cm$^{-1}$): 1738, 1676.

(b) Ethyl N-[3-(3-amidinophenyl)-2-(E)-propenyl]-N-[4-[1-(4,5-dihydro-3H-pyrrol-2-yl)piperidin-4-yloxy]-3-trifluoromethylphenyl]sulfamoylacetate dihydrochloride To a solution of ethyl N-[3-(3-amidinophenyl)-2-(E)-propenyl]-N-[4-(piperidin-4-yloxy)-3-trifluoromethylphenyl]sulfamoylacetate dihydrochloride (800 mg) obtained in example 77(a) in ethanol (20 ml) were added successively 5-methoxy-3,4-dihydro-2H-pyrrole (370 mg), which was prepared from 2-pyrrolidinone according to the method described in *Org. Prep. Proced. Int.*, 24, 147 (1992), and triethylamine (0.87 ml) at room temperature, and the resulting mixture was stirred at room temperature overnight. Because of the slow progress of the reaction, 5-methoxy-3,4-dihydro-2H-pyrrole (120 mg) and triethylamine (0.26 ml) were furthermore added successively and the resulting mixture was stirred at room temperature for 4 hours. After stirring, to the reaction mixture was added a 4N solution of hydrogen chloride in dioxane and the resulting mixture was evaporated in vacuo. The residue obtained was purified by preparative HPLC (YMC-Pack ODS-A; YMC, eluent: 26% acetonitrile/water). The amorphous solid obtained was dissolved in 1N hydrochloric acid, and the resulting mixture was evaporated to dryness in vacuo. The residue obtained was dissolved in water and then lyophilized to afford the title compound (622 mg, yield: 70%) as a colorless amorphous solid.

$^1$H NMR (400 MHz, DMSO-$d_6$) δ ppm: 1.22 (3H, t, J=7.0), 1.82 (2H, m), 2.00–2.15 (4H, m), 2.97 (2H, t, J=8.0), 3.53–3.64 (4H, m), 3.72 (2H, m), 4.19 (2H, q, J=7.0), 4.45 (2H, s), 4.50 (2H, d, J=6.0), 4.96 (1H, m), 6.46 (1H, dt, J=16.0, 6.0), 6.58 (1H, d, J=16.0), 7.44 (1H, d, J=10.0), 7.55 (1H, t, J=8.0), 7.67–7.75 (4H, m), 7.90 (1H, s);

IR (KBr, cm$^{-1}$): 1739, 1672, 1353, 1144.

Example 78

N-[3-(3-Amidinophenyl)-2-(E)-propenyl]-N-[4-[1-(4,5-dihydro-3H-pyrrol-2-yl)piperidin-4-yloxy]-3-trifluoromethylphenyl]sulfamoylacetic acid dihydrochloride (Exemplification Compound Number 613)

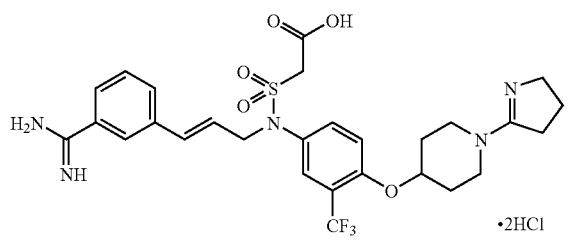

Ethyl N-[3-(3-amidinophenyl)-2-(E)-propenyl]-N-[4-[1-(4,5-dihydro-3H-pyrrol-2-yl)piperidin-4-yloxy]-3-trifluoromethylphenyl]sulfamoylacetate dihydrochloride (471 mg) obtained in example 77(b) was dissolved in 3N hydrochloric acid (20 ml) and the resulting mixture was stirred at 60° C. for 5.5 hours. After cooling to room temperature, the reaction mixture was evaporated in vacuo. The residue obtained was purified by preparative HPLC (YMC-Pack ODS-A; YMC, eluent: 20% acetonitrile/water). The amorphous solid obtained was dissolved in 1N hydrochloric acid and the resulting mixture was evaporated to dryness in vacuo. The residue obtained was dissolved in water and then lyophilized to afford the title compound (404 mg, yield: 89%) as a colorless amorphous solid.

$^1$H NMR (500 MHz, DMSO-$d_6$) δ ppm: 1.82 (2H, m), 2.00–2.15 (4H, m), 2.96 (2H, t, J=8.0), 3.49–3.64 (4H, m), 3.70 (2H, m), 4.19 (2H, s), 4.50 (2H, d, J=6.0), 4.95 (1H, m), 6.46 (1H, dt, J=16.0, 6.0), 6.57 (1H, d, J=16.0), 7.43 (1H, d, J=9.5), 7.54 (1H, t, J=8.0), 7.66–7.77 (4H, m), 7.89 (1H, s);

IR (KBr, cm$^{-1}$): 1739, 1672, 1353, 1144.

Example 79

Ethyl N-[3-(3-amidinophenyl)-2-(E)-propenyl]-N-[4-[1-(2,3,4,5-tetrahydropyridin-6-yl)piperidin-4-yloxy]-3-trifluoromethylphenyl]sulfamoylacetate dihydrochloride (Exemplification Compound Number 110)

To a solution of ethyl N-[3-(3-amidinophenyl)-2-(E)-propenyl]-N-[4-(piperidin-4-yloxy)-3-trifluoromethylphenyl]sulfamoylacetate dihydrochloride (900 mg) obtained in example 77(a) in ethanol (20 ml) were added successively 6-methoxy-2,3,4,5-tetrahydropyridine (480 mg), which was prepared from piperidin-2-one according to the method described in Org. Prep. Proced. Int., 24, 147 (1992), and triethylamine (0.98 ml) at room temperature and the resulting mixture was stirred at room temperature overnight. Because of the slow progress of the reaction, 6-ethoxy-2,3,4,5-tetrahydropyridine (480 mg) and triethylamine (0.98 ml) were furthermore added successively, and the resulting mixture was stirred at room temperature for one day and then at 40° C. for one day. After stirring, to the reaction mixture was added a 4N solution of hydrogen chloride in dioxane (2.5 ml) and the resulting mixture was evaporated in vacuo. The residue obtained was purified by preparative HPLC (YMC-Pack ODS-A; YMC, eluent: 25% acetonitrile/water). The amorphous solid obtained was dissolved in 1N hydrochloric acid, and the resulting mixture was evaporated to dryness in vacuo. The residue obtained was dissolved in water and then lyophilized to afford the title compound (429 mg, yield: 42%) as a colorless amorphous solid.

$^1$H NMR (400 MHz, DMSO-$d_6$) δ ppm: 1.22 (3H, t, J=7.0), 1.64–1.85 (6H, m), 1.99–2.10 (2H, m), 2.70 (2H, m), 3.27–3.39 (2H, m), 3.53–3.73 (4H, m), 4.19 (2H, q, J=7.0), 4.45 (2H, s), 4.50 (2H, d, J=6.0), 4.95 (1H, m), 6.45 (1H, dt, J=16.0, 6.0), 6.58 (1H, d, J=16.0), 7.43 (1H, d, J=10.0), 7.55 (1H, t, J=8.0), 7.65–7.75 (4H, m), 7.88 (1H, s);

IR (KBr, cm$^{-1}$): 1739, 1675, 1355, 1141.

Example 80

N-[3-(3-Amidinophenyl)-2-(E)-propenyl]-N-[4-[1-(2,3,4,5-tetrahydropyridin-6-yl)piperidin-4-yloxy]-3-trifluoromethylphenyl]sulfamoylacetic acid dihydrochloride (Exemplification Compound Number 614)

Ethyl N-[3-(3-amidinophenyl)-2-(E)-propenyl]-N-[4-[1-(2,3,4,5-tetrahydropyridin-6-yl)piperidin-4-yloxy]-3-trifluoromethylphenyl]sulfamoylacetate dihydrochloride (291 mg) obtained in example 79 was dissolved in 3N hydrochloric acid (20 ml) and the resulting mixture was stirred at 60° C. for 5.5 hours. After cooling to room temperature, the reaction mixture was evaporated in vacuo. The residue obtained was purified by preparative HPLC (YMC-Pack ODS-A; YMC, eluent: 22% acetonitrile/water). The amorphous solid obtained was dissolved in 1N hydrochloric acid and the resulting mixture was evaporated to dryness in vacuo. The residue obtained was dissolved in water and then lyophilized to afford the title compound (240 mg, yield: 86%) as a colorless amorphous solid.

$^1$H NMR (500 MHz, DMSO-$d_6$) δ ppm: 1.63–1.85 (6H, m), 2.03 (2H, m), 2.70 (2H, m), 3.20–3.48 (2H, m), 3.52–3.76 (4H, m), 4.12 (2H, s), 4.50 (2H, d, J=6.0), 4.94 (1H, m), 6.46 (1H, dt, J=16.0, 6.0), 6.56 (1H, d, J=16.0), 7.42 (1H, d, J=9.0), 7.54 (1H, t, J=8.0), 7.69 (1H, d, J=8.0), 7.71 (1H, d, J=8.0), 7.73–7.78 (2H, m), 7.89 (1H, s);

IR (KBr, cm$^{-1}$): 1732, 1675, 1352, 1143.

Example 81

Ethyl N-[3-(3-amidinophenyl)-2-(E)-propenyl]-N-[4-[1-(3,4,5,6-tetrahydro-2H-azepin-7-yl)piperidin-4-yloxy]-3-trifluoromethylphenyl]sulfamoylacetate dihydrochloride (Exemplification Compound Number 111)

To a solution of ethyl N-[3-(3-amidinophenyl)-2-(E)-propenyl]-N-[4-(piperidin-4-yloxy)-3-trifluoromethylphenyl]sulfamoylacetate dihydrochloride (900 mg) obtained in example 77(a) in ethanol (20 ml) were added successively 7-methoxy-3,4,5,6-tetrahydro-2H-azepine (540 mg) and triethylamine (0.98 ml) at room temperature and the resulting mixture was stirred at room temperature overnight. Because of the slow progress of the reaction, 7-methoxy-3,4,5,6-tetrahydro-2H-azepine (540 mg) and triethylamine (0.98 ml) were furthermore added successively and the resulting mixture was stirred at room temperature for 5 hours and then at 40° C. for one day. After stirring, to the reaction mixture was added a 4N solution of hydrogen chloride in dioxane and the resulting mixture was evaporated in vacuo. The residue obtained was purified by preparative HPLC (YMC-Pack ODS-A; YMC, eluent: 30% acetonitrile/water). The amorphous solid obtained was dissolved in 1N hydrochloric acid, and the resulting mixture was evaporated to dryness in vacuo. The residue obtained was dissolved in water and then lyophilized to afford the title compound (340 mg, yield: 33%) as a colorless amorphous solid.

$^1$H NMR (500 MHz, DMSO-$d_6$) δ ppm: 1.22 (3H, t, J=7.0), 1.52–1.67 (4H, m), 1.67–1.85 (4H, m), 2.06 (2H, m), 2.87 (2H, m), 3.48 (2H, m), 3.67–3.83 (4H, m), 4.19 (2H, q, J=7.0), 4.46 (2H, s), 4.50 (2H, d, J=6.0), 4.97 (1H, m), 6.46 (1H, dt, J=16.0, 6.0), 6.58 (1H, d, J=16.0), 7.44 (1H, d, J=9.5), 7.55 (1H, t, J=8.0), 7.67–7.75 (4H, m), 7.90 (1H, s);

IR (KBr, cm$^{-1}$): 1739, 1675, 1354, 1142.

Example 82

N-[3-(3-amidinophenyl)-2-(E)-propenyl]-N-[4-[1-(3,4,5,6-tetrahydro-2H-azepin-7-yl)piperidin-4-yloxy]-3-trifluoromethylphenyl]sulfamoylacetic acid dihydrochloride (Exemplification Compound Number 615)

Ethyl N-[3-(3-amidinophenyl)-2-(E)-propenyl]-N-[4-[1-(3,4,5,6-tetrahydro-2H-azepin-7-yl)piperidin-4-yloxy]-3-trifluoromethylphenyl]sulfamoylacetate dihydrochloride (307 mg) obtained in example 81 was dissolved in 3N hydrochloric acid (20 ml) and the resulting mixture was stirred at 60° C. for 6.5 hours. After cooling to room temperature, the reaction mixture was evaporated in vacuo. The residue obtained was purified by preparative HPLC (YMC-Pack ODS-A; YMC, eluent: 23% acetonitrile/water). The amorphous solid obtained was dissolved in 1N hydrochloric acid and the resulting mixture was evaporated to dryness in vacuo. The residue obtained was dissolved in water and then lyophilized to afford the title compound (218 mg, yield: 74%) as a colorless amorphous solid.

$^1$H NMR (500 MHz, DMSO-$d_6$) δ ppm: 1.46–1.67 (4H, m), 1.67–1.87 (4H, m), 2.07 (2H, m), 2.87 (2H, m), 3.42–3.52 (2H, m), 3.64–3.85 (4H, m), 4.27 (2H, s), 4.50 (2H, d, J=6.0), 4.96 (1H, m), 6.46 (1H, dt, J=16.0, 6.0), 6.58 (1H, d, J=16.0), 7.43 (1H, d, J=10.0), 7.55 (1H, t, J=8.0), 7.66–7.76 (4H, m), 7.89 (1H, s);

IR (KBr, cm$^{-1}$): 1733, 1676, 1351, 1144.

Example 83

Ethyl N-[3-(3-amidinophenyl)-2-(E)-propenyl]-N-[3-chloro-4-[1-(5,6-dihydro-2H-[1,4]thiazin-3-yl)piperidin-4-yloxy]phenyl]sulfamoylacetate dihydrochloride (Exemplification Compound Number 28)

To a solution of ethyl N-[3-(3-amidinophenyl)-2-(E)-propenyl]-N-[3-chloro-4-(piperidin-4-yloxy)phenyl]sulfamoylacetate dihydrochloride (0.25 g) obtained in example 47(a) in ethanol (10 ml) were added successively 5-ethoxy-3,6-dihydro-2H-[1,4]thiazine (0.24 g), which was prepared from 3-thiomorpholine according to the method described in *Indian J. Chem.*, 10, 323 (1972), and triethylamine (0.23 ml) at room temperature and the resulting mixture was stirred at room temperature for 4 hours, and then at 45° C. for 3 hours, and then allowed to stand at room temperature for 11 hours. The reaction mixture was further stirred at 45° C. for 12 hours and then allowed to stand at room temperature for 11 hours. After standing, to the reaction mixture was added a 4N solution of hydrogen chloride in dioxane (2 ml) and the resulting mixture was evaporated in vacuo. The residue obtained was purified by preparative HPLC (YMC-Pack ODS-A; YMC, eluent: 20% acetonitrile/water). Subsequently, to a solution of the amorphous solid obtained in ethanol (4 ml) was added a 4N solution of hydrogen chloride in dioxane (1 ml), and the resulting mixture was evaporated to dryness in vacuo to afford the title compound (0.07 g, yield: 24%) as a colorless amorphous solid.

$^1$H NMR (400 MHz, DMSO-$d_6$) δ ppm: 1.23 (3H, t, J=7.0), 1.73–1.82 (2H, m), 2.02–2.10 (2H, m), 2.91–2.96 (2H, m), 3.59–3.91 (8H, m), 4.19 (2H, q, J=7.0), 4.42 (2H, s), 4.47 (2H, d, J=6.0), 4.81–4.88 (1H, m), 6.44 (1H, dt, J=15.5, 6.0), 6.58 (1H, d, J=15.5), 7.33 (1H, d, J=9.0), 7.41 (1H, dd, J=9.0, 2.5), 7.51–7.60 (2H, m), 7.64–7.75 (2H, m), 7.87 (1H, s);

IR (KBr, cm$^{-1}$): 1737, 1674, 1633, 1350, 1155.

Example 84

Ethyl N-[3-(3-amidinophenyl)-2-(E)-propenyl]-N-[3-chloro-4-[1-2,3,5,6-tetrafluoropyridin-4-yl)piperidin-4-yloxy]phenyl]sulfamoylacetate dihydrochloride (Exemplification Compound Number 1045)

To a solution of ethyl N-[3-(3-amidinophenyl)-2-(E)-propenyl]-N-[3-chloro-4-(piperidin-4-yloxy)phenyl]sulfamoylacetate dihydrochloride (930 mg) obtained in example 47(a) in ethanol (20 ml) were added successively 2,3,5,6-tetrafluoropyridine (0.16 ml) and triethylamine (0.64 ml) at room temperature and the resulting mixture was stirred at room temperature for 5 hours. After stirring, to the reaction mixture was added a 4N solution of hydrogen chloride in dioxane and the resulting mixture was evaporated in vacuo. The residue obtained was purified by preparative HPLC (YMC-Pack ODS-A; YMC, eluent: 55% acetonitrile/water). The amorphous solid obtained was dissolved in 1N hydrochloric acid and the resulting mixture was evaporated to dryness in vacuo. The residue obtained was dissolved in water and then lyophilized to afford the title compound (893 mg, yield: 81%) as a colorless amorphous solid.

$^1$H NMR (500 MHz, DMSO-$d_6$) δ ppm: 1.23 (3H, t, J=7.0), 1.73–1.84 (2H, m), 2.01–2.12 (2H, m), 3.38–3.48 (2H, m), 3.59–3.69 (2H, m), 4.19 (2H, q, J=7.0), 4.42 (2H, s), 4.47 (2H, d, J=6.0), 4.80 (1H, m), 6.43 (1H, dt, J=16.0, 6.0), 6.59 (1H, d, J=16.0), 7.31 (1H, d, J=9.0), 7.40 (1H, dd, J=9.0, 2.5), 7.55 (1H, t, J=8.0), 7.59 (1H, d, J=2.5), 7.66 (1H, d, J=8.0), 7.74 (1H, d, J=8.0), 7.86 (1H, s);

IR (KBr, cm$^{-1}$); 1739, 1677, 1351, 1147.

Example 85

N-[3-(3-Amidinophenyl)-2-(E)-propenyl]-N-[3-chloro-4-[1-(2,3,5,6-tetrafluoropyridin-4-yl)piperidin-4-yloxy]phenyl]sulfamoylacetic acid dihydrochloride (Exemplification Compound Number 1063)

Ethyl N-[3-(3-amidinophenyl)-2-(E)-propenyl]-N-[3-chloro-4-[1-(2,3,5,6-tetrafluoropyridin-4-yl)piperidin-4-yloxy]phenyl]sulfamoylacetate dihydrochloride (356 mg)

obtained in example 84 was dissolved in a mixture of 3N hydrochloric acid (20 ml) and a 4N solution of hydrogen chloride in dioxane (20 ml), and the resulting mixture was stirred at 60° C. for 8.5 hours. After cooling to room temperature, the reaction mixture was evaporated in vacuo. The residue obtained was purified by preparative HPLC (YMC-Pack ODS-A; YMC, eluent: 40% acetonitrile/water~acetonitrile only). The amorphous solid obtained was dissolved in 1N hydrochloric acid and the resulting mixture was evaporated to dryness in vacuo. The residue obtained was dissolved in water and then lyophilized to afford the title compound (322 mg, yield: 94%) as a colorless amorphous solid.

$^1$H NMR (500 MHz, DMSO-$d_6$) δ ppm: 1.72–1.84 (2H, m), 2.00–2.12 (2H, m), 3.38–3.48 (2H, m), 3.59–3.69 (2H, m), 4.21 (2H, s), 4.47 (2H, d, J=6.0), 4.79 (1H, m), 6.44 (1H, dt, J=16.0, 6.0), 6.58 (1H, d, J=16.0), 7.31 (1H, d, J=9.0), 7.42 (1H, dd, J=9.0, 2.5), 7.55 (1H, t, J=8.0), 7.60 (1H, d, J=2.5), 7.66 (1H, d, J=8.0), 7.73 (1H, d, J=8.0), 7.86 (1H, s);

IR (KBr, cm$^{-1}$): 1678, 1346, 1147.

Example 86

Ethyl N-[3-(3-amidinophenyl)-2-(E)-propenyl]-N-[3-chloro-4-[1-(N-ethylformimidoyl)piperidin-4-yloxy]phenyl]sulfamoylacetate dihydrochloride (Exemplification Compound Number 1081)

To a solution of ethyl N-[3-(3-amidinophenyl)-2-(E)-propenyl]-N-[3-chloro-4-(piperidin-4-yloxy)phenyl]sulfamoylacetate dihydrochloride (0.38 g) obtained in example 47(a) in ethanol (20 ml) were added successively methyl N-ethylformimidate (0.09 g), which was prepared from N-ethylformamide according to the method described in *Angew. Chem.*, 75, 790 (1963), and triethylamine (0.30 ml) at room temperature, and the resulting mixture was stirred at room temperature for 46 hours. After stirring, to the reaction mixture was added a 4N solution of hydrogen chloride in dioxane (2 ml) and the reaction mixture was evaporated in vacuo. The residue obtained was purified by preparative HPLC (YMC-Pack ODS-A; YMC, eluent: 20% acetonitrile/water). Subsequently to a solution of the amorphous solid obtained in ethanol (5 ml) was added a 4N solution of hydrogen chloride in dioxane (1 ml), and the resulting mixture was evaporated to dryness in vacuo to afford the title compound (0.14 g, yield: 35%) as a colorless amorphous solid.

$^1$H NMR (400 MHz, DMSO-$d_6$) δ ppm: 1.16–1.27 (6H, m), 1.72–1.88 (2H, m), 1.99–2.10 (2H, m), 3.40–3.48 (2H, m), 3.51–3.73 (4H, m), 4.19 (2H, q, J=7.5), 4.42 (2H, s), 4.47 (2H, d, J=5.5), 4.79–4.85 (1H, m), 6.45 (1H, dt, J=16.0, 5.5), 6.58 (1H, d, J=16.0), 7.32 (1H, d, J=9.0), 7.41 (1H, dd, J=9.0, 2.5), 7.52–7.59 (2H, m), 7.65–7.75 (2H, m), 7.87 (1H, s), 8.11 (1H, d, J=13.5);

IR (KBr, cm$^{-1}$): 1738, 1697, 1675, 1350, 1156.

Example 87

N-[3-(3-Amidinophenyl)-2-(E)-propenyl]-N-[3-chloro-4-[1-(N-ethylformimidoyl)piperidin-4-yloxy]phenyl]sulfamoylacetic acid dihydrochloride (Exemplification Compound Number 1099)

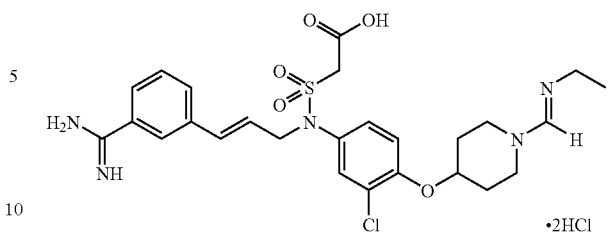

Ethyl N-[3-(3-amidinophenyl)-2-(E)-propenyl]-N-[3-chloro-4-[1-(N-ethylformimidoyl)piperidin-4-yloxy]phenyl]sulfamoylacetate dihydrochloride (0.38 g) obtained in example 86 was dissolved in 3N hydrochloric acid (14 ml) and the resulting mixture was stirred at 60° C. for 6 hours. After cooling to room temperature, the reaction mixture was evaporated in vacuo. The residue obtained was purified by preparative HPLC (YMC-Pack ODS-A; YMC, eluent: 18% acetonitrile/water). The amorphous solid obtained was dissolved in 1N hydrochloric acid (2 ml) and the resulting mixture was evaporated to dryness in vacuo. The residue obtained was dissolved in water and then lyophilized to afford the title compound (0.25 g, yield: 67%) as a colorless amorphous solid.

$^1$H NMR (400 MHz, DMSO-$d_6$) δ ppm: 1.19 (3H, t, J=7.0), 1.72–1.88 (2H, m), 1.98–2.09 (2H, m), 3.51–3.79 (6H, m), 4.28 (2H, s), 4.47 (2H, d, J=6.0), 4.80–4.87 (1H, m), 6.44(1H, dt, J=16.0, 6.0), 6.57 (1H, d, J=16.0), 7.32 (1H, d, J=9.0), 7.41 (1H, dd, J=9.0, 2.0), 7.52–7.60 (2H, m), 7.68–7.75 (2H, m), 7.89 (1H, s), 8.13 (1H, d, J=13.5);

IR (KBr, cm$^{-1}$): 1731, 1698, 1677, 1347, 1155.

Example 88

Ethyl N-[3-(3-amidinophenyl)-2-(E)-propenyl]-N-[3-chloro-4-[1-(4,5-dihydrooxazol-2-yl)piperidin-4-yloxy] phenyl]sulfamoylacetate dihydrochloride (Exemplification Compound Number 1009)

To a solution of ethyl N-[3-(3-amidinophenyl)-2-(E)-propenyl]-N-[3-chloro-4-(piperidin-4-yloxy)phenyl]sulfamoylacetate dihydrochloride (0.75 g) obtained in example 47(a) in ethanol (25 ml) were added successively 2-ethoxy-4,5-dihydrooxazole (0.28 g), which was prepared from 2-oxazolidone according to the method described in *Eur. J. Org. Chem.*, 10, 2645 (1999), and triethylamine (0.68 ml) at room temperature, and the resulting mixture was stirred at room temperature for 22 hours After stirring, to the reaction mixture was added a 4N solution of hydrogen chloride in dioxane (5 ml) and the resulting mixture was evaporated in vacuo. The residue obtained was purified by preparative HPLC (YMC-Pack ODS-A; YMC, eluent: 23% acetonitrile/water). Subsequently, to a solution of the amorphous solid obtained in ethanol (10 ml) was added a 4N solution of hydrogen chloride in dioxane (2 ml), and the resulting mixture was evaporated to dryness in vacuo to afford the title compound (0.56 g, yield: 67%) as a colorless amorphous solid.

$^1$H NMR (400 MHz, DMSO-$d_6$) δ ppm: 1.22 (3H, t, J=7.0), 1.75–1.86 (2H, m), 1.98–2.10 (2H, m), 3.51–3.78 (4H, m), 3.85 (2H, t, J=8.5), 4.19 (2H, q, J=7.0), 4.42 (2H, s), 4.47 (2H, d, J=6.0), 4.76–4.85 (3H, m), 6.44 (1H, dt, J=16.0, 6.0), 6.58 (1H, d, J=16.0), 7.32 (1H, d, J=9.0), 7.40 (1H, dd, J=9.0, 2.5), 7.52–7.60 (2H, m), 7.69 (1H, d, J=7.5), 7.73 (1H, d, J=7.5), 7.87 (1H, s);

MS (FAB, M$^+$-2HCl): 604.

Example 89

N-[3-(3-Amidinophenyl)-2-(E)-propenyl]-N-[3-chloro-4-[1-(4,5-dihydrooxazol-2-yl)piperidin-4-yloxy]phenyl]sulfamoylacetic acid dihydrochloride (Exemplification Compound Number 1027)

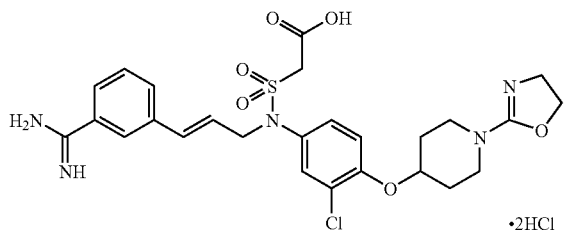

Ethyl N-[3-(3-amidinophenyl)-2-(E)-propenyl]-N-[3-chloro-4-[1-(4,5-dihydrooxazol-2-yl)piperidin-4-yloxy]phenyl]sulfamoylacetate dihydrochloride (0.29 g) obtained in example 88 was dissolved in 3N hydrochloric acid (12 ml), and the resulting mixture was stirred at 60° C. for 10 hours. After cooling to room temperature, the reaction mixture was evaporated in vacuo. The residue obtained was purified by preparative HPLC (YMC-Pack ODS-A; YMC, eluent: 17% acetonitrile/water). The amorphous solid obtained was dissolved in 1N hydrochloric acid (2 ml), and the resulting mixture was evaporated to dryness in vacuo to afford the title compound (0.23 g, yield: 82%) as a colorless amorphous solid.

$^1$H NMR (500 MHz, DMSO-$d_6$) δ ppm: 1.76–1.87 (2H, m), 1.98–2.10 (2H, m), 3.51–3.78 (4H, m), 3.85 (2H, t, J=8.5), 4.28 (2H, s), 4.47 (2H, d, J=5.5), 4.77–4.84 (3H, m), 6.44 (1H, dt, J=16.0, 5.5), 6.58 (1H, d, J=16.0), 7.31 (1H, d, J=9.0), 7.41 (1H, dd, J=9.0, 2.5), 7.52–7.61 (2H, m), 7.68 (1H, d, J=7.5), 7.73 (1H, d, J=7.5), 7.88 (1H, s);

IR (KBr, cm$^{-1}$): 1733, 1685, 1349, 1155.

Example 90

Ethyl N-[3-(3-amidinophenyl)-2-(E)-propenyl]-N-[3-chloro-4-(tropan-3-yloxy)phenyl]sulfamoylacetate dihydrochloride (Exemplification Compound Number 1117)

Hydrogen chloride was bubbled through a solution of ethyl N-[3-chloro-4-(tropan-3-yloxy)phenyl]-N-[3-(3-cyanophenyl)-2-(E)-propenyl]sulfamoylacetate (1.30 g) obtained in reference example 126 in a mixture of dichloromethane (25 ml) and ethanol (35 ml) under ice-cooling, and the resulting mixture was stirred at room temperature for 3.5 hours under sealed conditions and then evaporated in vacuo. Subsequently, to a solution of the residue obtained in ethanol (25 ml) were added successively an aqueous ammonium chloride solution (prepared by dissolving 0.40 g in 5 ml of water) and a 28% ammonia solution (0.90 ml), and the resulting mixture was stirred at room temperature overnight and evaporated in vacuo. The residue obtained was purified by preparative HPLC (YMC-Pack ODS-A; YMC, eluent: 22% acetonitrile/water). Subsequently, to a solution of the amorphous solid obtained in ethanol (15 ml) was added a 4N solution of hydrogen chloride in dioxane (1.40 ml), and the resulting mixture was evaporated to dryness in vacuo to afford the title compound (1.07 g, yield: 70%) as a colorless amorphous solid.

$^1$H NMR (500 MHz, DMSO-$d_6$) δ ppm: 1.23 (3H, t, J=7.0), 2.05–2.30 (8H, m), 2.66 (3H, s), 3.94 (2H, m), 4.19 (2H, q, J=7.0), 4.40 (2H, s), 4.47 (2H, d, J=6.0), 4.84 (1H, m), 6.43 (1H, dt, J=6.0, 16.0), 6.57 (1H, d, J=16.0), 7.35–7.45 (2H, m), 7.50–7.60 (2H, m), 7.69 (1H, m), 7.73 (1H, m), 7.88 (1H, m);

IR (KBr, cm$^{-1}$): 1737, 1675.

Example 91

N-[3-(3-Amidinophenyl)-2-(E)-propenyl]-N-[3-chloro-4-(tropan-3-yloxy)phenyl]sulfamoylacetic acid dihydrochloride (Exemplification Compound Number 1135)

Ethyl N-[3-(3-amidinophenyl)-2-(E)-propenyl]-N-[3-chloro-4-(tropan-3-yloxy)phenyl]sulfamoylacetate dihydrochloride (700 mg) obtained in example 90 was dissolved in 3N hydrochloric acid (20 ml) and the resulting mixture was stirred at 60° C. for 4 hours. After cooling to room temperature, the reaction mixture was evaporated in vacuo. The residue obtained was purified by preparative HPLC (YMC-Pack ODS-A; YMC, eluent: 15% acetonitrile/water). The amorphous solid obtained was dissolved in a mixture of 1N hydrochloric acid (3.3 ml) and water (10 ml), and the resulting mixture was evaporated to dryness in vacuo to afford the title compound (580 mg, yield: 86%) as a colorless amorphous solid.

$^1$H NMR (500 MHz, DMSO-$d_6$) δ ppm: 2.05–2.30 (8H, m), 2.66 (3H, s), 3.93 (2H, m), 4.27 (2H, s), 4.47 (2H, d, J=6.0), 4.83 (1H, m), 6.44 (1H, dt, J=6.0, 16.0), 6.57 (1H, d, J=16.0), 7.35–7.45 (2H, m), 7.50–7.60 (2H, m), 7.68 (1H, m), 7.73 (1H, m), 7.87 (1H, m);

IR (KBr, cm$^{-1}$): 1732, 1675.

Example 92

N-[3-(3-Amidinophenyl)-2-(E)-propenyl]-N-[3-chloro-4-[1-(3,4,5,6,7,8-hexahydro-2H-azonin-9-yl)piperidin-4-yloxy]phenyl]sulfamoylacetic acid dihydrochloride (Exemplification Compound Number 1171)

To a solution of ethyl N-[3-(3-amidinophenyl)-2-(E)-propenyl]-N-[3-chloro-4-(piperidin-4-yloxy)phenyl]sulfamoylacetate dihydrochloride (0.78 g) obtained in example 47(a) in ethanol (20 ml) were added successively 9-methoxy-3,4,5,6,7,8-hexahydro-2H-azonine (0.80 g), which was prepared from azonan-2-one according to the method described in Org. Prep. Proced. Int., 24, 147 (1992), and triethylamine (0.71 ml) at room temperature, and the resulting mixture was stirred at room temperature for 18 hours. Because of the slow progress of the reaction, 9-methoxy-3,4,5,6,7,8-hexahydro-2H-azonine (0.29 g) and triethylamine (0.53 ml) were furthermore added successively, and the resulting mixture was stirred at room temperature for 72 hours. To the reaction mixture was added a 4N solution of hydrogen chloride in dioxane (5 ml) and the resulting mixture was evaporated in vacuo. The residue obtained was purified by preparative HPLC (YMC-Pack ODS-A; YMC, eluent: 30% acetonitrile/water). Subsequently, to a solution of the amorphous solid obtained in ethanol (5 ml) was added a 4N solution of hydrogen chloride in dioxane (2 ml), and the resulting mixture was evaporated to dryness in vacuo. The residue obtained was dissolved in water and then lyophilized to afford a mixture (0.28 g) of ethyl N-[3-(3-amidinophenyl)-2-(E)-propenyl]-N-[3-chloro-4-[1-(3,4,5,6,7,8-hexahydro-2H-azonin-9-yl)piperidin-4-yloxy]phenyl]sulfamoylacetate dihydrochloride and impurities as a colorless amorphous solid.

Subsequently, the mixture obtained above was dissolved in 3N hydrochloric acid (10 ml) and the resulting mixture was stirred at 50° C. for 6 hours, allowed to stand at room temperature for 61 hours and then furthermore stirred at 50°

C. for 7 hours. After cooling to room temperature, the reaction mixute was evaporated in vacuo. The residue obtained was purified by preparative HPLC (YMC-Pack ODS-A; YMC, eluent: 23% acetonitrile/water). The amorphous solid obtained was dissolved in 1N hydrochloric acid (2 ml), and the resulting mixture was evaporated to dryness in vacuo to afford the title compound (0.09 g, yield: 58%) as a colorless amorphous solid.

$^1$H NMR (400 MHz, DMSO-$d_6$) δ ppm: 1.38–1.81 (12H, m), 2.00–2.09 (2H, m), 2.78–2.85 (2H, m), 3.48–3.57 (2H, m), 3.59–3.72 (2H, m), 3.73–3.86 (2H, m), 4.27 (2H, s), 4.46 (2H, d, J=5.5), 4.80–4.88 (1H, m), 6.44 (1H, dt, J=16.0, 5.5), 6.57 (1H, d, J=16.0), 7.31 (1H, d, J=9.0), 7.40 (1H, dd, J=9.0, 2.5), 7.51–7.60 (2H, m), 7.64–7.75 (2H, m), 7.87 (1H, s);

IR (KBr, cm$^{-1}$): 1733, 1675, 1627, 1352, 1156.

Example 93

Ethyl N-[3-(3-amidinophenyl)-2-(E)-propenyl]-N-[4-[1-(4,5-dihydrooxazol-2-yl)piperidin-4-yloxy]phenyl]sulfamoylacetate dihydrochloride (Exemplification Compound Number 1011)

To a solution of ethyl N-[3-(3-amidinophenyl)-2-(E)-propenyl]-N-[4-(piperidin-4-yloxy)phenyl]sulfamoylacetate dihydrochloride (533 mg) obtained in example 59(a) in ethanol (10 ml) were added successively 2-ethoxy-4,5-dihydrooxazole (235 mg), which was prepared from 2-oxazolidone according to the method described in *Eur. J. Org. Chem.*, 10, 2645 (1999), and triethylamine (0.43 ml) at room temperature, and the resulting mixture was stirred at room temperature overnight and then evaporated in vacuo. The residue obtained was purified by preparative HPLC (YMC-Pack ODS-A; YMC, eluent: 22% acetonitrile/water). Subsequently, to a solution of the amorphous solid obtained in ethanol (5 ml) was added a 4N solution of hydrogen chloride in dioxane (0.36 ml), and the resulting mixture was evaporated to dryness in vacuo to afford the title compound (278 mg, yield: 47%) as a colorless amorphous solid.

$^1$H NMR (400 MHz, DMSO-$d_6$) δ ppm: 1.23 (3H, t, J=7.0), 1.66–1.80 (2H, m), 1.94–2.10 (2H, m), 3.62–3.82 (4H, m), 3.85 (2H, t, J=8.5), 4.20 (2H, q, J=7.0), 4.34 (2H, s), 4.44 (2H, d, J=6.0), 4.68 (1H, m), 4.79 (2H, t, J=8.5), 6.44 (1H, dt, J=16.0, 6.0), 6.56 (1H, d, J=16.0), 7.04 (2H, d, J=9.0), 7.39 (2H, d, J=9.0), 7.54 (1H, t, J=8.0), 7.70 (2H, m), 7.88 (1H, s);

MS (FAB, M$^+$2 HCl): 570.

Example 94

N-[3-(3-Amidinophenyl)-2-(E)-propenyl]-N-[4-[1-(4,5-dihydrooxazol-2-yl)piperidin- 4-yloxyl]phenyl]sulfamoylacetic acid dihydrochloride (Exemplification Compound Number 1029)

Ethyl N-[3-(3-amidinophenyl)-2-(E)-propenyl]-N-[4-[1-(4,5-dihydrooxazol-2-yl)piperidin-4-yloxy]phenyl]sulfamoylacetate dihydrochloride (272 mg) obtained in example 93 was dissolved in 3N hydrochloric acid (10 ml) and stirred at 60° C. for 5 hours. After cooling to room temperature, the reaction mixture was evaporated in vacuo. The residue obtained was purified by preparative HPLC (YMC-Pack ODS-A; YMC, eluent: 15% acetonitrile/water). The amorphous solid obtained was dissolved in 1N hydrochloric acid (4 ml), and the resulting mixture was evaporated to dryness in vacuo to afford the title compound (209 mg, yield: 80%) as a colorless amorphous solid.

$^1$H NMR (400 MHz, DMSO-$d_6$) δ ppm: 1.65–1.81 (2H, m), 1.97–2.10 (2H, m), 3.43–3.62 (4H, m), 3.85 (2H, t, J=8.5), 4.21 (2H, s), 4.44 (2H, d, J=6.0), 4.68 (1H, m), 4.79 (2H, t, J=8.5), 6.44 (1H, dt, J=16.0, 6.0), 6.55 (1H, d, J=16.0), 7.03 (2H, d, J=9.0), 7.39 (2H, d, J=9.0), 7.54 (1H, t, J=8.0), 7.70 (2H, m), 7.88 (1H, s);

IR (KBr, cm$^{-1}$) 1687, 1346, 1156.

Example 95

Ethyl N-[3-(3-amidinophenyl)-2-fluoro-2-(Z)-propenyl]-N-[4-[1-(4,5-dihydro-3H-pyrrol-2-yl)piperidin-4-yloxy]phenyl]sulfamoylacetate dihydrochloride (Exemplification Compound Number 1462)

(a) Ethyl N-[3-(3-amidinophenyl)-2-fluoro-2-(Z)-propenyl]-N-[4-(piperidin-4-yloxy)phenyl]sulfamoylacetate Hydrogen chloride was bubbled through a solution of ethyl N-[4-(1-t-butoxycarbonylpiperidin-4-yloxy)phenyl]-N-[3-(3-cyanophenyl)-2-fluoro-2-(Z)-propenyl]sulfamoylacetate (1.41 g) obtained in reference example 128 in a mixture of dichloromethane (25 ml) and ethanol (25 ml) under ice-cooling, and the resulting mixture was stirred at room temperature for 10 hours under sealed conditions and then evaporated in vacuo. Subsequently, to a solution of the residue obtained in ethanol (30 ml) were added successively an aqueous ammonium chloride solution (prepared by dissolving 0.25 g in 10 ml of water) and a 28% ammonia solution (0.47 ml), and the resulting mixture was allowed to stand at room temperature for 8 hours. After standing, to the reaction mixture was added a 4N solution of hydrogen chloride in dioxane (1 ml) and the resulting mixture was evaporated in vacuo. The residue obtained was purified by preparative HPLC (YMC-Pack ODS-A; YMC, eluent: 20% acetonitrile/water) to afford the title compound (1.00 g, yield: 75%) as a colorless amorphous solid.

$^1$H NMR (500 MHz, DMSO-$d_6$) δ ppm: 1.24 (3H, t, J=7.0), 1.81 (2H, m), 2.08 (2H, m), 3.06 (2H, m), 3.22 (2H, m), 4.20 (2H, q, J=7.0), 4.36 (2H, s), 4.56 (2H, d, J=16.5), 4.65 (1H, m), 5.94 (1H, d, J=39.0), 7.05 (2H, d, J=9.5), 7.40 (2H, d, J=9.5), 7.56 (1H, d, J=8.0), 7.74 (2H, m), 7.81 (1H, s).

(b) Ethyl N-[3-(3-amidinophenyl)-2-fluoro-2-(Z)-propenyl]-N-[4-[1-(4,5-dihydro-3H-pyrrol-2-yl)piperidin-4-yloxy]phenyl]sulfamoylacetate dihydrochloride To a solution of ethyl N-[3-(3-amidinophenyl)-2-fluoro-2-(Z)-propenyl]-N-[4-(piperidin-4-yloxy)phenyl]sulfamoylacetate (1.27 g) obtained in example 97(a) in ethanol (50 ml) were added successively 5-methoxy-3,4-dihydro-2H-pyrrole (0.73 g), which was, prepared from 2-pyrrolidinone according to the method described in *Org. Prep. Proced. Int.*, 24, 147 (1992), and triethylamine (2.10 ml) at room temperature, and the resulting mixture was stirred at room temperature for 4 hours. At the end of this time, to the reaction mixture were furthermore added successively 5-methoxy-3,4-dihydro-2H-pyrrole (0.73 g) and triethylamine (2.10 ml), and the resulting mixture was allowed to stand at room temperature overnight and then evaporated in vacuo. The residue obtained was purified by preparative HPLC (YMC-Pack ODS-A; YMC, eluent: 20% acetonitrile/water). Subsequently, to a solution of the amorphous solid obtained in ethanol (5 ml) was added a 4N solution of hydrogen chloride in dioxane (0.80 ml), and the resulting mixture was evaporated to dryness in vacuo to afford the title compound (0.60 g, yield: 37%) as a colorless amorphous solid.

$^1$H NMR (500 MHz, DMSO-$d_6$) δ ppm: 1.24 (3H, t, J=7.0), 1.68–1.82 (2H, m), 2.02–2.13 (4H, m), 2.97 (2H, t, J=8.0), 3.47–3.53 (1H, m), 3.58–3.73 (4H, m), 3.85–3.92 (1H, m), 4.21 (2H, q, J=7.0), 4.37 (2H, s), 4.60 (2H, d, J=16.0), 4.71 (1H, m), 5.95 (1H, d, J=39.0), 7.07 (2H, d, J=9.0), 7.41 (2H, d, J=9.0), 7.59 (1H, t, J=8.0), 7.70 (1H, d, J=8.0), 7.76 (1H, d, J=8.0), 7.82 (1H, s);

IR (KBr, cm$^{-1}$): 1672, 1354, 1161.

Example 96

N-[3-(3-Amidinophenyl)-2-fluoro-2-(Z)-propenyl]-N-[4-[1-(4,5-dihydro- 3H-pyrrol-2-yl)piperidin-4-yloxy]phenyl] sulfamoylacetic acid dihydrochloride (Exemplification Compound Number 1484)

Ethyl N-[3-(3-amidinophenyl)-2-fluoro-2-(Z)-propenyl]-N-[4-[1-(4,5-dihydro-3H-pyrrol-2-yl)piperidin-4-yloxy] phenyl]sulfamoylacetate dihydrochloride (0.47 g) obtained in example 95(b) was dissolved in 3N hydrochloric acid (20 ml) and the resulting mixture was stirred at 70° C. for 2.5 hours. After cooling to room temperature, the reaction mixture was evaporated in vacuo. The residue obtained was purified by preparative HPLC (YMC-Pack ODS-A; YMC, eluent: 15% acetonitrile/water). The amorphous solid obtained was dissolved in 1N hydrochloric acid (2.5 ml), and the resulting mixture was evaporated to dryness in vacuo to afford the title compound (0.39 g, yield: 86%) as a colorless amorphous solid.

$^1$H NMR (500 MHz, DMSO-d$_6$) δ ppm: 1.68–1.81 (2H, m), 2.02–2.14 (4H, m), 2.96 (2H, t, J=8.0), 3.44–3.74 (6H, m), 4.23 (2H, s), 4.59 (2H, d, J=16.0), 4.71 (1H, m), 5.95 (1H, d, J=39.0), 7.06 (2H, d, J=9.0), 7.42 (2H, d, J=9.0), 7.59 (1H, t, J=8.0), 7.68 (1H, d, J=8.0), 7.76 (1H, d, J=8.0), 7.81 (1H, s);

IR (KBr, cm$^{-1}$) 1672, 1352, 1158.

Example 97

Ethyl N-[3-(3-amidinophenyl)-2-fluoro-2-(Z)-propenyl]-N-[3-carbamoyl-4-[1-(4,5-dihydro-3H-pyrrol-2-yl)piperidin-4-yloxy]phenyl]sulfamoylacetate dihydrochloride (Exemplification Compound Number 1472)

(a) Ethyl N-[3-(3-amidinophenyl)-2-fluoro-2-(Z)-propenyl]-N-[3-carbamoyl-4-(piperidin-4-yloxy)phenyl]sulfamoylacetate Hydrogen chloride was bubbled through a solution of ethyl N-[4-(1-t-butoxycarbonylpiperidin-4-yloxy)-3-carbamoylphenyl]-N-[3-(3-cyanophenyl)-2-fluoro-2-(Z)-propenyl]sulfamoylacetate (4.30 g) obtained in reference example 129 in a mixture of dichloromethane (35 ml) and ethanol (35 ml) under ice-cooling, and the resulting mixture was stirred at room temperature for 3 hours under sealed conditions and then evaporated in vacuo. Subsequently, to a solution of the residue obtained in ethanol (30 ml) were added successively an aqueous ammonium chloride solution (prepared by dissolving 0.80 g in 5 ml of water) and a 28% ammonia solution (1.80 ml), and the resulting mixture was allowed to stand at room temperature overnight and then evaporated in vacuo.

$^1$H NMR (500 MHz, DMSO-d$_6$) δ ppm: 1.24 (3H, t, J=7.0), 1.88–1.96 (2H, m), 2.09–2.17 (2H, m), 3.02–3.09 (2H, m), 3.17–3.24 (2H, m), 4.21 (2H, q, J=7.0), 4.40 (2H, s), 4.62 (2H, d, J=16.0), 4.81 (1H, m), 5.98 (1H, d, J=38.0), 7.26 (1H, d, J=9.0), 7.51 (1H, dd, J=9.0, 3.0), 7.57–7.71 (2H, m), 7.73–7.78 (2H, m), 7.81 (1H, s).

(b) Ethyl N-[3-(3-amidinophenyl)-2-fluoro-2-(Z)-propenyl]-N-[3-carbamoyl-4-[1-(4,5-dihydro-3H-pyrrol-2-yl)piperidin-4-yloxy]phenyl]sulfamoylacetate dihydrochloride To a solution of ethyl N-[3-(3-amidinophenyl)-2-fluoro-2-(Z)-propenyl]-N-[3-carbamoyl-4-(piperidin-4-yloxy)phenyl]sulfamoylacetate (1.20 g) obtained in example 99(a) in ethanol (40 ml) were added successively 5-methoxy-3,4-dihydro-2H-pyrrole (0.64 g), which was prepared from 2-pyrrolidinone according to the method described in Org. Prep. Proced. Int., 24, 147 (1992), and triethylamine (1.80 ml) at room temperature, and the resulting mixture was stirred at room temperature for 1 hour and allowed to stand at room temperature overnight and then evaporated in vacuo. The residue obtained was purified by preparative HPLC (YMC-Pack ODS-A; YMC, eluent: 15% acetonitrile/water). Subsequently, to a solution of the amorphous solid obtained in ethanol (5 ml) was added a 4N solution of hydrogen chloride in dioxane (1.60 ml), and the resulting mixture was evaporated to dryness in vacuo to afford the title compound (0.40 g, yield: 26%) as a colorless amorphous solid.

$^1$H NMR (500 MHz, DMSO-d$_6$) δ ppm: 1.24 (3H, t, J=7.0), 1.81–1.92 (2H, m), 2.02–2.14 (4H, m), 2.96 (2H, t, J=8.0), 3.48–3.88 (6H, m), 4.21 (2H, q, J=7.0), 4.40 (2H, s), 4.62 (2H, d, J=16.0), 4.87 (1H, m), 5.98 (1H, d, J=39.0), 7.30 (1H, d, J=9.0), 7.49–7.63 (2H, m), 7.68 (1H, d, J=8.0), 7.74–7.82 (3H, m);

IR (KBr, cm$^{-1}$): 1669, 1354, 1156.

Example 98

N-[3-(3-Amidinophenyl)-2-fluoro-2-(Z)-propenyl]-N-[3-carbamoyl-4-[1-(4,5-dihydro-3H-pyrrol-2-yl)piperidin-4-yloxy]phenyl]sulfamoylacetic acid dihydrochloride (Exemplification Compound Number 1494)

Ethyl N-[3-(3-amidinophenyl)-2-fluoro-2-(Z)-propenyl]-N-[3-carbamoyl-4-[1-(4,5-dihydro-3H-pyrrol-2-yl)piperidin-4-yloxy]phenyl]sulfamoylacetate (0.27 g) obtained in example 97(b) was dissolved in 3N hydrochloric acid (20 ml) and the resulting mixture was stirred at 70° C. for 2.5 hours. After cooling to room temperature, the reaction mixture was evaporated in vacuo. The residue obtained was purified by preparative HPLC (YMC-Pack ODS-A; YMC, eluent: 10% acetonitrile/water). The amorphous solid obtained was dissolved in 1N hydrochloric acid (1.2 ml), and the resulting mixture was evaporated to dryness in vacuo to afford the title compound (0.20 g, yield: 77%) as a colorless amorphous solid.

$^1$H NMR (500 MHz, DMSO-d$_6$) δ ppm: 1.82–1.93 (2H, m), 2.02–2.15 (4H, m), 2.96 (2H, t, J=8.0), 3.48–3.73 (5H, m), 3.78–3.88 (1H, m), 4.27 (2H, s), 4.62 (2H, d, J=16.0), 4.87 (1H, m), 5.98 (1H, d, J=39.0), 7.30 (1H, d, J=9.0), 7.49–7.71 (3H, m), 7.73–7.83 (3H, m);

IR (KBr, cm$^{-1}$): 1670, 1352, 1156.

Example 99

N-[3-(3-Amidinophenyl)-2-(E)-propenyl]-N-[3-carbamoyl-4-[1-(4,5-dihydro-3H-pyrrol-2-yl)piperidin-4-yloxy]phenyl]methanesulfonamide dihydrochloride (Exemplification Compound Number 1384)

(a) N-[3-(3-Amidinophenyl)-2-(E)-propenyl]-N-[3-carbamoyl-4-(piperidin-4-yloxy)phenyl]methanesulfonamide dihydrochloride Hydrogen chloride was bubbled through a solution of N-[4-(1-t-butoxycarbonylpiperidin-4-yloxy)-3-carbamoylphenyl]-N-[3-(3-cyanophenyl)-2-(E)-propenyl]methanesulfonamide (1.01 g) obtained in reference example 131 in a mixture of dichloromethane (7.5 ml) and ethanol (7.5 ml) under ice-cooling, and the resulting mixture was stirred at room temperature for 4 hours under sealed conditions and then evaporated in vacuo. Subsequently, to a solution of the residue obtained in ethanol (15 ml) were added successively an aqueous ammonium chloride solution (prepared by dissolving 0.24 g in 3 ml of water) and a 28% ammonia solution (0.43 ml), and the resulting mixture was allowed to stand at room temperature overnight and then evaporated in vacuo. To the residue obtained were added successively ethanol (10 ml) and a 4N solution of hydrogen chloride in dioxane (2 ml), and the resulting mixture was evaporated in vacuo. The residue obtained was purified by preparative HPLC (YMC-Pack ODS-A; YMC, eluent: 10% acetonitrile/water). Subsequently, to a solution of the amorphous solid obtained in ethanol (10 ml) was added a 4N solution of hydrogen chloride in dioxane (2 ml), and the resulting mixture was evaporated to dryness in vacuo. The residue obtained was dissolved in water and then lyophilized to afford the title compound (0.95 g, yield: 98%) as a pale yellow amorphous solid.

$^1$H NMR (500 MHz, DMSO-$d_6$) δ ppm: 1.87–1.97 (2H, m), 2.08–2.18 (2H, m), 3.06 (3H, s), 3.14–3.25 (2H, m), 3.65–3.74 (2H, m), 4.45 (2H, d, J=6.0), 4.80 (1H, m), 6.46 (1H, dt, J=16.0, 6.0), 6.59 (1H, d, J=16.0), 7.23 (1H, d, J=9.0), 7.48–7.59 (2H, m), 7.68–7.75 (3H, m), 7.90 (1H, s);

(b) N-[3-(3-Amidinophenyl)-2-(E)-propenyl]-N-[3-carbamoyl-4-[1-(4,5-dihydro-3H-pyrrol-2-yl)piperidin-4-yloxy]phenyl]methanesulfonamide dihydrochloride To a solution of N-[3-(3-amidinophenyl)-2-(E)-propenyl]-N-[3-carbamoyl-4-(piperidin-4-yloxy)phenyl]methanesulfonamide dihydrochloride (0.95 g) obtained in example 99(a) in ethanol (15 ml) were added successively 5-methoxy-3,4-dihydro-2H-pyrrole (0.52 g), which was prepared from 2-pyrrolidinone according to the method described in Org. Prep. Proced. Int., 24, 147 (1992), and triethylamine (1.20 ml) at room temperature, and the resulting mixture was allowed to stand at room temperature overnight, and at the end of this time, 5-methoxy-3,4-dihydro-2H-pyrrole (0.17 g) and triethylamine (0.24 ml) were furthermore added successively, and the resulting mixture was stirred at room temperature for 6 hours and then evaporated in vacuo. Subsequently, to the residue obtained were added successively ethanol (10 ml) and a 4N solution of hydrogen chloride in dioxane (4 ml), and the resulting mixture was evaporated in vacuo. The residue obtained was purified by preparative HPLC (YMC-Pack ODS-A; YMC, eluent: 10% acetonitrile/water). The amorphous solid obtained was dissolved in 1N hydrochloric acid (5 ml), and the resulting mixture was evaporated to dryness in vacuo. The residue obtained was dissolved in water and then lyophilized to afford the title compound (0.67 g, yield: 63%) as a colorless amorphous solid.

$^1$H NMR (400 MHz, DMSO-$d_6$) δ ppm: 1.79–1.92 (2H, m), 2.02–2.14 (4H, m), 2.99 (2H, t, J=8.0), 3.37 (3H, s), 3.41–3.58 (4H, m), 3.82–3.90 (2H, m), 4.46 (2H, d, J=6.0), 4.86 (1H, m), 6.47 (1H, dt, J=16.0, 6.0), 6.59 (1H, d, J=16.0), 7.26 (1H, d, J=9.0), 7.49–7.58 (2H, m), 7.67–7.77 (3H, m), 7.91 (1H, s);

IR (KBr, cm$^{-1}$): 1669, 1334, 1151.

Example 100

N-[3-(3-Amidinophenyl)-2-(E)-propenyl]-N-[3-carbamoyl-4-[1-(4,5-dihydro-3H-pyrrol-2-yl)piperidin-4-yloxy]phenyl]ethanesulfonamide dihydrochloride (Exemplification Compound Number 1406)

(a) N-[3-(3-Amidinophenyl)-2-(E)-propenyl]-N-[3-carbamoyl-4-(piperidin-4-yloxy)phenyl]ethanesulfonamide dihydrochloride Hydrogen chloride was bubbled through a solution of N-[4-(1-t-butoxycarbonylpiperidin-4-yloxy)-3-carbamoylphenyl]-N-[3-(3-cyanophenyl)-2-(E)-propenyl]ethanesulfonamide (1.08 g) obtained in reference example 132 in a mixture of dichloromethane (8 ml) and ethanol (8 ml) under ice-cooling, and the resulting mixture was stirred at room temperature for 4 hours under sealed conditions and then evaporated in vacuo. Subsequently, to a solution of the residue obtained in ethanol (16 ml) were added successively an aqueous ammonium chloride solution (prepared by dissolving 0.26 g in 3 ml of water) and a 28% ammonia solution (0.46 ml), and the resulting mixture was allowed to stand at room temperature overnight and then evaporated in vacuo. To the residue obtained were successively added ethanol (10 ml) and a 4N solution of hydrogen chloride in dioxane (2 ml) and the resulting mixture was evaporated in vacuo. The residue obtained was purified by preparative HPLC (YMC-Pack ODS-A; YMC, eluent: 10% acetonitrile/water). Subsequently, to a solution of the amorphous solid obtained in ethanol (10 ml) was added a 4N solution of hydrogen chloride in dioxane (2 ml), and the resulting mixture was evaporated to dryness in vacuo to afford the title compound (0.68 g, yield: 64%) as a pale yellow amorphous solid.

$^1$H NMR (400 MHz, DMSO-$d_6$) δ ppm: 1.26 (3H, t, J=7.5), 1.86–1.94 (2H, m), 2.07–2.14 (2H, m), 3.01–3.09 (2H, m), 3.13–3.23 (4H, m), 4.45 (2H, d, J=6.0), 4.77 (1H, m), 6.43 (1H, dt, J=16.0, 6.0), 6.55 (1H, d, J=16.0), 7.20 (1H, d, J=9.0), 7.46–7.75 (5H, m), 7.87 (1H, s).

(b) N-[3-(3-Amidinophenyl)-2-(E)-propenyl]-N-[3-carbamoyl-4-[1-(4,5-dihydro-3H-pyrrol-2-yl)piperidin-4-yloxy]phenyl]ethanesulfonamide dihydrochloride To a solution of N-[3-(3-amidinophenyl)-2-(E)-propenyl]-N-[3-carbamoyl-4-(piperidin- 4-yloxy)phenyl]ethanesulfonamide dihydrochloride (0.68 g) obtained in example 100(a) in ethanol (15 ml) were added successively 5-methoxy-3,4-dihydro-2H-pyrrole (0.36 g), which was prepared from 2-pyrrolidinone according to the method described in Org. Prep. Proced. Int., 24, 147 (1992), and triethylamine (0.85 ml) at room temperature and the resulting mixture was allowed to stand at room temperature overnight. At the end of this time, to the reaction mixture were furthermore added successively 5-methoxy-3,4-dihydro-2H-pyrrole (0.19 g) and triethylamine (0.34 ml) at room temperature, and the resulting mixture was stirred at room temperature for 5 hours and then evaporated in vacuo. Subsequently, to the residue obtained were successively added ethanol (10 ml) and a 4N solution of hydrogen chloride in dioxane (4 ml), and the resulting mixture was evaporated in vacuo. The residue obtained was purified by preparative HPLC (YMC-Pack ODS-A; YMC, eluent: 10% acetonitrile/water). To the amorphous solid obtained was added 1N hydrochloric acid (8 ml) and the resulting mixture was evaporated to dryness in vacuo. The residue obtained was dissolved in water and then lyophilized to afford the title compound (0.56 g, yield: 73%) as a pale brown amorphous solid.

$^1$H NMR (400 MHz, DMSO-$d_6$) δ ppm: 1.27 (3H, t, J=7.5), 1.79–1.91 (2H, m), 2.02–2.14 (4H, m), 2.97 (2H, t, J=7.0), 3.21 (2H, q, J=7.5), 3.47–3.73 (5H, m), 3.90 (1H, m), 4.47 (2H, d, J=6.0), 4.86 (1H, m), 6.46 (1H, dt, J=16.0, 6.0), 6.57 (1H, d, J=16.0), 7.26 (1H, d, J=9.0), 7.49–7.58 (2H, m), 7.69–7.76 (3H, m), 7.92 (1H, s);

IR (KBr, cm$^{-1}$): 1671, 1331, 1146.

Example 101

N-[3-(3-Amidinophenyl)-2-(E)-propenyl]-N-[3-carbamoyl-4-[1-(4,5-dihydrooxazol-2-yl)piperidin-4-yloxy]phenyl]methanesulfonamide dihydrochloride (Exemplification Compound Number 1211)

To a solution of N-[3-(3-amidinophenyl)-2-(E)-propenyl]-N-[3-carbamoyl-4-(piperidin-4-yloxy)phenyl]methanesulfonamide (0.32 g) obtained in example 99(a) in methanol (15 ml) were added successively 2-ethoxy-4,5-dihydrooxazole (0.21 g), which was prepared from 2-oxazolidone according to the method described in *Eur. J. Org. Chem.*, 10, 2645 (1999), and triethylamine (0.56 ml) at room temperature, and the resulting mixture was stirred at room temperature for 2 hours and allowed to stand at room temperature overnight and then evaporated in vacuo. The residue obtained was purified by preparative HPLC (YMC-Pack ODS-A; YMC, eluent: 12% acetonitrile/water). The amorphous solid obtained was dissolved in 1N hydrochloric acid (1.2 ml) and evaporated to dryness in vacuo to afford the title compound (0.15 g, yield: 59%) as a colorless amorphous solid.

$^1$H NMR (500 MHz, DMSO-$d_6$) δ ppm: 1.78–1.92 (2H, m), 1.98–2.11 (2H, m), 3.06 (3H, s), 3.47–3.88 (6H, m), 4.45 (2H, d, J=5.5), 4.76–4.85 (3H, m), 6.47 (1H, dt, J=16.0, 5.5), 6.59 (1H, d, J=16.0), 7.25 (1H, d, J=9.0), 7.49–7.58 (2H, m), 7.67–7.76 (3H, m), 7.91 (1H, s);

IR (KBr, cm$^{-1}$): 1686, 1334, 1151.

Example 102

N-[3-(3-Amidinophenyl)-2-(E)-propenyl]-N-[3-carbamoyl-4-[1-(4,5-dihydrothiazol-2-yl)piperidin-4-yloxy]phenyl]methanesulfonamide dihydrochloride (Exemplification Compound Number 1269)

To a solution of N-[3-(3-amidinophenyl)-2-(E)-propenyl]-N-[3-carbamoyl-4-(piperidin-4-yloxy)phenyl]methanesulfonamide (0.32 g) obtained in example 99(a) in a mixture of tetrahydrofuran (3 ml), 1,4-dioxane (3 ml) and water (3 ml) were added successively 2-chloroisothiocyanate (0.05 ml) and triethylamine (0.07 ml) under ice-cooling, and the resulting mixture was stirred at room temperature for 1.5 hours and allowed to stand at room temperature overnight and then evaporated in vacuo. The residue obtained was purified by preparative HPLC (YMC-Pack ODS-A; YMC, eluent: 12% acetonitrile/water). The amorphous solid obtained was dissolved in 1N hydrochloric acid (1.2 ml) and evaporated to dryness in vacuo to afford the title compound (0.15 g, yield: 59%) as a colorless amorphous solid.

$^1$H NMR (500 MHz, DMSO-$d_6$) δ ppm: 1.82–1.93 (2H, m), 2.02–2.12 (2H, m), 3.06 (3H, s), 3.52–3.63 (3H, m), 3.68–3.82 (2H, m), 3.91–4.02 (3H, m), 4.45 (2H, d, J=6.0), 4.85 (1H, m), 6.47 (1H, dt, J=16.0, 6.0), 6.59 (1H, d, J=16.0), 7.25 (1H, d, J=9.0), 7.49–7.58 (2H, m), 7.68–7.76 (3H, m), 7.91 (1H, s);

IR (KBr, cm$^{-1}$): 1673, 1632, 1333, 1151.

Example 103

Ethyl N-[3-chloro-4-(1-methylpiperidin-4-yloxy)phenyl]-N-[3-[3-(ethoxycarbonylamino)(imino)methylphenyl]-2-(E)-propenyl]sulfamoylacetate dihydrochloride To a solution of 4-nitrophenol (1.00 g) in dichloromethane (20 ml) were added dropwise ethyl chloroformate (0.70 ml) and pyridine (0.70 ml) under ice-cooling, and the resulting mixture was stirred at room temperature overnight and then evaporated in vacuo. To the residue obtained was added ethyl acetate, and the organic layer was washed successively with a saturated aqueous sodium hydrogencarbonate solution, a saturated aqueous sodium chloride solution, a saturated aqueous potassium hydrogensulfate solution and a saturated aqueous sodium chloride solution. The organic layer was dried over anhydrous magnesium sulfate and evaporated in vacuo. The residual solid obtained was collected by filtration using hexane to afford ethyl 4-nitrophenyl carbonate (1.44 g, yield: 95%) as a white solid.

Subsequently, to a solution of ethyl N-[3-(3-amidinophenyl)-2-(E)-propenyl]-N-[3-chloro-4-(1-methylpiperidin-4-yloxy)phenyl]sulfamoylacetate dihydrochloride (0.42 g) obtained in example 1 in water (5 ml) were added successively a solution of ethyl 4-nitrophenyl carbonate obtained above in dichloromethane (prepared by dissolving 0.14 g in 5 ml of dichloromethane) and sodium hydrogencarbonate (0.11 g), and the resulting mixture was stirred at room temperature for 3 hours. After stirring, a saturated aqueous sodium hydrogencarbonate solution was added, and the resulting mixture was extracted with ethyl acetate. The extract was washed with a saturated aqueous sodium hydrogencarbonate solution, dried over anhydrous magnesium sulfate and then evaporated in vacuo. The residue obtained was purified by chromatography on a silica gel column using a mixed solvent of dichloromethane and ethanol (1:1). Subsequently, to a solution of the amorphous solid obtained in ethanol (5 ml) was added 1N hydrochloric acid (1.4 ml), and the resulting mixture was evaporated to dryness in vacuo. The residue obtained was dissolved in water and then lyophilized to afford the title compound (0.36 g, yield: 78%) as a colorless amorphous solid.

$^1$H NMR (500 MHz, DMSO-$d_6$) δ ppm: 1.23 (3H, t, J=7.0), 1.33 (3H, t, J=7.0), 1.90–2.07 (2H, m), 2.15–2.25 (2H, m), 2.74 (3H, m), 3.00–3.10 (2H, m), 3.33 (1H, m), 3.40–3.50 (1H, m), 4.19 (2H, q, J=7.0), 4.35 (2H, q, J=7.0), 4.42 (2H, s), 4.47 (2H, d, J=6.0), 4.62 and 4.87 (total 1H, each m), 6.42 (1H, dt, J=16.0, 6.0), 6.59 (1H, d, J=16.0), 7.31 (1H, m), 7.40 (1H, m), 7.54 (1H, t, J=8.0), 7.59 (1H, m), 7.66 (1H, d, J=8.0), 7.75 (1H, d, J=8.0), 7.86 (1H, s);

IR (KBr, cm$^{-1}$): 1742, 1674, 1354, 1157.

Example 104

Ethyl N-[3-chloro-4-(1-methylpiperidin-4-yloxy)phenyl]-N-[3-[3-(imino)(4-methoxyphenoxycarbonylamino)methylphenyl]-2-(E)-propenyl]sulfamoylacetate dihydrochloride To a solution of 4-methoxyphenol (1.00 g) in dichloromethane (20 ml) were successively added dropwise 4-methoxyphenyl chloroformate (1.25 ml) and pyridine (0.72 ml) under ice-cooling, and the resulting mixture was stirred at room temperature overnight and then evaporated in vacuo. The residue obtained was diluted with ethyl acetate, and the organic layer was washed with a saturated aqueous sodium chloride solution. The organic layer was dried over anhydrous magnesium sulfate and evaporated to dryness in vacuo to afford bis(4-methoxyphenyl) dicarbonate (2.37 g, quantitative yield) as a white solid.

Subsequently, to a solution of ethyl N-[3-(3-amidinophenyl)-2-(E)-propenyl]-N-[3-chloro-4-(1-methylpiperidin-4-yloxy)phenyl]sulfamoylacetate dihydrochloride (0.50 g) obtained in example 1 in water (10 ml) were added successively a solution of bis(4-methoxyphenyl) dicarbonate obtained above in dichloromethane (prepared by dissolving 0.22 g in 10 ml of dichloromethane) and sodium hydrogencarbonate (0.14 g), and the resulting mixture was stirred at room temperature overnight. After stirring, to the reaction mixture were added water and sodium hydrogencarbonate, and the resulting mixture was extracted with ethyl acetate. The extract, was washed with a saturated aqueous sodium hydrogencarbonate solution, dried over anhydrous magnesium sulfate and evaporated in vacuo. The residue obtained was purified by chromatography on a silica gel column using a mixed solvent of dichloromethane and ethanol (5:2). Subsequently, to a solution of the amorphous solid obtained in ethanol (5 ml) was added 1N hydrochloric acid (1.6 ml), and the resulting mixture was evaporated to dryness in vacuo. The residue obtained was dissolved in water and then lyophilized to afford the title compound (0.42 g, yield: 67%) as a colorless amorphous solid.

$^1$H NMR (500 MHz, DMSO-$d_6$) δ ppm: 1.23 (3H, t, J=7.0), 1.83–1.93 (1H, m), 2.00–2.18 (2H, m), 2.20–2.27 (1H, m), 2.76 (3H, m), 3.00–3.10 (2H, m), 3.30–3.50 (2H, m), 3.77 (3H, s), 4.19 (2H, q, J=7.0), 4.42 (2H, s), 4.48 (2H, d, J=6.0), 4.60 and 4.85 (total 1H, each m), 6.39 (1H, dt, J=16.0, 6.0), 6.59 (1H, d, J=16.0), 6.99 (2H, d, J=9.0), 7.17 (2H, d, J=9.0), 7.31 (1H, m), 7.41 (1H, m), 7.51 (1H, t, J=7.5), 7.60 (1H, m), 7.69 (1H, d, J=7.5), 7.80 (1H, d, J=7.5), 7.97 (1H, s);

IR (KBr, cm$^{-1}$): 1740, 1671, 1354, 1161.

Example 105

Ethyl N-[3-[3-(t-butoxycarbonylamino)(imino)methylphenyl]-2-(E)-propenyl]-N-[3-chloro-4-(1-methylpiperidin-4-yloxy]phenyl]sulfamoylacetate To a solution of ethyl N-[3-(3-amidinophenyl)-2-(E)-propenyl]-N-[3-chloro-4-(1-methylpiperidin-4-yloxy)phenyl]sulfamoylacetate dihydrochloride (0.43 g) obtained in example 1 in water (10 ml) were added successively a solution of di-t-butyl dicarbonate in dichloromethane (prepared by dissolving 0.15 g in 10 ml of dichloromethane) and sodium hydrogencarbonate (0.12 g), and the resulting mixture was stirred at room temperature for 5 hours. After stirring, to the reaction mixture was added a saturated aqueous sodium hydrogencarbonate solution, and the resulting mixture was extracted with ethyl acetate. The extract was washed with a saturated aqueous sodium hydrogencarbonate solution, dried over anhydrous magnesium sulfate and evaporated in vacuo. The residue obtained was purified by chromatography on a silica gel column using a mixed solvent of dichloromethane and ethanol (5:1) to afford the title compound (0.36 g, yield: 81%) as a colorless amorphous solid.

$^1$H NMR (500 MHz, CDCl$_3$) δ ppm: 1.35 (3H, t, J=7.0), 1.54 (9H, s), 1.87–1.96 (2H, m), 1.97–2.06 (2H, m), 2.32 (3H, s), 2.39 (2H, m), 2.68 (2H, m), 3.99 (2H, s), 4.30 (2H, q, J=7.0), 4.41 (1H, m), 4.44 (2H, d, J=6.5), 6.22 (1H, dt, J=16.0, 6.5), 6.42 (1H, d, J=16.0), 6.91 (1H, d, J=9.0), 7.29 (1H, m), 7.34 (1H, t, J=8.0), 7.45 (1H, d, J=8.0), 7.52 (1H, d, J=2.5), 7.66 (1H, d, J=8.0), 7.78 (1H, s);

IR (KBr, cm$^{-1}$) 1740, 1655, 1365, 1163.

Example 106

Ethyl N-[3-chloro-4-(1-methylpiperidin-4-yloxy)phenyl]-N-[3-[3-(4-fluorophenoxycarbonylamino)(imino)methylphenyl]-2-(E)-propenyl]sulfamoylacetate To a solution of 4-fluorophenol (2.00 g) in dichloromethane (40 ml) were successively added dropwise a solution of 4-fluorophenyl chloroformate in dichloromethane (prepared by dissolving 2.35 ml in 5 ml of dichloromethane) and pyridine (1.59 ml) with stirring under ice-cooling, and the resulting mixture was stirred at room temperature for 1.5 hours and then evaporated in vacuo. To the residue obtained was added a saturated aqueous sodium chloride solution, and the resulting mixture was extracted with ethyl acetate. The extract was washed with an aqueous sodium chloride solution, dried over anhydrous magnesium sulfate and evaporated in vacuo. The white solid obtained was collected by filtration using hexane to afford bis(4-fluorophenyl) dicarbonate (4.25 g, yield: 95%) as a white solid.

Subsequently, to a solution of ethyl N-[3-(3-amidinophenyl)-2-(E)-propenyl]-N-[ 3-chloro-4-(1-methylpiperidin-4-yloxy)phenyl]sulfamoylacetate dihydrochloride (0.50 g) obtained in example 1 in water (10 ml) were added successively a solution of bis(4-fluorophenyl) dicarbonate obtained above in dichloromethane (prepared by dissolving 0.20 g in 10 ml of dichloromethane) and sodium hydrogencarbonate (0.20 g), and the resulting mixture was stirred at room temperature overnight. After stirring, a saturated aqueous sodium hydrogencarbonate solution was added and the resulting mixture was extracted with ethyl acetate. The extract was washed with a saturated aqueous sodium hydrogencarbonate solution; dried over anhydrous magnesium sulfate and evaporated in vacuo. The residue obtained was purified by chromatography on a silica gel column using a mixed solvent of dichloromethane and ethanol (1:1) to afford the title compound (0.47 g, yield: 85%) as a colorless amorphous solid.

$^1$H NMR (500 MHz, CDCl$_3$) δ ppm: 1.36 (3H, t, J=7.0), 1.86–1.95 (2H, m), 1.95–2.04 (2H, m), 2.31 (3H, s), 2.35 (2H, m), 2.66 (2H, m), 3.99 (2H, s), 4.31 (2H, q, J=7.0), 4.40 (1H, m), 4.46 (2H, d, J=6.5), 6.26 (1H, dt, J=16.0, 6.5), 6.47 (1H, d, J=16.0), 6.91 (1H, d, J=9.0), 7.08 (2H, m), 7.17 (2H, m), 7.31 (1H, dd, J=9.0, 2.5), 7.42 (1H, t, J=8.0), 7.53 (1H, d, J=2.5), 7.54 (1H, d, J=8.0), 7.75 (1H, d, J=8.0), 7.86 (1H, s);

IR (KBr, cm$^{-1}$): 1739, 1668, 1355, 1162.

Example 107

N-[3-Carbamoyl-4-[1-(4,5-dihydro-3H-pyrrol-2-yl)piperidin-4-yloxy]phenyl]-N-[3-[3-(ethoxycarbonylamino)(imino)methylphenyl]-2-(E)-propenyl]methanesulfonamide dihydrochloride To a solution of N-[3-(3-amidinophenyl)-2-(E)-propenyl]-N-[3-carbamoyl-4-[1-(4,5-dihydro-3H-pyrrol-2-yl)piperidin-4-yloxy]phenyl]methanesulfonamide dihydrochloride (0.23 g) obtained in example 99(b) in a mixture of dichloromethane (4.5 ml) and N,N-dimethylformamide (1.5 ml) were added successively ethyl 4-nitrophenyl carbonate (0.10 g) obtained in example 103 and triethylamine (0.16 ml) at room temperature, and the resulting mixture was stirred at room temperature overnight and then evaporated in vacuo. The residue obtained was purified by chromatography on a silica gel column using a mixed solvent of dichloromethane and methanol (50:0~47:3). Subsequently, to a solution of the oily product obtained in ethanol (2 ml) was added a 4N solution of hydrogen chloride in dioxane (0.5 ml), and the resulting mixture was evaporated to dryness in vacuo. The amorphous solid obtained was dissolved in dichloromethane, and the resulting mixture was extracted with 1N hydrochloric acid, and the aqueous layer collected was evaporated in vacuo. The residue obtained was dissolved in water and then lyophilized to afford the title compound (0.20 g, yield: 84%) as a colorless amorphous solid.

$^1$H NMR (400 MHz, DMSO-$d_6$) δ ppm 1.33 (3H, t, J=7.0), 1.80–1.92 (2H, m), 2.02–2.14 (4H, m), 2.96 (2H, t, J=7.5), 3.06 (3H, s), 3.47–3.73 (4H, m), 3.83–3.91 (2H, m), 4.35 (2H, q, J=7.0), 4.46 (2H, d, J=6.0), 4.87 (1H, m), 6.45 (1H, dt, J=16.0, 6.0), 6.60 (1H, d, J=16.0), 7.28 (1H, d, J=9.0), 7.49–7.69 (3H, m), 7.73–7.78 (2H, m), 7.88 (1H, s);

IR (KBr, cm$^{-1}$): 1754, 1667, 1334, 1151.

Example 108

N-[3-Carbamoyl-4-[1-(4,5-dihydro-3H-pyrrol-2-yl)piperidin-4-yloxy]phenyl]-N-[3-[3-(imino)(pivaloylamino)methylphenyl]-2-(E)-propenyl]methanesulfonamide To a solution of N-[3-(3-amidinophenyl)-2-(E)-propeyl]-N-[3-carbamoyl-4-(1-(4,5-dihydro-3H-pyrrol-2-yl)piperidin-4-yloxy]phenyl]methanesulfonamide dihydrochloride (0.20 g) obtained in example 99(b) in a mixture of dichloromethane (2.5 ml) and acetonitrile (2.5 ml) were added successively 4-nitrophenyl pivalate (0.09 g) and triethylamine (0.23 ml) with stirring under ice-cooling, and the resulting mixture was stirred at room temperature for 4 hours. After stirring, to the reaction mixture was added dichloromethane, and the organic layer was washed successively with a 1N aqueous sodium hydroxide solution and a saturated aqueous sodium chloride solution, dried over anhydrous sodium sulfate and evaporated in vacuo. The residue obtained was purified by chromatography on a silica gel column using a mixed solvent of dichloromethane and methanol (50:0~47:3) to afford the title compound (0.17 g, yield: 86%) as a colorless amorphous solid.

$^1$H NMR (400 MHz, CDCl$_3$) δ ppm: 1.28 (9H, s), 1.78–1.88 (2H, m), 1.96–2.05 (2H, m), 2.07–2.14 (2H, m), 2.51 (2H, t, J=8.0), 2.96 (3H, s), 3.22–3.31 (2H, m), 3.67–3.76 (4H, m), 4.44 (2H, d, J=6.5), 4.67 (1H, m), 6.23 (1H, dt, J=16.0, 6.5), 6.52 (1H, d, J=16.0), 7.01 (1H, d, J=9.0), 7.38 (1H, t, J=8.0), 7.45 (1H, d, J=8.0), 7.52 (1H, dd, J=9.0, 2.5), 7.82–7.88 (2H, m), 8.19 (1H, d, J=2.5);

IR (KBr, cm$^{-1}$): 1670, 1339, 1153.

Example 109

N-[3-[3-(Benzoylamino)(imino)methylphenyl]-2-(E)-propenyl]-N-[3-carbamoyl-4-[1-(4,5-dihydro-3H-pyrrol-2-yl)piperidin-4-yloxy]phenyl]methanesulfonamide To a solution of N-[3-(3-amidinophenyl)-2-(E)-propenyl]-N-[3-carbamoyl-4-[1-(4,5-dihydro-3H-pyrrol-2-yl)piperidin-4-yloxy]phenyl]methanesulfonamide dihydrochloride (0.30 g) obtained in example 99(b) in a mixture of dichloromethane (4 ml) and acetonitrile (4 ml) were added successively 4-nitrophenyl benzoate (0.15 g) and triethylamine (0.28 ml) with stirring under ice-cooling, and the resulting mixture was stirred at room temperature overnight. After stirring, the reaction mixture was diluted with dichloromethane, and the organic layer was washed successively with a 0.5N aqueous sodium hydroxide solution and a saturated aqueous sodium chloride solution, dried over anhydrous sodium sulfate and evaporated in vacuo. The residue obtained was purified by chromatography on a silica gel column using a mixed solvent of dichloromethane and methanol (50:0~47:3). The purified solid obtained was dissolved in water and then lyophilized to afford the title compound (0.24 g, yield: 75%) as a pale yellow amorphous solid.

$^1$H NMR (400 MHz, CDCl$_3$) δ ppm: 1.77–1.87 (2H, m), 1.94–2.12 (4H, m), 2.50 (2H, t, J=8.0), 2.97 (3H, s), 3.20–3.28 (2H, m), 3.65–3.74 (4H, m), 4.45 (2H, d, J=6.5), 4.66 (1H, m), 6.27 (1H, dt, J=15.5, 6.5), 6.56 (1H, d, J=15.5), 7.01 (1H, d, J=9.0), 7.42–7.56 (6H, m), 7.94–8.02 (2H, m), 8.20 (1H, d, J=2.5), 8.36 (2H, d, J=7.5);

IR (KBr, cm$^{-1}$): 1670, 1339, 1153.

Example 110

N-[3-[3-(Acetylamino)(imino)methylphenyl]-2-(E)-propenyl]-N-[3-carbamoyl-4-[1-(4,5-dihydro-3H-pyrrol-2-yl)piperidin-4-yloxy]phenyl]methanesulfonamide To a solution of N-[3-(3-amidinophenyl)-2-(E)-propenyl]-N-[3-carbamoyl-4-[1-(4,5-dihydro-3H-pyrrol-2-yl)piperidin-4-yloxy]phenyl]methanesulfonamide dihydrochloride (0.29 g) obtained in example 99(b) in a mixture of dichloromethane (3 ml) and acetonitrile (3 ml) were added successively 4-nitrophenyl acetate (0.09 g) and triethylamine (0.26 ml) with stirring under ice-cooling, and the resulting mixture was stirred at room temperature for 4 hours. After stirring, to the reaction mixture was added dichloromethane, and the organic layer was washed successively with a 0.5N aqueous sodium hydroxide solution and a saturated aqueous sodium chloride solution, dried over anhydrous sodium sulfate and evaporated in vacuo. The residue obtained was purified by chromatography on a silica gel column using a mixed solvent of dichloromethane and methanol (50:0~47:3). The solid obtained was dissolved in water and then lyophilized to afford the title compound (0.16 g, yield: 58%) as a pale yellow amorphous solid.

$^1$H NMR (400 MHz, CDCl$_3$) δ ppm: 1.78–1.88 (2H, m), 1.97–2.15 (4H, m), 2.30 (3H, s), 2.52 (2H, t, J=8.0), 2.96 (3H, s), 3.22–3.31 (2H, m), 3.66–3.77 (4H, m), 4.44 (2H, d, J=6.5), 4.68 (1H, m), 6.26 (1H, dt, J=15.5, 6.5), 6.50 (1H, d, J=15.5), 7.01 (1H, d, J=9.0), 7.37–7.53 (3H, m), 7.72–7.78 (2H, m), 8.18 (1H, d, J=3.0);

IR (KBr, cm$^{-1}$): 1668, 1338, 1152.

Example 111

N-[3-Carbamoyl-4-[1-(4,5-dihydro-3H-pyrrol-2-yl)piperidin-4-yloxyy]phenyl]-N-[3-[3-(imino)(4-methoxyphenoxycarbonylamino)methylphenyl]-2-(E)-propenyl]methanesulfonamide To a solution of 4-nitrophenol (1.00 g) in dichloromethane (30 ml) were added dropwise 4-methoxyphenyl chloroformate (1.10 ml) and pyridine (0.64 ml) with stirring under ice-cooling, and the resulting mixture was stirred at room temperature overnight and then evaporated in vacuo. To the residue obtained was added ethyl acetate, and the organic layer was washed with a saturated aqueous sodium chloride solution, dried over anhydrous sodium sulfate and evaporated in vacuo. The white solid obtained was collected by filtration using hexane to afford (4-methoxyphenyl)(4-nitrophenyl)carbonate (1.72 g, yield: 83%) as a white solid.

Subsequently, to a solution of N-[3-(3-amidinophenyl)-2-(E)-propenyl]-N-[3-carbamoyl-4-[1-(4,5-dihydro-3H-pyrrol-2-yl)piperidin-4-yloxy]phenyl]methanesulfonamide dihydrochloride (0.29 g) obtained in example 99(b) in a mixture of dichloromethane (3.5 ml) and acetonitrile (3.5 ml) were added successively (4-methoxyphenyl)(4-nitrophenyl)carbonate (0.15 g) obtained above and triethylamine (0.27 ml), and the resulting mixture was stirred at room temperature for 1.5 hours. After stirring, the reaction mixture was diluted with dichloromethane, and the organic layer was washed successively with a 0.5N aqueous sodium hydroxide solution and a saturated aqueous sodium chloride solution, dried over anhydrous sodium sulfate and evaporated in vacuo. The residue obtained was purified by chromatography on a silica gel column using a mixed solvent of dichloromethane and methanol (20:0~19:1). The purified product obtained was dissolved in water and then lyophilized to afford the title compound (0.23 g, yield: 69%) as a colorless amorphous solid.

¹H NMR (400 MHz, CDCl₃) δ ppm: 1.77–1.88 (2H, m), 1.94–2.13 (4H, m), 2.51 (2H, t, J=8.0), 2.97 (3H, s), 3.21–3.31 (2H, m), 3.64–3.84 (7H, m), 4.43 (2H, d, J=6.5), 4.68 (1H, m), 6.27 (1H, dt, J=15.5, 6.5), 6.51 (1H, d, J=15.5), 6.91 (2H, d, J=8.5), 7.01 (1H, d, J=9.0), 7.13 (2H, d, J=8.5), 7.40 (1H, t, J=7.5), 7.47–7.54 (2H, m), 7.80–7.90 (2H, m), 8.18 (1H, d, J=2.5);

IR (KBr, cm⁻¹): 1668, 1338, 1152.

Reference Example 1

3-Cyanocinnamaldehyde

To a solution of 3-cyanobenzaldehyde (4.5 g) in toluene (200 ml) was added (triphenylphosphoranylidene)acetaldehyde (13.6 g), and the resulting mixture was stirred at 70° C. for 4 hours and then evaporated in vacuo. The residue obtained was purified by chromatography on a silica gel column using dichloromethane as the eluent. The crude product obtained was recrystallized from a mixture of toluene and hexane to afford the title compound (3.09 g, yield: 57%) as pale yellowish needle crystals.

¹H NMR (500 MHz, CDCl₃) δ ppm: 6.76 (1H, dd, J=16.0, 7.5), 7.46 (1H, d, J=16.0), 7.58 (1H, t, J=8.0), 7.73 (1H, d, J=8.0), 7.80 (1H, d, J=8.0), 7.84 (1H, s), 9.75 (1H, d, J=7.5).

Reference Example 2

3-(3-Cyanophenyl)-2-(E)-propen-1-ol

To a solution of 3-cyanocinnamaldehyde (3.00 g) obtained in reference example 1 in a mixture of dichloromethane (30 ml) and ethanol (70 ml) were added successively sodium borohydride (1.32 g) and cerium chloride (2.49 g) under ice-cooling, and the resulting mixture was stirred at the same temperature for 1.5 hours. After stirring, to the reaction mixture was added a saturated aqueous ammonium chloride solution, and the resulting mixture was extracted with dichloromethane three times. The extract was washed with a saturated aqueous sodium chloride solution, dried over anhydrous sodium sulfate and evaporated in vacuo. The residue obtained was purified by chromatography on a silica gel column using a mixed solvent of hexane and ethyl acetate (3:2) as the eluent to afford the title compound (3.27 g, quantitative yield) as a pale yellow oil.

¹H NMR (500 MHz, CDCl₃) δ ppm: 4.37 (2H, m), 6.43 (1H, dt, J=16.0, 5.0), 6.62 (1H, d, J=16.0), 7.43 (1H, t, J=8.0), 7.52 (1H, d, J=8.0), 7.60 (1H, d, J=8.0), 7.65 (1H, s).

Reference Example 3

4-(1-t-Butoxycarbonylpiperidin-4-yloxy)-3-chloronitrobenzene

To a solution of 1-t-butoxycarbonyl-4-hydroxypiperidine (3.32 g), 2-chloro-4-nitrophenol (2.36 g) and triphenylphosphine (5.11 g) in dichloromethane (60 ml), diethyl azodicarboxylate (3.10 ml) was added dropwise with stirring under ice-cooling, and the resulting mixture was stirred at room temperature for 18 hours and then evaporated in vacuo. The residue obtained was purified by chromatography on a silica gel column using a mixed solvent of hexane and ethyl acetate (5:2) as the eluent to afford the title compound (3.90 g, yield: 76%) as a pale yellow solid.

¹H NMR (500 MHz, CDCl₃) δ ppm: 1.48 (9H, s), 1.84–1.98 (4H, m) 3.54 (2H, m), 3.62 (2H, m), 4.73 (1H, m), 7.00 (1H, d, J=9.0), 8.14 (1H, dd, J=9.0, 3.0), 8.31 (1H, d, J=3.0).

Reference Example 4

3-Chloro-4-(1-methylpiperidin-4-yloxy)nitrobenzene

To a suspension of 4-(1-t-butoxycarbonylpiperidin-4-yloxy)-3-chloronitrobenzene (1.50 g) obtained in reference example 3 in 90% formic acid (4.00 g) was added 37% formaldehyde (2.50 g), and the resulting mixture was stirred at 100° C. for 2 hours. After cooling to room temperature, the reaction mixture was neutralized with an aqueous potassium carbonate solution and extracted with ethyl acetate. The extract was washed with a saturated aqueous sodium chloride solution, dried over anhydrous magnesium sulfate and evaporated in vacuo to afford the title compound (1.12 g, yield: 98%) as a yellow solid.

¹H NMR (400 MHz, CDCl₃) δ ppm: 1.90–2.10 (4H, m), 2.33 (3H, s), 2.35–2.45 (2H, m), 2.60–2.70 (2H, m), 4.58 (1H, m), 6.98 (1H, d, J=9.0), 8.13 (1H, dd, J=9.0, 3.0), 8.30 (1H, d, J=3.0).

Reference Example 5

3-Chloro-4-(1-methylpiperidin-4-yloxy)aniline

To a solution of 3-chloro-4-(1-methylpiperidin-4-yloxy) nitrobenzene (8.48 g) obtained in reference example 4 in acetic acid (200 ml) was added tin powder (18.59 g) at room temperature, and the resulting mixture was stirred at room temperature overnight. After stirring, the reaction mixture was filtered, and the filtrate was evaporated in vacuo. The residue obtained was neutralized with an aqueous potassium carbonate solution and extracted with ethyl acetate five times. The extract was dried over anhydrous magnesium sulfate and evaporated in vacuo. The residue obtained was purified by chromatography on a silica gel column using a mixed solvent of dichloromethane and methanol (3:1) as the eluent to afford the title compound (6.95 g, yield: 92%) as a reddish brown solid.

¹H NMR (500 MHz, CDCl₃) δ ppm: 1.82–2.02 (4H, m), 2.20–2.30 (2H, m), 2.30 (3H, s), 2.68–2.78 (2H, m), 4.12 (1H, m), 6.51 (1H, dd, J=8.5, 3.0), 6.72 (1H, d, J=3.0), 6.81 (1H, d, J=8.5).

Reference Example 6

Ethyl N-[3-chloro-4-(1-methylpiperidin-4-yloxy)phenyl]sulfamoylacetate

To a solution of 3-chloro-4-(1-methylpiperidin-4-yloxy) aniline (6.95 g) obtained in reference example 5 in dichloromethane (150 ml) were successively added dropwise ethyl chlorosulfonylacetate (3.88 ml) and pyridine (4.67 ml) with stirring under ice-cooling, and the resulting mixture was stirred at room temperature for 5 hours. After stirring, to the reaction mixture was added water, and the resulting mixture was extracted with ethyl acetate three times. The extract was dried over anhydrous magnesium sulfate and evaporated in vacuo. The residue obtained was purified by chromatography on a silica gel column using a mixed solvent of dichloromethane and methanol (4:1~1:1) as the eluent to afford the title compound (9.12 g, yield: 81%) as a brown amorphous solid.

¹H NMR (500 MHz, CDCl₃) δ ppm: 1.34 (3H, t, J=7.0), 1.90–2.00 (2H, m), 2.00–2.10 (2H, m), 2.37 (3H, s), 2.40–2.50 (2H, m), 2.70–2.80 (2H, m), 3.92 (2H, s), 4.30 (2H, q, J=7.0), 4.41 (1H, m), 6.93 (1H, d, J=9.0), 7.21 (1H, dd, J=9.0, 2.5), 7.40 (1H, d, J=2.5).

Reference Example 7

Ethyl N-[3-chloro-4-(1-methylpiperidin-4-yloxy)phenyl]-N-[3-(3-cyanophenyl)-2-(E)-propenyl]sulfamoylacetate To a solution of 3-(3-cyanophenyl)-2-(E)-propen-1-ol (3.30 g) obtained in reference example 2, ethyl N-[3-chloro-4-(1-methylpiperidin-4-yloxy)phenyl]sulfamoylacetate (7.37 g) obtained in reference example 6 and triphenylphosphine (5.93 g) in dichloromethane (200 ml), diethyl azodicarboxylate (3.49 ml) was added dropwise with stirring under ice-cooling, and the resulting mixture was stirred at room temperature overnight and then evaporated in vacuo. The residue obtained was purified by chromatography on a silica gel column using a mixed solvent of methanol and ethyl acetate (1:3~2:1) as the eluent to afford the title compound (7.29 g, yield: 73%) as an orange-colored amorphous solid.

$^1$H NMR (500 MHz, CDCl$_3$) δ ppm: 1.36 (3H, t, J=7.0), 1.85–1.95 (2H, m), 1.95–2.05 (2H, m), 2.31 (3H, s), 2.30–2.40 (2H, m), 2.60–2.70 (2H, m), 3.99 (2H, s), 4.31 (2H, q, J=7.0), 4.40 (1H, m), 4.46 (2H, d, J=6.5), 6.22 (1H, dt, J=16.0, 6.5), 6.41 (1H, d, J=16.0), 6.92 (1H, d, J=9.0), 7.31 (1H, dd, J=9.0, 2.5), 7.40 (1H, t, J=8.0), 7.46–7.58 (4H, m).

Reference Example 8

3-Chloro-4-(piperidin-4-yloxy)nitrobenzene

To a solution of 4-(1-t-butoxycarbonylpiperidin-4-yloxy)-3-chloronitrobenzene (7.91 g) obtained in reference example 3 in dioxane (80 ml) was added a 4N solution of hydrogen chloride in dioxane (70 ml) at room temperature, and the resulting mixture was stirred at room temperature overnight and then evaporated in vacuo. The residue obtained was dissolved in water and neutralized with sodium hydrogencarbonate. The crystalline solid separated was collected by filtration to afford the title compound (8.06 g, quantitative yield) as pale yellow needle crystals.

$^1$H NMR (500 MHz, DMSO-d$_6$) δ ppm: 1.50–1.60 (2H, m), 1.90–2.00 (2H, m), 2.57–2.68 (2H, m), 2.90–3.00 (2H, m), 3.96 (1H, m), 7.45 (1H, d, J=9.0), 8.18 (1H, dd, J=9.0, 3.0), 8.31 (1H, d, J=3.0).

Reference Example 9

4-(1-Acetylpiperidin-4-yloxy)-3-chloronitrobenzene

To a solution of 3-chloro-4-(piperidin-4-yloxy)nitrobenzene (1.00 g) obtained in reference example 8 in pyridine (20 ml) was added dropwise acetic anhydride (0.55 ml) with stirring under ice-cooling, and the resulting mixture was stirred at room temperature for 3 hours. After stirring, to the reaction mixture was added water, and the resulting mixture was extracted with ethyl acetate. The extract was washed successively with an aqueous sodium hydrogencarbonate solution and a saturated aqueous sodium chloride solution and dried over anhydrous magnesium sulfate. The organic layer was evaporated in vacuo to afford the title compound (1.05 g, yield: 90%) as a pale yellow solid.

$^1$H NMR (500 MHz, CDCl$_3$) δ ppm: 1.88–2.03 (4H, m), 2.14 (3H, s), 3.50–3.63 (2H, m), 3.71 (1H, m), 3.94 (1H, m), 4.81 (1H, m), 7.01 (1H, d, J=9.0), 8.15 (1H, dd, J=9.0, 2.5), 8.32 (1H, d, J=2.5).

Reference Example 10

4-(1-Acetylpiperidin-4-yloxy)-3-chloroaniline

To a solution of 4-(1-acetylpiperidin-4-yloxy)-3-chloronitrobenzene (1.05 g) obtained in reference example 9 in acetic acid (30 ml) was added tin powder (2.09 g) at room temperature, and the resulting mixture was stirred at room temperature for 10 hours. After stirring, the reaction mixture was filtered, and the filtrate was evaporated in vacuo. The residue obtained was neutralized with an aqueous potassium carbonate solution and extracted with ethyl acetate five times. The organic layer was dried over anhydrous magnesium sulfate and evaporated in vacuo. The residue obtained was purified by chromatography on a silica gel column using a mixed solvent of ethyl acetate and methanol (15:1) as the eluent to afford the title compound (0.82 g, yield: 86%) as an orange-colored oil.

$^1$H NMR (500 MHz, CDCl$_3$) δ ppm: 1.78–1.94 (4H, m), 2.11 (3H, s), 3.33–3.43 (1H, m), 3.60–3.70 (1H, m), 3.70–3.82 (2H, m), 4.35 (1H, m), 6.53 (1H, dd, J=8.5, 3.0), 6.74 (1H, d, J=3.0), 6.81 (1H, d, J=8.5).

Reference Example 11

3-Chloro-4-(1-ethylpiperidin-4-yloxy)aniline

To a suspension of lithium aluminum hydride (230 mg) in tetrahydrofuran (5 ml) was added dropwise a solution of 4-(1-acetylpiperidin-4-yloxy)-3-chloroaniline obtained in reference example 10 in tetrahydrofuran (10 ml) with stirring under ice-cooling in a nitrogen atmosphere, and the resulting mixture was refluxed for 3.5 hours. After refluxing, to the reaction mixture was furthermore added lithium aluminum hydride (115 mg), and the resulting mixture was refluxed for a further 2 hours. After cooling to room temperature, to the reaction mixture was added sodium sulfate decahydrate, and the resulting mixture was furthermore stirred at room temperature overnight. After removing insoluble materials by filtration, the filtrate was evaporated in vacuo. The residue obtained was purified by chromatography on a silica gel column using a mixed solvent of dichloromethane and methanol (3:1~1:2) as the eluent to afford the title compound (448 mg, yield: 58%) as a brown oil.

$^1$H NMR (500 MHz, CDCl$_3$) δ ppm: 1.11 (3H, t, J=7.0), 1.82–1.93 (2H, m), 1.93–2.04 (2H, m), 2.29 (2H, m), 2.45 (2H, q, J=7.0), 2.78 (2H, m), 4.15 (1H, m), 6.51 (1H, dd, J=8.5, 3.0), 6.73 (1H, d, J=3.0), 6.81 (1H, d, J=8.5).

Reference Example 12

Ethyl N-[3-chloro-4-(1-ethylpiperidin-4-yloxy)phenyl]sulfamoylacetate

To a solution of 3-chloro-4-(1-ethylpiperidin-4-yloxy)aniline (853 mg) obtained in reference example 11 in dichloromethane (20 ml) were successively added dropwise ethyl chlorosulfonylacetate (0.45 ml) and pyridine (0.54 ml) with stirring under ice-cooling, and the resulting mixture was stirred at room temperature for 4 hours. After stirring, to the reaction mixture was added water, and the resulting mixture was extracted with ethyl acetate twice. The extract was dried over anhydrous magnesium sulfate and evaporated in vacuo. The residue obtained was purified by chromatography on a silica gel column using a mixed solvent of dichloromethane and methanol (3:1~1:1) as the eluent to afford the title compound (1113 mg, yield: 82%) as a yellowish brown amorphous solid.

$^1$H NMR (400 MHz, CDCl$_3$) δ ppm: 1.15 (3H, t, J=7.0), 1.34 (3H, t, J=7.0), 1.87–2.00 (2H, m), 2.00–2.13 (2H, m), 2.40–2.60 (4H, m), 2.70–2.83 (2H, m), 3.92 (2H, s), 4.30 (2H, q, J=7.0), 4.43 (1H, m), 6.93 (1H, d, J=9.0), 7.21 (1H, dd, J=9.0, 2.5), 7.40 (1H, d, J=2.5).

Reference Example 13

Ethyl N-[3-chloro-4-(1-ethylpiperidin-4-yloxy)phenyl]-N-[3-(3-cyanophenyl)-2-(E)-propenyl]sulfamoylacetate To a solution of 3-(3-cyanophenyl)-2-(E)-propen-1-ol (0.48 g) obtained in reference example 2, ethyl N-[3-chloro-4-(1-ethylpiperidin-4-yloxy)phenyl]sulfamoylacetate (1.11 g) obtained in reference example 12 and triphenylphosphine (0.87 g) in dichloromethane (20 ml), diethyl azodicarboxylate (0.51 ml) was added dropwise with stirring under ice-cooling, and the resulting mixture was stirred at room temperature overnight and then evaporated in vacuo. The residue obtained was purified by chromatography on a silica gel column using a mixed solvent of methanol and ethyl acetate (1:3~1:1) as the eluent to afford the title compound (1.24 g, yield: 83%) as an orange-colored amorphous solid.

$^1$H NMR (400 MHz, CDCl$_3$) δ ppm: 1.12 (3H, t, J=7.0), 1.36 (3H, t, J=7.0), 1.86–1.98 (2H, m), 1.98–2.10 (2H, m), 2.35–2.50 (2H, m), 2.48 (2H, q, J=7.0), 2.73 (2H, m), 3.99 (2H, s), 4.31 (2H, q, J=7.0), 4.43 (1H, m), 4.46 (2H, d, J=6.5), 6.22 (1H, dt, J=16.0, 6.5), 6.41 (1H, d, J=16.0), 6.93 (1H, d, J=9.0), 7.31 (1H, dd, J=9.0, 2.5), 7.40 (1H, t, J=7.5), 7.48–7.58 (4H, m).

Reference Example 14

3-Chloro-4-(1-isopropylpiperidin-4-yloxy)nitrobenzene

To a suspension of 3-chloro-4-(piperidin-4-yloxy)nitrobenzene (1.50 g) obtained in reference example 8 in acetone (20 ml) were successively added acetic acid (0.33 ml) and sodium cyanoborohydride (0.18 g) under ice-cooling, and the resulting mixture was stirred at room temperature for 4.5 hours. After stirring, to the reaction mixture was added sodium cyanoborohydride (0.18 g) and the resulting mixture was stirred at room temperature for 3 hours. After stirring, to the reaction mixture were furthermore added successively acetic acid (0.33 ml) and sodium cyanoborohydride (0.18 g), and the resulting mixture was stirred at room temperature overnight and then evaporated in vacuo. The residue obtained was neutralized with an aqueous potassium carbonate solution and extracted with ethyl acetate. The organic layer was dried over anhydrous magnesium sulfate and evaporated in vacuo to afford the title compound (1.36 g, yield: 78%) as a yellow solid.

$^1$H NMR (400 MHz, CDCl$_3$) ppm: 1.09 (6H, d, J=6.5), 1.90–2.00 (2H, m), 2.00–2.15 (2H, m), 2.45–2.60 (2H, m), 2.75–2.90 (3H, m), 4.59 (1H, m), 6.98 (1H, d, J=9.0), 8.13 (1H, dd, J=9.0, 3.0), 8.30 (1H, d, J=3.0).

Reference Example 15

3-Chloro-4-(1-isopropylpiperidin-4-yloxy)aniline

To a solution of 3-chloro-4-(1-isopropylpiperidin-4-yloxy)nitrobenzene (1.36 g) obtained in reference example 14 in acetic acid (30 ml) was added tin powder (2.70 g) at room temperature, and the resulting mixture was stirred at room temperature overnight. After stirring, the reaction mixture was filtered, and the filtrate was evaporated in vacuo. The residue obtained was neutralized with an aqueous potassium carbonate solution and extracted with ethyl acetate three times. The organic layer was dried over anhydrous magnesium sulfate and evaporated in vacuo. The residue obtained was purified by chromatography on a silica gel column using a mixed solvent of dichloromethane and methanol (5:1~1:1) as the eluent to afford the title compound (0.99 g, yield: 81%) as a brown oil.

$^1$H NMR (500 MHz, CDCl$_3$) δ ppm: 1.15 (6H, d, J=6.5), 1.80–2.20 (4H, m), 2.66 (2H, m), 2.97 (2H, m), 3.03 (1H, m), 4.27 (1H, m), 6.52 (1H, dd, J=8.5, 3.0), 6.73 (1H, d, J=3.0), 6.80 (1H, d, J=8.5).

Reference Example 16

Ethyl N-[3-chloro-4-(1-isopropylpiperidin-4-yloxy)phenyl]sulfamoylacetate

To a solution of 3-chloro-4-(1-isopropylpiperidin-4-yloxy)aniline (985 mg) obtained in reference example 15 in dichloromethane (20 ml) were successively added dropwise ethyl chlorosulfonylacetate (0.49 ml) and pyridine (0.59 ml) with stirring under ice-cooling, and the resulting mixture was stirred at room temperature for 4 hours. After stirring, to the reaction mixture was added water, and the resulting mixture was extracted with ethyl acetate twice. The organic layer was dried over anhydrous magnesium sulfate and evaporated in vacuo. The residue obtained was purified by chromatography on a silica gel column using a mixed solvent of dichloromethane and methanol (10:1~3:1) as the eluent to afford the title compound (1094 mg, yield: 71%) as an orange-colored amorphous solid.

$^1$H NMR (400 MHz, CDCl$_3$) δ ppm: 1.10 (6H, d, J=6.5), 1.33 (3H, t, J=7.0), 1.84–1.98 (2H, m), 1.98–2.12 (2H, m), 2.50 (2H, m), 2.76–2.90 (3H, m), 3.92 (2H, s), 4.29 (2H, q, J=7.0), 4.39 (1H, m), 6.93 (1H, d, J=9.0), 7.20 (1H, dd, J=9.0, 2.5), 7.39 (1H, d, J=2.5).

Reference Example 17

Ethyl N-[3-chloro-4-(1-isopropylpiperidin-4-yloxy)phenyl]-N-[3-(3-cyanophenyl)-2-(E)-propenyl]sulfamoylacetate To a solution of 3-(3-cyanophenyl)-2-(E)-propen-1-ol (0.46 g) obtained in reference example 2, ethyl N-[3-chloro-4-(1-isopropylpiperidin-4-yloxy)phenyl]sulfamoylacetate (1.09 g) obtained in reference example 16 and triphenylphosphine (0.82 g) in dichloromethane (30 ml), diethyl azodicarboxylate (0.48 ml) was added dropwise with stirring under ice-cooling, and the resulting mixture was stirred at room temperature overnight and then evaporated in vacuo. The residue obtained was purified by chromatography on a silica gel column using a mixed solvent of methanol and ethyl acetate (1:2~1:1) as the eluent to afford the title compound (1.17 g, yield: 80%) as a yellow oil.

$^1$H NMR (500 MHz, CDCl$_3$) δ ppm: 1.08 (6H, d, J=6.5), 1.36 (3H, t, J=7.0), 1.84–1.95 (2H, m), 1.95–2.09 (2H, m), 2.47 (2H, m), 2.72–2.88 (3H, m), 3.99 (2H, s), 4.31 (2H, q, J=7.0), 4.41 (1H, m), 4.46 (2H, d, J=6.5), 6.22 (1H, dt, J=16.0, 6.5), 6.41 (1H, d, J=16.0), 6.92 (1H, d, J=9.0), 7.31 (1H, dd, J=9.0, 2.5), 7.40 (1H, t, J=8.0), 7.48–7.58 (4H, m).

Reference Example 18

4-(1-Butylpiperidin-4-yloxy)-3-chloronitrobenzene

To a solution of 3-chloro-4-(piperidin-4-yloxy)nitrobenzene (1.50 g) obtained in reference example 8 and butylaldehyde (1.04 ml) in dichloromethane (30 ml) were added successively acetic acid (0.33 ml) and sodium cyanoborohydride (0.18 g) with stirring under ice-cooling, and the resulting mixture was stirred at room temperature for 3 hours. At the end of this time, to the reaction mixture was furthermore added sodium cyanoborohydride (0.18 g), and the resulting mixture was stirred at room temperature overnight and then evaporated in vacuo. The residue obtained was diluted with ethyl acetate, and the solution was washed successively with water, an aqueous sodium hydrogencarbonate solution and a saturated aqueous sodium chloride solution, dried over anhydrous magnesium sulfate and evaporated in vacuo. The residue obtained was purified by chromatography on a silica gel column using a mixed solvent of methanol and dichloromethane (1:20) as the eluent to afford the title compound (0.88 g, yield: 48%) as a yellow oil.

$^1$H NMR (500 MHz, CDCl$_3$) δ ppm: 0.94 (3H, t, J=7.5), 1.35 (2H, m), 1.53 (2H, m), 1.92–2.04 (2H, m), 2.04–2.15 (2H, m), 2.44 (2H, m), 2.53 (2H, m), 2.75 (2H, m), 4.62 (1H, m), 6.99 (1H, d, J=9.0), 8.13 (1H, dd, J=9.0, 2.5), 8.30 (1H, d, J=2.5).

Reference Example 19

4-(1-Butylpiperidin-4-yloxy)-3-chloroaniline

To a solution of 4-(1-butylpiperidin-4-yloxy)-3-chloronitrobenzene (1.48 g) obtained in reference example 18 in acetic acid (30 ml) was added tin powder (2.81 g) at room temperature, and the resulting mixture was stirred at the same temperature overnight. After stirring, the reaction mixture was filtered, and the filtrate was evaporated in vacuo. The residue obtained was neutralized with an aqueous sodium hydrogencarbonate solution and extracted with ethyl acetate twice. The organic layer was dried over anhydrous magnesium sulfate and evaporated in vacuo. The residue obtained was purified by chromatography on a silica gel column using a mixed solvent of dichloromethane and methanol (5:1~3:1) as the eluent to afford the title compound (1.09 g, yield: 82%) as a brown oil.

$^1$H NMR (500 MHz, CDCl$_3$) δ ppm: 0.93 (3H, t, J=7.5), 1.34 (2H, m), 1.60 (2H, m), 1.92–2.02 (2H, m), 2.08–2.18 (2H, m), 2.62 (2H, m), 2.79 (2H, m), 2.94 (2H, m), 4.31 (1H, m), 6.52 (1H, dd, J=8.5, 3.0), 6.73 (1H, d, J=3.0), 6.79 (1H, d, J=8.5).

Reference Example 20

Ethyl N-[4-(1-butylpiperidin-4-yloxy)-3-chlorophenyl]sulfamoylacetate

To a solution of 4-(1-butylpiperidin-4-yloxy)-3-chloroaniline (1.09 g) obtained in reference example 19 in dichloromethane (20 ml) were successively added dropwise ethyl chlorosulfonylacetate (0.52 ml) and pyridine (0.62 ml) with stirring under ice-cooling, and the resulting mixture was stirred at room temperature overnight and then evaporated in vacuo. The residue obtained was diluted with ethyl acetate, and the organic layer was washed with an aqueous sodium hydrogencarbonate solution, dried over anhydrous magnesium sulfate and evaporated in vacuo. The residue obtained was purified by chromatography on a silica gel column using a mixed solvent of dichloromethane and methanol (20:1~9:1) as the eluent to afford the title compound (1.41 g, yield: 84%) as a brown amorphous solid.

$^1$H NMR (500 MHz, CDCl$_3$) δ ppm: 0.93 (3H, t, J=7.5), 1.34 (3H, t, J=7.0), 1.28–1.38 (2H, m), 1.54 (2H, m), 1.86–1.99 (2H, m), 2.02–2.15 (2H, m), 2.40–2.60 (4H, m), 2.79 (2H, m), 3.92 (2H, s), 4.30 (2H, q, J=7.0), 4.41 (1H, m), 6.93 (1H, d, J=9.0), 7.21 (1H, dd, J=9.0, 2.5), 7.40 (1H, d, J=2.5).

Reference Example 21

Ethyl N-[4-(1-butylpiperidin-4-yloxy)-3-chlorophenyl]-N-[3-(3-cyanophenyl)-2-(E)-propenyl]sulfamoylacetate To a solution of 3-(3-cyanophenyl)-2-(E)-propen-1-ol (0.57 g) obtained in reference example 2, ethyl N-[4-(1-butylpiperidin-4-yloxy)-3-chlorophenyl]sulfamoylacetate (1.41 g) obtained in reference example 20 and triphenylphosphine (1.02 g) in dichloromethane (30 ml), diethyl azodicarboxylate (0.60 ml) was added dropwise with stirring under ice-cooling, and the resulting mixture was stirred at room temperature overnight and then evaporated in vacuo. The residue obtained was purified by chromatography on a silica gel column using a mixed solvent of methanol and ethyl acetate (1:20~1:10) as the eluent to afford the title compound (1.17 g, yield: 63%) as a yellowish brown oil.

$^1$H NMR (500 MHz, CDCl$_3$) δ ppm: 0.93 (3H, t, J=7.5), 1.36 (3H, t, J=7.0), 1.28–1.40 (2H, m), 1.48–1.60 (2H, m), 1.85–2.00 (2H, m), 2.00–2.15 (2H, m), 2.38–2.58 (4H, m), 2.77 (2H, m), 3.99 (2H, s), 4.31 (2H, q, J=7.0), 4.38–4.52 (1H, m), 4.46 (2H, d, J=6.5), 6.22 (1H, dt, J=16.0, 6.5), 6.41 (1H, d, J=16.0), 6.93 (1H, d, J=9.0), 7.31 (1H, dd, J=9.0, 2.5), 7.40 (1H, t, J=8.0), 7.48–7.58 (4H, m).

Reference Example 22

4-(1-Benzylpiperidin-4-yloxy)-3-chloronitrobenzene

To a solution of 3-chloro-4-(piperidin-4-yloxy)nitrobenzene (1.00 g) obtained in reference example 8 in N,N-dimethylformamide (20 ml) were added successively benzyl bromide (0.56 ml) and potassium carbonate (0.81 g) with stirring under ice-cooling, and the resulting mixture was stirred at room temperature for 5 hours. After stirring, the reaction mixture was diluted with ethyl acetate, and the organic layer was washed with a saturated aqueous sodium chloride solution, dried over anhydrous magnesium sulfate and evaporated in vacuo. The residue obtained was purified by chromatography on a silica gel column using a mixed solvent of hexane and ethyl acetate (2:5~ethyl acetate only) as the eluent to afford the title compound (1.02 g, yield: 75%) as a yellow oil.

$^1$H NMR (400 MHz, CDCl$_3$) δ ppm: 1.88–1.98 (2H, m), 1.98–2.08 (2H, m), 2.42 (2H, m), 2.72 (2H, m), 3.55 (2H, s), 4.58 (1H, m), 6.97 (1H, d, J=9.0), 7.23–7.37 (5H, m), 8.12 (1H, dd, J=9.0, 2.5), 8.30 (1H, d, J=2.5).

Reference Example 23

4-(1-Benzylpiperidin-4-yloxy)-3-chloroaniline

To a solution of 4-(1-benzylpiperidin-4-yloxy)-3-chloronitrobenzene (1.02 g) obtained in reference example 22 in acetic acid (40 ml) was added tin powder (1.75 g) at room temperature, and the resulting mixture was stirred at room temperature overnight. After stirring, the reaction mixture was filtered, and the filtrate was evaporated in vacuo. The residue obtained was neutralized with an aqueous sodium hydrogencarbonate solution and extracted with ethyl acetate twice. The extract was washed successively with an aqueous sodium hydrogencarbonate solution and a saturated aqueous sodium chloride solution, dried over anhydrous magnesium sulfate and evaporated in vacuo. The residue obtained was purified by chromatography on a silica gel column using a mixed solvent of ethyl acetate and methanol (10:1) as the eluent to afford the title compound (0.78 g, yield: 84%) as a brown oil.

$^1$H NMR (400 MHz, CDCl$_3$) δ ppm: 1.80–1.90 (2H, m), 1.90–2.00 (2H, m), 2.26 (2H, m), 2.76 (2H, m), 3.52 (2H, s), 4.12 (1H, m), 6.50 (1H, dd, J=8.5, 3.0), 6.72 (1H, d, J=3.0), 6.80 (1H, d, J=8.5), 7.25 (1H, m), 7.28–7.36 (4H, m).

Reference Example 24

Ethyl N-[4-(1-benzylpiperidin-4-yloxy)-3-chlorophenyl]sulfamoylacetate

To a solution of 4-(1-benzylpiperidin-4-yloxy)-3-chloroaniline (780 mg) obtained in reference example 23 in dichloromethane (20 ml) were successively added dropwise ethyl chlorosulfonylacetate (0.35 ml) and pyridine (0.40 ml) with stirring under ice-cooling, and the resulting mixture was stirred at room temperature for 2.5 hours and then evaporated in vacuo. The residue obtained was diluted with ethyl acetate, and the organic layer was washed successively with an aqueous sodium hydrogencarbonate solution and a saturated aqueous sodium chloride solution, dried over anhydrous magnesium sulfate and evaporated in vacuo. The residue obtained was purified by chromatography on a silica gel column using a mixed solvent of ethyl acetate and methanol (25:2) as the eluent to afford the title compound (1018 mg, yield: 89%) as a yellowish brown amorphous solid.

$^1$H NMR (400 MHz, CDCl$_3$) δ ppm: 1.33 (3H, t, J=7.0), 1.84–1.93 (2H, m), 1.93–2.02 (2H, m), 2.36 (2H, m), 2.73 (2H, m), 3.54 (2H, s), 3.91 (2H, s), 4.29 (2H, q, J=7.0), 4.37 (1H, m), 6.92 (1H, d, J=9.0), 7.19 (1H, dd, J=9.0, 2.5), 7.27 (1H, m), 7.29–7.37 (4H, m), 7.38 (1H, d, J=2.5).

Reference Example 25

Ethyl N-[4-(1-benzylpiperidin-4-yloxy)-3-chlorophenyl]-N-[3-(3-cyanophenyl)-2-(E)-propenyl]sulfamoylacetate To a solution of 3-(3-cyanophenyl)-2-(E)-propen-1-ol (0.36 g) obtained in reference example 2, ethyl N-[4-(1-benzylpiperidin-4-yloxy)-3-chlorophenyl]sulfamoylacetate (1.02 g) obtained in reference example 24 and triphenylphosphine (0.69 g) in dichloromethane (20 ml), diethyl azodicarboxylate (0.40 ml) was added dropwise with stirring under ice-cooling; and the resulting mixture was stirred at room temperature for 2 hours and then evaporated in vacuo. The residue obtained was purified by chromatography on a silica gel column using ethyl acetate as the eluent to afford the title compound (1.53 g, quantitative yield) as a yellowish brown oil.

$^1$H NMR (500 MHz, CDCl$_3$) δ ppm: 1.35 (3H, t, J=7.0), 1.84–1.93 (2H, m), 1.93–2.02 (2H, m), 2.36 (2H, m), 2.71 (2H, m), 3.53 (2H, s), 3.98 (2H, s), 4.30 (2H, q, J=7.0), 4.40 (1H, m), 4.46 (2H, d, J=6.5), 6.22 (1H, dt, J=16.0, 6.5), 6.41 (1H, d, J=16.0), 6.91 (1H, d, J=9.0), 7.23–7.37 (6H, m), 7.40 (1H, t, J=8.0), 7.44–7.58 (4H, m).

Reference Example 26

3-Chloro-4-(1-phenethylpiperidin-4-yloxy)nitrobenzene

To a solution of 3-chloro-4-(piperidin-4-yloxy)nitrobenzene (957 mg) obtained in reference example 8 in N,N-dimethylformamide (20 ml) were added successively phenethyl bromide (0.61 ml) and potassium carbonate (770 mg) with stirring under ice-cooling, and the resulting mixture was stirred at room temperature overnight. After stirring, the reaction mixture was diluted with ethyl acetate, and the organic layer was washed with a saturated aqueous sodium chloride solution, dried over anhydrous magnesium sulfate and evaporated in vacuo. The residue obtained was purified by chromatography on a silica gel column using a mixed solvent of hexane and ethyl acetate (1:5~ethyl acetate only) as the eluent to afford the title compound (936 mg, yield: 70%) as a pale yellow solid.

$^1$H NMR (400 MHz, CDCl$_3$) δ ppm: 1.93–2.03 (2H, m), 2.03–2.13 (2H, m), 2.46–2.59 (2H, m), 2.61–2.71 (2H, m), 2.73–2.88 (4H, m), 4.61 (1H, m), 6.99 (1H, d, J=9.0), 7.17–7.24 (3H, m), 7.24–7.34 (2H, m), 8.13 (1H, dd, J=9.0, 3.0), 8.31 (1H, d, J=3.0).

Reference Example 27

3-Chloro-4-(1-phenethylpiperidin-4-yloxy)aniline

To a solution of 3-chloro-4-(1-phenethylpiperidin-4-yloxy)nitrobenzene (936 mg) obtained in reference example 26 in acetic acid (40 ml) was added tin powder (1540 mg) at room temperature, and the resulting mixture was stirred at room temperature overnight. After stirring, the reaction mixture was filtered, and the filtrate was evaporated in vacuo. The residue obtained was neutralized with an aqueous sodium hydrogencarbonate solution and extracted with ethyl acetate twice. The extract was washed successively with an aqueous sodium hydrogencarbonate solution and a saturated aqueous sodium chloride solution, dried over anhydrous magnesium sulfate and evaporated in vacuo. The residue obtained was purified by chromatography on a silica gel column using a mixed solvent of ethyl acetate and methanol (10:1) as the eluent to afford the title compound (720 mg, yield: 84% o) as a pale yellow solid.

$^1$H NMR (400 MHz, CDCl$_3$) δ ppm: 1.83–1.95 (2H, m), 1.95–2.06 (2H, m), 2.37 (2H, m), 2.58–2.67 (2H, m), 2.77–2.91 (4H, m), 4.16 (1H, m), 6.52 (1H, dd, J=8.5, 3.0), 6.73 (1H, d, J=3.0), 6.82 (1H, d, J=8.5), 7.17–7.24 (3H, m), 7.24–7.32 (2H, m).

Reference Example 28

Ethyl N-[3-chloro-4-(1-phenethylpiperidin-4-yloxy)phenyl]sulfamoylacetate

To a solution of 3-chloro-4-(1-phenethylpiperidin-4-yloxy)aniline (720 mg) obtained in reference example 27 in dichloromethane (20 ml) were successively added dropwise ethyl chlorosulfonylacetate (0.31 ml) and pyridine (0.35 ml) with stirring under ice-cooling, and the resulting mixture was stirred at room temperature for 3 hours and then evaporated in vacuo. The residue obtained was diluted with ethyl acetate, and the organic layer was washed successively with an aqueous sodium hydrogencarbonate solution and a saturated aqueous sodium chloride solution, dried over anhydrous magnesium sulfate and evaporated in vacuo. The residue obtained was purified by chromatography on a silica gel column using a mixed solvent of ethyl acetate and methanol (25:2) as the eluent to afford the title compound (936 mg, yield: 89%) as a yellow amorphous solid.

$^1$H NMR (500 MHz, CDCl$_3$) δ ppm: 1.34 (3H, t, J=7.0), 1.88–1.98 (2H, m), 1.98–2.08 (2H, m), 2.48 (2H, m), 2.60–2.70 (2H, m), 2.76–2.89 (4H, m), 3.92 (2H, s), 4.30 (2H, q, J=7.0), 4.41 (1H, m), 6.93 (1H, d, J=9.0), 7.18–7.24 (4H, m), 7.24–7.33 (2H, m), 7.39 (1H, d, J=2.5).

Reference Example 29

Ethyl N-[3-chloro-4-(1-phenethylpiperidin-4-yloxy)phenyl]-N-[3-(3-cyanophenyl)-2-(E)-propenyl]sulfamoylacetate To a solution of 3-(3-cyanophenyl)-2-(E)-propen-1-ol (325 mg) obtained in reference example 2, ethyl N-[3-chloro-4-(1-phenethylpiperidin-4-yloxy)phenyl]sulfamoylacetate (936 mg) obtained in reference example 28 and triphenylphosphine (610 mg) in dichloromethane (20 ml), diethyl azodicarboxylate (0.36 ml) was added dropwise with stirring under ice-cooling, and the resulting mixture was stirred at room temperature for 4 hours and then evaporated in vacuo. The residue obtained was purified by chromatography on a silica gel column using a mixed solvent of ethyl acetate and dichloromethane (1:2~ethyl acetate only) as the eluent to afford the title compound (1013 mg, yield: 84%) as a pale yellow amorphous solid.

$^1$H NMR (500 MHz, CDCl$_3$) δ ppm: 1.36 (3H, t, J=7.0), 1.87–1.98 (2H, m), 1.98–2.09 (2H, m), 2.47 (2H, m), 2.60–2.68 (2H, m), 2.76–2.87 (4H, m), 3.99 (2H, s), 4.31 (2H, q, J=7.0), 4.43 (1H, m), 4.46 (2H, d, J=6.5), 6.22 (1H, dt, J=16.0, 6.5), 6.41 (1H, d, J=16.0), 6.93 (1H, d, J=9.0), 7.17–7.23 (3H, m), 7.23–7.34 (3H, m), 7.40 (1H, t, J=8.0), 7.48–7.58 (4H, m).

Reference Example 30

3-Chloro-4-(1-phenylpiperidin-4-yloxy)nitrobenzene

3-Chloro-4-(piperidin-4-yloxy)nitrobenzene (2.68 g) obtained in reference example 8, bromobenzene (1.97 g), 2-(di-t-butylphosphino)biphenyl (0.62 g), tris(dibenzylideneacetone)dipalladium (0.95 g) and sodium t-butoxide (1.20 g) were suspended in toluene (30 ml) and the resulting mixture was stirred at 80° C. for 2 hours. After cooling to room temperature, insoluble materials were filtered off and the filtrate was evaporated in vacuo. The residue obtained was diluted with ethyl acetate, and the organic layer was washed successively with an aqueous sodium hydrogencarbonate solution and a saturated aqueous sodium chloride solution, dried over anhydrous sodium sulfate and evaporated in vacuo. The residue obtained was purified by chromatography on a silica gel column using a mixed solvent of hexane and ethyl acetate (4:1) as the eluent to afford the title compound (1.86 g, yield: 54%) as a yellow solid.

$^1$H NMR (400 MHz, CDCl$_3$) δ ppm: 2.00–2.10 (2H, m), 2.11–2.21 (2H, m), 3.24 (2H, m), 3.48 (2H, m), 4.73 (1H, m), 6.88 (1H, t, J=7.5), 6.95–7.00 (2H, m), 7.03 (1H, d, J=9.0), 7.25–7.32 (2H, m), 8.15 (1H, dd, J=9.0, 3.0), 8.31 (1H, d, J=3.0).

Reference Example 31

3-Chloro-4-(1-phenylpiperidin-4-yloxy)aniline

To a solution of 3-chloro-4-(1-phenylpiperidin-4-yloxy)nitrobenzene (1.86 g) obtained in reference example 30 in acetic acid (35 ml) was added tin powder (3.32 g) at room temperature, and the resulting mixture was stirred at room temperature for 1 hour. After stirring, the reaction mixture was filtered, and the filtrate was evaporated in vacuo. The residue obtained was diluted with ethyl acetate, and the organic layer was washed successively with an aqueous sodium hydrogencarbonate solution and a saturated aqueous sodium chloride solution. The organic layer was dried over anhydrous magnesium sulfate and evaporated in vacuo to afford the title compound (1.69 g, quantitative yield) as a pale yellow solid.

$^1$H NMR (400 MHz, CDCl$_3$) δ ppm: 1.90–2.01 (2H, m), 2.03–2.12 (2H, m), 3.07 (2H, m), 3.55 (2H, m), 4.27 (1H, m), 6.53 (1H, dd, J=8.5, 3.0), 6.74 (1H, d, J=3.0), 6.81–6.87 (1H, m), 6.84 (1H, d, J=8.5), 6.96 (2H, d, J=8.0), 7.23–7.29 (2H, m).

Reference Example 32

Ethyl N-[3-chloro-4-(1-phenylpiperidin-4-yloxy)phenyl]sulfamoylacetate

To a solution of 3-chloro-4-(1-phenylpiperidin-4-yloxy)aniline (1.69 g) obtained in reference example 31 in dichloromethane (25 ml) were successively added dropwise a solution of ethyl chlorosulfonylacetate (1.15 g) in dichloromethane (5 ml) and pyridine (0.50 ml) with stirring under ice-cooling, and the resulting mixture was stirred at room temperature for 2 hours. After stirring, to the reaction mixture was added a saturated aqueous sodium chloride solution, and the resulting mixture was extracted with ethyl acetate. The extract was washed with a saturated aqueous sodium chloride solution, dried over anhydrous sodium sulfate and evaporated in vacuo. The residue obtained was purified by chromatography on a silica gel column using a mixed solvent of ethyl acetate and hexane (2:3) as the eluent to afford the title compound (2.23 g, yield: 88%) as a colorless oil.

$^1$H NMR (400 MHz, CDCl$_3$) δ ppm: 1.34 (3H, t, J=7.0), 1.95–2.05 (2H, m), 2.06–2.15 (2H, m), 3.17 (2H, m), 3.50 (2H, m), 3.92 (2H, s), 4.30 (2H, q, J=7.0), 4.52 (1H, m), 6.86 (1H, t, J=7.5), 6.94–7.00 (2H, m), 6.97 (1H, d, J=9.0), 7.23 (1H, dd, J=9.0, 2.5), 7.25–7.30 (2H, m), 7.40 (1H, d, J=2.5).

Reference Example 33

Ethyl N-[3-chloro-4-(1-phenylpiperidin-4-yloxy)phenyl]-N-[3-(3-cyanophenyl)-2-(E)-propenyl]sulfamoylacetate To a solution of 3-(3-cyanophenyl)-2-(E)-propen-1-ol (0.41 g) obtained in reference example 2, ethyl N-[3-chloro-4-(1-phenylpiperidin-4-yloxy)phenyl]sulfamoylacetate (1.16 g) obtained in reference example 32 and triphenylphosphine (0.87 g) in dichloromethane (25 ml), diethyl azodicarboxylate (0.52 ml) was added dropwise with stirring under ice-cooling, and the resulting mixture was stirred at room temperature for 1 hour and then evaporated in vacuo. The residue obtained was purified by chromatography on a silica gel column using a mixed solvent of ethyl acetate and dichloromethane (1:12) as the eluent to afford the title compound (1.45 g, yield: 95%) as a colorless amorphous solid.

$^1$H NMR (400 MHz, CDCl$_3$) δ ppm: 1.36 (3H, t, J=7.0), 1.95–2.05 (2H, m), 2.06–2.16 (2H, m), 3.18 (2H, m), 3.49 (2H, m), 3.99 (2H, s), 4.31 (2H, q, J=7.0), 4.47 (2H, d, J=6.0), 4.55 (1H, m), 6.23 (1H, dt, J=16.0, 6.0), 6.42 (1H, d, J=16.0), 6.86 (1H, t, J=7.5), 6.93–6.99 (2H, m), 6.97 (1H, d, J=9.0), 7.24–7.30 (2H, m), 7.33 (1H, dd, J=9.0, 2.5), 7.41 (1H, t, J=7.5), 7.49–7.58 (4H, m).

Reference Example 34

3-Chloro-4-(1-methoxycarbonylmethylpiperidin-4-yloxy)nitrobenzene

To a solution of 3-chloro-4-(piperidin-4-yloxy)nitrobenzene (1.00 g) obtained in reference example 8 in N,N-dimethylformamide (20 ml) were added successively methyl bromoacetate (0.43 ml) and potassium carbonate (0.81 g) with stirring under ice-cooling, and the resulting mixture was stirred at room temperature overnight. After stirring, the reaction mixture was diluted with ethyl acetate, and the organic layer was washed with a saturated aqueous sodium chloride solution, dried over anhydrous magnesium sulfate and evaporated in vacuo. The residue obtained was purified by chromatography on a silica gel column using ethyl acetate as the eluent to afford the title compound (1.16 g, yield: 90%) as a yellow oil.

$^1$H NMR (400 MHz, CDCl$_3$) δ ppm: 1.93–2.04 (2H, m), 2.04–2.15 (2H, m), 2.59–2.69 (2H, m), 2.73–2.83 (2H, m), 3.29 (2H, s), 3.74 (3H, s), 4.62 (1H, m), 6.98 (1H, d, J=9.0), 8.13 (1H, dd, J=9.0, 2.5), 8.31 (1H, d, J=2.5).

Reference Example 35

3-Chloro-4-(1-methoxycarbonylmethylpiperidin-4-yloxy)aniline

To a solution of 3-chloro-4-(1-methoxycarbonylmethylpiperidin-4-yloxy)nitrobenzene (1.16 g) obtained in reference example 34 in acetic acid (30 ml) was added tin powder (2.09 g) at room temperature, and the resulting mixture was stirred at room temperature overnight. After stirring, the reaction mixture was filtered, and the filtrate was evaporated in vacuo. The residue obtained was diluted with ethyl acetate, and the organic layer was washed successively with an aqueous sodium hydrogencarbonate solution and a saturated aqueous sodium chloride solution, dried over anhydrous magnesium sulfate and evaporated in vacuo. The residue obtained was purified by chromatography on a silica gel column using a mixed solvent of ethyl acetate and methanol (25:1) as the eluent to afford the title compound (0.79 g, yield: 75%) as a yellow oil.

$^1$H NMR (500 MHz, CDCl$_3$) δ ppm: 1.87–1.95 (2H, m), 1.95–2.03 (2H, m), 2.43–2.53 (2H, m), 2.77–2.86 (2H, m), 3.25 (2H, s), 3.73 (3H, s), 4.17 (1H, m), 6.51 (1H, dd, J=8.5, 3.0), 6.73 (1H, d, J=3.0), 6.80 (1H, d, J=8.5).

Reference Example 36

Ethyl N-[3-chloro-4-(1-methoxycarbonylmethylpiperidin-4-yloxy)phenyl]sulfamoylacetate To a solution of 3-chloro-4-(1-methoxycarbonylmethylpiperidin-4-yloxy)aniline (0.79 g) obtained in reference example 35 in dichloromethane (20 ml) were successively added dropwise ethyl chlorosulfonylacetate (0.37 ml) and pyridine (0.43 ml) with stirring under ice-cooling, and the resulting mixture was stirred at room temperature overnight and then evaporated in vacuo. The residue obtained was diluted with ethyl acetate, and the organic layer was washed with a saturated aqueous sodium hydrogencarbonate solution, dried over anhydrous magnesium sulfate and evaporated in vacuo. The residue obtained was purified by chromatography on a silica gel column using ethyl acetate as the eluent to afford the title compound (1.06 g, yield: 89%) as a yellow oil.

$^1$H NMR (500 MHz, CDCl$_3$) δ ppm: 1.34 (3H, t, J=7.0), 1.90–1.99 (2H, m), 1.99–2.08 (2H, m), 2.53–2.62 (2H, m), 2.75–2.84 (2H, m), 3.27 (2H, s), 3.74 (3H, s), 3.91 (2H, s), 4.30 (2H, q, J=7.0), 4.41 (1H, m), 6.92 (1H, d, J=9.0), 7.20 (1H, dd, J=9.0, 2.5), 7.39 (1H, d, J=2.5).

Reference Example 37

Ethyl N-[3-chloro-4-(1-methoxycarbonylmethylpiperidin-4-yloxy)phenyl]-N-[3-(3-cyanophenyl)-2-(E)-propenyl]sulfamoylacetate To a solution of 3-(3-cyanophenyl)-2-(E)-propen-1-ol (0.39 g) obtained in reference example 2, ethyl N-[3-chloro-4-(1-methoxycarbonylmethylpiperidin-4-yloxy)phenyl]sulfamoylacetate (1.06 g) obtained in reference example 36 and triphenylphosphine (0.74 g) in dichloromethane (30 ml), diethyl azodicarboxylate (0.44 ml) was added dropwise with stirring under ice-cooling, and the resulting mixture was stirred at room temperature overnight and then evaporated in vacuo. The residue obtained was purified by chromatography on a silica gel column using ethyl acetate as the eluent to afford the title compound (1.70 g, quantitative yield) as a yellow oil.

$^1$H NMR (500 MHz, CDCl$_3$) δ ppm: 1.36 (3H, t, J=7.0), 1.90–1.99 (2H, m), 1.99–2.08 (2H, m), 2.54–2.63 (2H, m), 2.75–2.84 (2H, m), 3.27 (2H, s), 3.73 (3H, s), 3.98 (2H, s), 4.31 (2H, q, J=7.0), 4.45 (1H, m), 4.46 (2H, d, J=6.5), 6.22 (1H, dt, J=16.0, 6.5), 6.41 (1H, d, J=16.0), 6.92 (1H, d, J=9.0), 7.31 (1H, dd, J=9.0, 2.5), 7.40 (1H, t, J=8.0), 7.44–7.58 (4H, m).

Reference Example 38

Ethyl N-[4-(1-acetylpiperidin-4-yloxy)-3-chlorophenyl]sulfamoylacetate

To a solution of 4-(1-acetylpiperidin-4-yloxy)-3-chloroaniline (650 mg) obtained in reference example 10 in dichloromethane (20 ml) were successively added dropwise ethyl chlorosulfonylacetate (0.33 ml) and pyridine (0.39 ml) with stirring under ice-cooling, and the resulting mixture was stirred at room temperature for 3.5 hours and then evaporated in vacuo. The residue obtained was diluted with ethyl acetate, and the organic layer was washed successively with a saturated aqueous sodium hydrogencarbonate solution and a saturated aqueous sodium chloride solution, dried over anhydrous magnesium sulfate and evaporated in vacuo. The residue obtained was purified by chromatography on a silica gel column (eluent: ethyl acetate only~a mixed solvent of ethyl acetate and methanol (10:1)) to afford the title compound (773 mg, yield: 76%) as an orange-colored oil.

$^1$H NMR (400 MHz, CDCl$_3$) δ ppm: 1.34 (3H, t, J=7.0), 1.82–1.98 (4H, m), 2.13 (3H, s), 3.47 (1H, m), 3.63 (1H, m), 3.72 (1H, m), 3.84 (1H, m), 3.92 (2H, s), 4.30 (2H, q, J=7.0), 4.60 (1H, m), 6.94 (1H, d, J=9.0), 7.23 (1H, dd, J=9.0, 2.5), 7.41 (1H, d, J=2.5).

Reference Example 39

Ethyl N-[4-(1-acetylpiperidin-4-yloxy)-3-chlorophenyl]-N-[3-(3-cyanophenyl)-2-(E)-propenyl]sulfamoylacetate To a solution of 3-(3-cyanophenyl)-2-(E)-propen-1-ol (323 mg) obtained in reference example 2, ethyl N-[4-(1-acetylpiperidin-4-yloxy)-3-chlorophenyl]sulfamoylacetate (773 mg) obtained in reference example 38 and triphenylphosphine (581 mg) in dichloromethane (20 ml), diethyl azodicarboxylate (0.34 ml) was added dropwise with stirring under ice-cooling, and the resulting mixture was stirred at room temperature overnight and then evaporated in vacuo. The residue obtained was purified by chromatography on a silica gel column (eluent: ethyl acetate only~a mixed solvent of ethyl acetate and methanol (9:1)) to afford the title compound (733 mg, yield: 71%) as a pale yellow amorphous solid.

$^1$H NMR (500 MHz, CDCl$_3$) δ ppm: 1.36 (3H, t, J=7.0), 1.82–1.98 (4H, m), 2.12 (3H, s), 3.48 (1H, m), 3.61 (1H, m), 3.70 (1H, m), 3.85 (1H, m), 3.99 (2H, s), 4.31 (2H, q, J=7.0), 4.47 (2H, d, J=6.5), 4.63 (1H, m), 6.22 (1H, dt, J=16.0, 6.5), 6.42 (1H, d, J=16.0), 6.94 (1H, d, J=9.0), 7.34 (1H, dd, J=9.0, 2.5), 7.41 (1H, t, J=8.0), 7.48–7.58 (4H, m).

Reference Example 40

4-(1-Carbamoylpiperidin-4-yloxy)-3-chloronitrobenzene

To a solution of 3-chloro-4-(piperidin-4-yloxy)nitrobenzene (500 mg) obtained in reference example 8 in N,N-dimethylformamide (10 ml) was added potassium cyanate (790 mg) with stirring under ice-cooling, and the resulting mixture was stirred at room temperature overnight. At the end of this time, to the reaction mixture was furthermore added potassium cyanate (790 mg), and the resulting mixture was stirred at 40° C. overnight. Furthermore, to the reaction mixture was added a 4N solution of hydrogen chloride in dioxane (1.0 ml), and the resulting mixture was stirred at room temperature for 1 hour. After stirring, the reaction mixture was diluted with ethyl acetate, and the organic layer was washed successively with an aqueous sodium hydrogencarbonate solution and a saturated aqueous sodium chloride solution and evaporated in vacuo to afford the title compound (523 mg, yield: 88%) as a pale yellow solid.

$^1$H NMR (400 MHz, CDCl$_3$) δ ppm: 1.53–1.67 (2H, m), 1.86–2.00 (2H, m), 3.18–3.31 (2H, m), 3.51–3.64 (2H, m), 4.92 (1H, m), 7.49 (1H, d, J=9.0), 8.20 (1H, dd, J=9.0, 2.5), 8.33 (1H, d, J=2.5).

Reference Example 41

4-(1-Carbamoylpiperidin-4-yloxy)-3-chloroaniline

To a solution of 4-(1-carbamoylpiperidin-4-yloxy)-3-chloronitrobenzene (1.25 g) obtained in reference example 40 in acetic acid (30 ml) was added tin powder (2.47 g) at room temperature, and the resulting mixture was stirred at room temperature overnight. After stirring, the reaction mixture was filtered, and the filtrate was evaporated in vacuo. The residue obtained was diluted with ethyl acetate, and the organic layer was washed with an aqueous sodium hydrogencarbonate solution, dried over anhydrous magnesium sulfate and evaporated in vacuo. The residue obtained was purified by chromatography on a silica gel column using a mixed solvent of dichloromethane and methanol (20:1) as the eluent to afford the title compound (0.91 g, yield: 81%) as a pale orange-colored amorphous solid.

$^1$H NMR (500 MHz, CDCl$_3$) δ ppm: 1.80–1.96 (4H, m), 3.30–3.40 (2H, m), 3.62–3.72 (2H, m), 4.33 (1H, m), 6.52 (1H, dd, J=8.5, 3.0), 6.74 (1H, d, J=3.0), 6.81 (1H, d, J=8.5).

Reference Example 42

Ethyl N-[4-(1-carbamoylpiperidin-4-yloxy)-3-chlorophenyl]sulfamoylacetate

To a solution of 4-(1-carbamoylpiperidin-4-yloxy)-3-chloroaniline (907 mg) obtained in reference example 41 in dichloromethane (20 ml) were successively added dropwise ethyl chlorosulfonylacetate (0.45 ml) and diisopropylethylamine (0.88 ml) with stirring under ice-cooling, and the resulting mixture was stirred at room temperature overnight. After stirring, furthermore ethyl chlorosulfonylacetate (0.05 ml) was added and the resulting mixture was stirred at room temperature for 2 hours and then evaporated in vacuo. The residue obtained was diluted with ethyl acetate, and the organic layer was washed with a saturated aqueous sodium hydrogencarbonate solution, dried over anhydrous magnesium sulfate and evaporated in vacuo. The residue obtained was purified by chromatography on a silica gel column using a mixed solvent of dichloromethane and methanol (30:1~20:1) as the eluent to afford the title compound (809 mg, yield: 57%) as a pale yellow amorphous solid.

$^1$H NMR (400 MHz, CDCl$_3$) δ ppm: 1.34 (3H, t, J=7.0), 1.83–1.99 (4H, m), 3.47 (2H, m), 3.61 (2H, m), 3.92 (2H, s), 4.30 (2H, q, J=7.0), 4.58 (1H, m), 6.94 (1H, d, J=9.0), 7.23 (1H, dd, J=9.0, 2.5), 7.41 (1H, d, J=2.5).

Reference Example 43

Ethyl N-[4-(1-carbamoylpiperidin-4-yloxy)-3-chlorophenyl]-N-[3-(3-cyanophenyl)-2-(E)-propenyl]sulfamoylacetate To a solution of 3-(3-cyanophenyl)-2-(E)-propen-1-ol (322 mg) obtained in reference example 2, ethyl N-[4-(1-carbamoylpiperidin-4-yloxy)-3-chlorophenyl]sulfamoylacetate (809 mg) obtained in reference example 42 and triphenylphosphine (610 mg) in dichloromethane (20 ml), diethyl azodicarboxylate (0.36 ml) was added dropwise with stirring under ice-cooling, and the resulting mixture was stirred at room temperature overnight and then evaporated in vacuo. The residue obtained was purified by chromatography on a silica gel column using a mixed solvent of ethyl acetate and methanol (10:1) as the eluent to afford the title compound (1015 mg, yield: 94%) as a pale yellow amorphous solid.

$^1$H NMR (500 MHz, CDCl$_3$) δ ppm: 1.36 (3H, t, J=7.0), 1.84–1.99 (4H, m), 3.48 (2H, m), 3.59 (2H, m), 3.99 (2H, s), 4.31 (2H, q, J=7.0), 4.47 (2H, d, J=6.5), 4.62 (1H, m), 6.22 (1H, dt, J=16.0, 6.5), 6.41 (1H, d, J=16.0), 6.94 (1H, d, J=9.0), 7.33 (1H, dd, J=9.0, 2.5), 7.41 (1H, t, J=8.0), 7.49–7.57 (4H, m).

Reference Example 44

3-Chloro-4-(1-methanesulfonylpiperidin-4-yloxy)nitrobenzene

To a suspension of 3-chloro-4-(piperidin-4-yloxy)nitrobenzene (1.00 g) obtained in reference example 8 in dichloromethane (20 ml) were added successively methanesulfonyl chloride (0.33 ml) and triethylamine (1.09 ml) with stirring under ice-cooling, and the resulting mixture was stirred at room temperature for 2 hours. After stirring, the reaction mixture was diluted with ethyl acetate, and the organic layer was washed with a saturated aqueous sodium chloride solution, dried over anhydrous magnesium sulfate and evaporated in vacuo. The residue obtained was purified by chromatography on a silica gel column using a mixed solvent of ethyl acetate and hexane (1:1) as the eluent to afford the title compound (0.96 g, yield: 73%) as a colorless amorphous solid.

$^1$H NMR (500 MHz, CDCl$_3$) δ ppm: 2.06–2.14 (4H, m), 2.84 (3H, s), 3.29 (2H, m), 3.55 (2H, m), 4.82 (1H, m), 7.00 (1H, d, J=9.0), 8.16 (1H, dd, J=9.0, 2.5), 8.33 (1H, d, J=2.5).

Reference Example 45

3-Chloro-4-(1-methanesulfonylpiperidin-4-yloxy)aniline

To a solution of 3-chloro-4-(1-methanesulfonylpiperidin-4-yloxy)nitrobenzene (955 mg) obtained in reference example 44 in acetic acid (30 ml) was added tin powder (1690 mg) at room temperature, and the resulting mixture was stirred at room temperature overnight. After stirring, the reaction mixture was filtered, and the filtrate was evaporated in vacuo. The residue obtained was diluted with ethyl acetate, and the organic layer was washed with an aqueous sodium hydrogencarbonate solution, dried over anhydrous magnesium sulfate and evaporated in vacuo. The residue obtained was purified by chromatography on a silica gel column using a mixed solvent of ethyl acetate and hexane (5:3) as the eluent to afford the title compound (737 mg, yield: 85%) as a yellow amorphous solid.

$^1$H NMR (500 MHz, CDCl$_3$) δ ppm; 1.92–2.08 (4H, m), 2.81 (3H, s), 3.33–3.45 (4H, m), 4.38 (1H, m), 6.54 (1H, dd, J=8.5, 3.0), 6.74 (1H, d, J=3.0), 6.80 (1H, d, J=8.5).

Reference Example 46

Ethyl N-[3-chloro-4-(1-methanesulfonylpiperidin-4-yloxy)phenyl]sulfamoylacetate

To a solution of 3-chloro-4-(1-methanesulfonylpiperidin-4-yloxy)aniline (737 mg) obtained in reference example 45 in dichloromethane (20 ml) were successively added dropwise ethyl chlorosulfonylacetate (0.33 ml) and pyridine (0.39 ml) with stirring under ice-cooling, and the resulting mixture was stirred at room temperature for 1 hour. After stirring, the reaction mixture was diluted with ethyl acetate, and the organic layer was washed successively with a saturated aqueous sodium hydrogencarbonate solution and a saturated aqueous sodium chloride solution, dried over anhydrous magnesium sulfate and evaporated in vacuo. The residue obtained was purified by chromatography on a silica gel column using a mixed solvent of ethyl acetate and hexane (3:2) as the eluent to afford the title compound (805 mg, yield: 73%) as a pink amorphous solid.

$^1$H NMR (400 MHz, CDCl$_3$) δ ppm: 1.26 (3H, t, J=7.0), 1.96–2.10 (4H, m), 2.82 (3H, s), 3.31 (2H, m), 3.47 (2H, m), 3.92 (2H, s), 4.30 (2H, q, J=7.0), 4.62 (1H, m), 6.93 (1H, d, J=9.0), 7.23 (1H, dd, J=9.0, 2.5), 7.42 (1H, d, J=2.5).

Reference Example 47

Ethyl N-[4-(1-carbamoylpiperidin-4-yloxy)-3-chlorophenyl]-N-[3-(3-cyanophenyl)-2-(E)-propenyl]sulfamoylacetate To a solution of 3-(3-cyanophenyl)-2-(E)-propen-1-ol (296 mg) obtained in reference example 2, ethyl N-[3-chloro-4-(1-methanesulfonylpiperidin-4-yloxy)phenyl]sulfamoylacetate (805 mg) obtained in reference example 46 and triphenylphosphine (560 mg) in dichloromethane (20 ml), diethyl azodicarboxylate (0.33 ml) was added dropwise with stirring under ice-cooling, and the resulting mixture was stirred at room temperature for 5 hours and then evaporated in vacuo. The residue obtained was purified by chromatography on a silica gel column using a mixed solvent of dichloromethane and ethyl acetate (20:1~10:1) as the eluent to afford the title compound (835 mg, yield: 79%) as a colorless amorphous solid.

$^1$H NMR (400 MHz, CDCl$_3$) δ ppm: 1.36 (3H, t, J=7.0), 1.96–2.09 (4H, m), 2.82 (3H, s), 3.30 (2H, m), 3.48 (2H, m), 3.99 (2H, s), 4.31 (2H, q, J=7.0), 4.47 (2H, d, J=6.5), 4.65 (1H, m), 6.22 (1H, dt, J=16.0, 6.5), 6.42 (1H, d, J=16.0), 6.94 (1H, d, J=9.0), 7.35 (1H, dd, J=9.0, 2.5), 7.41 (1H, t, J=7.5), 7.50–7.55 (2H, m), 7.56 (1H, s), 7.56 (1H, d, J=2.5).

Reference Example 48

3-Chloro-4-[1-(2-pyridyl)piperidin-4-yloxy]nitrobenzene

To a suspension of 3-chloro-4-(piperidin-4-yloxy)nitrobenzene (3.00 g) obtained in reference example 8 in pyridine (30 ml) was added 2-bromopyridine (1.25 ml) at room temperature, and the resulting mixture was stirred at 150° C. for 16 hours. After cooling to room temperature, the reaction mixture was diluted with ethyl acetate, and the organic layer was washed with a saturated aqueous sodium chloride solution, dried over anhydrous magnesium sulfate and evaporated in vacuo. The residue obtained was purified by chromatography on a silica gel column using a mixed solvent of ethyl acetate and hexane (1:2) as the eluent to afford the title compound (0.80 g, yield: 20%) as a yellow solid.

$^1$H NMR (500 MHz, CDCl$_3$) δ ppm: 1.93–2.06 (2H, m), 2.06–2.17 (2H, m), 3.60–3.72 (2H, m), 3.79–3.90 (2H, m), 4.79 (1H, m), 6.64 (1H, dd, J=7.0, 5.0), 6.71 (1H, d, J=8.5), 7.04 (1H, d, J=9.0), 7.50 (1H, m), 8.16 (1H, dd, J=9.0, 3.0), 8.20 (1H, dd, J=5.0, 2.0), 8.32 (1H, d, J=3.0).

Reference Example 49

3-Chloro-4-[1-(2-pyridyl)piperidin-4-yloxy]aniline

To a solution of 3-chloro-4-[1-(2-pyridyl)piperidin-4-yloxy]nitrobenzene (796 mg) obtained in reference example 48 in acetic acid (40 ml) was added tin powder (1420 mg) at room temperature, and the resulting mixture was stirred at room temperature overnight. After stirring, the reaction mixture was filtered, and the filtrate was evaporated in vacuo. The residue obtained was diluted with ethyl acetate, and the organic layer was washed with an aqueous sodium hydrogencarbonate solution, dried over anhydrous magnesium sulfate and evaporated in vacuo. The residue obtained was purified by chromatography on a silica gel column using a mixed solvent of ethyl acetate and hexane (1:1) as the eluent to afford the title compound (680 mg, yield: 94%) as a pale reddish purple oil.

$^1$H NMR (400 MHz, CDCl$_3$) δ ppm: 1.83–1.95 (2H, m), 1.97–2.07 (2H, m), 3.41 (2H, m), 3.95 (2H, m), 4.34 (1H, m), 6.53 (1H, dd, J=8.5, 3.0), 6.59 (1H, dd, J=7.0, 5.5), 6.69 (1H, d, J=8.5), 6.74 (1H, d, J=3.0), 6.85 (1H, d, J=8.5), 7.47 (1H, m), 8.19 (1H, m).

Reference Example 50

Ethyl N-[3-chloro-4-[1-(2-pyridyl)piperidin-4-yloxy]phenyl]sulfamoylacetate

To a solution of 3-chloro-4-[1-(2-pyridyl)piperidin-4-yloxy]aniline (680 mg) obtained in reference example 49 in dichloromethane (20 ml) were successively added dropwise ethyl chlorosulfonylacetate (0.32 ml) and pyridine (0.36 ml) with stirring under ice-cooling, and the resulting mixture was stirred at room temperature overnight. After stirring, the reaction mixture was diluted with ethyl acetate, and the organic layer was washed successively with a saturated aqueous sodium hydrogencarbonate solution and a saturated aqueous sodium chloride solution, dried over anhydrous magnesium sulfate and evaporated in vacuo. The residue obtained was purified by chromatography on a silica gel column using a mixed solvent of ethyl acetate and hexane (1:1) as the eluent to afford the title compound (858 mg, yield: 85%) as a pale yellow amorphous solid.

$^1$H NMR (500 MHz, CDCl$_3$) δ ppm: 1.34 (3H, t, J=7.0), 1.88–1.98 (2H, m), 1.98–2.08 (2H, m), 3.56 (2H, m), 3.86 (2H, m), 3.92 (2H, s), 4.30 (2H, q, J=7.0), 4.58 (1H, m), 6.61 (1H, m), 6.70 (1H, d, J=8.5), 6.97 (1H, d, J=9.0), 7.23 (1H, dd, J=9.0, 2.5), 7.40 (1H, d, J=2.5), 7.48 (1H, m), 8.19 (1H, m).

Reference Example 51

Ethyl N-[3-chloro-4-[1-(2-pyridyl)piperidin-4-yloxy]phenyl]-N-[3-(3-cyanophenyl)-2-(E)-propenyl]sulfamoylacetate To a solution of 3-(3-cyanophenyl)-2-(E)-propen-1-ol (316 mg) obtained in reference example 2, ethyl N-[3-chloro-4-[1-(2-pyridyl)piperidin-4-yloxy]phenyl]sulfamoylacetate (858 mg) obtained in reference example 50 and triphenylphosphine (590 mg) in dichloromethane (20 ml), diethyl azodicarboxylate (0.35 ml) was added dropwise with stirring under ice-cooling, and the resulting mixture was stirred at room temperature overnight and then evaporated in vacuo. The residue obtained was purified by chromatography on a silica gel column using a mixed solvent of dichloromethane and ethyl acetate (10:1) as the eluent to afford the title compound (1100 mg, yield: 98%) as a colorless amorphous solid.

$^1$H NMR (500 MHz, CDCl$_3$) δ ppm: 1.36 (3H, t, J=7.0), 1.88–1.98 (2H, m), 1.98–2.08 (2H, m), 3.57 (2H, m), 3.84 (2H, m), 4.00 (2H, s), 4.31 (2H, q, J=7.0), 4.47 (2H, d, J=6.5), 4.61 (1H, m), 6.23 (1H, dt, J=16.0, 6.5), 6.42 (1H, d, J=16.0), 6.61 (1H, dd, J=7.0, 5.0), 6.69 (1H, d, J=8.5), 6.97

(1H, d, J=9.0), 7.33 (1H, dd, J=9.0, 2.5), 7.41 (1H, t, J=8.0), 7.48 (1H, m), 7.50–7.58 (4H, m), 8.19 (1H, m).

Reference Example 52

3-Chloro-4-[1-(3-pyridyl)piperidin-4-yloxy]nitrobenzene

3-Chloro-4-(piperidin-4-yloxy)nitrobenzene (2.72 g) obtained in reference example 8, 3-bromopyridine (2.01 g), 2-(di-t-butylphosphino)biphenyl (0.32 g), tris(dibenzylideneacetone)dipalladium (0.49 g) and sodium t-butoxide (1.22 g) were suspended in toluene (30 ml) and stirred at 70° C. for 2 hours. After cooling to room temperature, insoluble materials were filtered off and the filtrate was evaporated in vacuo. The residue obtained was diluted with ethyl acetate, and the organic layer was washed successively with an aqueous sodium hydrogencarbonate solution and a saturated aqueous sodium chloride solution, dried over anhydrous sodium sulfate and evaporated in vacuo. The residue obtained was purified by chromatography on a silica gel column using a mixed solvent of dichloromethane and methanol (9:1) as the eluent to afford the title compound (1.56 g, yield: 44%) as a yellow solid.
$^1$H NMR (400 MHz, CDCl$_3$) δ ppm: 2.03–2.22 (4H, m), 3.31 (2H, m), 3.49 (2H, m), 4.77 (1H, m), 7.03 (1H, d, J=9.0), 7.18 (1H, dd, J=8.5, 4.5), 7.24 (1H, m), 8.12 (1H, dd, J=4.5, 1.5), 8.16 (1H, dd, J=9.0, 3.0), 8.32 (1H, d, J=3.0), 8.36 (1H, d, J=3.0).

Reference Example 53

3-Chloro-4-[1-(3-pyridyl)piperidin-4-yloxy]aniline

To a solution of 3-chloro-4-[1-(3-pyridyl)piperidin-4-yloxy]nitrobenzene (1.54 g) obtained in reference example 52 in acetic acid (30 ml) was added tin powder (2.74 g) at room temperature, and the resulting mixture was stirred at room temperature for 1 hour. After stirring, the reaction mixture was filtered, and the filtrate was evaporated in vacuo. The residue obtained was diluted with ethyl acetate, and the organic layer was washed successively with a saturated aqueous sodium hydrogencarbonate solution and a saturated aqueous sodium chloride solution, dried over anhydrous sodium sulfate and evaporated in vacuo. The residue obtained was purified by chromatography on a silica gel column using a mixed solvent of dichloromethane and methanol (9:1) as the eluent to afford the title compound (1.39 g, yield: 99%) as a yellow oil.
$^1$H NMR (400 MHz, CDCl$_3$) δ ppm: 1.92–2.11 (4H, m), 3.14 (2H, m), 3.56 (2H, m), 4.31 (1H, m), 6.53 (1H, dd, J=9.0, 2.0), 6.74 (1H, d, J=2.0), 6.84 (1H, d, J=9.0), 7.16 (1H, dd, J=8.5, 4.5), 7.21 (1H, m), 8.08 (1H, d, J=4.5), 8.34 (1H, d, J=2.5).

Reference Example 54

Ethyl N-[3-chloro-4-[1-(3-pyridyl)piperidin-4-yloxy]phenyl]sulfamoylacetate

To a solution of 3-chloro-4-[1-(3-pyridyl)piperidin-4-yloxy]aniline (1.38 g) obtained in reference example 53 in dichloromethane (20 ml) were successively added dropwise a solution of ethyl chlorosulfonylacetate (0.93 g) in dichloromethane (5 ml) and pyridine (0.37 ml) with stirring under ice-cooling, and the resulting mixture was stirred at room temperature for 2 hours and then evaporated in vacuo. The residue obtained was purified by chromatography on a silica gel column using a mixed solvent of dichloromethane and methanol (9:1) as the eluent to afford the title compound (1.61 g, yield: 78%) as a pale brown amorphous solid.
$^1$H NMR (400 MHz, CDCl$_3$) δ ppm: 1.33 (3H, t, J=7.0), 1.97–2.15 (4H, m), 3.24 (2H, m), 3.51 (2H, m), 3.93 (2H, s), 4.29 (2H, q, J=7.0), 4.56 (1H, m), 6.97 (1H, d, J=9.0), 7.18 (1H, dd, J=8.5, 4.0), 7.21–7.28 (2H, m), 7.42 (1H, d, J=2.5), 8.10 (1H, d, J=4.0), 8.35 (1H,s).

Reference Example 55

Ethyl N-[3-chloro-4-[1-(3-pyridyl)piperidin-4-yloxy]phenyl]-N-[3-(3-cyanophenyl)-2-(E)-propenyl]sulfamoylacetate To a solution of 3-(3-cyanophenyl)-2-(E)-propen-1-ol (294 mg) obtained in reference example 2, ethyl N-(3-chloro-4-[1-(3-pyridyl)piperidin-4-yloxy]phenyl]sulfamoylacetate (840 mg) obtained in reference example 54 and triphenylphosphine (630 mg) in dichloromethane (20 ml), diethyl azodicarboxylate (0.38 ml) was added dropwise with stirring under ice-cooling, and the resulting mixture was stirred at room temperature overnight and then evaporated in vacuo. The residue obtained was purified by chromatography on a silica gel column using a mixed solvent of dichloromethane and methanol (97:3) as the eluent to afford the title compound (2060 mg, quantitative yield) as a yellow amorphous solid.
$^1$H NMR (400 MHz, CDCl$_3$) δ ppm: 1.36 (3H, t, J=7.0), 1.97–2.16 (4H, m), 3.25 (2H, m), 3.49 (2H, m), 4.00 (2H, s), 4.31 (2H, q, J=7.0), 4.47 (2H, d, J=6.5), 4.60 (1H, m), 6.23 (1H, dt, J=16.0, 6.5), 6.42 (1H, d, J=16.0), 6.97 (1H, d, J=9.0), 7.34 (1H, dd, J=9.0, 2.5), 7.41 (1H, t, J=8.0), 7.44–7.71 (6H, m), 8.10 (1H, m), 8.35(1H, m).

Reference Example 56

3-Chloro-4-[1-(4-pyridyl)piperidin-4-yloxy]nitrobenzene

To a solution of 3-chloro-4-(piperidin-4-yloxy)nitrobenzene (3.00 g) obtained in reference example 8 in N,N-dimethylformamide (30 ml) were added successively 4-bromopyridine (2.50 g) and N-methylmorpholine (5.14 ml) with stirring at room temperature, and the resulting mixture was stirred at 150° C. for 7 hours. After cooling to room temperature, the reaction mixture was diluted with ethyl acetate, and the organic layer was washed with a saturated aqueous sodium hydrogencarbonate solution, dried over anhydrous magnesium sulfate and evaporated in vacuo. The residue obtained was purified by chromatography on a silica gel column using a mixed solvent of dichloromethane and methanol (30:1~10:1) as the eluent to afford the title compound (1.27 g, yield: 33%) as a dark yellow amorphous solid.
$^1$H NMR (500 MHz, CDCl$_3$) δ ppm: 1.98–2.14 (4H, m), 3.46–3.55 (2H, m), 3.58–3.67 (2H, m), 4.83 (1H, m), 6.72 (2H, d, J=6.5), 7.03 (1H, d, J=9.0), 8.16 (1H, dd, J=9.0, 3.0), 8.28 (2H, d, J=6.5), 8.32 (1H, d, J=3.0).

Reference Example 57

3-Chloro-4-[1-(4-pyridyl)piperidin-4-yloxy]aniline

To a solution of 3-chloro-4-[1-(4-pyridyl)piperidin-4-yloxy]nitrobenzene (1.26 g) obtained in reference example 56 in acetic acid (50 ml) was added tin powder (2.24 g) at room temperature, and the resulting mixture was stirred at room temperature overnight. After stirring, the reaction mixture was filtered, and the filtrate was evaporated in vacuo. The residue obtained was neutralized with an aqueous potassium carbonate solution and extracted with ethyl acetate three times. The organic layer was dried over anhydrous magnesium sulfate and evaporated in vacuo. The residue obtained was purified by chromatography on a silica gel column using a mixed solvent of dichloromethane and methanol (10:1~1:1) as the eluent to afford the title compound (0.85 g, yield: 74%) as a pale yellow solid.

$^1$H NMR (500 MHz, CDCl$_3$) δ ppm: 1.85–2.05 (4H, m), 3.30–3.38 (2H, m), 3.65–3.73 (2H, m), 4.37 (1H, m), 6.54 (1H, dd, J=8.5, 3.0), 6.69 (2H, dd, J=5.0, 1.5), 6.74 (1H, d, J=3.0), 6.83 (1H, d, J=8.5), 8.25 (2H, dd, J=5.0, 1.5).

Reference Example 58

Ethyl N-[3-chloro-4-[1-(4-pyridyl)piperidin-4-yloxy]phenyl]sulfamoylacetate

To a solution of 3-chloro-4-[1-(4-pyridyl)piperidin-4-yloxy]aniline (854 mg) obtained in reference example 57 in dichloromethane (20 ml) were successively added dropwise ethyl chlorosulfonylacetate (0.40 ml) and pyridine (0.45 ml) with stirring under ice-cooling, and the resulting mixture was stirred at room temperature overnight and then evaporated in vacuo. The residue obtained was neutralized with an aqueous potassium carbonate solution and extracted with ethyl acetate twice. The extract was washed with a saturated sodium hydrogencarbonate solution, dried over anhydrous magnesium sulfate and evaporated in vacuo. The residue obtained was purified by chromatography on a silica gel column using a mixed solvent of dichloromethane and methanol (5:1~2:1) as the eluent to afford the title compound (888 mg, yield: 70%) as a yellow amorphous solid.

$^1$H NMR (500 MHz, CDCl$_3$) δ ppm: 1.33 (3H, t, J=7.0), 1.94–2.07 (4H, m), 3.47 (2H, m), 3.65 (2H, m), 3.93 (2H, s), 4.29 (2H, q, J=7.0), 4.63 (1H, m), 6.72 (2H, dd, J=5.0, 1.5), 6.96 (1H, d, J=9.0), 7.25 (1H, dd, J=9.0, 2.5), 7.43 (1H, d, J=2.5), 8.26 (2H, dd, J=5.0, 1.5).

Reference Example 59

Ethyl N-[3-chloro-4-[1-(4-pyridyl)piperidin-4-yloxy]phenyl]-N-[3-(3-cyanophenyl)-2-(E)-propenyl]sulfamoylacetate To a solution of 3-(3-cyanophenyl)-2-(E)-propen-1-ol (327 mg) obtained in reference example 2, ethyl N-[3-chloro-4-[1-(4-pyridyl)piperidin-4-yloxy]phenyl]sulfamoylacetate (887 mg) obtained in reference example 58 and triphenylphosphine (620 mg) in dichloromethane (20 ml), diethyl azodicarboxylate (0.36 ml) was added dropwise with stirring under ice-cooling, and the resulting mixture was stirred at room temperature overnight and then evaporated in vacuo. The residue obtained was purified by chromatography on a silica gel column using a mixed solvent of dichloromethane and methanol (20:1~10:1) as the eluent to afford the title compound (637 mg, yield: 55%) as a colorless amorphous solid.

$^1$H NMR (500 MHz, CDCl$_3$) δ ppm: 1.36 (3H, t, J=7.0), 1.97–2.07 (4H, m), 3.45 (2H, m), 3.62 (2H, m), 4.00 (2H, s), 4.31 (2H, q, J=7.0), 4.47 (2H, d, J=6.0), 4.65 (1H, m), 6.22 (1H, dt, J=16.0, 6.0), 6.42 (1H, d, J=16.0), 6.70 (2H, d, J=6.5), 6.96 (1H, d, J=9.0), 7.34 (1H, dd, J=9.0, 2.5), 7.41 (1H, t, J=7.5), 7.53 (2H, m), 7.56 (1H, s), 7.56 (1H, d, J=2.5), 8.27 (2H, d, J=6.5).

Reference Example 60

3-Chloro-4-[1-(2-pyrimidyl)piperidin-4-yloxy]nitrobenzene

To a solution of 3-chloro-4-(piperidin-4-yloxy)nitrobenzene (2.50 g) obtained in reference example 8 in ethanol (30 ml) was added 2-chloropyrimidine (1.12 g) at room temperature, and the resulting mixture was stirred at 30° C. for 8 hours. After cooling to room temperature, the crystalline solid separated was collected by filtration to afford a mixture of the title compound and 2-chloropyrimidine. Subsequently, to this mixture was added dichloromethane, and the insoluble material was filtered off. The filtrate was evaporated in vacuo to afford the title compound (1.29 g, yield: 39%) as a pale yellow solid.

$^1$H NMR (500 MHz, CDCl$_3$) δ ppm: 1.90–2.00 (2H, m), 2.00–2.10 (2H, m), 3.92–4.00 (2H, m), 4.00–4.08 (2H, m), 4.82 (1H, m), 6.51 (1H, t, J=5.0), 7.04 (1H, d, J=9.0), 8.16 (1H, dd, J=9.0, 3.0), 8.32 (1H, d, J=3.0), 8.33 (2H, d, J=5.0).

Reference Example 61

3-Chloro-4-[1-(2-pyrimidyl)piperidin-4-yloxy]aniline

To a solution of 3-chloro-4-[1-(2-pyrimidyl)piperidin-4-yloxy]nitrobenzene (1.29 g) obtained in reference example 60 in acetic acid (40 ml) was added tin powder (2.28 g) at room temperature, and the resulting mixture was stirred at room temperature overnight. After stirring, the reaction mixture was filtered, and the filtrate was evaporated in vacuo. The residue obtained was neutralized with a saturated aqueous sodium hydrogencarbonate solution and extracted with ethyl acetate three times. The extract was washed with a saturated sodium chloride solution, dried over anhydrous magnesium sulfate and evaporated in vacuo. The residue obtained was purified by chromatography on a silica gel column using a mixed solvent of ethyl acetate and hexane (2:1) as the eluent to afford the title compound (1.01 g, yield: 86%) as a brown oil.

$^1$H NMR (500 MHz, CDCl$_3$) δ ppm: 1.80–1.90 (2H, m), 1.92–2.02 (2H, m), 3.67 (2H, m), 4.20 (2H, m), 4.37 (1H, m), 6.46 (1H, t, J=4.5), 6.53 (1H, dd, J=8.5, 3.0), 6.74 (1H, d, J=3.0), 6.85 (1H, d, J=8.5), 8.30 (2H, d, J=4.5).

Reference Example 62

Ethyl N-[3-chloro-4-[1-(2-pyrimidyl)piperidin-4-yloxy]phenyl]sulfamoylacetate

To a solution of 3-chloro-4-[1-(2-pyrimidyl)piperidin-4-yloxy]aniline (1.01 g) obtained in reference example 61 in dichloromethane (30 ml) were successively added dropwise ethyl chlorosulfonylacetate (0.47 ml) and pyridine (0.53 ml) with stirring under ice-cooling, and the resulting mixture was stirred at room temperature for 1 hour and then evaporated in vacuo. The residue obtained was neutralized with a saturated aqueous sodium hydrogencarbonate solution and extracted with ethyl acetate. The extract was washed with a saturated sodium chloride solution, dried over anhydrous magnesium sulfate and evaporated in vacuo. The residue obtained was purified by chromatography on a silica gel column using a mixed solvent of hexane and ethyl acetate (2:1~1:1) as the eluent to afford the title compound (1.29 g, yield: 85%) as a pale brown amorphous solid.

$^1$H NMR (500 MHz, CDCl$_3$) δ ppm: 1.34 (3H, t, J=7.0), 1.85–1.95 (2H, m), 1.95–2.05 (2H, m), 3.85 (2H, m), 3.93 (2H, s), 4.09 (2H, m), 4.30 (2H, q, J=7.0), 4.61 (1H, m), 6.48 (1H, t, J=4.5), 6.98 (1H, d, J=9.0), 7.23 (1H, dd, J=9.0, 2.5), 7.41 (1H, d, J=2.5), 8.32 (2H, d, J=4.5).

Reference Example 63

Ethyl N-[3-chloro-4-[1-(2-pyrimidyl)piperidin-4-yloxy]phenyl]-N-[3-(3-cyanophenyl)-2-(E)-propenyl]sulfamoylacetate To a solution of 3-(3-cyanophenyl)-2-(E)-propen-1-ol (0.47 g) obtained in reference example 2, ethyl N-[3-chloro-4-[1-(2-pyrimidyl)piperidin-4-yloxy]phenyl]sulfamoylacetate (1.29 g) obtained in reference example 62 and triphenylphosphine (0.89 g) in dichloromethane (30 ml), diethyl azodicarboxylate (0.52 ml) was added dropwise with stirring under ice-cooling, and the resulting mixture was stirred at room temperature overnight and then evaporated in vacuo. The residue obtained was purified by chromatography on a silica gel column using a mixed solvent of dichloromethane and ethyl acetate (9:1) as the eluent to afford the title compound (1.59 g, yield: 94%) as a colorless amorphous solid.

$^1$H NMR (500 MHz, CDCl$_3$) δ ppm: 1.36 (3H, t, J=7.0), 1.85–1.95 (2H, m), 1.95–2.05 (2H, m), 3.87 (2H, m), 4.00 (2H, s), 4.06 (2H, m), 4.31 (2H, q, J=7.0), 4.47 (2H, d, J=6.5), 4.64 (1H, m), 6.23 (1H, dt, J=16.0, 6.5), 6.43 (1H, d, J=16.0), 6.48(1H, t, J=4.5), 6.98 (1H, d, J=9.0), 7.34 (1H, dd, J=9.0, 2.5), 7.41 (1H, t, J=8.0), 7.50–7.55 (2H, m), 7.55 (1H, d, J=2.5), 7.57 (1H, s), 8.31 (2H, d, J=4.5).

Reference Example 64

3-Chloro-4-[1-(3-pyridylmethyl)piperidin-4-yloxy]nitrobenzene

To a solution of 3-chloro-4-(piperidin-4-yloxy)nitrobenzene (1.00 g) obtained in reference example 8 in N,N-dimethylformamide (20 ml) were added successively 3-(bromomethyl)pyridine hydrobromide (1.08 g) and potassium carbonate (1.08 g) at room temperature, and the resulting mixture was stirred at room temperature for 2 hours. After stirring, the reaction mixture was diluted with ethyl acetate, and the organic layer was washed successively with a saturated aqueous sodium hydrogencarbonate solution and a saturated aqueous sodium chloride solution, dried over anhydrous magnesium sulfate and evaporated in vacuo. The residue obtained was purified by chromatography on a silica gel column using a mixed solvent of dichloromethane and methanol (25:1) as the eluent to afford the title compound (0.98 g, yield: 72%) as a yellow oil.

$^1$H NMR (500 MHz, CDCl$_3$) δ ppm: 1.88–1.98 (2H, m), 1.98–2.08 (2H, m), 2.39–2.49 (2H, m), 2.65–2.75 (2H, m), 3.56 (2H, s), 4.60 (1H, m), 6.97 (1H, d, J=9.0), 7.27 (1H, dd, J=8.0, 5.0), 7.68 (1H, d, J=8.0), 8.12 (1H, dd, J=9.0, 3.0), 8.30 (1H, d, J=3.0), 8.52 (1H, dd, J=5.0, 1.5), 8.56 (1H, d, J=1.5).

Reference Example 65

3-Chloro-4-[1-(3-pyridylmethyl)piperidin-4-yloxy]aniline

To a solution of 3-chloro-4-[1-(3-pyridylmethyl)piperidin-4-yloxy]nitrobenzene (980 mg) obtained in reference example 64 in acetic acid (50 ml) was added tin powder (1670 mg) at room temperature, and the resulting mixture was stirred at room temperature overnight. After stirring, the reaction mixture was filtered, and the filtrate was evaporated in vacuo. The residue obtained was neutralized with a saturated aqueous sodium hydrogencarbonate solution and extracted with ethyl acetate three times. The extract was washed with a saturated sodium chloride solution, dried over anhydrous magnesium sulfate and evaporated in vacuo. The residue obtained was purified by chromatography on a silica gel column using a mixed solvent of dichloromethane and methanol (10:1~5:1) as the eluent to afford the title compound (874 mg, yield: 98%) as a pale yellow oil.

$^1$H NMR (500 MHz, CDCl$_3$) δ ppm: 1.80–1.90 (2H, m), 1.90–2.00 (2H, m), 2.32 (2H, m), 2.76 (2H, m), 3.55 (2H, s), 4.16 (1H, m), 6.51 (1H, dd, J=8.5, 3.0), 6.72 (1H, d, J=3.0), 6.80 (1H, d, J=8.5), 7.27 (1H, m), 7.70 (1H, d, J=7.5), 8.51 (1H, d, J=6.5), 8.55 (1H, s).

Reference Example 66

Ethyl N-[3-chloro-4-[1-(3-pyridylmethyl)piperidin-4-yloxy]phenyl]sulfamoylacetate To a solution of 3-chloro-4-[1-(3-pyridylmethyl)piperidin-4-yloxy]aniline (874 mg) obtained in reference example 65 in dichloromethane (20 ml) were successively added dropwise ethyl chlorosulfonylacetate (0.39 ml) and pyridine (0.44 ml) with stirring under ice-cooling, and the resulting mixture was stirred at room temperature for 3 hour and evaporated in vacuo. The residue obtained was neutralized with a saturated aqueous sodium hydrogencarbonate solution and extracted with ethyl acetate. The extract was washed with a saturated aqueous sodium chloride solution, dried over anhydrous magnesium sulfate and evaporated in vacuo. The residue obtained was purified by chromatography on a silica gel column using a mixed solvent of dichloromethane and methanol (20:1~10:1) as the eluent to afford the title compound (770 mg, yield: 60%) as a yellow amorphous solid.

$^1$H NMR (500 MHz, CDCl$_3$) δ ppm: 1.33 (3H, t, J=7.0), 1.84–1.93 (2H, m), 1.93–2.02 (2H, m), 2.38 (2H, m), 2.72 (2H, m), 3.55 (2H, s), 3.91 (2H, s), 4.29 (2H, q, J=7.0), 4.39 (1H, m), 6.92 (1H, d, J=9.0), 7.20 (1H, dd, J=9.0, 2.5), 7.27 (1H, m), 7.39 (1H, d, J=2.5), 7.69 (1H, d, J=7.5), 8.51 (1H, d, J=3.5), 8.56 (1H, s).

Reference Example 67

Ethyl N-[3-chloro-4-[1-(3-pyridylmethyl)piperidin-4-yloxy]phenyl]-N-[3-(3-cyanophenyl)-2-(E)-propenyl]sulfamoylacetate To a solution of 3-(3-cyanophenyl)-2-(E)-propen-1-ol (275 mg) obtained in reference example 2, ethyl N-[3-chloro-4-[1-(3-pyridylmethyl)piperidin-4-yloxy]phenyl]sulfamoylacetate (770 mg) obtained in reference example 66 and triphenylphosphine (520 mg) in dichloromethane (20 ml), diethyl azodicarboxylate (0.30 ml) was added dropwise with stirring under ice-cooling, and the resulting mixture was stirred at room temperature overnight and then evaporated in vacuo. The residue obtained was purified by chromatography on a silica gel column using a mixed solvent of ethyl acetate and methanol (10:1~5:1) as the eluent to afford the title compound (949 mg, yield: 95%) as a pale yellow amorphous solid.

$^1$H NMR (500 MHz, CDCl$_3$) δ ppm: 1.36 (3H, t, J=7.0), 1.84–1.93 (2H, m), 1.93–2.02 (2H, m), 2.38 (2H, m), 2.70 (2H, m), 3.54 (2H, s), 3.98 (2H, s), 4.31 (2H, q, J=7.0), 4.42 (1H, m), 4.46 (2H, d, J=6.5), 6.22 (1H, dt, J=16.0, 6.5), 6.41 (1H, d, J=16.0), 6.92 (1H, d, J=9.0), 7.26 (1H, dd, J=7.5, 5.0), 7.30 (1H, dd, J=9.0, 2.5), 7.40 (1H, t, J=7.5), 7.48–7.54 (3H, m), 7.55 (1H, s), 7.68 (1H, d, J=7.5), 8.51 (1H, dd, J=5.0, 1.5), 8.55 (1H, d, J=1.5).

Reference Example 68

4-(1-t-Butoxycarbonylpiperidin-4-yloxy)-3-chloroaniline

To a solution of 4-(1-t-butoxycarbonylpiperidin-4-yloxy)-3-chloronitrobenzene (2.40 g) obtained in reference example 3 in acetic acid (50 ml) was added zinc powder (5.60 g) in four portions with stirring at room temperature, and the resulting mixture was stirred at room temperature for 2 hours. After stirring, the reaction mixture was filtered, and the filtrate was evaporated in vacuo. The residue obtained was purified by chromatography on a silica gel column using a mixed solvent of hexane and ethyl acetate (1:1) as the eluent to afford the title compound (1.99 g, yield: 87%) as an orange-colored oil.

$^1$H NMR (500 MHz, CDCl$_3$) δ ppm: 1.47 (9H, s), 1.77 (2H, m), 1.87 (2H, m), 3.31 (2H, m), 3.72 (2H, m), 4.26 (1H, m), 6.52 (1H, dd, J=9.0, 3.0), 6.73 (1H, d, J=3.0), 6.80 (1H, d, J=9.0).

Reference Example 69

Ethyl N-[4-(1-t-butoxycarbonylpiperidin-4-yloxy)-3-chlorophenyl]sulfamoylacetate To a solution of 4-(1-t-butoxycarbonylpiperidin-4-yloxy)-3-chloroaniline (1.50 g) obtained in reference example 68 in dichloromethane (20 ml) were successively added dropwise ethyl chlorosulfonylacetate (0.74 ml) and pyridine (0.56 ml) with stirring under ice-cooling, and the resulting mixture was stirred at room temperature for 5 hours and then evaporated in vacuo. The residue obtained was purified by chromatography on a silica gel column using a mixed solvent of hexane and ethyl acetate (3:2) as the eluent to afford the title compound (1.19 g, yield: 54%) as a pale red oil.

$^1$H NMR (500 MHz, CDCl$_3$) δ ppm: 1.34 (3H, t, J=7.0), 1.47 (9H, s), 1.79–1.92 (4H, m), 3.46 (2H, m), 3.64 (2H, m), 3.92 (2H, s), 4.30 (2H, q, J=7.0), 4.52 (1H, m), 6.94 (1H, d, J=9.0), 7.22 (1H, dd, J=9.0, 2.5), 7.40 (1H, d, J=2.5).

Reference Example 70

Ethyl N-[4-(1-t-butoxycarbonylpiperidin-4-yloxy)-3-chlorophenyl]-N-[3-(3-cyanophenyl)-2-(E)-propenyl]sulfamoylacetate To a solution of 3-(3-cyanophenyl)-2-(E)-propen-1-ol (0.40 g) obtained in reference example 2, ethyl N-[4-(1-t-butoxycarbonylpiperidin-4-yloxy)-3-chlorophenyl]sulfamoylacetate (1.19 g) obtained in reference example 69 and triphenylphosphine (0.79 g) in dichloromethane (20 ml), diethyl azodicarboxylate (0.50 ml) was added dropwise with stirring under ice-cooling, and the resulting mixture was stirred at room temperature overnight and then evaporated in vacuo. The residue obtained was purified by chromatography on a silica gel column using a mixed solvent of dichloromethane and ethyl acetate (10:1) as the eluent to afford the title compound (1.20 g, yield: 78%) as a pale red amorphous solid.

$^1$H NMR (500 MHz, CDCl$_3$) δ ppm: 1.36 (3H, t, J=7.0), 1.47 (9H, s), 1.79–1.92 (4H, m), 3.47 (2H, m), 3.62 (2H, m), 3.99 (2H, s), 4.31 (2H, q, J=7.0), 4.47 (2H, d, J=6.5), 4.55 (1H, m), 6.23 (1H, dt, J=16.0, 6.5), 6.41 (1H, d, J=16.0), 6.94 (1H, d, J=9.0), 7.32 (1H, dd, J=9.0, 3.0), 7.41 (1H, t, J=7.5), 7.50–7.58 (4H, m).

Reference Example 71

Ethyl N-[4-(piperidin-4-yloxy)-3-chlorophenyl]-N-[3-(3-cyanophenyl)-2-(E)-propenyl]sulfamoylacetate To a solution of ethyl N-[4-(1-t-butoxycarbonylpiperidin-4-yloxy)-3-chlorophenyl]-N-[3-(3-cyanophenyl)-2-(E)-propenyl]sulfamoylacetate (1.25 g) obtained in reference example 70 in ethanol (15 ml) was added a 4N solution of hydrogen chloride in dioxane (15 ml) at room temperature, and the resulting mixture was stirred at room temperature for 4 hours and then evaporated in vacuo. Subsequently, the residue obtained was diluted with ethyl acetate, and the organic layer was washed successively with a saturated aqueous sodium hydrogencarbonate solution and a saturated aqueous sodium chloride solution. The organic layer was dried over anhydrous magnesium sulfate and evaporated in vacuo to afford the title compound (1.10 g, quantitative yield) as a pale yellow oil.

$^1$H NMR (500 MHz, CDCl$_3$) δ ppm: 1.36 (3H, t, J=7.0), 1.76–1.88 (2H, m), 2.00–2.10 (2H, m), 2.85 (2H, m), 3.20 (2H, m), 3.99 (2H, s), 4.31 (2H, q, J=7.0), 4.46 (2H, d, J=6.5), 4.50 (1H, m), 6.22 (1H, dt, J=16.0, 6.5), 6.41 (1H, d, J=16.0), 6.93 (1H, d, J=9.0), 7.32 (1H, dd, J=9.0, 2.5), 7.40 (1H, t, J=8.0), 7.49–7.59 (4H, m).

Reference Example 72

Ethyl N-[3-chloro-4-[1-(4-pyridylmethyl)piperidin-4-yloxy]phenyl]-N-[3-(3-cyanophenyl)-2-(E)-propenyl]sulfamoylacetate To a solution of ethyl N-[4-(piperidin-4-yloxy)-3-chlorophenyl]-N-[3-(3-cyanophenyl)-2-(E)-propenyl]sulfamoylacetate (1.10 g) obtained in reference example 71 in N,N-dimethylformamide (30 ml) were added successively 4-(bromomethyl)pyridine hydrobromide (0.59 g) and potassium carbonate (0.59 g) with stirring at room temperature, and the resulting mixture was stirred at room temperature overnight. After stirring, the reaction mixture was diluted with ethyl acetate, and the organic layer was washed with a saturated aqueous sodium chloride solution, dried over anhydrous magnesium sulfate and evaporated in vacuo. The residue obtained was purified by chromatography on a silica gel column using a mixed solvent of ethyl acetate and methanol (10:1) as the eluent to afford the title compound (0.97 g, yield: 75%) as a pale yellow amorphous solid.

$^1$H NMR (500 MHz, CDCl$_3$) δ ppm: 1.36 (3H, t, J=7.0), 1.86–1.95 (2H, m), 1.95–2.04 (2H, m), 2.38 (2H, m), 2.70 (2H, m), 3.53 (2H, s), 3.98 (2H, s), 4.31 (2H, q, J=7.0), 4.43 (1H, m), 4.46 (2H, d, J=6.5), 6.22 (1H, dt, J=16.0, 6.5), 6.41 (1H, d, J=16.0), 6.92 (1H, d, J=9.0), 7.28 (2H, d, J=6.0), 7.31 (1H, dd, J=9.0, 2.5), 7.40 (1H, t, J=8.0), 7.49–7.54 (2H, m), 7.53 (1H, d, J=2.5), 7.55 (1H, s), 8.54 (2H, d, J=6.0).

Reference Example 73

2-(2-Bromoethyl)pyridine

To a solution of 2-pyridineethanol (1.00 ml) in tetrahydrofuran (20 ml) were successively added triphenylphosphine (3.51 g) and carbon tetrabromide (4.44 g) with stirring at room temperature, and the resulting mixture was stirred at room temperature overnight. After stirring, to the reaction mixture was added diethyl ether, and insoluble materials were filtered off, and the organic layer was washed successively with a saturated aqueous sodium hydrogencarbonate solution and a saturated aqueous sodium chloride solution, dried over anhydrous magnesium sulfate and evaporated in vacuo. The residue obtained was purified by chromatography on a silica gel column using a mixed solvent of hexane and ethyl acetate (1:3) as the eluent to afford the title compound (1.30 g, yield: 78%) as a yellow oil.

$^1$H NMR (400 MHz, CDCl$_3$) δ ppm: 3.34 (2H, t, J=7.0), 3.78 (2H, t, J=7.0), 7.15–7.23 (2H, m), 7.64 (1H, m), 8.57 (1H, m).

Reference Example 74

3-Chloro-4-[1-[2-(2-pyridyl)ethyl]piperidin-4-yloxy]nitrobenzene

To a solution of 3-chloro-4-(piperidin-4-yloxy)nitrobenzene (1.50 g) obtained in reference example 8 in N,N-dimethylformamide (30 ml) were added successively 2-(2-bromoethyl)pyridine (1.30 g) obtained in reference example 73 and potassium carbonate (1.21 g) at room temperature, and the resulting mixture was stirred at the same temperature overnight. After stirring, the reaction mixture was diluted with ethyl acetate, and the organic layer was washed with a saturated aqueous sodium chloride solution, dried over anhydrous magnesium sulfate and evaporated in vacuo. The residue obtained was purified by chromatography on a silica gel column using a mixed solvent of dichloromethane and methanol (10:1~5:1) as the eluent to afford the title compound (1.57 g, yield: 74%) as a yellow solid.

$^1$H NMR (500 MHz, CDCl$_3$) δ ppm: 1.89–2.00 (2H, m), 2.00–2.11 (2H, m), 2.52 (2H, m), 2.75–2.85 (2H, m), 2.83 (2H, m), 3.01 (2H, m), 4.59 (1H, m), 6.99 (1H, d, J=9.0), 7.13 (1H, dd, J=7.5, 5.0), 7.20 (1H, d, J=8.0), 7.61 (1H, m), 8.13 (1H, dd, J=9.0, 3.0), 8.30 (1H, d, J=3.0), 8.53 (1H, d, J=5.0).

Reference Example 75

3-Chloro-4-[1-[2-(2-pyridyl)ethyl]piperidin-4-yloxy]aniline

To a solution of 3-chloro-4-[1-[2-(2-pyridyl)ethyl]piperidin-4-yloxy]nitrobenzene (1.57 g) obtained in reference example 74 in acetic acid (50 ml) was added tin powder (2.58 g) at room temperature, and the resulting mixture was stirred at room temperature overnight. After stirring, the reaction mixture was filtered, and the filtrate was evaporated in vacuo. The residue obtained was neutralized with a saturated aqueous sodium hydrogencarbonate solution and extracted with ethyl acetate three times. The extract was washed with a saturated aqueous sodium chloride solution, dried over anhydrous magnesium sulfate and evaporated in vacuo. The residue obtained was purified by chromatography on a silica gel column using a mixed solvent of dichloromethane and methanol (5:1~1:1) as the eluent to afford the title compound (1.26 g, yield: 87%) as a pale yellow amorphous solid.

$^1$H NMR (500 MHz, CDCl$_3$) δ ppm: 1.82–1.94 (2H, m), 1.94–2.06 (2H, m), 2.40 (2H, m), 2.81 (2H, m), 2.89 (2H, m), 3.02 (2H, m), 4.15 (1H, m), 6.51 (1H, dd, J=8.5, 3.0), 6.73 (1H, d, J=3.0), 6.81 (1H, d, J=8.5), 7.12 (1H, dd, J=7.5, 5.0), 7.20 (1H, d, J=8.0), 7.60 (1H, m), 8.52 (1H, d, J=5.0).

Reference Example 76

Ethyl N-[3-chloro-4-[1-[2-(2-pyridyl)ethyl]piperidin-4-yloxy]phenyl]sulfamoylacetate To a solution of 3-chloro-4-[1-[2-(2-pyridyl)ethyl]piperidin-4-yloxy]aniline (1.26 g) obtained in reference example 75 in dichloromethane (30 ml) were successively added dropwise ethyl chlorosulfonylacetate (0.54 ml) and pyridine (0.61 ml) with stirring under ice-cooling, and the resulting mixture was stirred at room temperature for 2 hours and evaporated in vacuo. The residue obtained was neutralized with a saturated aqueous sodium hydrogencarbonate solution and extracted with ethyl acetate three times, and the extract was dried over anhydrous magnesium sulfate and evaporated in vacuo. The residue obtained was purified by chromatography on a silica gel column using a mixed solvent of dichloromethane and methanol (10:1~5:1) as the eluent to afford the title compound (1.50 g, yield: 82%) as a pale yellow amorphous solid.

$^1$H NMR (500 MHz, CDCl$_3$) δ ppm: 1.33 (3H, t, J=7.0), 1.86–1.97 (2H, m), 1.97–2.08 (2H, m), 2.50 (2H, m), 2.77–2.92 (4H, m), 3.03 (2H, m), 3.92 (2H, s), 4.29 (2H, q, J=7.0), 4.40 (1H, m), 6.93 (1H, d, J=9.0), 7.13 (1H, m), 7.21 (1H, dd, J=9.0, 2.5), 7.17–7.24 (1H, m), 7.40 (1H, d, J=2.5), 7.61 (1H, m), 8.53 (1H, d, J=5.0).

Reference Example 77

Ethyl N-[3-chloro-4-[1-[2-(2-pyridyl)ethyl]piperidin-4-yloxy]phenyl]-N-[3-(3-cyanophenyl)-2-(E)-propenyl]sulfamoylacetate To a solution of 3-(3-cyanophenyl)-2-(E)-propen-1-ol (0.52 g) obtained in reference example 2, ethyl N-[3-chloro-4-[1-[2-(2-pyridyl)ethyl]piperidin-4-yloxy]phenyl]sulfamoylacetate (1.50 g) obtained in reference example 76 and triphenylphosphine (0.98 g) in dichloromethane (40 ml), diethyl azodicarboxylate (0.57 ml) was added dropwise with stirring under ice-cooling, and the resulting mixture was stirred at room temperature overnight and then evaporated in vacuo. The residue obtained was purified by chromatography on a silica gel column using a mixed solvent of dichloromethane and methanol (30:1~10:1) as the eluent to afford the title compound (1.73 g, yield: 89%) as a pale yellow amorphous solid.

$^1$H NMR (500 MHz, CDCl$_3$) δ ppm: 1.36 (3H, t, J=7.0), 1.86–1.98 (2H, m), 1.98–2.10 (2H, m), 2.51 (2H, m), 2.78–2.92 (4H, m), 3.03 (2H, m), 3.99 (2H, s), 4.31 (2H, q, J=7.0), 4.43 (1H, m), 4.46 (2H, d, J=6.5), 6.22 (1H, dt, J=16.0, 6.5), 6.41 (1H, d, J=16.0), 6.93 (1H, d, J=9.0), 7.12 (1H, m), 7.20 (1H, d, J=8.0), 7.31 (1H, dd, J=9.0, 2.5), 7.40 (1H, t, J=8.0), 7.49–7.55 (3H, m), 7.56 (1H, s), 7.60 (1H, m), 8.53 (1H, d, J=4.5).

Reference Example 78

3-Chloro-4-(1-cyclopentylpiperidin-4-yloxy)nitrobenzene

To a solution of 3-chloro-4-(piperidin-4-yloxy)nitrobenzene (4.00 g) obtained in reference example 8 in N,N-dimethylformamide (70 ml) were added successively cyclopentyl bromide (1.96 ml) and potassium carbonate (3.23 g) at room temperature, and the resulting mixture was stirred at 100° C. for 7 hours. Because of the slow progress of the reaction, cyclopentyl bromide (0.70 ml) was added, and the resulting mixture was stirred furthermore at 100° C. for 2 hours and then at 120° C. for 5 hours. After cooling to room temperature, the reaction mixture was diluted with ethyl acetate, and the organic layer was washed with a saturated aqueous sodium chloride solution, dried over anhydrous magnesium sulfate and evaporated in vacuo. The residue obtained was purified by chromatography on a silica gel column using a mixed solvent of dichloromethane and methanol (30:1~10:1) as the eluent to afford the title compound (2.35 g, yield: 46%) as a brown oil.

$^1$H NMR (500 MHz, CDCl$_3$) δ ppm: 1.37–1.48 (2H, m), 1.50–1.61 (2H, m), 1.65–1.76 (2H, m), 1.85–2.00 (4H, m), 2.00–2.10 (2H, m), 2.50 (2H, m), 2.57 (1H, m), 2.75 (2H, m), 4.59 (1H, m), 6.98 (1H, d, J=9.0), 8.13 (1H, dd, J=9.0, 3.0), 8.30 (1H, d, J=3.0).

Reference Example 79

3-Chloro-4-(1-cyclopentylpiperidin-4-yloxy)aniline

To a solution of 3-chloro-4-(1-cyclopentylpiperidin-4-yloxy)nitrobenzene (2.35 g) obtained in reference example 78 in acetic acid (50 ml) was added tin powder (4.29 g) at room temperature, and the resulting mixture was stirred at room temperature overnight. After stirring, the reaction mixture was filtered, and the filtrate was evaporated in vacuo. Subsequently, to the residue obtained was added a saturated aqueous sodium hydrogencarbonate solution, and the resulting mixture was extracted with ethyl acetate five times. The extract was washed with a saturated sodium chloride solution, dried over anhydrous magnesium sulfate and evaporated in vacuo. The residue obtained was purified by chromatography on a silica gel column using a mixed solvent of dichloromethane and methanol (5:1~1:1) as the eluent to afford the title compound (1.97 g, yield: 92%) as a pale brown amorphous solid.

$^1$H NMR (500 MHz, CDCl$_3$) δ ppm: 1.48–1.61 (2H, m), 1.61–1.78 (4H, m), 1.86–2.02 (4H, m), 2.06–2.19 (2H, m), 2.76 (2H, m), 2.85 (1H, m), 2.94 (2H, m), 4.29 (1H, m), 6.52 (1H, dd, J=8.5, 2.5), 6.73 (1H, d, J=2.5), 6.79 (1H, d, J=8.5).

Reference Example 80

Ethyl N-[3-chloro-4-(1-cyclopentylpiperidin-4-yloxy) phenyl]sulfamoylacetate

To a solution of 3-chloro-4-(1-cyclopentylpiperidin-4-yloxy)aniline (1.97 g) obtained in reference example 79 in dichloromethane (40 ml) were successively added dropwise ethyl chlorosulfonylacetate (0.94 ml) and pyridine (1.08 ml) with stirring under ice-cooling, and the resulting mixture was stirred at room temperature for 3 hours and evaporated in vacuo. The residue obtained was diluted with ethyl acetate, and the organic layer was washed successively with a saturated aqueous sodium hydrogencarbonate solution and a saturated aqueous sodium chloride solution, dried over anhydrous magnesium sulfate and evaporated in vacuo. The residue obtained was purified by chromatography on a silica gel column using a mixture of dichloromethane and methanol (25:1~10:1) as the eluent to afford the title compound (1.09 g, yield: 37%) as a pale brown amorphous solid.

$^1$H NMR (500 MHz, CDCl$_3$) δ ppm: 1.33 (3H, t, J=7.0), 1.38–1.62 (4H, m), 1.62–1.77 (2H, m), 1.80–1.96 (4H, m), 1.96–2.09 (2H, m), 2.47 (2H, m), 2.59 (1H, m), 2.79 (2H, m), 3.92 (2H, s), 4.29 (2H, q, J=7.0), 4.39 (1H, m), 6.92 (1H, d, J=9.0), 7.20 (1H, dd, J=9.0, 2.5), 7.39 (1H, d, J=2.5).

Reference Example 81

Ethyl N-[3-chloro-4-(1-cyclopentylpiperidin-4-yloxy) phenyl]-N-[3-(3-cyanophenyl)-2-(E)-propenyl]sulfamoylacetate To a solution of 3-(3-cyanophenyl)-2-(E)-propen-1-ol (0.39 g) obtained in reference example 2, ethyl N-[3-chloro-4-(1-cyclopentylpiperidin-4-yloxy)phenyl]sulfamoylacetate (1.09 g) obtained in reference example 80 and triphenylphosphine (0.77 g) in dichloromethane (30 ml), diethyl azodicarboxylate (0.45 ml) was added dropwise with stirring under ice-cooling, and the resulting mixture was stirred at room temperature overnight and then evaporated in vacuo. The residue obtained was purified by chromatography on a silica gel column using a mixed solvent of ethyl acetate and methanol (10:1~5:1) as the eluent to afford the title compound (1.30 g, yield: 91%) as a yellowish brown amorphous solid.

$^1$H NMR (500 MHz, CDCl$_3$) δ ppm: 1.36 (3H, t, J=7.0), 1.40–1.61 (4H, m), 1.64–1.80 (2H, m), 1.83–1.99 (4H, m), 1.99–2.14 (2H, m), 2.40–2.68 (3H, m), 2.68–2.87 (2H, m), 3.99 (2H, s), 4.31 (2H, q, J=7.0), 4.46 (1H, m), 4.46 (2H, d, J=6.5), 6.22 (1H, dt, J=16.0, 6.5), 6.41 (1H, d, J=16.0), 6.92 (1H, d, J=9.0), 7.31 (1H, dd, J=9.0, 2.5), 7.40 (1H, t, J=8.0), 7.48–7.55 (3H, m), 7.56 (1H, s).

Reference Example 82

1-t-Butoxycarbonyl-2-methyl-4-piperidone ethylene ketal

To a solution of 4-piperidone ethylene ketal (9.6 g) in acetone (100 ml) was added di-t-butyl dicarbonate (16.0 g) with stirring under ice-cooling, and the resulting mixture was stirred at room temperature for 1 hour and then evaporated in vacuo. The residue obtained was diluted with diethyl ether, and the organic layer was washed successively with water and a saturated aqueous sodium chloride solution. The organic layer was dried over anhydrous magnesium sulfate and evaporated in vacuo to afford 1-t-butoxycarbonyl-4-piperidone ethylene ketal (17.4 g) as a pale yellow solid.

Subsequently, to a solution of 1-t-butoxycarbonyl-4-piperidone ethylene ketal obtained above in diethyl ether (200 ml) were successively added dropwise N,N,N',N'-tetramethylethylenediamine (13.0 ml) and a 1N solution of s-butyllithium in a mixture of cyclohexane and hexane (88.0 ml) with stirring at −78° C., and the resulting mixture was stirred at at −30° C. for 30 minutes. After cooling to −78° C. again, to the reaction mixture was added methyl iodide with stirring, and the resulting mixture was stirred at room temperature for 3 hours. After stirring, water was poured gradually into the reaction mixture, and the resulting mixture was extracted with diethyl ether. The extract was washed successively with water and a saturated sodium chloride solution, dried over anhydrous magnesium sulfate and evaporated in vacuo. The residue obtained was purified by chromatography on a silica gel column using a mixed solvent of hexane and ethyl acetate (9:1) as the eluent to afford the title compound (6.0 g, yield: 34%) as a colorless oil.

$^1$H NMR (500 MHz, CDCl$_3$) δ ppm: 1.23 (3H, d, J=7.0), 1.46 (9H, s), 1.55–1.70 (4H, m), 1.85–1.90 (1H, m), 3.05–3.15 (1H, m), 3.90–4.05 (4H, m), 4.47 (1H, m).

Reference Example 83

1-t-Butoxycarbonyl-2-methyl-4-piperidone

To a solution of 1-t-butoxycarbonyl-2-methyl-4-piperidone ethylene ketal (6.00 g) obtained in reference example 82 in acetone (150 ml) was added p-toluenensulfonic acid monohydrate (4.40 g) with stirring under ice-cooling, and the resulting mixture was stirred at room temperature overnight. After stirring, the reaction mixture was diluted with ethyl acetate, and the organic layer was washed successively with a saturated sodium hydrogencarbonate solution and a saturated aqueous sodium chloride solution. The organic layer was dried over anhydrous magnesium sulfate and evaporated in vacuo to afford the title compound (2.40 g, yield: 48%) as a yellow oil.

$^1$H NMR (500 MHz, CDCl$_3$) δ ppm: 1.18 (3H, d, J=7.0), 1.49 (9H, s), 2.20–2.30 (1H, m), 2.30–2.40 (1H, m), 2.45–2.55 (1H, m), 2.65–2.70 (1H, m), 3.25–3.35 (1H, m), 3.90–4.05 (1H, m), 4.20–4.30 (1H, m).

Reference Example 84

1-t-Butoxycarbonyl-4-hydroxy-2-methylpiperidine

To a suspension of lithium aluminum hydride (1.30 g) in tetrahydrofuran (50 ml) was added dropwise 1-t-butoxycarbonyl-2-methyl-4-piperidone (2.40 g) obtained in reference example 83 with stirring under ice-cooling in a nitrogen atmosphere, and the resulting mixture was stirred at room temperature for 1 hour under a nitrogen atmosphere. After stirring, to the reaction mixture was added sodium sulfate decahydrate, and the resulting mixture was furthermore stirred at room temperature for 1 hour. After removing insoluble materials by filtration, the filtrate was evaporated in vacuo. The residue obtained was purified by chromatography on a silica gel column using a mixed solvent of hexane and ethyl acetate (1:1) as the eluent to afford a low polar compound (0.95 g, yield: 39%) and a high polar compound (1.02 g, yield: 42%) of the title compound, separately, as yellow oily products.

High polar compound; $^1$H NMR (500 MHz, CDCl$_3$) δ ppm: 1.14 (3H, d, J=7.0), 1.30–1.40 (1H, m), 1.45–1.55 (1H, m), 1.46 (9H, s), 1.80–1.85 (1H, m), 1.90–1.95 (1H, m), 2.85–2.95 (1H, m), 3.90–4.00 (1H, m), 4.00–4.10 (1H, m), 4.45–4.55 (1H, m).

Low polar compound; $^1$H NMR (500 MHz, CDCl$_3$) δ ppm: 1.33 (3H, d, J=7.0), 1.46 (9H, s), 1.60–1.75 (3H, m), 1.80–1.90 (1H, m), 3.20–3.30 (1H, m), 3.80–3.85 (1H, m), 4.15–4.20 (1H, m), 4.25–4.35 (1H, m).

Reference Example 85

4-(1-t-Butoxycarbonyl-2-methylpiperidin-4-yloxy)-3-chloronitrobenzene

To a solution of the high polar compound of 1-t-butoxycarbonyl-4-hydroxy-2-methylpiperidine (1.02 g) obtained in reference example 84, 2-chloro-4-nitrophenol (0.83 g) and triphenylphosphine (1.62 g) in dichloromethane (60 ml), diethyl azodicarboxylate (0.97 ml) was added dropwise with stirring under ice-cooling, and the resulting mixture was stirred at room temperature for 8 hours. Because of the slow progress of the reaction, to the reaction mixture were successively added triphenylphosphine (1.62 g) and diethyl azodicarboxylate (0.97 ml), and the resulting mixture was stirred at room temperature overnight and then evaporated in vacuo. The residue obtained was purified by chromatography on a silica gel column using a mixed solvent of hexane and ethyl acetate (4:1) as the eluent to afford the title compound (1.15 g, yield: 76%) as a yellow oil.

$^1$H NMR (500 MHz, CDCl$_3$) δ ppm: 1.35 (3H, d, J=7.0), 1.48 (9H, s), 1.75–1.85 (1H, m), 1.95–2.05 (3H, m), 3.25–3.35 (1H, m), 3.90–4.00 (1H, m), 4.35–4.45 (1H, m), 4.87 (1H, m), 6.97 (1H, d, J=9.0), 8.15 (1H, dd, J=9.0, 2.5), 8.32 (1H, d, J=2.5).

Reference Example 86

3-Chloro-4-(1,2-dimethylpiperidin-4-yloxy)nitrobenzene

To a suspension of 4-(1-t-butoxycarbonyl-2-methylpiperidin-4-yloxy)-3-chloronitrobenzene (1.15 g) obtained in reference example 85 in 90% formic acid (3.10 g) was added 37% formaldehyde (2.50 g), and the resulting mixture was stirred at 100° C. for 2 hours. After cooling to room temperature, the reaction mixture was neutralized with an aqueous potassium carbonate solution and extracted with ethyl acetate. The extract was washed with a saturated aqueous sodium chloride solution, dried over anhydrous magnesium sulfate and evaporated in vacuo. The residue obtained was purified by chromatography on a silica gel column using a mixed solvent of dichloromethane and methanol (9:1) as the eluent to afford the title compound (0.80 g, yield: 90%) as a yellow oil.

$^1$H NMR (500 MHz, CDCl$_3$) δ ppm: 1.18 (3H, d, J=6.0), 1.64 (1H, m), 1.85–1.95 (1H, m), 2.05–2.25 (4H, m), 2.32 (3H, s), 3.00 (1H, m), 4.39 (1H, m), 6.99 (1H, d, J=9.0), 8.12 (1H, dd, J=9.0, 2.5), 8.30 (1H, d, J=2.5).

Reference Example 87

3-Chloro-4-(1,2-dimethylpiperidin-4-yloxy)aniline

To a solution of 3-chloro-4-(1,2-dimethylpiperidin-4-yloxy)nitrobenzene (800 mg) obtained in reference example 86 in acetic acid (20 ml) was added tin powder (1700 mg) with stirring at room temperature, and the resulting mixture was stirred at room temperature for 4 hours. After stirring, the reaction mixture was filtered, and the filtrate was evaporated in vacuo. Subsequently, to the residue obtained was added a saturated aqueous potassium carbonate solution, and the resulting mixture was extracted with ethyl acetate. The extract was washed with a saturated sodium chloride solution, dried over anhydrous magnesium sulfate and evaporated in vacuo to afford the title compound (690 mg, yield: 96%) as a reddish brown oil.

$^1$H NMR (500 MHz, CDCl$_3$) δ ppm: 1.13 (3H, d, J=6.0), 1.52 (1H, m), 1.75–1.85 (1H, m), 1.90–2.15 (4H, m), 2.27 (3H, s), 2.93 (1H, m), 3.95 (1H, m), 6.50 (1H, dd, J=8.5, 3.0), 6.72 (1H, d, J=3.0), 6.83 (1H, d, J=8.5).

Reference Example 88

Ethyl N-[3-chloro-4-(1,2-dimethylpiperidin-4-yloxy)phenyl]sulfamoylacetate

To a solution of 3-chloro-4-(1,2-dimethylpiperidin-4-yloxy)aniline (690 mg) obtained in reference example 87 in dichloromethane (20 ml) were successively added dropwise ethyl chlorosulfonylacetate (0.40 ml) and pyridine (0.25 ml) with stirring under ice-cooling, and the resulting mixture was stirred at room temperature for 1 hour and evaporated in vacuo. The residue obtained was purified by chromatography on a silica gel column using a mixed solvent of dichloromethane and methanol (9:1~3:1) as the eluent to afford the title compound (800 mg, yield: 73%) as a yellow amorphous solid.

$^1$H NMR (500 MHz, CDCl$_3$) δ ppm: 1.18 (3H, t, J=7.0), 1.26 (3H, m), 1.55–1.70 (1H, m), 1.75–1.90 (1H, m), 2.15–2.30 (2H, m), 2.55–2.75 (3H, m), 2.80–3.30 (3H, m), 4.11 (2H, q, J=7.0), 4.20 (2H, s), 4.45–4.55 (1H, m), 7.17 (1H, dd, J=9.0, 2.5), 7.27 (1H, d, J=9.0), 7.29 (1H, d, J=2.5).

Reference Example 89

Ethyl N-[3-chloro-4-(1,2-dimethylpiperidin-4-yloxy)phenyl]-N-[3-(3-cyanophenyl)-2-(E)-propenyl]sulfamoylacetate To a solution of 3-(3-cyanophenyl)-2-(E)-propen-1-ol (320 mg) obtained in reference example 2, ethyl N-[3-chloro-4-(1,2-dimethylpiperidin-4-yloxy)phenyl]sulfamoylacetate (800 mg) obtained in reference example 88 and triphenylphosphine (680 mg) in dichloromethane (20 ml), diethyl azodicarboxylate (0.40 ml) was added dropwise with stirring under ice-cooling, and the resulting mixture was stirred at room temperature for 4 hours and then evaporated in vacuo. The residue obtained was purified by chromatography on a silica gel column (eluent: mixed solvent of dichloromethane and ethyl acetate (4:1)~mixed solvent of dichloromethane and methanol (9:1)) to afford the title compound (1100 mg, quantitative yield) as a yellow amorphous solid.

$^1$H NMR (500 MHz, CDCl$_3$) δ ppm: 1.14 (3H, d, J=6.0), 1.36 (3H, t, J=7.0), 1.50–1.65 (1H, m), 1.75–1.90 (1H, m), 1.95–2.20 (4H, m), 2.29 (3H, s), 2.95 (1H, m), 3.98 (2H, s), 4.21 (1H, m), 4.31 (2H, q, J=7.0), 4.46 (2H, d, J=6.5), 6.22

(1H, dt, J=16.0, 6.5), 6.41 (1H, d, J=16.0), 6.94 (1H, m), 7.31 (1H, m), 7.40 (1H, m), 7.45–7.50 (1H, m), 7.50–7.60 (2H, m), 7.65–7.70 (1H, m).

Reference Example 90

Indolizin-7-ol

To a suspension of lithium aluminum hydride (2.30 g) in tetrahydrofuran (50 ml) was added dropwise indolizin-7-one (2.80 g), which was prepared from 4,4-diethoxybutylamine and diethyl 1,3-acetonedicarboxylate according to the method described in Heterocycles, 43, 1391 (1996), with stirring under ice-cooling under a nitrogen atmosphere, and the resulting mixture was stirred at the same temperature for 1 hour. After stirring, to the reaction mixture was added sodium sulfate decahydrate, and the resulting mixture was furthermore stirred at room temperature for 1 hour. After removing insoluble materials by filtration, the filtrate was evaporated in vacuo. The residue obtained was purified by chromatography on a silica gel column using a mixed solvent of dichloromethane and methanol (4:1) as the eluent to afford the title compound (1.70 g, yield: 59%) as a yellow oil.

$^1$H NMR (500 MHz, CDCl$_3$) δ ppm: 1.24 (1H, m), 1.40–1.50 (1H, m), 1.55–1.80 (2H, m), 1.80–2.00 (4H, m), 2.00–2.15 (3H, m), 3.00–3.15 (2H, m), 3.65 (1H, m).

Reference Example 91

3-Chloro-4-methoxymethoxyaniline

To a solution of 2-chloro-4-nitrophenol (5.2 g) in N,N-dimethylformamide (50 ml) were successively added methoxymethyl chloride (2.7 ml) and triethylamine (5.0 ml) with stirring under ice-cooling, and the resulting mixture was stirred at room temperature for 1 hour. After stirring, to the reaction mixture was added water, and the resulting mixture was extracted with ethyl acetate. The extract was washed successively with water and a saturated aqueous sodium chloride solution, dried over anhydrous magnesium sulfate and evaporated in vacuo to afford 3-chloro-4-methoxymethoxynitrobenzene (8.1 g) as a yellow oil.

Subsequently, to a solution of 3-chloro-4-methoxymethoxynitrobenzene obtained above in a mixed solvent of acetone (100 ml) and water (100 ml) were added successively zinc powder (9.8 g) and ammonium chloride (8.0 g) with stirring at room temperature, and the resulting mixture was stirred at 60° C. for 40 minutes. After stirring, the reaction mixture was filtered, and the filtrate was evaporated in vacuo and then the residue obtained was extracted with ethyl acetate. The extract was washed with a saturated aqueous sodium chloride solution, dried over anhydrous magnesium sulfate and evaporated in vacuo to afford the title compound (5.4 g, yield: 96%) as a yellow oil.

$^1$H NMR (500 MHz, CDCl$_3$) δ ppm: 3.53 (3H, s), 5.11 (2H, s), 6.52 (1H, dd, J=8.5, 3.0), 6.73 (1H, d, J=3.0), 6.98 (1H, d, J=8.5).

Reference Example 92

Ethyl N-(3-chloro-4-methoxymethoxyphenyl)sulfamoylacetate

To a solution of 3-chloro-4-methoxymethoxyaniline (5.4 g) obtained in reference example 91 in dichloromethane (50 ml) were successively added dropwise ethyl chlorosulfonylacetate (4.7 ml) and pyridine (2.9 ml) with stirring under ice-cooling, and the resulting mixture was stirred at room temperature for 30 minutes. After stirring, to the reaction mixture was added water, and the resulting mixture was extracted with ethyl acetate. The extract was washed successively with water and a saturated aqueous sodium chloride solution, dried over anhydrous magnesium sulfate and evaporated in vacuo. The residue obtained was purified by chromatography on a silica gel column using a mixed solvent of dichloromethane and methanol (19:1) as the eluent to afford the title compound (8.0 g, yield: 82%) as a reddish brown oil.

$^1$H NMR (500 MHz, CDCl$_3$) δ ppm: 1.34 (3H, t, J=7.0), 3.52 (3H, s), 3.92 (2H, s), 4.30 (2H, q, J=7.0), 5.24 (2H, s), 7.15–7.25 (2H, m), 7.41 (1H, m).

Reference Example 93

Ethyl N-[3-chloro-4-methoxymethoxyphenyl]-N-[3-(3-cyanophenyl)-2-(E)-propenyl]sulfamoylacetate To a solution of 3-(3-cyanophenyl)-2-(E)-propen-1-ol (1.6 g) obtained in reference example 2, ethyl N-(3-chloro-4-methoxymethoxyphenyl)sulfamoylacetate (3.4 g) obtained in reference example 92 and triphenylphosphine (3.2 g) in dichloromethane (50 ml), diethyl azodicarboxylate (1.9 ml) was added dropwise with stirring under ice-cooling, and the resulting mixture was stirred at room temperature for 40 minutes and then evaporated in vacuo. The residue obtained was purified by chromatography on a silica gel column using a mixed solvent of dichloromethane and ethyl acetate (19:1) as the eluent to afford the title compound (3.9 g, yield: 81%) as a yellow oil.

$^1$H NMR (500 MHz, CDCl$_3$) δ ppm: 1.36 (3H, t, J=7.0), 3.51 (3H, s), 3.99 (2H, s), 4.31 (2H, q, J=7.0), 4.47 (2H, d, J=6.5), 5.25 (2H, s), 6.22 (1H, dt, J=15.5, 6.5), 6.42 (1H, d, J=15.5), 7.20 (1H, m), 7.34 (1H, m), 7.41 (1H, m), 7.50–7.60 (4H, m).

Reference Example 94

Ethyl N-[3-chloro-4-hydroxyphenyl]-N-[3-(3-cyanophenyl)-2-(E)-propenyl]sulfamoylacetate To a solution of ethyl N-[3-chloro-4-methoxymethoxyphenyl]-N-[3-(3-cyanophenyl)-2-(E)-propenyl]sulfamoylacetate (3.9 g) obtained in reference example 93 in a mixed solvent of ethyl acetate (50 ml) and dioxane (50 ml) was added a 4N solution of hydrogen chloride in dioxane (25 ml) with stirring under ice-cooling, and the resulting mixture was stirred at room temperature overnight. After stirring, the reaction mixture was neutralized with an aqueous sodium hydrogencarbonate solution and extracted with ethyl acetate. The extract was washed successively with water and a saturated aqueous sodium chloride solution, dried over anhydrous magnesium sulfate and evaporated in vacuo to afford the title compound (3.6 g, quantitative yield) as a yellow oil.

$^1$H NMR (500 MHz, CDCl$_3$) δ ppm: 1.36 (3H, t, J=7.0), 3.98 (2H, s), 4.31 (2H, q, J=7.0), 4.46 (2H, d, J=6.5), 6.22 (1H, dt, J=16.0, 6.5), 6.40 (1H, d, J=16.0), 7.03 (1H, m), 7.32 (1H, m), 7.41 (1H, m), 7.50–7.60 (4H, m).

Reference Example 95

Ethyl N-[3-chloro-4-(indolizin-7-yloxy)phenyl]-N-[3-(3-cyanophenyl)-2-(E)-propenyl]sulfamoylacetate To a solution of ethyl N-[3-chloro-4-hydroxyphenyl]-N-[3-(3-cyanophenyl)-2-(E)-propenyl]sulfamoylacetate (2.0 g) obtained in reference example 94, indolizin-7-ol (1.7 g) obtained in reference example 90 and triphenylphosphine (3.2 g) in dichloromethane (60 ml), diethyl azodicarboxylate (1.9 ml) was added dropwise with stirring under ice-cooling, and the resulting mixture was stirred at room temperature for 6 hours. Because of the slow progress of the reaction, to the reaction mixture were furthermore added successively triphenylphosphine (3.2 g) and diethyl azodicarboxylate (1.9 ml), and the resulting mixture was stirred at room temperature overnight and then evaporated in vacuo. The residue obtained was purified by chromatography on a silica gel column using a mixed solvent of ethyl acetate and methanol (2:1) as the eluent to afford the title compound (0.6 g) containing impurities as an orange-colored oil.

Reference Example 96

Ethyl N-(4-methoxymethoxyphenyl)sulfamoylacetate

To a solution of 4-methoxymethoxyaniline (20.9 g) in dichloromethane (400 ml) were successively added dropwise ethyl chlorosulfonylacetate (18.0 ml) and pyridine (33 ml) with stirring under ice-cooling, and the resulting mixture was stirred at room temperature overnight. After stirring, to the reaction mixture was added water, and the resulting mixture was extracted with ethyl acetate. The extract was washed with a saturated aqueous sodium chloride solution, dried over anhydrous magnesium sulfate and evaporated in vacuo. The residue obtained was purified by chromatography on a silica gel column using a mixed solvent of hexane and ethyl acetate (3:2) as the eluent to afford the title compound (28.0 g, yield: 67%) as a brown oil.

$^1$H NMR (500 MHz, CDCl$_3$) δ ppm: 1.33 (3H, t, J=7.0), 3.48 (3H, s), 3.90 (2H, s), 4.29 (2H, q, J=7.0), 5.16 (2H, s), 7.03 (2H, d, J=9.0), 7.28 (2H, d, J=9.0).

Reference Example 97

Ethyl N-[3-(3-cyanophenyl)-2-(E)-propenyl]-N-(4-methoxymethoxyphenyl)sulfamoylacetate To a solution of 3-(3-cyanophenyl)-2-(E)-propen-1-ol (0.53 g) obtained in reference example 2, ethyl N-(4-methoxymethoxyphenyl)sulfamoylacetate (1.00 g) obtained in reference example 96 and triphenylphosphine (1.12 g) in dichloromethane (30 ml), diethyl azodicarboxylate (0.66 ml) was added dropwise with stirring under ice-cooling, and the resulting mixture was stirred at room temperature for 3.5 hours and then evaporated in vacuo. The residue obtained was purified by chromatography on a silica gel column using a mixed solvent of hexane and ethyl acetate (3:2) as the eluent to afford the title compound (1.38 g, yield: 94%) as a yellow oil.

$^1$H NMR (270 MHz, CDCl$_3$) δ ppm: 1.37 (3H, t, J=7.0), 3.48 (3H, s), 3.99 (2H, s), 4.32 (2H, q, J=7.0), 4.49 (2H, d, J=6.0), 5.18 (2H, s), 6.25 (1H, dt, J=16.0, 6.0), 6.42 (1H, d, J=16.0), 7.06 (2H, d, J=9.0), 7.40 (1H, t, J=7.0), 7.41 (2H, d, J=9.0), 7.52 (1H, d, J=7.0), 7.54 (1H, d, J=7.0), 7.56 (1H, s).

Reference Example 98

Ethyl N-[3-(3-cyanophenyl)-2-(E)-propenyl]-N-(4-hydroxyphenyl)sulfamoylacetate

To a solution of ethyl N-[3-(3-cyanophenyl)-2-(E)-propenyl]-N-(4-methoxymethoxyphenyl)sulfamoylacetate (10.7 g) obtained in reference example 97 in ethyl acetate (120 ml) was added a 4N solution of hydrogen chloride in ethyl acetate (80 ml) with stirring under ice-cooling, and the resulting mixture was stirred at room temperature for 4 hours and then evaporated in vacuo. The residue obtained was diluted with ethyl acetate, and the organic layer was washed successively with water and a saturated aqueous sodium chloride solution, dried over anhydrous magnesium sulfate and evaporated in vacuo. The residue obtained was purified by chromatography on a silica gel column using a mixed solvent of hexane and ethyl acetate (1:1) as the eluent to afford the title compound (9.1 g, yield: 95%) as a yellow oil.

$^1$H NMR (270 MHz, CDCl$_3$) δ ppm: 1.35 (3H, t, J=7.0), 3.98 (2H, s), 4.30 (2H, q, J=7.0), 4.46 (2H, d, J=6.0), 6.23 (1H, dt, J=16.0, 6.0), 6.39 (1H, d, J=16.0), 6.84 (2H, d, J=9.0), 7.34 (2H, d, J=9.0), 7.39 (1H, t, J=7.5), 7.50 (2H, m), 7.54 (1H, s).

Reference Example 99

Ethyl N-[3-(3-cyanophenyl)-2-(E)-propenyl]-N-[4-(1-methylpiperidin-4-yloxy)phenyl]sulfamoylacetate To a solution of ethyl N-[3-(3-cyanophenyl)-2-(E)-propenyl]-N-(4-hydroxyphenyl)sulfamoylacetate (700 mg) obtained in reference example 98, 4-hydroxy-1-methylpiperidine (410 mg) and triphenylphosphine (920 mg) in dichloromethane (20 ml), diethyl azodicarboxylate (0.55 ml) was added dropwise with stirring under ice-cooling, and the resulting mixture was stirred at room temperature overnight. Because of the slow progress of the reaction, 4-hydroxy-1-methylpiperidine (410 mg), triphenylphosphine (920 mg) and diethyl azodicarboxylate (0.55 ml) were added furthermore, and the resulting mixture was stirred at the same temperature for 4 hours and then evaporated in vacuo. The residue obtained was purified by chromatography on a silica gel column using a mixed solvent of ethyl acetate and methanol (2:1~1:1) as the eluent to afford the title compound (690 mg, yield: 79%) as a yellow oil.

$^1$H NMR (400 MHz, CDCl$_3$) δ ppm: 1.35 (3H, t, J=7.0), 1.70–1.90 (2H, m), 1.95–2.05 (2H, m), 2.31 (3H, s), 2.65–2.75 (2H, m), 2.85–2.95 (2H, m), 3.98 (2H, s), 4.25–4.35 (1H, m), 4.30 (2H, q, J=7.0), 4.47 (2H, d, J=6.5), 6.23 (1H, dt, J=16.0, 6.5), 6.40 (1H, d, J=16.0), 6.90 (2H, d, J=9.0), 7.35–7.45 (1H, m), 7.38 (2H, d, J=9.0), 7.45–7.55 (3H, m).

Reference Example 100

4-(1-t-Butoxycarbonylpiperidin-4-yloxy)-3-trifluoromethylnitrobenzene

To a solution of 1-t-butoxycarbonyl-4-hydroxypiperidine (1.45 g), 2-trifluoromethyl-4-nitrophenol (1.38 g), which was prepared from 3-trifluoromethylnitrobenzene according to the method described in J. Org. Chem., 63, 4199 (1998), and triphenylphosphine (2.27 g) in dichloromethane (65 ml), diethyl azodicarboxylate (1.4 ml) was added dropwise with stirring under ice-cooling, and the resulting mixture was stirred at room temperature overnight and then evaporated in vacuo. The residue obtained was purified by chromatography on a silica gel column using dichloromethane as the eluent to afford the title compound (2.28 g, yield: 88%) as a pale yellow oil.

$^1$H NMR (500 MHz, CDCl$_3$) δ ppm: 1.49 (9H, s), 1.88–1.99 (4H, m), 3.51 (2H, m), 3.64 (2H, m), 4.83 (1H, m), 7.09 (1H, d, J=9.0), 8.41 (1H, dd, J=9.0, 3.0), 8.53 (1H, d, J=3.0).

Reference Example 101

4-(1-Methylpiperidin-4-yloxy)-3-trifluoromethylnitrobenzene

To a suspension of 4-(1-t-butoxycarbonylpiperidin-4-yloxy)-3-trifluoromethylnitrobenzene (2.45 g) obtained in reference example 100 in 90% formic acid (8.80 g) was added 37% formaldehyde (5.50 g), and the resulting mixture was stirred at 100° C. for 6 hours. After cooling to room temperature, the reaction mixture was neutralized with an aqueous sodium hydrogencarbonate solution and extracted with ethyl acetate. The extract was washed with a saturated aqueous sodium chloride solution, dried over anhydrous magnesium sulfate and evaporated in vacuo. The residue obtained was purified by chromatography on a silica gel column using a mixed solvent of dichloromethane and methanol (10:1) as the eluent to afford the title compound (1.82 g, yield: 95%) as a yellow oil.

$^1$H NMR (500 MHz, CDCl$_3$) δ ppm: 1.94–2.02 (2H, m), 2.02–2.10 (2H, m), 2.33 (3H, s), 2.40–2.53 (2H, m), 2.53–2.65 (2H, m), 4.68 (1H, m), 7.07 (1H, d, J=9.0), 8.39 (1H, dd, J=9.0, 3.0), 8.51 (1H, d, J=3.0).

Reference Example 102

4-(1-Methylpiperidin-4-yloxy)-3-trifluoromethylaniline

To a solution of 4-(1-methylpiperidin-4-yloxy)-3-trifluoromethylnitrobenzene (1.82 g) obtained in reference example 101 in ethanol (30 ml) was added palladium on carbon (0.18 g), and the resulting mixture was stirred at room temperature under a hydrogen atmosphere for 4.5 hours. At the end of this time, the reaction mixture was filtered, and the filtrate was evaporated in vacuo. The residue obtained was purified by chromatography on a silica gel column using a mixed solvent of dichloromethane and methanol (10:1~1:1) as the eluent to afford the title compound (1.55 g, yield: 95%) as a pale brown solid.

$^1$H NMR (500 MHz, CDCl$_3$) δ ppm: 1.85–2.00 (4H, m), 2.29 (3H, s), 2.25–2.40 (2H, m), 2.55–2.70 (2H, m), 4.31 (1H, m), 6.78 (1H, dd, J=8.5, 3.0), 6.83 (1H, d, J=8.5), 6.91 (1H, d, J=3.0).

Reference Example 103

Ethyl N-[4-(1-methylpiperidin-4-yloxy)-3-trifluoromethylphenyl]sulfamoylacetate

To a solution of 4-(1-methylpiperidin-4-yloxy)-3-trifluoromethylaniline (1.55 g) obtained in reference example 102 in dichloromethane (30 ml) were successively added dropwise ethyl chlorosulfonylacetate (0.76 ml) and pyridine (0.91 ml) with stirring under ice-cooling, and the resulting mixture was stirred at room temperature for 1 hour. After stirring, to the reaction mixture was added water, and the resulting mixture was extracted with ethyl acetate three times. The extract was washed with a saturated aqueous sodium chloride solution, dried over anhydrous magnesium sulfate and evaporated in vacuo. The residue obtained was purified by chromatography on a silica gel column using a mixed solvent of dichloromethane and methanol (10:1~5:1) as the eluent to afford the title compound (2.39 g, quantitative yield) as a pale brown amorphous solid.

$^1$H NMR (400 MHz, CDCl$_3$) δ ppm: 1.34 (3H, t, J=7.0), 2.00–2.15 (2H, m), 2.35–2.50 (2H, m), 2.62 (3H, s), 2.80–3.15 (4H, m), 3.92 (2H, s), 4.30 (2H, q, J=7.0), 4.72 (1H, m), 6.98 (1H, d, J=9.0), 7.55 (1H, dd, J=9.0, 2.5), 7.62 (1H, d, J=2.5).

Reference Example 104

Ethyl N-[3-(3-cyanophenyl)-2-(E)-propenyl]-N-[4-(1-methylpiperidin-4-yloxy)-3-trifluoromethylphenyl]sulfamoylacetate To a solution of 3-(3-cyanophenyl)-2-(E)-propen-1-ol (500 mg) obtained in reference example 2, ethyl N-[4-(1-methylpiperidin-4-yloxy)-3-trifluoromethylphenyl]sulfamoylacetate (1333 mg) obtained in reference example 0.103 and triphenylphosphine (990 mg) in dichloromethane (30 ml), diethyl azodicarboxylate (0.58 ml) was added dropwise with stirring under ice-cooling, and the resulting mixture was stirred at room temperature for 4 hours and then evaporated in vacuo. The residue obtained was purified by chromatography on a silica gel column using a mixed solvent of dichloromethane and methanol (15:1) as the eluent to afford the title compound (755 mg, yield: 43%) as a pale yellow amorphous solid.

$^1$H NMR (400 MHz, CDCl$_3$) δ ppm: 1.35 (3H, t, J=7.0), 1.90–2.10 (4H, m), 2.33 (3H, m), 2.40–2.50 (2H, m), 2.55–2.65 (2H, m), 3.98 (2H, s), 4.31 (2H, q, J=7.0), 4.47 (2H, d, J=6.5), 4.53 (1H, m), 6.23 (1H, dt, J=16.0, 6.5), 6.41 (1H, d, J=16.0), 6.98 (1H, d, J=9.0), 7.41 (1H, t, J=7.5), 7.50–7.60 (4H, m), 7.71 (1H, d, J=2.5).

Reference Example 105

4-(1-t-Butoxycarbonylpiperidin-4-yloxy)nitrobenzene

To a solution of 1-t-butoxycarbonyl-4-hydroxypiperidine (50.1 g) in N,N-dimethylacetamide (550 ml) was added sodium hydride (10.5 g) with stirring under ice-cooling, and the resulting mixture was stirred at the same temperature for 30 minutes. At the end of this time, to the reaction mixture was added dropwise a solution of 4-fluoronitrobenzene (42.2 g) in N,N-dimethylacetamide (100 ml) with stirring at the same temperature, and the resulting mixture was furthermore stirred at room temperature overnight. After stirring, to the reaction mixture was added water and the resulting mixture was extracted with ethyl acetate. The extract was washed with a saturated aqueous sodium chloride solution, dried over anhydrous magnesium sulfate and evaporated in vacuo. The residue obtained was purified by chromatography on a silica gel column using a mixed solvent of hexane and ethyl acetate (13:7) as the eluent to afford the title compound (75.1 g, yield: 93%) as a pale yellow solid.

$^1$H NMR (400 MHz, CDCl$_3$) δ ppm: 1.43 (9H, s), 1.76 (2H, m), 1.91 (2H, m), 3.34 (2H, m), 3.65 (2H, m), 4.56 (1H, m), 6.91 (2H, d, J=9.0), 8.15 (2H, d, J=9.0).

Reference Example 106

4-(1-t-Butoxycarbonylpiperidin-4-yloxy)aniline

To a solution of 4-(1-t-butoxycarbonylpiperidin-4-yloxy)nitrobenzene (11.9 g) obtained in reference example 105 in methanol (100 ml) was added palladium on carbon (1.9 g), and the resulting mixture was stirred at room temperature under a hydrogen atmosphere for 4 hours. At the end of this time, the reaction mixture was filtered, and the filtrate was evaporated in vacuo. The residue obtained was purified by chromatography on a silica gel column using a mixed solvent of hexane and ethyl acetate (1:1) as the eluent to afford the title compound (10.7 g, yield: 99%) as a pale red solid.

$^1$H NMR (400 MHz, CDCl$_3$) δ ppm: 1.46 (9H, s), 1.71 (2H, m), 1.87 (2H, m), 3.27 (2H, m), 3.71 (2H, m), 4.26 (1H, m), 6.63 (2H, d, J=8.5), 6.76 (2H, d, J=8.5).

Reference Example 107

Ethyl N-[4-(1-t-butoxycarbonylpiperidin-4-yloxy)phenyl]sulfamoylacetate

To a solution of 4-(1-t-butoxycarbonylpiperidin-4-yloxy)aniline (4.39 g) obtained in reference example 106 in dichloromethane (30 ml) were successively added dropwise ethyl chlorosulfonylacetate (2.4 ml) and pyridine (2.4 ml) with stirring under ice-cooling, and the resulting mixture was stirred at room temperature overnight and then evaporated in vacuo. The residue obtained was purified by chromatography on a silica gel column using a mixed solvent of hexane and ethyl acetate (3:2) as the eluent to afford the title compound (4.96 g, yield: 75%) as a pale red oil.

$^1$H NMR (400 MHz, CDCl$_3$) δ ppm: 1.33 (3H, t, J=7.0), 1.47 (9H, s), 1.75 (2H, m), 1.90 (2H, m), 3.34 (2H, m), 3.69 (2H, m), 3.89 (2H, s), 4.29 (2H, q, J=7.0), 4.44 (1H, m), 6.89 (2H, d, J=8.5), 7.27 (2H, d, J=8.5).

Reference Example 108

Ethyl N-[4-(1-t-butoxycarbonylpiperidin-4-yloxy)phenyl]-N-[3-(3-cyanophenyl)-2-(E)-propenyl]sulfamoylacetate To a solution of 3-(3-cyanophenyl)-2-(E)-propen-1-ol (0.80 g) obtained in reference example 2, ethyl N-[4-(1-t-butoxycarbonylpiperidin-4-yloxy)phenyl]sulfamoylacetate (2.21 g) obtained in reference example 107 and triphenylphosphine (1.70 g) in dichloromethane (40 ml), diethyl azodicarboxylate (1.0 ml) was added dropwise with stirring under ice-cooling, and the resulting mixture was stirred at the same temperature for 2 hours and then evaporated in vacuo. The residue obtained was purified by chromatography on a silica gel column using a mixed solvent of dichloromethane and ethyl acetate (10:1) as the eluent to afford the title compound (2.15 g, yield: 74%) as a colorless oil.

$^1$H NMR (500 MHz, CDCl$_3$) δ ppm: 1.35 (3H, t, J=7.0), 1.47 (9H, s), 1.75 (2H, m), 1.90 (2H, m), 3.34 (2H, m), 3.68 (2H, m), 3.98 (2H, s), 4.30 (2H, q, J=7.0), 4.45 (1H, m), 4.47 (2H, d, J=6.0), 6.24 (1H, dt, J=15.5, 6.0), 6.40 (1H, d, J=15.5), 6.90 (2H, d, J=8.5), 7.39 (3H, m), 7.51 (2H, m), 7.55 (1H, s).

Reference Example 109

4-(1-t-Butoxycarbonylpiperidin-4-yloxy)-3-methylnitrobenzene

To a solution of 1-t-butoxycarbonyl-4-hydroxypiperidine (3.62 g), 2-methyl-4-nitrophenol (2.55 g) and triphenylphosphine (5.25 g) in dichloromethane (100 ml), diethyl azodicarboxylate (3.2 ml) was added dropwise with stirring under ice-cooling, and the resulting mixture was stirred at room temperature overnight and then evaporated in vacuo. The residue obtained was purified by chromatography on a silica gel column using dichloromethane as the eluent to afford the title compound (4.07 g) containing impurities as a pale yellow oil.

$^1$H NMR (500 MHz, CDCl$_3$) δ ppm: 1.48 (9H, s), 1.84 (2H, m), 1.95 (2H, m), 2.29 (3H, s), 3.49 (2H, m), 3.62 (2H, m), 4.66 (1H, m), 6.86 (1H, d, J=8.5), 8.07 (2H, m).

Reference Example 110

4-(1-t-Butoxycarbonylpiperidin-4-yloxy)-3-methylaniline

To a solution of 4-(1-t-butoxycarbonylpiperidin-4-yloxy)-3-methylnitrobenzene (4.07 g) obtained in reference example 109 in methanol (40 ml) was added palladium on carbon (0.41 g), and the resulting mixture was stirred at room temperature under a hydrogen atmosphere for 4 hours. At the end of this time, the reaction mixture was filtered, and the filtrate was evaporated in vacuo. The residue obtained was purified by chromatography on a silica gel column using hexane and ethyl acetate (3:2) as the eluent to afford the title compound (2.73 g, overall yield in two steps from reference example 109 to reference example 110: 53%) as a pale red oil.

$^1$H NMR (500 MHz, CDCl$_3$) δ ppm: 1.47 (9H, s), 1.74 (2H, m), 1.87 (2H, m), 2.17 (3H, s), 3.30 (2H, m), 3.68 (2H, m), 4.25 (1H, m), 6.47 (1H, dd, J=8.5, 2.5), 6.53 (1H, d, J=2.5), 6.68 (1H, d, J=8.5).

Reference Example 111

Ethyl N-[4-(1-t-butoxycarbonylpiperidin-4-yloxy)-3-methylphenyl]sulfamoylacetate To a solution of 4-(1-t-butoxycarbonylpiperidin-4-yloxy)-3-methylaniline (1.63 g) obtained in reference example 110 in dichloromethane (30 ml) were successively added dropwise ethyl chlorosulfonylacetate (0.86 ml) and pyridine (0.81 ml) with stirring under ice-cooling, and the resulting mixture was stirred at room temperature for 5 hours and then evaporated in vacuo. The residue obtained was purified by chromatography on a silica gel column using a mixed solvent of hexane and ethyl acetate (3:2) as the eluent to afford the title compound (1.84 g, yield: 76%) as a pale brown amorphous solid.

$^1$H NMR (500 MHz, CDCl$_3$) δ ppm: 1.34 (3H, t, J=7.0), 1.47 (9H, s), 1.78 (2H, m), 1.89 (2H, m), 2.22 (3H, s), 3.43 (2H, m), 3.62 (2H, m), 3.90 (2H, s), 4.29 (2H, q, J=7.0), 4.48 (1H, m), 6.79 (1H, d, J=8.0), 7.12 (2H, m).

Reference Example 112

Ethyl N-[4-(1-t-butoxycarbonylpiperidin-4-yloxy)-3-methylphenyl]-N-[3-(3-cyanophenyl)-2-(E)-propenyl]sulfamoylacetate To a solution of 3-(3-cyanophenyl)-2-(E)-propen-1-ol (0.64 g) obtained in reference example 2, ethyl N-[4-(1-t-butoxycarbonylpiperidin-4-yloxy)-3-methylphenyl]sulfamoylacetate (1.84 g) obtained in reference example 111 and triphenylphosphine (1.26 g) in dichloromethane (40 ml), diethyl azodicarboxylate (0.76 ml) was added dropwise with stirring under ice-cooling, and the resulting mixture was stirred at the same temperature for 1 hour and then evaporated in vacuo. The residue obtained was purified by chromatography on a silica gel column using a mixed solvent of dichloromethane and ethyl acetate (12:1) as the eluent to afford the title compound (1.90 g, yield: 79%) as a colorless amorphous solid.

$^1$H NMR (500 MHz, CDCl$_3$) δ ppm: 1.36 (3H, t, J=7.0), 1.47 (9H, s), 1.78 (2H, m), 1.89 (2H, m), 2.21 (3H, s), 3.44 (2H, m), 3.60 (2H, m), 3.99 (2H, s), 4.31 (2H, q, J=7.0), 4.46 (2H, d, J=6.5), 4.50 (1H, m), 6.24 (1H, dt, J=16.0, 6.5), 6.41 (1H, d, J=16.0), 6.80 (1H, d, J=8.0), 7.24 (2H, m), 7.40 (1H, t, J=8.0), 7.50 (1H, d, J=7.5), 7.52 (1H, d, J=8.0), 7.56 (1H, s).

Reference Example 113

Ethyl 5-nitrosalicylate

To a solution of 5-nitrosalicylic acid (10.8 g) in ethanol (100 ml) was added concentrated sulfuric acid (92.0 g) with stirring at room temperature, and the resulting mixture was refluxed for 7.5 hours. After cooling to room temperature, the reaction mixture was neutralized with an aqueous sodium hydroxide solution and extracted with ethyl acetate. The extract was washed successively with a saturated aqueous sodium hydrogencarbonate solution, 0.5N hydrochloric acid and a saturated aqueous sodium chloride solution. The organic layer was dried over anhydrous magnesium sulfate and evaporated in vacuo to afford the title compound (10.7 g, yield: 85%) as a pale yellow solid.

$^1$H NMR (400 MHz, CDCl$_3$) δ ppm: 1.47 (3H, t, J=7.0), 4.49 (2H, q, J=7.0), 7.09 (1H, d, J=9.0), 8.33 (1H, dd, J=9.0, 3.0), 8.79 (1H, d, J=3.0).

Reference Example 114

4-(1-t-Butoxycarbonylpiperidin-4-yloxy)-3-ethoxycarbonylnitrobenzene

To a solution of 1-t-butoxycarbonyl-4-hydroxypiperidine (10.2 g), ethyl 5-nitrosalicylate (10.7 g) obtained in reference example 113 and triphenylphosphine (11.3 g) in dichloromethane (200 ml), diethyl azodicarboxylate (10.4 ml) was added dropwise with stirring under ice-cooling, and the resulting mixture was stirred at room temperature for 4 hours and then evaporated in vacuo. The residue obtained was purified by chromatography on a silica gel column using a mixed solvent of hexane and ethyl acetate (3:1) as the eluent, and the yellow solid obtained was collected by filtration using hexane to afford the title compound (12.3 g, yield: 61%) as a white solid.

$^1$H NMR (400 MHz, CDCl$_3$) δ ppm: 1.40 (3H, t, J=7.0), 1.47 (9H, s), 1.91 (4H, m), 3.58 (4H, m), 4.39 (2H, q, J=7.0), 4.79 (1H, m), 7.04 (1H, d, J=9.0), 8.32 (1H, dd, J=9.0, 3.0), 8.69 (1H, d, J=3.0).

Reference Example 115

4-(1-t-Butoxycarbonylpiperidin-4-yloxy)-3-carboxynitrobenzene

To a solution of 4-(1-t-butoxycarbonylpiperidin-4-yloxy)-3-ethoxycarbonylnitrobenzene (1.0 g) obtained in reference example 114 in ethanol (10 ml) was added an aqueous potassium hydroxide solution (prepared by dissolving 0.2 g in 0.5 ml of water) at room temperature, and the resulting mixture was refluxed for 2 hours. After cooling to room temperature, the reaction mixture was neutralized with 1N hydrochloric acid and extracted with ethyl acetate. The extract was washed successively with water and a saturated aqueous sodium chloride solution. The organic layer was dried over anhydrous magnesium sulfate and evaporated in vacuo to afford the title compound (0.9 g, yield: 96%) as a pale yellow solid.

$^1$H NMR (500 MHz, CDCl$_3$) δ ppm: 1.48 (9H, s), 1.85–1.95 (2H, m), 2.00–2.10 (2H, m), 3.45–3.55 (2H, m), 3.65–3.75 (2H, m), 4.87 (1H, m), 7.13 (1H, d, J=9.0), 8.39 (1H, dd, J=9.0, 3.0), 8.93 (1H, d, J=3.0).

Reference Example 116

4 (1-t-Butoxycarbonylpiperidin-4-yloxy)-3-carbamoylnitrobenzene

To a solution of 4-(1-t-butoxycarbonylpiperidin-4-yloxy)-3-carboxynitrobenzene (0.9 g) obtained in reference example 115 in dichloromethane (20 ml) were added successively isobutyl chloroformate (0.3 ml) and triethylamine (0.4 ml) with stirring under ice-cooling, and the resulting mixture was stirred at the same temperature for 1 hour. Furthermore, to the reaction mixture was added a 28% ammonia solution (0.2 ml), and the resulting mixture was stirred at room temperature for 1 hour and then evaporated in vacuo. The residue obtained was purified by chromatography on a silica gel column using a mixed solvent of dichloromethane and methanol (19:1) as the eluent to afford the title compound (0.9 g, yield: 98%) as a pale yellow amorphous solid.

$^1$H NMR (500 MHz, CDCl$_3$) δ ppm: 1.48 (9H, s), 1.80–1.90 (2H, m), 2.05–2.20 (2H, m), 3.30–3.40 (2H, m), 3.75–3.90 (2H, m), 4.81 (1H, m), 7.11 (1H, d, J=9.0), 8.33 (1H, dd, J=9.0, 3.0), 9.09 (1H, d, J=3.0).

Reference Example 117

4-(1-t-Butoxycarbonylpiperidin-4-yloxy)-3-carbamoylaniline

To a solution of 4-(1-t-butoxycarbonylpiperidin-4-yloxy)-3-carbamoylnitrobenzene (5.7 g) obtained in reference example 116 in methanol (80 ml) was added palladium on carbon (0.6 g), and the resulting mixture was stirred at room temperature under a hydrogen atmosphere for 2.5 hours. At the end of this time, the reaction mixture was filtered, and the filtrate was evaporated in vacuo. The residue obtained was purified by chromatography on a silica gel column using a mixed solvent of dichloromethane and methanol (19:1) as the eluent to afford the title compound (4.8 g, yield: 91%) as a pale yellow amorphous solid.

$^1$H NMR (500 MHz, CDCl$_3$) δ ppm: 1.47 (9H, s), 1.65–1.80 (2H, m), 1.95–2.05 (2H, m), 3.19 (2H, m), 3.75–3.85 (2H, m), 4.44 (1H, m), 6.78 (1H, dd, J=9.0, 3.0), 6.84 (1H, d, J=9.0), 7.50 (1H, d, J=3.0).

Reference Example 118

Ethyl N-[4-(1-t-butoxycarbonylpiperidin-4-yloxy)-3-carbamoylphenyl]sulfamoylacetate To a solution of 4-(1-t-butoxycarbonylpiperidin-4-yloxy)-3-carbamoylaniline (4.8 g) obtained in reference example 117 in dichloromethane (80 ml) were successively added dropwise ethyl chlorosulfonylacetate (2.5 ml) and pyridine (2.3 ml) with stirring under ice-cooling, and the resulting mixture was stirred at room temperature for 6 hours and then evaporated in vacuo. The residue obtained was purified by chromatography on a silica gel column using a mixed solvent of dichloromethane and methanol (19:1) as the eluent. The orange-colored solid obtained was collected by filtration using diethyl ether to afford the title compound (3.7 g, yield: 53%) as a pale yellow solid.

$^1$H NMR (500 MHz, CDCl$_3$) δ ppm: 1.32 (3H, t, J=7.0), 1.47 (9H, s), 1.70–1.85 (2H, m), 2.00–2.15 (2H, m), 3.27 (2H, m), 3.75–3.85 (2H, m), 3.94 (2H, s), 4.28 (2H, q, J=7.0), 4.65 (1H, m), 7.02 (1H, d, J=9.0), 7.59 (1H, dd, J=9.0, 3.0), 8.12 (1H, d, J=3.0).

Reference Example 119

Ethyl N-[4-(1-t-butoxycarbonylpiperidin-4-yloxy)-3-carbamoylphenyl]-N-[3-(3-cyanophenyl)-2-(E)-propenyl]sulfamoylacetate To a solution of 3-(3-cyanophenyl)-2-(E)-propen-1-ol (0.7 g) obtained in reference example 2, ethyl N-[4-(1-t-butoxycarbonylpiperidin-4-yloxy)-3-carbamoylphenyl]sulfamoylacetate (2.0 g) obtained in reference example 118 and triphenylphosphine (1.5 g) in dichloromethane (30 ml), diethyl azodicarboxylate (0.9 ml) was added dropwise with stirring under ice-cooling, and the resulting mixture was stirred at room temperature for 8 hours and then evaporated in vacuo. The residue obtained was purified by chromatography on a silica gel column using a mixed solvent of hexane and ethyl acetate (1:2) as the eluent to afford the title compound (2.5 g, yield: 94%) as a yellow amorphous solid.

$^1$H NMR (500 MHz, CDCl$_3$) δ ppm: 1.36 (3H, t, J=7.0), 1.47 (9H, s), 1.75–1.85 (2H, m), 2.00–2.10 (2H, m), 3.27 (2H, m), 3.75–3.85 (2H, m), 3.99 (2H, s), 4.31 (2H, q, J=7.0), 4.53 (2H, d, J=7.0), 4.66 (1H, m), 6.22 (1H, dt, J=16.0, 7.0), 6.42 (1H, d, J=16.0), 7.01 (1H, m), 7.39 (1H, m), 7.45–7.60 (2H, m), 7.65–7.75 (2H, m), 8.32 (1H, m).

Reference Example 120

4-(1-t-Butoxycarbonylpiperidin-4-yloxy)-3-trifluoromethylaniline

To a solution of 4-(1-t-butoxycarbonylpiperidin-4-yloxy)-3-trifluoromethylnitrobenzene (2.28 g) obtained in reference example 100 in methanol (50 ml) was added palladium on carbon (0.20 g), and the resulting mixture was stirred at room temperature under a hydrogen atmosphere for 5 hours. At the end of this time, the reaction mixture was filtered, and the filtrate was evaporated in vacuo. The residue obtained was purified by chromatography on a silica gel column using a mixed solvent of hexane and ethyl acetate (3:2) as the eluent to afford the title compound (1.69 g, yield: 80%) as a pale red oil.

$^1$H NMR (500 MHz, CDCl$_3$) δ ppm: 1.47 (9H, s), 1.76–1.88 (4H, m), 3.43 (2H, m), 3.59 (2H, m), 4.46 (1H, m), 6.78 (1H, dd, J=9.0, 3.0), 6.83 (1H, d, J=9.0), 6.91 (1H, d, J=3.0).

Reference Example 121

Ethyl N-[4-(1-t-butoxycarbonylpiperidin-4-yloxy)-3-trifluoromethylphenyl]sulfamoylacetate To a solution of 4-(1-t-butoxycarbonylpiperidin-4-yloxy)-3-trifluoromethylaniline (1.69 g) obtained in reference example 120 in dichloromethane (20 ml) were successively added dropwise ethyl chlorosulfonylacetate (0.76 ml) and pyridine (0.49 ml) with stirring under ice-cooling, and the resulting mixture was stirred at room temperature for 3 hours and then evaporated in vacuo. The residue obtained was purified by chromatography on a silica gel column using a mixed solvent of hexane and ethyl acetate (3:2) as the eluent to afford the title compound (1.74 g, yield: 73%) as a pale red oil.

$^1$H NMR (500 MHz, CDCl$_3$) δ ppm: 1.34 (3H, t, J=7.0), 1.48 (9H, s), 1.83–1.94 (4H, m), 3.48–3.60 (4H, m), 3.91 (2H, s), 4.31 (2H, q, J=7.0), 4.65 (1H, m), 6.99 (1H, d, J=9.0), 7.52 (1H, dd, J=9.0, 2.5), 7.56 (1H, d, J=2.5).

Reference Example 122

Ethyl N-[4-(1-t-butoxycarbonylpiperidin-4-yloxy)-3-trifluoromethylphenyl]-N-[3-(3-cyanophenyl)-2-(E)-propenyl]sulfamoylacetate To a solution of 3-(3-cyanophenyl)-2-(E)-propen-1-ol (0.57 g) obtained in reference example 2, ethyl N-[4-(1-t-butoxycarbonylpiperidin-4-yloxy)-3-trifluoromethylphenyl]sulfamoylacetate (1.74 g) obtained in reference example 121 and triphenylphosphine (1.07 g) in dichloromethane (27 ml), diethyl azodicarboxylate (0.65 ml) was added dropwise with stirring under ice-cooling, and the resulting mixture was stirred at room temperature for 3 hours and then evaporated in vacuo. The residue obtained was purified by chromatography on a silica gel column using a mixed solvent of dichloromethane and ethyl acetate (12:1) as the eluent to afford the title compound (2.06 g, yield: 93%) as a colorless amorphous solid.

$^1$H NMR (500 MHz, CDCl$_3$) δ ppm: 1.35 (3H, t, J=7.0), 1.47 (9H, s), 1.82–1.92 (4H, m), 3.46–3.62 (4H, m), 3.98 (2H, s), 4.31 (2H, q, J=7.0), 4.48 (2H, d, J=6.5), 4.66 (1H, m), 6.22 (1H, dt, J=16.0, 6.5), 6.41 (1H, d, J=16.0), 6.98 (1H, d, J=7.5), 7.41 (1H, dd, J=8.0, 7.5), 7.52 (2H, m), 7.57 (1H, s), 7.58 (1H, dd, J=9.0, 2.0), 7.72 (1H, d, J=2.0).

Reference Example 123

3-Chloro-4-(tropan-3-yloxy)nitrobenzene

To a solution of 3-tropanol (6.7 g), 2-chloro-4-nitrophenol (8.2 g) and triphenylphosphine (16.1 g) in a mixture of dichloromethane (200 ml) and tetrahydrofuran (50 ml), diethyl azodicarboxylate (9.7 ml) was added dropwise with stirring under ice-cooling, and the resulting mixture was stirred at room temperature overnight and then evaporated in vacuo. The residue obtained was purified by chromatography on a silica gel column using a mixed solvent of dichloromethane and methanol (19:1) as the eluent to afford the title compound (8.5 g, yield: 60%) as a pale yellow amorphous solid.

$^1$H NMR (500 MHz, CDCl$_3$) δ ppm: 1.65–1.75 (2H, m), 2.00–2.10 (4H, m), 2.15–2.25 (2H, m), 2.46 (3H, s), 3.35–3.45 (2H, m), 4.68 (1H, m), 6.98 (1H, d, J=9.0), 8.11 (1H, dd, J=3.0, 9.0), 8.28 (1H, d, J=3.0).

Reference Example 124

3-Chloro-4-(tropan-3-yloxy)aniline

To a solution of 3-chloro-4-(tropan-3-yloxy)nitrobenzene (8.5 g) obtained in reference example 123 in acetic acid (500 ml) was added tin powder (17.0 g) at room temperature, and the resulting mixture was stirred at room temperature overnight. After stirring, the reaction mixture was filtered, and the filtrate was neutralized with an aqueous potassium carbonate solution and extracted with ethyl acetate. The extract was washed with a saturated sodium chloride solution, dried over anhydrous magnesium sulfate and evaporated in vacuo. The residue obtained was purified by chromatography on a silica gel column using a mixed solvent of dichloromethane and methanol (3:1) as the eluent to afford the title compound (2.5 g, yield: 32%) as a colorless solid.

$^1$H NMR (500 MHz, CDCl$_3$) δ ppm: 1.50–1.60 (2H, m), 1.85–1.95 (4H, m), 2.00–2.10 (2H, m), 2.38 (3H, s), 3.20–3.30 (2H, m), 4.23 (1H, m), 6.49 (1H, dd, J=3.0, 8.5), 6.71 (1H, d, J=3.0) 6.81 (1H, d, J=8.5).

Reference Example 125

Ethyl N-[3-chloro-4-(tropan-3-yloxy)phenyl]sulfamoylacetate

To a solution of 3-chloro-4-(tropan-3-yloxy)aniline (2.5 g) obtained in reference example 124 in dichloromethane (50 ml) were successively added dropwise ethyl chlorosulfonylacetate (1.5 ml) and pyridine (0.9 ml) with stirring under ice-cooling, and the resulting mixture was stirred at room temperature for 3.5 hours and then evaporated in vacuo. The residue obtained was purified by chromatography on a silica gel column using a mixed solvent of dichloromethane and methanol (4:1) as the eluent to afford the title compound (3.5 g, yield: 89%) as a pale brown amorphous solid.

$^1$H NMR (500 MHz, CDCl$_3$) δ ppm: 1.32 (3H, t, J=7.0), 1.95–2.05 (2H, m), 2.20–2.25 (2H, m), 2.30–2.75 (4H, m), 2.84 (3H, s), 3.89 (2H, m), 3.98 (2H, s), 4.28 (2H, q, J=7.0), 4.49 (1H, m), 6.95 (1H, d, J=8.5), 7.25 (1H, dd, J=2.5, 8.5), 7.45 (1H, d, J=2.5).

Reference Example 126

Ethyl N-[3-chloro-4-(tropan-3-yloxy)phenyl]-N-[3-(3-cyanophenyl)-2-(E)-propenyl]sulfamoylacetate To a solution of 3-(3-cyanophenyl)-2-(E)-propen-1-ol (1.4 g) obtained in reference example 2, ethyl N-[3-chloro-4-(tropan-3-yloxy)phenyl]sulfamoylacetate (3.5 g) obtained in reference example 125 and triphenylphosphine (2.9 g) in dichloromethane (50 ml), diethyl azodicarboxylate (1.8 ml) was added dropwise with stirring under ice-cooling, and the resulting mixture was stirred at room temperature overnight and then evaporated in vacuo. The residue obtained was purified by chromatography on a silica gel column using a mixed solvent of dichloromethane and methanol (19:1~9:1) as the eluent to afford the title compound (1.3 g, yield: 27%) as a yellow amorphous solid.

$^1$H NMR (500 MHz, CDCl$_3$) δ ppm: 1.36 (3H, t, J=7.0), 1.55–1.65 (2H, m), 1.90–2.00 (4H, m), 2.05–2.15 (2H, m), 2.37 (3H, s), 3.27 (2H, m), 3.98 (2H, s), 4.31 (2H, q, J=7.0), 4.46 (2H, d, J=6.5), 4.50 (1H, m), 6.21 (1H, dt, J=6.5, 16.0), 6.41 (1H, d, J=16.0), 6.94 (1H, m), 7.29 (1H, m), 7.40 (1H, m), 7.50–7.60 (4H, m).

Reference Example 127

3-(3-Cyanophenyl)-2-fluoro-2-(Z)-propen-1-ol

To a solution of 2-diethylphosphono-2-fluoroacetic acid (4.35 g), which was prepared by the method described in J. Organomet. Chem., 332, 1 (1987), in tetrahydrofuran (90 ml) was added dropwise a 1.6 N solution of butyllithium in hexane (28 ml) with stirring at −78° C., and the resulting mixture was stirred at the same temperature for 1 hour. After stirring, to the reaction mixture was added dropwise a solution of 3-cyanobenzaldehyde (2.66 g) in tetrahydrofuran (10 ml) over a 10-minute interval, and the resulting mixture was stirred at the same temperature for 3 hours. Subsequently, the reaction temperature was raised up to 0° C., and after adding water, the aqueous layer was separated by partitioning. The organic layer separated by partitioning was extracted with a saturated aqueous sodium hydrogencarbonate solution twice. These extracts were combined with the aqueous layer separated above and adjusted to pH 4 with concentrated hydrochloric acid and then extracted with t-butyl methyl ether five times. The extract was dried over anhydrous sodium sulfate and evaporated in vacuo to afford the intermediate (3.47 g) as a white solid.

Subsequently, to a solution of the intermediate (1.15 g) obtained above and triethylamine (0.92 ml) in dichloromethane (10 ml) was added ethyl chlorocarbonate (0.63 ml) under ice-cooling, and the resulting mixture was stirred at room temperature for 15 minutes and evaporated in vacuo. To the residue obtained was added ethyl acetate, and insoluble materials were filtered off and the filtrate was evaporated in vacuo. Furthermore, to a solution of the residue obtained in tetrahydrofuran (10 ml) was added an aqueous sodium borohydride solution (prepared by dissolving 0.45 g in 5 ml of water) with stirring under ice-cooling, and the resulting mixture was stirred at room temperature for 18 hours. After stirring, to the reaction mixture was added a saturated ammonium chloride solution, and the resulting mixture was extracted with t-butyl methyl ether three times. The extract was washed with a saturated sodium chloride solution, dried over anhydrous sodium sulfate and evaporated in vacuo. The residue obtained was purified by chromatography on a silica gel column using a mixed solvent of hexane and ethyl acetate (3:2) as the eluent to afford the title compound (0.33 g, yield: 31%) as a colorless solid.

$^1$H NMR (500 MHz, CDCl$_3$) δ ppm: 4.32 (2H, dd, J=12.5, 5.5), 5.82 (1H, d, J=37.5), 7.45 (1H, t, J=8.0), 7.53 (1H, d, J=8.0), 7.70 (1H, d, J=8.0), 7.81 (1H, s).

Reference Example 128

Ethyl N-[4-(1-t-butoxycarbonylpiperidin-4-yloxy)phenyl]-N-[3-(3-cyanophenyl)-2-fluoro-2-(Z)-propenyl]sulfamoylacetate To a solution of 3-(3-cyanophenyl)-2-fluoro-2-(Z)-propen-1-ol (0.45 g) obtained in reference example 127, ethyl N-[4-(1-t-butoxycarbonylpiperidin-4-yloxy)phenyl]sulfamoylacetate (1.12 g) obtained in reference example 107 and triphenylphosphine (0.80 g) in dichloromethane (20 ml), diethyl azodicarboxylate (0.48 ml) was added dropwise with stirring under ice-cooling, and the resulting mixture was stirred at the same temperature for 2 hours and then evaporated in vacuo. The residue obtained was purified by chromatography on a silica gel column using a mixed solvent of dichloromethane and ethyl acetate (15:1) as the eluent to afford the title compound (1.40 g, yield: 92%) as a colorless oil.

$^1$H NMR (400 MHz, CDCl$_3$) δ ppm: 1.35 (3H, t, J=7.0), 1.47 (9H, s), 1.74 (2H, m), 1.90 (2H, m), 3.34 (2H, m), 3.68 (2H, m), 4.00 (2H, s), 4.30 (2H, q, J=7.0), 4.46 (1H, m), 4.54 (2H, d, J=15.0), 5.62 (1H, d, J=36.5), 6.92 (2H, d, J=9.5), 7.42 (3H, m), 7.51 (1H, d, J=7.0), 7.63 (1H, d, J=8.0), 7.71 (1H, s).

Reference Example 129

Ethyl N-[4-[(1-t-butoxycarbonylpiperidin-4-yloxy)-3-carbamoylphenyl]-N-[3-(3-cyanophenyl)-2-fluoro-2-(Z)-propenyl]sulfamoylacetate To a solution of 3-(3-cyanophenyl)-2-fluoro-2-(Z)-propen-1-ol (0.80 g) obtained in reference example 127, ethyl N-[4-(1-t-butoxycarbonylpiperidin-4-yloxy)-3-carbamoylphenyl]sulfamoylacetate (2.20 g) obtained in reference example 118 and triphenylphosphine (1.50 g) in dichloromethane (50 ml), diethyl azodicarboxylate (0.86 ml) was added dropwise with stirring under ice-cooling, and the resulting mixture was stirred at room temperature for 2.5 hours and then evaporated in vacuo. The residue obtained was purified by chromatography on a silica gel column using a mixed solvent of hexane and ethyl acetate (1:4~1:2) as the eluent to afford the title compound (3.40 g, quantitative yield) as a pale yellow amorphous solid.

$^1$H NMR (500 MHz, CDCl$_3$) δ ppm: 1.36 (3H, t, J=7.0), 1.47 (9H, s), 1.75–1.84 (2H, m), 2.02–2.10 (2H, m), 3.23–3.30 (2H, m), 3.76–3.84 (2H, m), 4.01 (2H, s), 4.31 (2H, q, J=7.0), 4.57–4.70 (3H, m), 5.65 (1H, d, J=36.5), 7.03 (1H, d, J=9.0), 7.38–7.74 (5H, m), 8.35 (1H, d, J=3.0).

Reference Example 130

3-[3-[N-[4-(1-t-Butoxycarbonylpiperidin-4-yloxy)-3-carbamoylphenyl]amino]-1-(E)-propenyl]benzonitrile 3-Cyanocinnamaldehyde (0.64 g) obtained in reference example 1, 4-(1-t-butoxycarbonylpiperidin-4-yloxy)-3-carbamoylaniline (1.36 g) obtained in reference example 117 and powdered molecular sieves 5A (5.06 g) were suspended in toluene (30 ml) and refluxed for 2.5 hours. After cooling to room temperature, the reaction mixture was filtered with celite, and the filtrate was evaporated in vacuo to afford the imine derivative.

Subsequently, to a suspension of the imine derivative obtained above in ethanol (30 ml) were added successively sodium borohydride (0.31 g) and cerium chloride (0.32 g) under ice-cooling, and the resulting mixture was stirred at room temperature overnight. After stirring, to the reaction mixture was added furthermore sodium borohydride (0.16 g), and the resulting mixture was stirred at room temperature for 30 minutes. After stirring, to the reaction mixture was added a saturated aqueous ammonium chloride solution, and the resulting mixture was extracted with ethyl acetate. The extract was washed with water, dried over anhydrous sodium sulfate and evaporated in vacuo. The residue obtained was purified by chromatography on a silica gel column using a mixed solvent of hexane and ethyl acetate (7:3~0:10) as the eluent to afford the title compound (1.77 g, yield: 92%) as a colorless oil.

$^1$H NMR (400 MHz, CDCl$_3$) δ ppm: 1.47 (9H, s), 1.68–1.79 (2H, m), 1.98–2.17 (2H, m), 3.14–3.22 (2H, m), 3.78–3.88 (2H, m), 3.99 (2H, d, J=5.5), 4.45 (1H, m), 6.38 (1H, dt, J=16.0, 5.5), 6.60 (1H, d, J=16.0), 6.75 (1H, dd, J=9.0, 3.0), 6.89 (1H, d, J=9.0), 7.41 (1H, t, J=8.0), 7.49–7.53 (2H, m), 7.58 (1H, d, J=8.0), 7.63 (1H, s).

Reference Example 131

N-[4-(1-t-Butoxycarbonylpiperidin-4-yloxy)-3-carbamoylphenyl]-N-[3-(3-cyanophenyl)-2-(E)-propenyl]methanesulfonamide To a solution of 3-[3-[N-[4-(1-t-butoxycarbonylpiperidin-4-yloxy)-3-carbamoylphenyl]amino]-1-(E)-propenyl]benzonitrile (0.85 g) obtained in reference example 130 in dichloromethane (15 ml) were successively added dropwise methanesulfonyl chloride (0.17 ml) and pyridine (0.29 ml) with stirring under ice-cooling, and the resulting mixture was stirred at room temperature overnight. After stirring, to the reaction mixture was added methanol (3 ml), and the resulting mixture was evaporated in vacuo. The residue obtained was purified by chromatography on a silica gel column using a mixed solvent of dichloromethane and methanol (10:0~9:1) as the eluent to afford the title compound (1.01 g, quantitative yield) as a colorless oil.

$^1$H NMR (400 MHz, CDCl$_3$) δ ppm: 1.48 (9H, s), 1.74–1.85 (2H, m), 2.03–2.12 (2H, m), 2.96 (3H, s), 3.23–3.32 (2H, m), 3.75–3.85 (2H, m), 4.46 (2H, d, J=6.5), 4.68 (1H, m), 6.24 (1H, dt, J=16.0, 6.5), 6.48 (1H, d, J=16.0), 7.02 (1H, d, J=9.0), 7.41 (1H, t, J=7.5), 7.49–7.57 (4H, m), 8.18 (1H, d, J=3.0).

Reference Example 132

N-[4-(1-t-Butoxycarbonylpiperidin-4-yloxy)-3-carbamoylphenyl]-N-[3-(3-cyanophenyl)-2-(E)-propenyl]ethanesulfonamide To a suspension of 3-[3-[N-[4-(1-t-butoxycarbonylpiperidin-4-yloxy)-3-carbamoylphenyl]amino]-1-(E)-propenyl] benzonitrile (0.92 g) obtained in reference example 130 in dichloromethane (15 ml) were successively added dropwise ethanesulfonyl chloride (0.22 ml) and pyridine (0.31 ml) with stirring under ice-cooling, and the resulting mixture was stirred at room temperature overnight. At the end of this time, to the reaction mixture were furthermore added dropwise ethanesulfonyl chloride (0.04 ml) and pyridine (0.16 ml) with stirring under ice-cooling, and the resulting mixture was stirred at room temperature for 5 hours. After stirring, to the reaction mixture was added methanol (3 ml), and the resulting mixture was evaporated in vacuo. The residue obtained was purified by chromatography on a silica gel column using a mixed solvent of dichloromethane and methanol (10:0~9:1) as the eluent to afford the title compound (1.08 g, yield: 90%) as a yellow oil.

$^1$H NMR (500 MHz, CDCl$_3$) δ ppm: 1.42 (3H, t, J=7.5), 1.47 (9H, s), 1.72–1.82 (2H, m), 2.03–2.10 (2H, m), 3.08 (2H, q, J=7.5), 3.22–3.31 (2H, m), 3.74–3.83 (2H, m), 4.48 (2H, d, J=6.5), 4.66 (1H, m), 6.24 (1H, dt, J=16.0, 6.5), 6.44 (1H, d, J=16.0), 7.00 (1H, d, J=9.0), 7.39 (1H, t, J=7.5), 7.48–7.55 (4H, m), 8.16 (1H, d, J=3.0).

Test Example 1

Determination of Anti-factor Xa Activity

Anti-factor Xa activity was determined according to methods described by Hara et al. [Thrombo. Haemost., 71, 314 (1994)], which were slightly modified. S-2222, a coloring substrate (0.4 mM, Daiichi Pure Chemicals Co., Ltd.) and the test compounds were mixed in Tris hydrochloride buffered solution (50 mM, pH: 8.4) containing NaCl (0.9%). To this solution, human factor-Xa (0.25 unit/ml, Cosmobio Co., Ltd.) was added and the reaction was started. In the control group, distilled water was added to the Tris-buffered solution instead of the test compound. The reaction mixture (in total: 0.1 ml) was incubated at room temperature for 5 minutes. Optical absorbance of the reaction mixture was continuously determined at 405 nm with a 96-well microplate reader (Model 550, Biorad) and increase in the absorbance for 5 minutes was calculated as an indicator of factor Xa activity. To assess anti-factor Xa activities of the test compounds, concentrations of the test compounds to inhibit the factor Xa activity by 50% (IC$_{50}$) were calculated.

As the results, the tested benzamidine derivatives of general formula (1) exerted excellent inhibitory actions against activated blood coagulation factor X activity. Compounds with IC$_{50}$ values of less than 15 nM are listed in Table 2. In this table, compound A indicates N-[4-[1-acetimidoyl-4-piperidyloxy]phenyl]-N-[2-(3-amidinophenoxy) ethyl]sulfamoyl acetic acid dihydrochloride, which was described in WO98/31661 (EP976722).

TABLE 2

| Test Compounds | Inhibitory Action against Factor Xa Activity (IC$_{50}$ (nM)) |
|---|---|
| Compound of Example 4 | 10 |
| Compound of Example 10 | 15 |
| Compound of Example 12 | 13 |
| Compound of Example 27 | 7.9 |
| Compound of Example 28 | 6.4 |
| Compound of Example 36 | 13 |
| Compound of Example 38 | 12 |
| Compound of Example 42 | 11 |
| Compound of Example 45 | 7.9 |
| Compound of Example 46 | 11 |
| Compound of Example 47 | 6.1 |
| Compound of Example 48 | 5.8 |
| Compound of Example 49 | 6.8 |
| Compound of Example 50 | 6.3 |
| Compound of Example 51 | 6.9 |
| Compound of Example 52 | 7.8 |
| Compound of Example 53 | 6.8 |
| Compound of Example 54 | 7 |
| Compound of Example 56 | 10 |
| Compound of Example 60 | 14 |
| Compound of Example 65 | 12 |
| Compound of Example 66 | 8.3 |
| Compound of Example 67 | 15 |
| Compound of Example 68 | 15 |
| Compound of Example 72 | 9.8 |
| Compound of Example 77 | 12 |
| Compound of Example 78 | 11 |
| Compound of Example 79 | 15 |

TABLE 2-continued

| Test Compounds | Inhibitory Action against Factor Xa Activity (IC$_{50}$ (nM)) |
| --- | --- |
| Compound of Example 80 | 11 |
| Compound of Example 83 | 13 |
| Compound of Example 86 | 15 |
| Compound of Example 87 | 13 |
| Compound of Example 89 | 11 |
| Compound A | 130 |

Test Example 2

Determination of Anti-trypsin Activity

Anti-trypsin activity was determined according to methods described by Taniuchi et al. [Thromb. Haemost., 79, 543 (1998)], which were partially modified. S-2222, a coloring substrate (5 µl, final concentration: 0.4 mM, Daiichi Pure Chemicals Co., Ltd.) and the test compound (5 µl) were mixed with Tris hydrochloride buffered solution (50 mM, 85 µl, pH: 8.4) containing NaCl (0.9%). To this solution, bovine trypsin (5 µl, final concentration: 0.25 µg-protein/ml, Sigma) was added and the reaction was started. In the control group, distilled water was added to the Tris-buffered solution instead of the test compound. The reaction mixture (in total: 0.1 ml) was incubated at room temperature. Optical absorbance was continuously determined at 405 nm with a 96-well microplate reader (Model 550, Biorad) and increase in the absorbance for 5 minutes was calculated as an indicator of trypsin activity. To assess anti-trypsin activities of the test compounds, concentrations of the test compounds to inhibit the trypsin activity by 50% (IC$_{50}$) were calculated. The results are shown in Table 3.

TABLE 3

| Test Compounds | Inhibitory Action against Trypsin Activity (IC$_{50}$ (nM)) |
| --- | --- |
| Compound of Example 27 | 540 |
| Compound of Example 28 | 650 |
| Compound of Example 42 | 7300 |
| Compound of Example 47 | 790 |
| Compound of Example 48 | 1200 |
| Compound of Example 49 | 860 |
| Compound of Example 50 | 1200 |
| Compound of Example 53 | 2100 |
| Compound of Example 54 | 2200 |
| Compound of Example 60 | 3100 |
| Compound of Example 65 | 2300 |
| Compound of Example 66 | 5600 |
| Compound of Example 72 | 4400 |
| Compound of Example 77 | 3700 |
| Compound of Example 78 | 5300 |
| Compound of Example 87 | 3500 |
| Compound of Example 89 | 2000 |

Formulation Example 1

Hard Capsules 50 mg of powdered of compound of Example 27, 128.7 mg of lactose, 70 mg of cellulose, and 1.3 mg of magnesium stearate are well mixed and filtrated through a sieve of 60 mesh. Each capsule is manufactured by addition of the filtrated powder into a hard gelatin capsule (No. 3) of 250 mg weight.

Formulation Example 2

Tablets 50 mg of powdered compound of Example 27, 124 mg of lactose, 25 mg of crystalline cellulose, and 1 mg of magnesium stearate are well mixed and a tablet of 200 mg weight is manufactured using a tableting machine. If desired, the tablet can be coated.

Formulation Example 3

Injections

Compound of Example 27 of 1.5 wt % is mixed in 10 vol % propylene glycol and the volume is adjusted with sterilized distilled water for injection so as to be a constant volume. The solution is sterilized and manufactured as injections.

Compounds of general formula (1), and pharmacologically acceptable salts and prodrugs thereof of the present invention exhibit excellent inhibitory activities against activated blood coagulation factor X and with low toxicities, and they are useful as remedies [particularly as prevention or therapeutic agents (particularly as therapeutic agents) for blood coagulation-related diseases (for example, thrombotic diseases such as cerebral infarction, myocardial infarction, and peripheral circulatory disorders)].

In cases where the compounds of general formula (1) or pharmacologically acceptable salts thereof of the present invention are used as prevention or therapeutic agents for disorders described above, the compounds expressed as general formula (I) described above or pharmacologically acceptable salts thereof themselves may be orally administered as such formulations as tablets, capsules, granules, powders, or syrups or non-orally administered as such formulations as injections or suppositories by mixing, if necessary, with a pharmaceutically acceptable diluent and excipient, etc.

Preparations are prepared by conventionally known methods using additive agents (carriers) such as excipients (for instance, organic excipients including sugar derivatives such as lactose, sucrose, glucose, mannitol and sorbitol; starch derivatives such as corn starch, potato starch, α-starch and dextrin; cellulose derivatives such as crystalline cellulose; gum Arabic; dextran; pullulan; and inorganic excipients including silicate derivatives such as light anhydrous silicic acid, synthetic aluminum silicate, calcium silicate and magnesium aluminometasilicate; phosphates such as calcium hydrogen-phosphate; carbonates such as calcium carbonate; sulfates such as calcium sulfate), lubricants (for instance, stearic acid, metal salts of stearic acid such as calcium stearate and magnesium stearate; talc; colloidal silica; waxes such as beeswax and spermaceti; boric acid; adipic acid; sulfates such as sodium sulfate; glycol; fumaric acid; sodium benzoate; DL-leucine; laurylsufates such as sodium lauryl sulfate and magnesium lauryl sulfate; silicates such as silicic anhydride and silicic hydrate; and starch derivatives described above can be listed), binders (for instance, hydroxypropylcellulose, hydroxypropylmethylcellulose, polyvinylpyrrolidone, Macrogol and similar excipients described above), disintegrators (for instance, cellulose derivatives such as low-substituted hydroxypropylcellulose, carboxymethylcellulose, calcium carboxymethylcellulose and internal crosslinked-sodium carboxymethylcellulose; chemically modified starch/cellulose derivatives such as carboxymethylstarch, sodium carboxymethylstarch, crosslinked polyvinylpyrrolidone), emulsifiers (for instance, colloidal clay such as bentonite and veegum; metal hydroxides such as magnesium hydroxide and aluminum hydroxide; anionic surfactants such as sodium lauryl sulfate and calcium stearate; cationic surfactants such as benzalkonium chloride; and non-ionic surfactants such as polyoxyethylenealkyl ethers, polyoxyethylene sorbitan fatty acid esters and sucrose esters of fatty acids), stabilizers (for instance, para-oxy benzoates such as methyl parahydroxybenzoate and propyl parahydroxybenzoate; alcohols such as chlorobutanol, benzylalcohol and phenylethylalcohol; benzalkonium chloride; phenols such as phenol and cresol; thimerosal; dehydroacetic acid; and sorbic acid), flavors (for instance, conventionally employed sweeteners, acidifiers and flavors), and diluents, etc.

The usage amount varies depending on the symptom, age, etc. of the patient (human). For example, in the case of oral administration, it is desirable to administer 1 mg (preferably 10 mg) as a lower limit and 1000 mg (preferably 500 mg) as an upper limit per one time for an adult and one to six times a day depending on the symptom. In the case of intravenous administration, it is desirable to administer 0.5 mg (preferably 5 mg) as a lower limit and 500 mg (preferably 250 mg) as an upper limit per one time for an adult and one to six times a day depending on the symptom.

The above dosage ranges are based on an adult human. The dosage range for warm-blooded animals who differ in weight from an adult human would be proportional to the respective average weight of an adult human and a non-human, warm-blooded animal.

The invention claimed is:

1. A compound of a formula (1), or a pharmacologically acceptable salt or prodrug thereof:

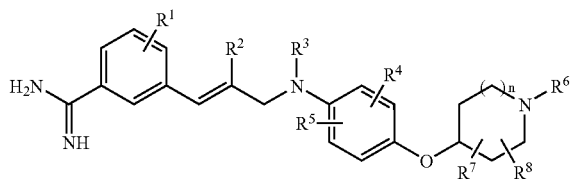

(1)

wherein
$R^1$ represents a hydrogen atom, a halogen atom, an alkyl group having from 1 to 6 carbon atoms or a hydroxyl group;
$R^2$ represents a hydrogen atom or a halogen atom;
$R^3$ represents an alkoxycarbonylalkylsulfonyl group having from 3 to 13 carbon atoms or a carboxyalkylsulfonyl group having from 2 to 7 carbon atoms;
$R^4$ and $R^5$ are the same or different and each of $R^4$ and $R^5$ represents a hydrogen atom, a halogen atom, an unsubstituted alkyl group having from 1 to 6 carbon atoms, an alkyl group having from 1 to 6 carbon atoms substituted with a halogen atom, an alkoxy group having from 1 to 6 carbon atoms, a carboxyl group, an alkoxycarbonyl group having from 2 to 7 carbon atoms, a carbamoyl group, a monoalkylcarbamoyl group having from 2 to 7 carbon atoms or a dialkylcarbamoyl group having from 3 to 13 carbon atoms;
$R^6$ represents a hydrogen atom, an unsubstituted alkyl group having from 1 to 6 carbon atoms, a cycloalkyl group having from 3 to 8 carbon atoms, an aralkyl group having from 7 to 16 carbon atoms, an alkyl group having from 1 to 6 carbon atoms substituted with a heterocycle, a carboxyalkyl group having from 2 to 7 carbon atoms, an alkoxycarbonylalkyl group having from 3 to 13 carbon atoms, an aliphatic acyl group having from 2 to 7 carbon atoms, an aromatic acyl group having from 7 to 11 carbon atoms, a carbamoyl group, an alkylsulfonyl group having from 1 to 6 carbon atoms, an aryl group having from 6 to 10 carbon atoms, a heterocycle, a formimidoyl group, a 1-iminoalkyl group having from 3 to 7 carbon atoms, an N-alkylformimidoyl group having from 2 to 7 carbon atoms or an iminoarylmethyl group having from 7 to 11 carbon atoms;
each of $R^7$ and $R^8$ represents a hydrogen atom or an alkyl group having from 1 to 6 carbon atoms; or
$R^6$ and $R^7$ taken together or $R^7$ and $R^8$ taken together form an alkylene group having from 2 to 5 carbon atoms; and
n represents 0, 1 or 2.

2. The compound according to claim 1, wherein $R^1$ is a hydrogen atom or a hydroxyl group or a pharmacologically acceptable salt thereof.

3. The compound according to claim 1, wherein $R^2$ is a hydrogen atom or a pharmacologically acceptable salt thereof.

4. The compound according to claim 1, wherein $R^3$ is an ethoxycarbonylmethanesulfonyl group or a carboxymethanesulfonyl group or a pharmacologically acceptable salt thereof.

5. The compound according to claim 1, wherein $R^4$ and $R^5$ are the same or different and each of $R^4$ and $R^5$ is a hydrogen atom, a halogen atom, an unsubstituted alkyl group having from 1 to 6 carbon atoms, an alkyl group having from 1 to 6 carbon atoms substituted with a halogen atom or a carbamoyl group or a pharmacologically acceptable salt thereof.

6. The compound according to claim 1, wherein $R^4$ and $R^5$ are the same or different and each of $R^4$ and $R^5$ is a hydrogen atom, a chlorine atom, a methyl group, a trifluoromethyl group or a carbamoyl group or a pharmacologically acceptable salt thereof.

7. The compound according to claim 1, wherein $R^6$ is an unsubstituted alkyl group having from 1 to 6 carbon atoms, a cycloalkyl group having from 3 to 8 carbon atoms, an aralkyl group having from 7 to 16 carbon atoms, an alkyl group having from 1 to 6 carbon atoms substituted with a heterocycle, an aryl group having from 6 to 10 carbon atoms, a heterocycle, a formimidoyl group, a 1-iminoalkyl group having from 3 to 7 carbon atoms, an iminoarylmethyl group having from 7 to 11 carbon atoms, or an N-alkylformimidoyl group having from 2 to 7 carbon atoms or a pharmacologically acceptable salt thereof.

8. The compound according to claim 1, wherein $R^6$ is a methyl, ethyl or isopropyl group, a cyclopentyl group, a benzyl or phenethyl group, a 2-pyridylmethyl, 3-pyridylmethyl, 4-pyridylmethyl, 2-(2-pyridyl)ethyl, 2-(3-pyridyl)ethyl or 2-(4-pyridyl)ethyl group, a phenyl group, a 4,5-dihydro-3H-pyrrol-2-yl, 2,3,4,5-tetrahydropyridin-6-yl, 4,5-dihydrooxazol-2-yl, 5,6-dihydro-2H-[1,4]thiazin-3-yl or 4-pyridyl group, a formimidoyl group, a 1-iminopropyl group, an iminophenylmethyl group or an N-ethylformimidoyl group or a pharmacologically acceptable salt thereof.

9. The compound according to claim 1, wherein each of $R^7$ and $R^8$ is a hydrogen atom or an alkyl group having from 1 to 6 carbon atoms or a pharmacologically acceptable salt thereof.

10. The compound according to claim 1, wherein $R^6$ and $R^7$ taken together or $R^7$ and $R^8$ taken together form an alkylene group having from 2 to 5 carbon atoms or a pharmacologically acceptable salt thereof.

11. The compound according to claim 1, wherein $R^6$ and $R^7$ taken together or $R^7$ and $R^8$ taken together form an ethylene or trimethylene group or a pharmacologically acceptable salt thereof.

12. The compound according to claim 1, wherein n is 1, or a pharmacologically acceptable salt thereof.

13. The compound according to claim 1, wherein said compound is ethyl N-8 3-(3-amidinophenyl)-2-(E)-propenyl]-N-[3-chloro-4-[1-(4-pyridyl)piperidin-4-yloxy]phenyl] sulfamoylacetate dihydrochloride, or a pharmacologically acceptable salt or prodrug thereof.

14. The compound according to claim 1, wherein the compound is ethyl N-[3-(3-amidinophenyl)-2-(E)-propenyl-N-[3-chloro-4-(1-formimidoylpiperidin-4-yloxy)phenyl] sulfamoylacetate dihydrochloride or a pharmacologically acceptable salt or prodrug thereof.

15. The compound according to claim 1, wherein the compound is ethyl N-[3-(3-amidinophenyl)-2-(E)-propenyl-N-[3-chloro-4-(1-iminopropyl)piperidin-4-yloxy)phenyl] sulfamoylacetate dihydrochloride or a pharmacologically acceptable salt or prodrug thereof.

16. The compound according to claim 1, wherein the compound is ethyl N-[3-(3-amidinophenyl)-2-(E)-propenyl]-N-[3-chloro-4-[1-(4,5-dihydro-3H-pyrrol-2-yl)piperidin-4-yloxy]phenyl]sulfamoylacetate dihydrochloride or a pharmacologically acceptable salt or prodrug thereof.

17. The compound according to claim 1, wherein the compound is ethyl N-[3-(3-amidinophenyl)-2-(E)-propenyl]-N-[4-[1-(4,5-dihydro-3H-pyrrol-2-yl)piperidin-4-yloxy]-3-methylphenyl]sulfamoylacetate dihydrochloride or a pharmacologically acceptable salt or prodrug thereof.

18. The compound according to claim 1, wherein the compound is ethyl N-[3-(3-amidinophenyl)-2-(E)-propenyl]-N-[4-[1-(4,5-dihydro-3H-pyrrol-2-yl)piperidin-4-yloxy]-3-trifluoromethylphenyl]sulfamoylacetate dihydrochloride or a pharmacologically acceptable salt or prodrug thereof.

19. The compound according to claim 1, wherein the compound is N-[3-(3-amidinophenyl)-2-(E)-propenyl]-N-[3-chloro-4-(1-isopropylpiperidin-4-yloxy)phenyl]sulfamoylacetic acid dihydrochloride or a pharmacologically acceptable salt or prodrug thereof.

20. The compound according to claim 1, wherein the compound is N-[3-(3-amidinophenyl)-2-(E)-propenyl]-N-[3-chloro-4-[1-(4-pyridyl)piperidin-4-yloxy]phenyl]sulfamoylacetic acid dihydrochloride or a pharmacologically acceptable salt or prodrug thereof.

21. The compound according to claim 1, wherein the compound is N-[3-(3-amidinophenyl)-2-(E)-propenyl]-N-[3-chloro-4-(1-cyclopentylpiperidin-4-yloxy)phenyl]sulfamoylacetic acid dihydrochloride or a pharmacologically acceptable salt or prodrug thereof.

22. The compound according to claim 1, wherein the compound is N-[3-(3-amidinophenyl)-2-(E)-propenyl]-N-[3-chloro-4-(indolizin-7-yloxy)phenyl]sulfamoylacetic acid dihydrochloride or a pharmacologically acceptable salt or prodrug thereof.

23. The compound according to claim 1, wherein the compound is N-[3-(3-amidinophenyl)-2-(E)-propenyl]-N-[chloro-4-(1-formimidoylpiperidin-4-yloxy)phenyl]sulfamoylacetic acid dihydrochloride or a pharmacologically acceptable salt or prodrug thereof.

24. The compound according to claim 1, wherein the compound is N-[3-(3-amidinophenyl)-2-(E)-propenyl]-N-[chloro-4-[1-(1-iminopropyl)piperidin-4-yloxy]phenyl]sulfamoylacetic acid dihydrochloride or a pharmacologically acceptable salt or prodrug thereof.

25. The compound according to claim 1, wherein the compound is N-[3-(3-amidinophenyl)-2-(E)-propenyl]-N-[3-chloro-4-[1-(4,5-dihydro-3H-pyrrol-2-yl)piperidin-4-yloxy]phenyl]sulfamoylacetic acid dihydrochloride or a pharmacologically acceptable salt or prodrug thereof.

26. The compound according to claim 1, wherein the compound is N-[3-(3-amidinophenyl)-2-(E)-propenyl]-N-[4-[1-(4,5-dihydro-3H-pyrrol-2-yl)piperidin-4-yloxy]-3-methylphenyl]sulfamoylacetic acid dihydrochloride or a pharmacologically acceptable salt or prodrug thereof.

27. The compound according to claim 1, wherein the compound is N-[3-(3-amidinophenyl)-2-(E)-propenyl]-N-[4-[1-(4,5-dihydro-3H-pyrrol-2-yl)piperidin-4-yloxy]phenyl]sulfamoylacetic acid dihydrochloride or a pharmacologically acceptable salt or prodrug thereof.

28. The compound according to claim 1, wherein the compound is N-[3-(3-amidinophenyl)-2-(E)-propenyl]-N-[4-(1-methylpiperidin-4-yloxy)-3-trifluoromethylphenyl] sulfamoylacetic acid dihydrochloride or a pharmacologically acceptable salt or prodrug thereof.

29. The compound according to claim 1, wherein the compound is N-[3-(3-amidinophenyl)-2-(E)-propenyl]-N-[4-[1-(4,5-dihydro-3H-pyrrol-2-yl)piperidin-4-yloxy]-3-trifluoromethylphenyl]sulfamoylacetic acid dihydrochloride or a pharmacologically acceptable salt or prodrug thereof.

30. The compound according to claim 1, wherein the compound is N-[3-(3-amidinophenyl)-2-(E)-propenyl]-N-[3-carbamoyl-4-[1-(4,5-dihydro-3H-pyrrol-2-yl)piperidin-4-yloxy]phenyl]sulfamoylacetic acid dihydrochloride or a pharmacologically acceptable salt or prodrug thereof.

31. The compound according to claim 1, wherein the compound is N-[3-(3-amidinophenyl)-2-(E)-propenyl]-N-[3-chloro-4-[1-(4,5-dihydrooxazol-2-yl)piperidin-4-yloxy] phenyl]sulfamoylacetic acid dihydrochloride or a pharmacologically acceptable salt or prodrug thereof.

32. The compound according to claim 1, wherein the compound is N-[3-(3-amidinophenyl)-2-(E)-propenyl]-N-[4-[1-(4,5-dihydrooxazol-2-yl)piperidin-4-yloxy]phenyl] sulfamoylacetic acid dihydrochloride or a pharmacologically acceptable salt or prodrug thereof.

33. The compound according to claim 1, wherein the compound is N-[3-(3-amidinophenyl)-2-(E)-propenyl]-N-[3-chloro-4-[1-(N-ethylformimidoyl)piperidin-4-yloxy]phenyl]sulfamoylacetic acid dihydrochloride or a pharmacologically acceptable salt or prodrug thereof.

34. A pharmaceutical composition for the treatment of a blood coagulation-related disease, a cerebral embolus, a myocardial infarction, or a peripheral circulatory disease comprising an effective pharmaceutical amount of the compound according to any one of claims 1 to 3, or 4 to 33 or a pharmacologically acceptable salt thereof or a prodrug thereof, in combination with a pharmaceutically acceptable carrier.

* * * * *